US006734301B2

(12) United States Patent
Ennis et al.

(10) Patent No.: US 6,734,301 B2
(45) Date of Patent: May 11, 2004

(54) 2,3,4,5-TETRAHYDRO-1H-[1,4]DIAZEPINO[1,7-A]INDOLE COMPOUNDS

(75) Inventors: Michael Dalton Ennis, Portage, MI (US); Robert Louis Hoffman, Kalamazoo, MI (US); Nabil B. Ghazal, Grand Rapids, MI (US); Rebecca M. Olson, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/803,242

(22) Filed: Mar. 8, 2001

(65) Prior Publication Data

US 2002/0002161 A1 Jan. 3, 2002

Related U.S. Application Data

(60) Provisional application No. 60/189,103, filed on Mar. 14, 2000.

(51) Int. Cl.[7] .................. C07D 487/12; A61K 31/55; A61P 25/00
(52) U.S. Cl. ..................... 540/561; 514/220
(58) Field of Search .............. 514/220; 540/561

(56) References Cited

U.S. PATENT DOCUMENTS

| | | | | |
|---|---|---|---|---|
| 3,689,503 | A | 9/1972 | Reynolds et al. | ... 260/326.13 R |
| 3,867,374 | A | 2/1975 | Reynolds et al. | ..... 260/239 BC |
| 4,210,590 | A | 7/1980 | Maryanoff et al. | .. 260/326.11 R |
| 4,673,674 | A | 6/1987 | Gadient | ...................... 514/220 |

FOREIGN PATENT DOCUMENTS

SU 460724 A 7/1989

OTHER PUBLICATIONS

Baxter, Gordon. "5–HT$_2$ receptor subtypes: a family re–united?." *Trends in Pharmacological Sciences.* vol. 16, pp. 105–110, 1995.
Beletskaya, I.P. "The Cross–coupling Reactions of Organic Halides with Organic Derivatives of Tin, Mercury and Copper Catalyzed by Palladium." *Journal of Organometallic Chemistry.* vol. 250, pp. 551–564, 1983.

Bös, Michael. "Novel agonists of 5HT$_{2c}$ Receptors. Synthesis and Biological Evaluation of Substituted 2–(Indol–1–yl)–1–methylethylamines and 2–(Indeno [1,2–b] pyrrol–1–yl) methylethylamines. Improved Therapeutics for Obsessive Compulsive Disorder." *Journal of Medicinal Chemistry.* vol. 40, No 17, Pp. 2762–2769, 1997.
Bromidge, Steven M. "Novel and Selective 5–HT$_{2C/2B}$ Receptor Antagonists as Potential Anxiolytic Agents: Synthesis, Quantitative Structure–Activity Relationships, and Molecular Modeling of Substituted 1–(3–Pyridylcarbamoyl) indolines." *Journal of Medicinal Chemistry*,vol. 41, No. 10, pp. 1598–1612, 1998.
Dekeyne, A., et al. "Discriminative stimulus properties of the novel serotonin (5–HT)$_{2C}$ receptor agonist, RO 60–0175: a pharmacological analysis." *Neuropharmacology.* vol. 38, Pp. 415–423, 1999.
De Meijere, A. and F. E. Meyer. *Angewandte Chemie International Edition.* vol. 33, Pp. 2379, 1994.
Gilchrist, TL., Et. Al. "Benzocarbapenems From Ethyl Indole–2–acetate." *Tetrahedron Letters.* vol. 36, No. 47, Pp. 8693–8696, 1995.
Glennon, et al. *Neuroscience and Behavioral Reviews,* vol. 14, Pp. 35, 1990.
Heck, R.F., et al. *Journal of Organic Chemistry.* vol. 39, Pp. 3318, 1974.
Hoyer, Daniel., et al. "VII. International Union of Pharmacology Classification of Receptors for 5–Hydroxythryptamine (Serotonin)." *Pharmacological Reviews.* vol. 46, No. 2, Pp. 157–203, 1994.
Jenck, F. et al. "The role of 5–HT$_{2c}$ receptors in affective disorders." *Expert Opinion on Investigational Drugs.* vol. 7, No. 10, Pp. 1587–1599, 1998.
Kennett, G.A. *IDrugs.* vol. 1, No. 4, Pp. 456–470, 1998.
Martin, J.R. et al. "5–HT$_{2C}$ Receptor Agonists: Pharmacological Characteristics and Therapeutic Potential." *The Journal of Pharmacology and Experimental Therapeutics.* vol. 286, No. 2, Pp. 913–924, 1998.
Snieckus, V. *Chemical Reviews.* vol. 90, Pp. 897, 1990.
Yang, Bryant H. " Palladium–catalyzed amination of aryl halides and sulfonates." *Journal of Organometallic Chemistry.* vol. 576, Pp. 125–146, 1999.

*Primary Examiner*—Brenda Coleman
(74) *Attorney, Agent, or Firm*—Mary J. Hosley

(57) ABSTRACT

Certain 2,3,4,5-tetrahydro-1H-[1,4]diazepino[1,7-a]indoles are 5-HT ligands and are useful for treating diseases wherein modulation of 5-HT activity is desired.

8 Claims, No Drawings

2,3,4,5-TETRAHYDRO-1H-[1,4]DIAZEPINO[1,7-A]INDOLE COMPOUNDS

CROSS-REFERENCE TO RELATED APPLICATIONS

This application claims the benefit of U.S. Provisional Application Serial No. 60/189103, filed Mar. 14, 2000, under 37 CFR 1.53(c).

BACKGROUND OF THE INVENTION

1. Field of the Invention

The present invention provides novel diazepinoindole compounds of Formula I. These compounds are 5-HT ligands and are useful for treating diseases wherein modulation of 5-HT activity is desired.

2. Technology Description

Serotonin has been implicated in a number of diseases and conditions that originate in the central nervous system. These include diseases and conditions related to sleeping, eating, perceiving pain, controlling body temperature, controlling blood pressure, depression, anxiety, schizophrenia, and other bodily states. Serotonin also plays an important role in peripheral systems, such as the gastrointestinal system, where it has been found to mediate a variety of contractile, secretory, and electrophysiologic effects.

As a result of the broad distribution of serotonin within the body, there is a tremendous interest in drugs that affect serotonergic systems. In particular, agonists, partial agonists and antagonists are of interest for the treatment of a wide range of disorders, including anxiety, depression, hypertension, migraine, obesity, compulsive disorders, schizophrenia, autism, neurodegenerative disorders (e.g. Alzheimer's disease, Parkinsonism, and Huntington's chorea), and chemotherapy-induced vomiting.

The major classes of serotonin receptors ($5\text{-HT}_{1\text{-}7}$) contain fourteen to eighteen separate receptor subtypes that have been formally classified. See Glennon, et al., *Neuroscience and Behavioral Reviews*, 1990, 14, 35; and D. Hoyer, et al. *Pharmacol. Rev.* 1994, 46, 157–203.

For example, the $5\text{-HT}_2$ family of receptors is comprised of $5\text{-HT}_{2A}$, $5\text{-HT}_{2B}$, and $5\text{-HT}_{2C}$ subtypes, which have been grouped together on the basis of primary structure, secondary messenger system, and operational profile. All three subtypes are G-protein coupled, activate phospholipase C as a principal transduction mechanism, and contain a seven-transmembrane domain structure. There are distinct differences in the distribution of the three $5\text{-HT}_2$ subtypes. The $5\text{-HT}_{2B}$ and $5\text{-HT}_{2A}$ receptors are widely distributed in the periphery, while the $5\text{-HT}_{2C}$ receptor has been found only in the central nervous system, being highly expressed in many regions of the human brain. See G. Baxter, et al. *Trends in Pharmacol. Sci.* 1995, 16, 105–110.

Subtype $5\text{-HT}_{2A}$ has been associated with effects including vasoconstriction, platelet aggregation, and bronchoconstriction, while subtype $5\text{-HT}_{2C}$ has been associated with diseases that include depression, anxiety, obsessive compulsive disorder, panic disorders, phobias, psychiatric syndromes, and obesity. Very little is known about the pharmocologic role of the $5\text{-HT}_{2B}$ receptor. See F. Jenck, et al., *Exp. Opin. Invest. Drugs*, 1998, 7, 1587–1599; M. Bos, et al., *J. Med. Chem.*, 1997, 40, 2762–2769; J. R. Martin, et al., *The Journal of Pharmacology and Experimental Therapeutics*, 1998, 286, 913–924; S. M. Bromidge, et al., *J. Med. Chem.*, 1998, 41, 1598–1612; G. A. Kennett, *Drugs*, 1998, 1, 4, 456–470; and A. Dekeyne, et al., *Neuropharmacology*, 1999, 38, 415–423.

The following references possibly suggest molecules containing both indole groups and cyclic rings wherein the indolyl nitrogen atom and an additional nitrogen atom form a part of the cyclic ring: SU 460724 and U.S. Pat. No. 4,673,674. However, the molecules described in the above-described references contain additional substituents that the inventors of the instant invention have discovered are not required, and potentially not desired. U.S. Pat. No. 4,210,590 suggests the reduction of indole compounds to indoline compounds to yield compounds having biological and/or pharmacological properties. U.S. Pat. Nos. 3,689,503 and 3,867,374 disclose 2,3,4,5-tetrahydro-1H-[1,4]-diazepino[1,2-a]indole compounds and their use in treating central nervous system diseases or disorders.

Despite the above teachings, there is currently a need for pharmaceutical agents that are useful in treating diseases and conditions that are associated with 5-HT receptors.

BRIEF SUMMARY OF THE INVENTION

In accordance with the present invention novel compounds which demonstrate useful biological activity, and particularly activity as 5-HT receptor ligands are provided. More specifically, the compounds are unsubstituted or substituted 2,3,4,5-tetrahydro-1H-[1,4]-diazepino[1,7-a] indoles.

A first embodiment of the present invention provides compounds of formula I:

A compound of formula I:

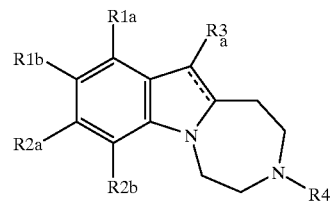

where a is a single bond or double bond, and where
R1a, R1b, R2a and R2b are each independently
(a) H, Cl, Br, I, F, CN, $CF_3$, $OCF_3$, OR5, CONR5R6, COR5, CO2R5, $Y(CH_2)_m XR5$ or $YC(O)(CH_2)_m XR5$, where m=0–3, $Y=CH_2$, S, O, or NR6, $X=CH_2$, S, O, NR6;
(b) $(CH2)_p Ar$ where p=0–3 and Ar is aryl or heteroaryl optionally substituted with one or more of the following: H, halogen, CN, $NO_2$, OR7, $CF_3$, $OCF_3$, SR7, $SO_2 R7$, $SO_2 NR7R8$, NR7R8, CONR7R8, NR7COR8, NR7CONR8R9, $CO_2 R7$, COR7, COR7, or R7; or
(c) linear or branched $C_1$–$C_8$ alkyl, linear or branched $C_2$–$C_8$ alkenyl, linear or branched $C_2$–$C_8$ alkynyl, $C_3$–$C_8$ cycloalkyl, $C_3$–$C_8$ cycloalkenyl, or $C_3$–$C_8$ cycloalkynyl; wherein any of these groups may be optionally substituted with one or more of the following: halogen, CN, $NO_2$, COR7, OR7, NR7R8, SR7, CO2R7, CONR7R8 or NR7COR8; and where
R3 is
(a) H, Cl, Br, I, F, CN, $CF_3$, $OCF_3$, alkyl, Ar, OR5, SR5, CHO, CONR5R6, COR5, CO2R5, $(Y)_o (CH2)_n XR5$, C(O)C(O)XR5, $(Y)_o (CH_2)_n C(O)XR5$, $C(O)(CH2)_n XR5$, $(Y)_o (CH2)_n N(R6)C(O)R5$, $(Y)_o (CH2)_n N(R6) S(O)_2 R5$, $(Y)_o (CH2)_n N(R6)C(O)OR5$, $(Y)_o (CH2)_n N(R6)C(O)NR5R6$ where o=0 or 1, n=0–3, $X=CH_2$, S, O, or NR6 and $Y=CH_2$, S, O or NR6, where Ar is aryl or heteroaryl optionally substituted with one or more of the following: H, halogen, CN, $NO_2$, OR7, $CF_3$, $OCF_3$, SR7, $SO_2R7$, $SO_2NR7R8$, NR7R8, CONR7R8, NR7COR8, NR7CONR8R9, $CO_2R7$, COR7, or R7; or (b) linear or branched $C_1$–$C_8$ alkyl, linear or branched $C_2$–$C_8$ alkenyl, linear or branched $C_2$–$C_8$ alkynyl, $C_3$–$C_8$ cycloalkyl, $C_3$–$C_8$ cycloalkenyl, or $C_3$–$C_8$ cycloalkynyl; wherein any of these groups may be optionally substituted with one or more of the following: halogen, CN, $NO_2$, COR10, OR10, NR10R8, SR10, CO2R10, CONR10R8 or NR10COR8; and where R4, R5 and R6 are each independently (a) H, linear or branched $C_1$–$C_8$ alkyl, linear or branched $C_2$–$C_8$ alkenyl, linear or branched $C_2$–$C_8$ alkynyl, $C_3$–$C_8$ cycloalkyl, $C_3$–$C_8$ cycloalkenyl, or $C_3$–$C_8$ cycloalkynyl; wherein any of these groups other than H may be optionally substituted with one or more of the following: halogen, CN, $NO_2$, COR10, OR10, NR10R11, SR10, CO2R10, CONR10R11 or NR10COR11; or where R5 and R6 are linked to form a 3 to 8 member ring; or (b) $(CH_2)_p$Ar where p=0–3 and Ar is aryl or heteroaryl optionally substituted with one or more of the following: H, halogen, CN, $NO_2$, OR7, $CF_3$, $OCF_3$, SR7, $SO_2R7$, $SO_2NR7R8$, NR7R8, CONR7R8, NR7COR8, NR7CONR8R9, $CO_2R7$, COR7, or R7; and where R7, R8, and R9 are each independently (a) H, linear or branched $C_1$–$C_8$ alkyl, linear or branched $C_2$–$C_8$ alkenyl, linear or branched $C_2$–$C_8$ alkynyl, $C_3$–$C_8$ cycloalkyl, $C_3$–$C_8$ cycloalkenyl, or $C_3$–$C_8$ cycloalkynyl groups, wherein any of these groups other than H may be optionally substituted with halogen, CN, $NO_2$, COR10, OR10, NR10R11, SR10, CO2R10, CONR10R11, NR10COR11, NR10CONR11R12, or where R7, R8, or R9 are linked to form a ring; or (b) $(CH2)_p$Ar where p=0–3 and Ar is aryl or heteroaryl optionally substituted with one or more of the following: H, halogen, CN, $NO_2$, OR10, $CF_3$, $OCF_3$, SR10, $SO_2R10$, $SO_2NR10R11$, NR10R11, CONR10R11, NR10COR11, NR10CONR11R12, $CO_2R10$, COR10, or R10; and where R10, R11 and R12 are each independently H, linear or branched $C_1$–$C_8$ alkyl, linear or branched $C_2$–$C_8$ alkenyl, linear or branched $C_2$–$C_8$ alkynyl, $C_3$–$C_8$ cycloalkyl, $C_3$–$C_8$ cycloalkenyl, or $C_3$–$C_8$ cycloalkynyl;

or a stereoisomer or pharmaceutically acceptable salt thereof.

In particularly preferred embodiments, R1a, R1b, R2a, R2b and R4 are H and R3 is selected from either H, —C(O)C(O)XAr, —$CH_2$C(O)XAr or —C(O)$CH_2$XAr where X and Ar are as defined above.

Another embodiment of the present invention provides a pharmaceutical composition comprising a compound of formula I, or a pharmaceutically acceptable salt thereof, and a pharmaceutically acceptable carrier. In preferred embodiments, the composition preferably comprises a therapeutically effective amount of the compound or salt.

Still another embodiment of the present invention provides a method for treating a disease or condition in a mammal (e.g. animal or human) wherein a 5-HT receptor is implicated and modulation of a 5-HT function is desired comprising administering to the mammal a therapeutically effective amount of a compound of formula I, or a pharmaceutically acceptable salt thereof.

Yet another embodiment of the present invention provides a method for treating or preventing diseases or disorders of the central nervous system comprising administering a therapeutically effective amount of a compound of formula I, or a pharmaceutically acceptable salt thereof to the mammal. Specific diseases or disorders for which the compound of formula I may have activity include, but are not limited to the following: obesity, depression, schizophrenia, a stress related disease, panic disorder, a phobia, obsessive compulsive disorder, post-traumatic-stress syndrome, immune system depression, incontinence, a stress induced problem with the urinary, gastrointestinal or cardiovascular system, neurodegenerative disorders, autism, chemotherapy-induced vomiting, hypertension, migraine headaches, cluster headaches, sexual dysfunction in a mammal, addictive disorder and withdrawal syndrome, an adjustment disorder, an age-associated learning and mental disorder, anorexia nervosa, apathy, an attention-deficit disorder due to general medical conditions, attention-deficit hyperactivity disorder, bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, a movement disorder, oppositional defiant disorder, a pain disorder, peripheral neuropathy, post-traumatic stress disorder, premenstrual dysphoric disorder, a psychotic disorder, seasonal affective disorder, a sleep disorder, a specific developmental disorder, and selective serotonin reuptake inhibition (SSRI) "poop out" syndrome.

A further embodiment of the present invention comprises the use of a compound of formula (I) or a pharmaceutically acceptable salt thereof to prepare a medicament for treating or preventing diseases or disorders of the central nervous system.

A final embodiment of the present invention comprises a method for modulating 5-HT receptor function with an effective amount of a compound of formula I, or a pharmaceutically acceptable salt thereof.

An object of the present invention is to provide novel compounds having biological activity.

Still another object of the present invention is to provide a method for treating a disease or condition in a mammal wherein a 5-HT receptor is implicated and modulation of a 5-HT function is desired by using the novel compounds of the present invention.

A further object of the present invention is to provide a method for treating or preventing diseases of the central nervous system by using the novel compounds of the present invention.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

1. Terminology Definitions

The following definitions are used, unless otherwise described: halo is fluoro, chloro, bromo, or iodo. Alkyl, alkoxy, etc. denote both straight and branched groups; but reference to an individual group or moiety such as "propyl"

embraces only the straight chain group or moiety, a branched chain isomer such as "isopropyl" being specifically referred to. When alkyl can be partially unsaturated, the alkyl chain may comprise one or more (e.g. 1, 2, 3, or 4) double or triple bonds in the chain.

Aryl denotes a phenyl group or moiety or an ortho-fused bicyclic carbocyclic group optionally substituted with one or more of the following; O, S, N, halogen, or $C_{1-4}$alkyl or moiety having about nine to ten ring atoms in which at least one ring is aromatic. Heteroaryl denotes a group or moiety of a monocyclic or polycyclic aromatic ring containing five or six ring atoms consisting of carbon and 1, 2, 3, or 4 heteroatoms each selected from the group consisting of non-peroxide oxygen, sulfur, and N(X) wherein X is absent or is H, O, $C_{1-4}$alkyl, phenyl or benzyl.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine activity using the standard tests described herein, or using other similar tests which are well known in the art.

To the extent that any pharmaceutically active compound is disclosed or claimed, it is expressly intended to include all active metabolites produced in vivo.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

To the extent that any numerical range is recited in connection with any aspect of the inventive compounds (e.g., dosages, treatment regimens, etc.) it expressly includes all numerals, integer and fractional, falling within the range.

Specific and preferred values listed below for groups or moieties, substituents, and ranges, are for illustration only; they do not exclude other defined values or other values within defined ranges.

2. The Invention
The present invention comprises compounds of formula I:
A compound of formula I:

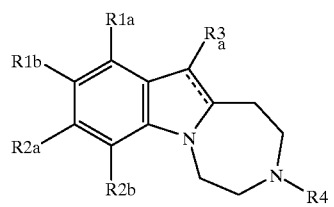

where a is a single bond or double bond, and where
R1a, R1b, R2a and R2b are each independently
(a) H, Cl, Br, I, F, CN, $CF_3$, $OCF_3$, OR5, CONR5R6, COR5, CO2R5, $Y(CH_2)_m XR5$ or $YC(O)(CH_2)_m XR5$, where m=0–3, Y=$CH_2$, S, O, or NR6, X=$CH_2$, S, O, NR6;
(b) $(CH2)_p Ar$ where p=0–3 and Ar is aryl or heteroaryl optionally substituted with one or more of the following: H, halogen, CN, $NO_2$, OR7, $CF_3$, $OCF_3$, SR7, $SO_2R7$, $SO_2NR7R8$, NR7R8, CONR7R8, NR7COR8, NR7CONR8R9, $CO_2R7$, COR7, or R7; or
(c) linear or branched $C_1$–$C_8$ alkyl, linear or branched $C_2$–$C_8$ alkenyl, linear or branched $C_2$–$C_8$ alkynyl, $C_3$–$C_8$ cycloalkyl, $C_3$–$C_8$ cycloalkenyl, or $C_3$–$C_8$ cycloalkynyl; wherein any of these groups may be optionally substituted with one or more of the following: halogen, CN, $NO_2$, COR7, OR7, NR7R8, SR7, $CO2R7$, CONR7R8 or NR7COR8; and where
R3 is
(a) H, Cl, Br, I, F, CN, $CF_3$, $OCF_3$, alkyl, Ar, OR5, SR5, CHO, CONR5R6, COR5, CO2R5, $(Y)_o(CH2)_n XR5$, $C(O)C(O)XR5$, $(Y)_o(CH_2)_n C(O)XR5$, $C(O)(CH2)_n XR5$, $(Y)_o(CH2)_n N(R6)C(O)R5$, $(Y)_o(CH2)_n N(R6) S(O)_2 R5$, $(Y)_o(CH2)_n N(R6)C(O)OR5$, $(Y)_o(CH2)_n N(R6)C(O)NR5R6$ where o=0 or 1, n=0–3, X=$CH_2$, S, O, or NR6 and Y=$CH_2$, S, O or NR6, where Ar is aryl or heteroaryl optionally substituted with one or more of the following: H, halogen, CN, $NO_2$, OR7, $CF_3$, $OCF_3$, SR7, $SO_2R7$, $SO_2NR7R8$, NR7R8, CONR7R8, NR7COR8, NR7CONR8R9, $CO_2R7$, COR7, or R7; or
(b) linear or branched $C_1$–$C_8$ alkyl, linear or branched $C_2$–$C_8$ alkenyl, linear or branched $C_2$–$C_8$ alkynyl, $C_3$–$C_8$ cycloalkyl, $C_3$–$C_8$ cycloalkenyl, or $C_3$–$C_8$ cycloalkynyl; wherein any of these groups may be optionally substituted with one or more of the following: halogen, CN, $NO_2$, COR10, OR10, NR10R8, SR10, CO2R10, CONR10R8 or NR10COR8; and where
R4, R5 and R6 are each independently
(a) H, linear or branched $C_1$–$C_8$ alkyl, linear or branched $C_2$–$C_8$ alkenyl, linear or branched $C_2$–$C_8$ alkynyl, $C_3$–$C_8$ cycloalkyl, $C_3$–$C_8$ cycloalkenyl, or $C_3$–$C_8$ cycloalkynyl; wherein any of these groups other than H may be optionally substituted with one or more of the following: halogen, CN, $NO_2$, COR10, OR10, NR10R11, SR10, CO2R10, CONR10R11 or NR10COR11; or where R5 and R6 are linked to form a 3 to 8 member ring; or
(b) $(CH_2)_p Ar$ where p=0–3 and Ar is aryl or heteroaryl optionally substituted with one or more of the following: H, halogen, CN, $NO_2$, OR7, $CF_3$, $OCF_3$, SR7, SO$_2$R7, SO$_2$NR7R8, NR7R8, CONR7R8, NR7COR8, NR7CONR8R9, CO$_2$R7, COR7, or R7; and where R7, R8, and R9 are each independently
  (a) H, linear or branched C$_1$–C$_8$ alkyl, linear or branched C$_2$–C$_8$ alkenyl, linear or branched C$_2$–C$_8$ alkynyl, C$_3$–C$_8$ cycloalkyl, C$_3$–C$_8$ cycloalkenyl, or C$_3$–C$_8$ cycloalkynyl groups, wherein any of these groups other than H may be optionally substituted with halogen, CN, NO$_2$, COR10, OR10, NR10R11, SR10, CO$_2$R10, CONR10R11, NR10COR11, NR10CONR11R12, or where R7, R8, or R9 are linked to form a ring; or
  (b) (CH2)$_p$Ar where p=0–3 and Ar is aryl or heteroaryl optionally substituted with one or more of the following: H, halogen, CN, NO$_2$, OR10, CF$_3$, OCF$_3$, SR10, SO$_2$R10, SO$_2$NR10R11, NR10R11, CONR10R11, NR10COR11, NR10CONR11R12, CO$_2$R10, COR10, or R10; and where R10, R11 and R12 are each independently H, linear or branched C$_1$–C$_8$ alkyl, linear or branched C$_2$–C$_8$ alkenyl, linear or branched C$_2$–C$_8$ alkynyl, C$_3$–C$_8$ cycloalkyl, C$_3$–C$_8$ cycloalkenyl, or C$_3$–C$_8$ cycloalkynyl;

or a stereoisomer or pharmaceutically acceptable salt thereof.

Compounds of this formula are 5-HT receptor ligands, and as such may be useful in treating animals (including humans, food animals, companion animals and other animals) against diseases and disorders of the central nervous system.

In particularly preferred embodiments, R1a, R1b, R2a, R2b and R4 are H and R3 is selected from either H, —C(O)C(O)XAr, —CH$_2$C(O)XAr or —C(O)CH$_2$XAr where X and Ar are as defined above. Even more preferred embodiments comprise the above definition where X is CH$_2$, S, O, or NR6 and Ar is phenyl or heteroaryl optionally substituted with one or more of the following: H, halogen, CN, NO$_2$, OR7, CF$_3$, OCF$_3$, SR7, SO$_2$R7, NR7R8, CONR7R8, COR7, or R7 where R7 and R8 are each independently H, linear, branched or cyclic C$_1$–C$_8$ alkyl, alkenyl, or alkynyl groups, or (CH2)$_p$Ph where p=0–3.

The names of compounds falling within the scope of the present invention include, but are not limited to the following:

2,3,4,5-tetrahydro-1H-[1,4]diazepino[1,7-a]indole hydrochloride
8-bromo-2,3,4,5-tetrahydro-1H-[1,4]diazepino[1,7-a]indole hydrochloride
2,3,4,5-tetrahydro-1H-[1,4]diazepino[1,7-a]indole-11-carbaldehyde
2-oxo-2-(2,3,4,5-tetrahydro-1H-[1,4]diazepino[1,7-a]indol-11-yl)acetamide
2,2,2-trifluoro-1-(2,3,4,5-tetrahydro-1H-[1,4]diazepino[1,7-a]indol-11-yl)-1-ethanoe
11-methyl-2,3,4,5-tetrahydro-1H-[1,4]diazepino[1,7-a]indole hydrochloride
11-chloro-2,3,4,5-tetrahydro-1H-[1,4]diazepino[1,7-a]indole hydrochloride
2,3,4,5-tetrahydro-1H-[1,4]diazepino[1,7-a]indole-11-carbonitrile
8-bromo-2,3,4,5-tetrahydro-1H-[1,4]diazepino[1,7-a]indole-11-carbaldehyde
1-(8-bromo-2,3,4,5-tetrahydro-1H-[1,4]diazepino[1,7-a]indol-11-yl)-2,2,2-trifluoro-1-ethanone
2,3,4,5-tetrahydro-1H-[1,4]diazepino[1,7-a]indole-11-carboxamide
1-(2,3,4,5-tetrahydro-1H-[1,4]diazepino[1,7-a]indol-11-yl)-1-ethanone hydrochloride
3-methyl-2,3,4,5-tetrahydro-1H-[1,4]diazepino[1,7-a]indole
3-ethyl-2,3,4,5-tetrahydro-1H-[1,4]diazepino[1,7-a]indole
3-benzyl-2,3,4,5-tetrahydro-1H-[1,4]diazepino[1,7-a]indole
10-methoxy-2,3,4,5-tetrahydro-1H-[1,4]diazepino[1,7-a]indole hydrochloride
ethyl 2-(3-benzyl-2,3,4,5-tetrahydro-1H-[1,4]diazepino[1,7-a]indol-11-yl)-2-oxoacetate
3-propyl-2,3,4,5-tetrahydro-1H-[1,4]diazepino[1,7-a]indole hydrochloride
2-(2,3,4,5-tetrahydro-1H-[1,4]diazepino[1,7-a]indol-11-yl)-1-ethanamine
2-(3-benzyl-2,3,4,5-tetrahydro-1H-[1,4]diazepino[1,7-a]indol-11-yl)-1-ethanol
3-benzyl-11-(2-phenoxyethyl)-2,3,4,5-tetrahydro-1H-[1,4]diazepino[1,7-a]indole
11-(2-phenoxyethyl)-2,3,4,5-tetrahydro-1H-[1,4]diazepino[1,7-a]indole
3-benzyl-11-[2-(2-methoxyphenoxy)ethyl]-2,3,4,5-tetrahydro-1H-[1,4]diazepino[1,7-a]indole
3-benzyl-11-[2-(2-fluorophenoxy)ethyl]-2,3,4,5-tetrahydro-1H-[1,4]diazepino[1,7-a]indole
3-benzyl-11-[2-(8-quinolinyloxy)ethyl]-2,3,4,5-tetrahydro-1H-[1,4]diazepino[1,7-a]indole
2-(2,3,4,5-tetrahydro-1H-[1,4]diazepino[1,7-a]indol-11-yl)-1-ethanol
3-benzyl-11-[2-(2-methoxy-4-methylphenoxy)ethyl]-2,3,4,5-tetrahydro-1H-[1,4]diazepino[1,7-a]indole
3-benzyl-11-[2-(2-fluoro-6-methoxyphenoxy)ethyl]-2,3,4,5-tetrahydro-1H-[1,4]diazepino[1,7-a]indole
11-[2-(2-methoxyphenoxy)ethyl]-2,3,4,5-tetrahydro-1H-[1,4]diazepino[1,7-a]indole
11-[2-(2-methoxyphenoxy)ethyl]-2,3,4,5-tetrahydro-1H-[1,4]diazepino[1,7-a]indole hydrochloride
11-[2-(2-fluorophenoxy)ethyl]-2,3,4,5-tetrahydro-1H-[1,4]diazepino[1,7-a]indole
11-[2-(2-methoxy-4-methylphenoxy)ethyl]-2,3,4,5-tetrahydro-1H-[1,4]diazepino[1,7-a]indole
11-[2-(2-fluoro-6-methoxyphenoxy)ethyl]-2,3,4,5-tetrahydro-1H-[1,4]diazepino[1,7-a]indole
3-benzyl-11-[2-(2-chlorophenoxy)ethyl]-2,3,4,5-tetrahydro-1H-[1,4]diazepino[1,7-a]indole
3-benzyl-11-[2-(4-bromo-2-methoxyphenoxy)ethyl]-2,3,4,5-tetrahydro-1H-[1,4]diazepino[1,7-a]indole
N-benzyl-2-(3-benzyl-2,3,4,5-tetrahydro-1H-[1,4]diazepino[1,7-a]indol-11-yl)-1-ethanamine
11-[2-(2-chlorophenoxy)ethyl]-2,3,4,5-tetrahydro-1H-[1,4]diazepino[1,7-a]indole
11-[2-(4-bromo-2-methoxyphenoxy)ethyl]-2,3,4,5-tetrahydro-1H-[1,4]diazepino[1,7-a]indole
2-phenoxy-1-(2,3,4,5-tetrahydro-1H-[1,4]diazepino[1,7-a]indol-11-yl)-1-ethanone
N-(4-methoxyphenyl)-2-oxo-2-(2,3,4,5-tetrahydro-1H-[1,4]diazepino[1,7-a]indol-11-yl)acetamide
4-methoxy-N-[2-(2,3,4,5-tetrahydro-1H-[1,4]diazepino[1,7-a]indol-11-yl)ethyl]aniline dihydrochloride
2-hydroxy-N-(4-methoxyphenyl)-2-(2,3,4,5-tetrahydro-1H-[1,4]diazepino[1,7-a]indol-11-yl)acetamide
2-(2-methoxyphenoxy)-1-(2,3,4,5-tetrahydro-1H-[1,4]diazepino[1,7-a]indol-11-yl)-1-ethanone
2-(4-bromo-2-methoxyphenoxy)-1-(2,3,4,5-tetrahydro-1H-[1,4]diazepino[1,7-a]indol-11-yl)-1-ethanone
N-(4-methoxyphenyl)-2-(2,3,4,5-tetrahydro-1H-[1,4]diazepino[1,7-a]indol-11-yl)acetamide
2-(4-methoxyanilino)-1-(2,3,4,5-tetrahydro-1H-[1,4]diazepino[1,7-a]indol-11-yl)-1-ethanone dihydrochloride N-(2,4-difluorophenyl)-2-oxo-2-(2,3,4,5-tetrahydro-1H-[1,4]diazepino[1,7-a]indol-11-yl)acetamide
N-(3-chloro-4-methoxyphenyl)-2-oxo-2-(2,3,4,5-tetrahydro-1H-[1,4]diazepino[1,7-a]indol-11-yl)acetamide
2-oxo-N-phenyl-2-(2,3,4,5-tetrahydro-1H-[1,4]diazepino[1,7-a]indol-11-yl)acetamide
N-(2-naphthyl)-2-oxo-2-(2,3,4,5-tetrahydro-1H-[1,4]diazepino[1,7-a]indol-11-yl)acetamide
N-(2,4-difluorophenyl)-2-(2,3,4,5-tetrahydro-1H-[1,4]diazepino[1,7-a]indol-11-yl)acetamide
8-phenyl-2,3,4,5-tetrahydro-1H-[1,4]diazepino[1,7-a]indole
8-(2,4-dichlorophenyl)-2,3,4,5-tetrahydro-1H-[1,4]diazepino[1,7-a]indole
8-(4-fluorophenyl)-2,3,4,5-tetrahydro-1H-[1,4]diazepino[1,7-a]indole
8-(4-chlorophenyl)-2,3,4,5-tetrahydro-1H-[1,4]diazepino[1,7-a]indole
8-(2-chlorophenyl)-2,3,4,5-tetrahydro-1H-[1,4]diazepino[1,7-a]indole
8-(2-methoxyphenyl)-2,3,4,5-tetrahydro-1H-[1,4]diazepino[1,7-a]indole
8-[2-chloro-4-(trifluoromethyl)phenyl]-2,3,4,5-tetrahydro-1H-[1,4]diazepino[1,7-a]indole
8-(2,4-dimethylphenyl)-2,3,4,5tetrahydro-1H-[1,4]diazepino[1,7-a]indole
8-(2-chloro-4-methoxyphenyl)-2,3,4,5-tetrahydro-1H-[1,4]diazepino[1,7-a]indole
8-(4-isopropylphenyl)-2,3,4,5tetrahydro-1H-[1,4]diazepino[1,7-a]indole
8-(4-butylphenyl)-2,3,4,5-tetrahydro-1H-[1,4]diazepino[1,7-a]indole
8-(5-fluoro-4-methoxy-2-methylphenyl)-2,3,4,5-tetrahydro-1H-[1,4]diazepino[1,7-a]indole
8-(4-methoxy-2-methylphenyl)-2,3,4,5-tetrahydro-1H-[1,4]diazepino[1,7-a]indole
8-[2-chloro-4-(trifluoromethoxy)phenyl]-2,3,4,5-tetrahydro-1H-[1,4]diazepino[1,7-a]indole
8-(2,4,5-trimethylphenyl)-2,3,4,5-tetrahydro-1H-[1,4]diazepino[1,7-a]indole
8-(3-chlorophenyl)-2,3,4,5-tetrahydro-1H-[1,4]diazepino[1,7-a]indole
8-(4-methylphenyl)-2,3,4,5-tetrahydro-1H-[1,4]diazepino[1,7-a]indole
8-(4-chloro-2-methylphenyl)-2,3,4,5-tetrahydro-1H-[1,4]diazepino[1,7-a]indole
8-(2,5-dichlorophenyl)-2,3,4,5-tetrahydro-1H-[1,4]diazepino[1,7-a]indole
8-(4-isopropyl-2-methoxyphenyl)-2,3,4,5-tetrahydro-1H-[1,4]diazepino[1,7-a]indole
8-(2,6-dichlorophenyl)-2,3,4,5-tetrahydro-1H-[1,4]diazepino[1,7-a]indole
8-(2,6-difluorophenyl)-2,3,4,5-tetrahydro-1H-[1,4]diazepino[1,7-a]indole
8-[4-methoxy-2-(trifluoromethyl)phenyl]-2,3,4,5-tetrahydro-1H-[1,4]diazepino[1,7-a]indole
8-[2-(trifluoromethyl)phenyl]-2,3,4,5-tetrahydro-1H-[1,4]diazepino[1,7-a]indole
8-(4-pyridinyl)-2,3,4,5-tetrahydro-1H-[1,4]diazepino[1,7-a]indole
8-(2-furyl)-2,3,4,5-tetrahydro-1H-[1,4]diazepino[1,7-a]indole
2-(2,3,4,5-tetrahydro-1H-[1,4]diazepino[1,7-a]indol-8-yl)benzenethiol
8-(2,3-dichlorophenyl)-2,3,4,5-tetrahydro-1H-[1,4]diazepino[1,7-a]indole
8-(4-ethylphenyl)-2,3,4,5-tetrahydro-1H-[1,4]diazepino[1,7-a]indole
8-(2,4-dimethoxyphenyl)-2,3,4,5-tetrahydro-1H-[1,4]diazepino[1,7-a]indole
8-(3-chloro-2-fluorophenyl)-2,3,4,5-tetrahydro-1H-[1,4]diazepino[1,7-a]indole
8-(4-methoxyphenyl)-2,3,4,5-tetrahydro-1H-[1,4]diazepino[1,7-a]indole
8-[4-(methylsulfanyl)phenyl]-2,3,4,5-tetrahydro-1H-[1,4]diazepino[1,7-a]indole
4-(2,3,4,5-tetrahydro-1H-[1,4]diazepino[1,7-a]indol-8-yl)benzonitrile
8-[3-(trifluoromethyl)phenyl]-2,3,4,5-tetrahydro-1H-[1,4]diazepino[1,7-a]indole
8-(2-naphthyl)-2,3,4,5-tetrahydro-1H-[1,4]diazepino[1,7-a]indole
1-[4-(2,3,4,5-tetrahydro-1H-[1,4]diazepino[1,7-a]indol-8-yl)phenyl]ethanone
N-[3-(2,3,4,5-tetrahydro-1H-[1,4]diazepino[1,7-a]indol-8-yl)phenyl]acetamide
8-(2,3-dimethylphenyl)-2,3,4,5-tetrahydro-1H-[1,4]diazepino[1,7-a]indole
8-(5-fluoro-2-methylphenyl)-2,3,4,5-tetrahydro-1H-[1,4]diazepino[1,7-a]indole
8-(2-fluoro-5-methylphenyl)-2,3,4,5-tetrahydro-1H-[1,4]diazepino[1,7-a]indole
8-(5-fluoro-2-methoxylphenyl)-2,3,4,5-tetrahydro-1H-[1,4]diazepino[1,7-a]indole
8-(3-chloro-2-methylphenyl)-2,3,4,5-tetrahydro-1H-[1,4]diazepino[1,7-a]indole
8-(3-nitrophenyl)-2,3,4,5-tetrahydro-1H-[1,4]diazepino[1,7-a]indole
8-(2-nitrophenyl)-2,3,4,5-tetrahydro-1H-[1,4]diazepino[1,7-a]indole
8-(2-chloro-3-methylphenyl)-2,3,4,5-tetrahydro-1H-[1,4]diazepino[1,7-a]indole
8-(2-methoxylphenyl)-2,3,4,5-tetrahydro-1H-[1,4]diazepino[1,7-a]indole
8-(4-ethoxy-2-methylphenyl)-2,3,4,5-tetrahydro-1H-[1,4]diazepino[1,7-a]indole
8-(4-fluoro-2-methylphenyl)-2,3,4,5-tetrahydro-1H-[1,4]diazepino[1,7-a]indole
8-(2-chloro-6-fluorophenyl)-2,3,4,5-tetrahydro-1H-[1,4]diazepino[1,7-a]indole
8-[2-chloro-4-(difluoromethoxy)phenyl]-2,3,4,5-tetrahydro-1H-[1,4]diazepino[1,7-a]indole
8-[4-(trifluoromethyl)phenyl]-2,3,4,5-tetrahydro-1H-[1,4]diazepino[1,7-a]indole
8-[4-(trifluoromethoxy)phenyl]-2,3,4,5-tetrahydro-1H-[1,4]diazepino[1,7-a]indole
8-(6-fluoro-2,4-dimethoxylphenyl)-2,3,4,5-tetrahydro-1H-[1,4]diazepino[1,7-a]indole
8-(2-methylphenyl)-2,3,4,5-tetrahydro-1H-[1,4]diazepino[1,7-a]indole
8-[6-fluoro-2-(trifluoromethyl)phenyl]-2,3,4,5-tetrahydro-1H-[1,4]diazepino[1,7-a]indole
8-[2-(methylsulfanyl)phenyl]-2,3,4,5-tetrahydro-1H-[1,4]diazepino[1,7-a]indole
8-(2,4,6-trifluorophenyl)-2,3,4,5-tetrahydro-1H-[1,4]diazepino[1,7-a]indole
8-(2,4,6-trichlorophenyl)-2,3,4,5-tetrahydro-1H-[1,4]diazepino[1,7-a]indole
8-(2,6-dichloro-4-methoxyphenyl)-2,3,4,5-tetrahydro-1H-[1,4]diazepino[1,7-a]indole
8-(2,3,4-trifluorophenyl)-2,3,4,5-tetrahydro-1H-[1,4]diazepino[1,7-a]indole
8-(4-chloro-2,6-difluorophenyl)-2,3,4,5-tetrahydro-1H-[1,4]diazepino[1,7-a]indole
8-(2,3,4,6-tetrafluorophenyl)-2,3,4,5-tetrahydro-1H-[1,4]diazepino[1,7-a]indole 8-(2,3,4,5,6-pentafluorophenyl)-2,3,4,5-tetrahydro-1H-[1,4]
diazepino[1,7-a]indole
8-[2,6-di(trifluoromethyl)phenyl]-2,3,4,5-tetrahydro-1H-[1,
4]diazepino[1,7-a]indole
8-[2-(trifluoromethoxy)phenyl]-2,3,4,5-tetrahydro-1H-[1,4]
diazepino[1,7-a]indole
8-[4-ethoxy-2-(trifluoromethoxy)phenyl]-2,3,4,5-
tetrahydro-1H-[1,4]diazepino[1,7-a]indole
8-[4-isopropoxy-2-(trifluoromethyl)phenyl]-2,3,4,5-
tetrahydro-1H-[1,4]diazepino[1,7-a]indole
8-[4-chloro-2-(trifluoromethyl)phenyl]-2,3,4,5-tetrahydro-
1H-[1,4]diazepino[1,7-a]indole
8-[4-fluoro-2-(trifluoromethyl)phenyl]-2,3,4,5-tetrahydro-
1H-[1,4]diazepino[1,7-a]indole
8-[2-chloro-4-ethoxyphenyl]-2,3,4,5-tetrahydro-1H-[1,4]
diazepino[1,7-a]indole
8-[2-chloro-4-isopropoxyphenyl]-2,3,4,5-tetrahydro-1H-[1,
4]diazepino[1,7-a]indole
8-(2-ethyl-4-methoxyphenyl)-2,3,4,5-tetrahydro-1H-[1,4]
diazepino[1,7-a]indole
5-methoxy-2-(2,3,4,5-tetrahydro-1H-[1,4]diazepino[1,7-a]
indol-8-yl)benzaldehyde
8-[4-methoxy-2-(1-hydroxyethyl)phenyl]-2,3,4,5-
tetrahydro-1H-[1,4]diazepino[1,7-a]indole
8-[4-methoxy-2-(1-methoxyethyl)phenyl]-2,3,4,5-
tetrahydro-1H-[1,4]diazepino[1,7-a]indole
1-[5-methoxy-2-(2,3,4,5-tetrahydro-1H-[1,4]diazepino[1,7-
a]indol-8-yl)phenyl]ethanone
[5-methoxy-2-(2,3,4,5-tetrahydro-1H-[1,4]diazepino[1,7-a]
indol-8-yl)phenyl]methanol
8-[4-methoxy-2-(methoxymethyl)phenyl]-2,3,4,5-
tetrahydro-1H-[1,4]diazepino[1,7-a]indole
1-[5-methoxy-2-(2,3,4,5-tetrahydro-1H-[1,4]diazepino[1,7-
a]indol-8-yl)phenyl]-1-propanol
1-[5-methoxy-2-(2,3,4,5-tetrahydro-1H-[1,4]diazepino[1,7-
a]indol-8-yl)phenyl]-1-propanone
methyl (2Z)-3-[5-methoxy-2-(2,3,4,5-tetrahydro-1H-[1,4]
diazepino[1,7-a]indol-8-yl)phenyl]-2-propanoate
methyl 3-[5-methoxy-2-(2,3,4,5-tetrahydro-1H-[1,4]
diazepino[1,7-a]indol-8-yl)phenyl]propanoate
(2Z)-3-[5-methoxy-2-(2,3,4,5-tetrahydro-1H-[1,4]diazepino
[1,7-a]indol-8-yl)phenyl]-2-propen-1-ol
methyl (2E)-3-[5-methoxy-2-(2,3,4,5-tetrahydro-1H-[1,4]
diazepino[1,7-a]indol-8-yl)phenyl]-2-propenoate
(2E)-3-[5-methoxy-2-(2,3,4,5-tetrahydro-1H-[1,4]diazepino
[1,7-a]indol-8-yl)phenyl]-2-propen-1-ol
8-[4-methoxy-2-(2-methoxyethyl)phenyl]-2,3,4,5-
tetrahydro-1H-[1,4]diazepino[1,7-a]indole
8-(2-fluoro-4-methoxyphenyl)-2,3,4,5-tetrahydro-1H-[1,4]
diazepino[1,7-a]indole
8-(2-chloro-4-fluorophenyl)-2,3,4,5-tetrahydro-1H-[1,4]
diazepino[1,7-a]indole
8-benzyl-2,3,4,5-tetrahydro-1H-[1,4]diazepino[1,7-a]indole
8-(2-fluorobenzyl)-2,3,4,5-tetrahydro-1H-[1,4]diazepino[1,
7-a]indole
8-(3-fluorobenzyl)-2,3,4,5-tetrahydro-1H-[1,4]diazepino[1,
7-a]indole
8-(4-fluorobenzyl)-2,3,4,5-tetrahydro-1H-[1,4]diazepino[1,
7-a]indole
8-(3-methoxybenzyl)-2,3,4,5-tetrahydro-1H-[1,4]diazepino
[1,7-a]indole
3-(2,3,4,5-tetrahydro-1H-[1,4]diazepino[1,7-a]indol-8-
ylmethyl)phenol
8-(2-methoxybenzyl)-2,3,4,5-tetrahydro-1H-[1,4]diazepino
[1,7-a]indole
2-(2,3,4,5-tetrahydro-1H-[1,4]diazepino[1,7-a]indol-8-
ylmethyl)phenol methyl 2-methoxy-6-(2,3,4,5-tetrahydro-1H-[1,4]diazepino
[1,7-a]indol-8-yl)benzoate
3-(2,3,4,5-tetrahydro-1H-[1,4]diazepino[1,7-a]indol-8-yl)
benzonitrile
3-methyl-4-(2,3,4,5-tetrahydro-1H-[1,4]diazepino[1,7-a]
indol-8-yl)benzonitrile
2-methyl-3-(2,3,4,5-tetrahydro-1H-[1,4]diazepino[1,7-a]
indol-8-yl)benzonitrile
2-(2,3,4,5-tetrahydro-1H-[1,4]diazepino[1,7-a]indol-8-yl)
benzonitrile
3-trifluoromethyl-4-(2,3,4,5-tetrahydro-1H-[1,4]diazepino
[1,7-a]indol-8-yl)benzonitrile
3-(2,3,4,5-tetrahydro-1H-[1,4]diazepino[1,7-a]indol-8-yl)
benzaldehyde
[3-(2,3,4,5-tetrahydro-1H-[1,4]diazepino[1,7-a]indol-8-yl)
phenyl]methanol
8-[3-(methoxymethyl)phenyl]-2,3,4,5-tetrahydro-1H-[1,4]
diazepino[1,7-a]indole
N,N-dimethyl[3-(2,3,4,5-tetrahydro-1H-[1,4]diazepino[1,7-
a]indol-8-yl)phenyl]methanamine
2-fluoro-5-(2,3,4,5-tetrahydro-1H-[1,4]diazepino[1,7-a]
indol-8-yl)benzonitrile
2-fluoro-5-(2,3,4,5-tetrahydro-1H-[1,4]diazepino[1,7-a]
indol-8-yl)benzamide
8-phenyl-2,3,4,5,11,11a-hexahydro-1H-[1,4]diazepino[1,7-
a]indole
8-(2,4-dichlorophenyl)-2,3,4,5,11,11a-hexahydro-1H-[1,4]
diazepino[1,7-a]indole
8-(4-fluorophenyl)-2,3,4,5,11,11a-hexahydro-1H-[1,4]
diazepino[1,7-a]indole
8-(4-chlorophenyl)-2,3,4,5,11,11a-hexahydro-1H-[1,4]
diazepino[1,7-a]indole
8-(2-chlorophenyl)-2,3,4,5,11,11a-hexahydro-1H-[1,4]
diazepino[1,7-a]indole
8-(2-methoxyphenyl)-2,3,4,5,11,11a-hexahydro-1H-[1,4]
diazepino[1,7-a]indole
8-[2-chloro-4-(trifluoromethyl)phenyl]-2,3,4,5,11,11a-
hexahydro-1H-[1,4]diazepino[1,7-a]indole
8-(2,4-dimethylphenyl)-2,3,4,5,11,11a-hexahydro-1H-[1,4]
diazepino[1,7-a]indole
8-(2-chloro-4-methoxyphenyl)-2,3,4,5,11,11a-hexahydro-
1H-[1,4]diazepino[1,7-a]indole
8-(4-isopropylphenyl)-2,3,4,5,11,11a-hexahydro-1H-[1,4]
diazepino[1,7-a]indole
8-(4-butylphenyl)-2,3,4,5,11,11a-hexahydro-1H-[1,4]
diazepino[1,7-a]indole
8-(5-fluoro-4-methoxy-2-methylphenyl)-2,3,4,5,11,11a-
hexahydro-1H-[1,4]diazepino[1,7-a]indole
8-(4-methoxy-2-methylphenyl)-2,3,4,5,11,11a-hexahydro-
1H-[1,4]diazepino[1,7-a]indole
8-[2-chloro-4-(trifluoromethoxy)phenyl]-2,3,4,5,11,11a-
hexahydro-1H-[1,4]diazepino[1,7-a]indole
8-(2,4,5-trimethylphenyl)-2,3,4,5,11,11a-hexahydro-1H-[1,
4]diazepino[1,7-a]indole
8-(3-chlorophenyl)-2,3,4,5,11,11a-hexahydro-1H-[1,4]
diazepino[1,7-a]indole
8-(4-methylphenyl)-2,3,4,5,11,11a-hexahydro-1H-[1,4]
diazepino[1,7-a]indole
8-(4-chloro-2-methylphenyl)-2,3,4,5,11,11a-hexahydro-1H-
[1,4]diazepino[1,7-a]indole
8-(2,5-dichlorophenyl)-2,3,4,5,11,11a-hexahydro-1H-[1,4]
diazepino[1,7-a]indole
8-(4-isopropyl-2-methoxyphenyl)-2,3,4,5,11,11a-
hexahydro-1H-[1,4]diazepino[1,7-a]indole
8-(2,6-dichlorophenyl)-2,3,4,5,11,11a-hexahydro-1H-[1,4]
diazepino[1,7-a]indole
8-(2,6-difluorophenyl)-2,3,4,5,11,11a-hexahydro-1H-[1,4]
diazepino[1,7-a]indole 8-[4-methoxy-2-(trifluoromethyl)phenyl]-2,3,4,5,11,11a-hexahydro-1H-[1,4]diazepino[1,7-a]indole 8-[2-(trifluoromethyl)phenyl]-2,3,4,5,11,11a-hexahydro-1H-[1,4]diazepino[1,7-a]indole 8-(4-pyridinyl)-2,3,4,5,11,11a-hexahydro-1H-[1,4]diazepino[1,7-a]indole 8-(2-furyl)-2,3,4,5,11,11a-hexahydro-1H-[1,4]diazepino[1,7-a]indole 2-(2,3,4,5,11,11a-hexahydro-1H-[1,4]diazepino[1,7-a]indol-8-yl)benzenethiol 8-(2,3-dichlorophenyl)-2,3,4,5,11,11a-hexahydro-1H-[1,4]diazepino[1,7-a]indole 8-(4-ethylphenyl)-2,3,4,5,11,11a-hexahydro-1H-[1,4]diazepino[1,7-a]indole 8-(2,4-dimethoxyphenyl)-2,3,4,5,11,11a-hexahydro-1H-[1,4]diazepino[1,7-a]indole 8-(3-chloro-2-fluorophenyl)-2,3,4,5,11,11a-hexahydro-1H-[1,4]diazepino[1,7-a]indole 8-(4-methoxyphenyl)-2,3,4,5,11,11a-hexahydro-1H-[1,4]diazepino[1,7-a]indole 8-[4-(methylsulfanyl)phenyl]-2,3,4,5,11,11a-hexahydro-1H-[1,4]diazepino[1,7-a]indole 4-(2,3,4,5,11,11a-hexahydro-1H-[1,4]diazepino[1,7-a]indol-8-yl)benzonitrile 8-[3-(trifluoromethyl)phenyl]-2,3,4,5,11,11a-hexahydro-1H-[1,4]diazepino[1,7-a]indole 8-(2-naphthyl)-2,3,4,5,11,11a-hexahydro-1H-[1,4]diazepino[1,7-a]indole 1-[4-(2,3,4,5,11,11a-hexahydro-1H-[1,4]diazepino[1,7-a]indol-8-yl)phenyl]ethanone N-[3-(2,3,4,5,11,11a-hexahydro-1H-[1,4]diazepino[1,7-a]indol-8-yl)phenyl]acetamide 8-(2,3-dimethylphenyl)-2,3,4,5,11,11a-hexahydro-1H-[1,4]diazepino[1,7-a]indole 8-(5-fluoro-2-methylphenyl)-2,3,4,5,11,11a-hexahydro-1H-[1,4]diazepino[1,7-a]indole 8-(2-fluoro-5-methylphenyl)-2,3,4,5,11,11a-hexahydro-1H-[1,4]diazepino[1,7-a]indole 8-(5-fluoro-2-methoxylphenyl)-2,3,4,5,11,11a-hexahydro-1H-[1,4]diazepino[1,7-a]indole 8-(3-chloro-2-methylphenyl)-2,3,4,5,11,11a-hexahydro-1H-[1,4]diazepino[1,7-a]indole 8-(3-nitrophenyl)-2,3,4,5,11,11a-hexahydro-1H-[1,4]diazepino[1,7-a]indole 8-(2-nitrophenyl)-2,3,4,5,11,11a-hexahydro-1H-[1,4]diazepino[1,7-a]indole 8-(2-chloro-3-methylphenyl)-2,3,4,5,11,11a-hexahydro-1H-[1,4]diazepino[1,7-a]indole 8-(2-methoxyphenyl)-2,3,4,5,11,11a-hexahydro-1H-[1,4]diazepino[1,7-a]indole 8-(4-ethoxy-2-methylphenyl)-2,3,4,5,11,11a-hexahydro-1H-[1,4]diazepino[1,7-a]indole 8-(4-fluoro-2-methylphenyl)-2,3,4,5,11,11a-hexahydro-1H-[1,4]diazepino[1,7-a]indole 8-(2-chloro-6-fluorophenyl)-2,3,4,5,11,11a-hexahydro-1H-[1,4]diazepino[1,7-a]indole 8-[2-chloro-4-(difluoromethoxy)phenyl]-2,3,4,5,11,11a-hexahydro-1H-[1,4]diazepino[1,7-a]indole 8-[4-(trifluoromethyl)phenyl]-2,3,4,5,11,11a-hexahydro-1H-[1,4]diazepino[1,7-a]indole 8-[4-(trifluoromethoxy)phenyl]-2,3,4,5,11,11a-hexahydro-1H-[1,4]diazepino[1,7-a]indole 8-(6-fluoro-2,4-dimethoxylphenyl)-2,3,4,5,11,11a-hexahydro-1H-[1,4]diazepino[1,7-a]indole 8-(2-methylphenyl)-2,3,4,5,11,11a-hexahydro-1H-[1,4]diazepino[1,7-a]indole 8-[6-fluoro-2-(trifluoromethyl)phenyl]-2,3,4,5,11,11a-hexahydro-1H-[1,4]diazepino[1,7-a]indole 8-[2-(methylsulfanyl)phenyl]-2,3,4,5,11,11a-hexahydro-1H-[1,4]diazepino[1,7-a]indole 8-(2,4,6-trifluorophenyl)-2,3,4,5,11,11a-hexahydro-1H-[1,4]diazepino[1,7-a]indole 8-(2,4,6-trichlorophenyl)-2,3,4,5,11,11a-hexahydro-1H-[1,4]diazepino[1,7-a]indole 8-(2,6-dichloro-4-methoxyphenyl)-2,3,4,5,11,11a-hexahydro-1H-[1,4]diazepino[1,7-a]indole 8-(2,3,4-trifluorophenyl)-2,3,4,5,11,11a-hexahydro-1H-[1,4]diazepino[1,7-a]indole 8-(4-chloro-2,6-difluorophenyl)-2,3,4,5,11,11a-hexahydro-1H-[1,4]diazepino[1,7-a]indole 8-(2,3,4,6-tetrafluorophenyl)-2,3,4,5,11,11a-hexahydro-1H-[1,4]diazepino[1,7-a]indole 8-(2,3,4,5,6-pentafluorophenyl)-2,3,4,5,11,11a-hexahydro-1H-[1,4]diazepino[1,7-a]indole 8-[2,6-di(trifluoromethyl)phenyl]-2,3,4,5,11,11a-hexahydro-1H-[1,4]diazepino[1,7-a]indole 8-[2-(trifluoromethoxy)phenyl]-2,3,4,5,11,11a-hexahydro-1H-[1,4]diazepino[1,7-a]indole 8-[4-ethoxy-2-(trifluoromethoxy)phenyl]-2,3,4,5,11,11a-hexahydro-1H-[1,4]diazepino[1,7-a]indole 8-[4-isopropoxy-2-(trifluoromethyl)phenyl]-2,3,4,5,11,11a-hexahydro-1H-[1,4]diazepino[1,7-a]indole 8-[4-chloro-2-(trifluoromethyl)phenyl]-2,3,4,5,11,11a-hexahydro-1H-[1,4]diazepino[1,7-a]indole 8-[4-fluoro-2-(trifluoromethyl)phenyl]-2,3,4,5,11,11a-hexahydro-1H-[1,4]diazepino[1,7-a]indole 8-(2-chloro-4-ethoxyphenyl)-2,3,4,5,11,11a-hexahydro-1H-[1,4]diazepino[1,7-a]indole 8-[2-chloro-4-isopropoxyphenyl]-2,3,4,5,11,11a-hexahydro-1H-[1,4]diazepino[1,7-a]indole 8-(2-ethyl-4-methoxyphenyl)-2,3,4,5,11,11a-hexahydro-1H-[1,4]diazepino[1,7-a]indole 5-methoxy-2-(2,3,4,5,11,11a-hexahydro-1H-[1,4]diazepino[1,7-a]indol-8-yl)benzaldehyde 8-[4-methoxy-2-(1-hydroxyethyl)phenyl]-2,3,4,5,11,11a-hexahydro-1H-[1,4]diazepino[1,7-a]indole 8-[4-methoxy-2-(1-methoxyethyl)phenyl]-2,3,4,5,11,11a-hexahydro-1H-[1,4]diazepino[1,7-a]indole 1-[5-methoxy-2-(2,3,4,5,11,11a-hexahydro-1H-[1,4]diazepino[1,7-a]indol-8-yl)phenyl]ethanol

[5-methoxy-2-(2,3,4,5,11,11a-hexahydro-1H-[1,4]diazepino[1,7-a]indol-8-yl)phenyl]methanol 8-[4-methoxy-2-(methoxymethyl)phenyl]-2,3,4,5,11,11a-hexahydro-1H-[1,4]diazepino[1,7-a]indole 1-[5-methoxy-2-(2,3,4,5,11,11a-hexahydro-1H-[1,4]diazepino[1,7-a]indol-8-yl)phenyl]-1-propanol 1-[5-methoxy-2-(2,3,4,5,11,11a-hexahydro-1H-[1,4]diazepino[1,7-a]indol-8-yl)phenyl]-1-propanone methyl (2Z)-3-[5-methoxy-2-(2,3,4,5,11,11a-hexahydro-1H-[1,4]diazepino[1,7-a]indol-8-yl)phenyl]-2-propenoate methyl 3-[5-methoxy-2-(2,3,4,5,11,11a-hexahydro-1H-[1,4]diazepino[1,7-a]indol-8-yl)phenyl]propnoate (2Z)-3-[5-methoxy-2-(2,3,4,5,11,11a-hexahydro-1H-[1,4]diazepino[1,7-a]indol-8-yl)phenyl]-2-propen-1-ol methyl (2E)-3-[5-methoxy-2-(2,3,4,5,11,11a-hexahydro-1H-[1,4]diazepino[1,7-a]indol-8-yl)phenyl]-2-propenoate (2E)-3-[5-methoxy-2-(2,3,4,5,11,11a-hexahydro-1H-[1,4]diazepino[1,7-a]indol-8-yl)phenyl]-2-propen-1-ol 8-[4-methoxy-2-(2-methoxyethyl)phenyl]-2,3,4,5,11,11a-hexahydro-1H-[1,4]diazepino[1,7-a]indole 8-(2-fluoro-4-methoxyphenyl)-2,3,4,5,11,11a-hexahydro-1H-[1,4]diazepino[1,7-a]indole 8-(2-chloro-4-fluorophenyl)-2,3,4,5,11,11a-hexahydro-1H-[1,4]diazepino[1,7-a]indole 8-benzyl-2,3,4,5,11,11a-hexahydro-1H-[1,4]diazepino[1,7-a]indole 8-(2-fluorobenzyl)-2,3,4,5,11,11a-hexahydro-1H-[1,4]diazepino[1,7-a]indole 8-(3-fluorobenzyl)-2,3,4,5,11,11a-hexahydro-1H-[1,4]diazepino[1,7-a]indole 8-(4-fluorobenzyl)-2,3,4,5,11,11a-hexahydro-1H-[1,4]diazepino[1,7-a]indole 8-(3-methoxybenzyl)-2,3,4,5,11,11a-hexahydro-1H-[1,4]diazepino[1,7-a]indole 3-(2,3,4,5,11,11a-hexahydro-1H-[1,4]diazepino[1,7-a]indol-8-ylmethyl)phenol 8-(2-methoxybenzyl)-2,3,4,5,11,11a-hexahydro-1H-[1,4]diazepino[1,7-a]indole 2-(2,3,4,5,11,11a-hexahydro-1H-[1,4]diazepino[1,7-a]indol-8-ylmethyl)phenol methyl 2-methoxy-6-(2,3,4,5,11,11a-hexahydro-1H-[1,4]diazepino[1,7-a]indol-8-yl)benzoate 3-(2,3,4,5,11,11a-hexahydro-1H-[1,4]diazepino[1,7-a]indol-8-yl)benzonitrile 3-methyl-4-(2,3,4,5,11,11a-hexahydro-1H-[1,4]diazepino[1,7-a]indol-8-yl)benzonitrile 2-methyl-3-(2,3,4,5,11,11a-hexahydro-1H-[1,4]diazepino[1,7-a]indol-8-yl)benzonitrile 2-(2,3,4,5,11,11a-hexahydro-1H-[1,4]diazepino[1,7-a]indol-8-yl)benzonitrile 3-trifluoromethyl-4-(2,3,4,5,11,11a-hexahydro-1H-[1,4]diazepino[1,7-a]indol-8-yl)benzonitrile 3-(2,3,4,5,11,11a-hexahydro-1H-[1,4]diazepino[1,7-a]indol-8-yl)benzaldehyde

[3-(2,3,4,5,11,11a-hexahydro-1H-[1,4]diazepino[1,7-a]indol-8-yl)phenyl]methanol

8-[3-(methoxymethyl)phenyl]-2,3,4,5,11,11a-hexahydro-1H-[1,4]diazepino[1,7-a]indole N,N-dimethyl[3-(2,3,4,5,11,11a-hexahydro-1H-[1,4]diazepino[1,7-a]indol-8-yl)phenyl]methanamine 2-fluoro-5-(2,3,4,5,11,11a-hexahydro-1H -[1,4]diazepino[1,7-a]indol-8-yl)benzonitrile 2-fluoro-5-(2,3,4,5,11,11a-hexahydro-1H-[1,4]diazepino[1,7-a]indol-8-yl)benzamide 7-phenyl-2,3,4,5-tetrahydro-1H-[1,4]diazepino[1,7-a]indole 7-(2,4-dichlorophenyl)-2,3,4,5-tetrahydro-1H-[1,4]diazepino[1,7-a]indole 7-(4-fluorophenyl)-2,3,4,5-tetrahydro-1H-[1,4]diazepino[1,7-a]indole 7-(4-chlorophenyl)-2,3,4,5-tetrahydro-1H-[1,4]diazepino[1,7-a]indole 7-(2-chlorophenyl)-2,3,4,5-tetrahydro-1H-[1,4]diazepino[1,7-a]indole 7-(2-methoxyphenyl)-2,3,4,5-tetrahydro-1H-[1,4]diazepino[1,7-a]indole 7-[2-chloro-4-(trifluoromethyl)phenyl]-2,3,4,5-tetrahydro-1H-[1,4]diazepino[1,7-a]indole 7-(2,4-dimethylphenyl)-2,3,4,5-tetrahydro-1H-[1,4]diazepino[1,7-a]indole 7-(2-chloro-4-methoxyphenyl)-2,3,4,5-tetrahydro-1H-[1,4]diazepino[1,7-a]indole 7-(4-isopropylphenyl)-2,3,4,5-tetrahydro-1H-[1,4]diazepino[1,7-a]indole 7-(4-butylphenyl)-2,3,4,5-tetrahydro-1H-[1,4]diazepino[1,7-a]indole 7-(5-fluoro-4-methoxy-2-methylphenyl)-2,3,4,5-tetrahydro-1H-[1,4]diazepino[1,7-a]indole 7-(4-methoxy-2-methylphenyl)-2,3,4,5-tetrahydro-1H-[1,4]diazepino[1,7-a]indole 7-[2-chloro-4-(trifluoromethoxy)phenyl]-2,3,4,5-tetrahydro-1H-[1,4]diazepino[1,7-a]indole 7-(2,4,5-trimethylphenyl)-2,3,4,5-tetrahydro-1H-[1,4]diazepino[1,7-a]indole 7-(3-chlorophenyl)-2,3,4,5-tetrahydro-1H-[1,4]diazepino[1,7-a]indole 7-(4-methylphenyl)-2,3,4,5-tetrahydro-1H-[1,4]diazepino[1,7-a]indole 7-(4-chloro-2-methylphenyl)-2,3,4,5-tetrahydro-1H-[1,4]diazepino[1,7-a]indole 7-(2,5-dichlorophenyl)-2,3,4,5-tetrahydro-1H-[1,4]diazepino[1,7-a]indole 7(4-isopropyl-2-methoxyphenyl)-2,3,4,5-tetrahydro-1H-[1,4]diazepino[1,7-a]indole 7-(2,6-dichlorophenyl)-2,3,4,5-tetrahydro-1H-[1,4]diazepino[1,7-a]indole 7-(2,6-difluorophenyl)-2,3,4,5-tetrahydro-1H-[1,4]diazepino[1,7-a]indole 7-[4-methoxy-2-(trifluoromethyl)phenyl]-2,3,4,5-tetrahydro-1H-[1,4]diazepino[1,7-a]indole 7-[2-(trifluoromethyl)phenyl]-2,3,4,5-tetrahydro-1H-[1,4]diazepino[1,7-a]indole 7-(4-pyridinyl)-2,3,4,5-tetrahydro-1H-[1,4]diazepino[1,7-a]indole 7-(2-furyl)-2,3,4,5-tetrahydro-1H-[1,4]diazepino[1,7-a]indole 2-(2,3,4,5-tetrahydro-1H-[1,4]diazepino[1,7-a]indol-7-yl)benzenethiol 7-(2,3-dichlorophenyl)-2,3,4,5-tetrahydro-1H-[1,4]diazepino[1,7-a]indole 7-(4-ethylphenyl)-2,3,4,5-tetrahydro-1H-[1,4]diazepino[1,7-a]indole 7-(2,4-dimethoxyphenyl)-2,3,4,5-tetrahydro-1H-[1,4]diazepino[1,7-a]indole 7-(3-chloro-2-fluorophenyl)-2,3,4,5-tetrahydro-1H-[1,4]diazepino[1,7-a]indole 7-(4-methoxyphenyl)-2,3,4,5-tetrahydro-1H-[1,4]diazepino[1,7-a]indole 7-[4-(methylsulfanyl)phenyl]-2,3,4,5-tetrahydro-1H-[1,4]diazepino[1,7-a]indole 4-(2,3,4,5-tetrahydro-1H-[1,4]diazepino[1,7-a]indol-7-yl)benzonitrile 7-[3-(trifluoromethyl)phenyl]-2,3,4,5-tetrahydro-1H-[1,4]diazepino[1,7-a]indole 7-(2-naphthyl)-2,3,4,5-tetrahydro-1H-[1,4]diazepino[1,7-a]indole 1-[4-(2,3,4,5-tetrahydro-1H-[1,4]diazepino[1,7-a]indol-7-yl)phenyl]ethanone N-[3-(2,3,4,5-tetrahydro-1H-[1,4]diazepino[1,7-a]indol-7-yl)phenyl]acetamide 7-(2,3-dimethylphenyl)-2,3,4,5-tetrahydro-1H-[1,4]diazepino[1,7-a]indole 7-(5-fluoro-2-methylphenyl)-2,3,4,5-tetrahydro-1H-[1,4]diazepino[1,7-a]indole 7-(2-fluoro-5-methylphenyl)-2,3,4,5-tetrahydro-1H-[1,4]diazepino[1,7-a]indole 7-(5-fluoro-2-methoxylphenyl)-2,3,4,5-tetrahydro-1H-[1,4]diazepino[1,7-a]indole 7-(3-chloro-2-methylphenyl)-2,3,4,5-tetrahydro-1H-[1,4]diazepino[1,7-a]indole 7-(3-nitrophenyl)-2,3,4,5-tetrahydro-1H-[1,4]diazepino[1,7-a]indole 7-(2-nitrophenyl)-2,3,4,5-tetrahydro-1H-[1,4]diazepino[1,7-a]indole 7-(2-chloro-3-methylphenyl)-2,3,4,5-tetrahydro-1H-[1,4]diazepino[1,7-a]indole 7-(2-methoxylphenyl)-2,3,4,5-tetrahydro-1H-[1,4]diazepino[1,7-a]indole 7-(4-ethoxy-2-methylphenyl)-2,3,4,5-tetrahydro-1H-[14]diazepino[1,7-a]indole 7-(4-fluoro-2-methylphenyl)-2,3,4,5-tetrahydro-1H-[1,4]diazepino[1,7-a]indole
7-(2-chloro-6-fluorophenyl)-2,3,4,5-tetrahydro-1H-[1,4]diazepino[1,7-a]indole
7-[2-chloro-4-(difluoromethoxy)phenyl]-2,3,4,5-tetrahydro-1H-[1,4]diazepino[1,7-a]indole
7-[4-(trifluoromethyl)phenyl]-2,3,4,5-tetrahydro-1H-[1,4]diazepino[1,7-a]indole
7-[4-(trifluoromethoxy)phenyl]-2,3,4,5-tetrahydro-1H-[1,4]diazepino[1,7-a]indole
7-(6-fluoro-2,4-dimethoxyphenyl)-2,3,4,5-tetrahydro-1H-[1,4]diazepino[1,7-a]indole
7-(2-methylphenyl)-2,3,4,5-tetrahydro-1H-[1,4]diazepino[1,7-a]indole
7-[6-fluoro-2-(trifluoromethyl)phenyl]-2,3,4,5-tetrahydro-1H-[1,4]diazepino[1,7-a]indole
7-[2-(methylsulfanyl)phenyl]-2,3,4,5-tetrahydro-1H-[1,4]diazepino[1,7-a]indole
7-(2,4,6-trifluorophenyl)-2,3,4,5-tetrahydro-1H-[1,4]diazepino[1,7-a]indole
7-(2,4,6trichlorophenyl)-2,3,4,5-tetrahydro-1H-[1,4]diazepino[1,7-a]indole
7-(2,6-dichloro-4-methoxyphenyl)-2,3,4,5-tetrahydro-1H-[1,4]diazepino[1,7-a]indole
7-(2,3,4-trifluorophenyl)-2,3,4,5-tetrahydro-1H-[1,4]diazepino[1,7-a]indole
7-(4-chloro-2,6-difluorophenyl)-2,3,4,5-tetrahydro-1H-[1,4]diazepino[1,7-a]indole
7-(2,3,4,6-tetrafluorophenyl)-2,3,4,5-tetrahydro-1H-[1,4]diazepino[1,7-a]indole
7-(2,3,4,5,6-pentafluorophenyl)-2,3,4,5-tetrahydro-1H-[1,4]diazepino[1,7-a]indole
7-[2,6-di(trifluoromethyl)phenyl]-2,3,4,5-tetrahydro-1H-[1,4]diazepino[1,7-a]indole
7-[2-(trifluoromethoxy)phenyl]-2,3,4,5-tetrahydro-1H-[1,4]diazepino[1,7-a]indole
7-[4-ethoxy-2-(trifluoromethoxy)phenyl]-2,3,4,5-tetrahydro-1H-[1,4]diazepino[1,7-a]indole
7-[4-isopropoxy-2-(trifluoromethyl)phenyl]-2,3,4,5-tetrahydro-1H-[1,4]diazepino[1,7-a]indole
7-[4-chloro-2-(trifluoromethyl)phenyl]-2,3,4,5-tetrahydro-1H-[1,4]diazepino[1,7-a]indole
7-[4-fluoro-2-(trifluoromethyl)phenyl]-2,3,4,5-tetrahydro-1H-[1,4]diazepino[1,7-a]indole
7-(2-chloro-4-ethoxyphenyl)-2,3,4,5-tetrahydro-1H-[1,4]diazepino[1,7-a]indole
7-(2-chloro-4-isopropoxyphenyl)-2,3,4,5-tetrahydro-1H-[1,4]diazepino[1,7-a]indole
7-(2-ethyl-4-methoxyphenyl)-2,3,4,5-tetrahydro-1H-[1,4]diazepino[1,7-a]indole
5-methoxy-2-(2,3,4,5-tetrahydro-1H-[1,4]diazepino[1,7-a]indol-7-yl)benzaldehyde
7-[4-methoxy-2-(1-hydroxyethyl)phenyl]-2,3,4,5-tetrahydro-1H-[1,4]diazepino[1,7-a]indole
7-[4-methoxy-2-(1-methoxyethyl)phenyl]-2,3,4,5-tetrahydro-1H-[1,4]diazepino[1,7-a]indole
1-[5-methoxy-2-(2,3,4,5-tetrahydro-1H-[1,4]diazepino[1,7-a]indol-7-yl)phenyl]ethanone
[5-methoxy-2-(2,3,4,5-tetrahydro-1H-[1,4]diazepino[1,7-a]indol-7-yl)phenyl]methanol
7-[4-methoxy-2-(methoxymethyl)phenyl]-2,3,4,5-tetrahydro-1H-[1,4]diazepino[1,7-a]indole
1-[5-methoxy-2-(2,3,4,5-tetrahydro-1H-[1,4]diazepino[1,7-a]indol-7-yl)phenyl]-1-propanol
1-[5-methoxy-2-(2,3,4,5-tetrahydro-1H-[1,4]diazepino[1,7-a]indol-7-yl)phenyl]-1-propanoate
methyl (2Z)-3-[5-methoxy-2-(2,3,4,5-tetrahydro-1H-[1,4]diazepino[1,7-a]indol-7-yl)phenyl]-2-propenoate
methyl 3-[5-methoxy-2-(2,3,4,5-tetrahydro-1H-[1,4]diazepino[1,7-a]indol-7-yl)phenyl]propanoate
(2Z)-3-[5-methoxy-2-(2,3,4,5-tetrahydro-1H-[1,4]diazepino[1,7-a]indol-7-yl)phenyl]-2-propen-1-ol
methyl (2E)-3-[5-methoxy-2-(2,3,4,5-tetrahydro-1H-[1,4]diazepino[1,7-a]indol-7-yl)phenyl]-2-propenoate
(2E)-3-[5-methoxy-2-(2,3,4,5-tetrahydro-1H-[1,4]diazepino[1,7-a]indol-7-yl)phenyl]-2-propen-1-ol
7-[4-methoxy-2-(2-methoxyethyl)phenyl]-2,3,4,5-tetrahydro-1H-[1,4]diazepino[1,7-a]indole
7-(2-fluoro-4-methoxyphenyl)-2,3,4,5-tetrahydro-1H-[1,4]diazepino[1,7-a]indole
7-(2-chloro-4-fluorophenyl)-2,3,4,5-tetrahydro-1H-[1,4]diazepino[1,7-a]indole
7-benzyl-2,3,4,5-tetrahydro-1H-[1,4]diazepino[1,7-a]indole
7-(2-fluorobenzyl)-2,3,4,5-tetrahydro-1H-[1,4]diazepino[1,7-a]indole
7-(3-fluorobenzyl)-2,3,4,5-tetrahydro-1H-[1,4]diazepino[1,7-a]indole
7-(4-fluorobenzyl)-2,3,4,5-tetrahydro-1H-[1,4]diazepino[1,7-a]indole
7-(3-methoxybenzyl)-2,3,4,5-tetrahydro-1H-[1,4]diazepino[1,7-a]indole
3-(2,3,4,5-tetrahydro-1H-[1,4]diazepino[1,7-a]indol-7-ylmethyl)phenol
7-(2-methoxybenzyl)-2,3,4,5-tetrahydro-1H-[1,4]diazepino[1,7-a]indole
2-(2,3,4,5-tetrahydro-1H-[1,4]diazepino[1,7-a]indol-7-ylmethyl)phenol
methyl 2-methoxy-6-(2,3,4,5-tetrahydro-1H-[1,4]diazepino[1,7-a]indol-7-yl)benzoate
3-(2,3,4,5-tetrahydro-1H-[1,4]diazepino[1,7-a]indol-7-yl)benzonitrile
3-methyl-4-(2,3,4,5-tetrahydro-1H-[1,4]diazepino[1,7-a]indol-7-yl)benzonitrile
2-methyl-3-(2,3,4,5-tetrahydro-1H -[1,4]diazepino[1,7-a]indol-7-yl)benzonitrile
2-(2,3,4,5-tetrahydro-1H-[1,4]diazepino[1,7-a]indol-7-yl)benzonitrile
3-trifluoromethyl-4-(2,3,4,5-tetrahydro-1H-[1,4]diazepino[1,7-a]indol-7-yl)benzonitrile
3-(2,3,4,5-tetrahydro-1H-[1,4]diazepino[1,7-a]indol-7-yl)benzaldehyde
[3-(2,3,4,5-tetrahydro-1H-[1,4]diazepino[1,7-a]indol-7-yl)phenyl]methanol
7-[3-(methoxymethyl)phenyl]-2,3,4,5-tetrahydro-1H-[1,4]diazepino[1,7-a]indole
N,N-dimethyl[3-(2,3,4,5-tetrahydro-1H-[1,4]diazepino[1,7-a]indol-7-yl)phenyl]methanamine
2-fluoro-5-(2,3,4,5-tetrahydro-1H-[1,4]diazepino[1,7-a]indol-7-yl)benzonitrile
2-fluoro-5-(2,3,4,5-tetrahydro-1H-[1,4]diazepino[1,7-a]indol-7-yl)benzamide
7-phenyl-2,3,4,5,11,11a-hexahydro-1H-[1,4]diazepino[1,7-a]indole
7-(2,4-dichlorophenyl)-2,3,4,5,11,11a-hexahydro-1H-[1,4]diazepino[1,7-a]indole
7-(4-fluorophenyl)-2,3,4,5,11,11a-hexahydro-1H-[1,4]diazepino[1,7-a]indole
7-(4-chlorophenyl)-2,3,4,5,11,11a-hexahydro-1H-[1,4]diazepino[1,7-a]indole
7-(2-chlorophenyl)-2,3,4,5,11,11a-hexahydro-1H-[1,4]diazepino[1,7-a]indole
7-(2-methoxyphenyl)-2,3,4,5,11,11a-hexahydro-1H-[1,4]diazepino[1,7-a]indole
7-[2-chloro-4-(trifluoromethyl)phenyl]-2,3,4,5,11,11a-hexahydro-1H-[1,4]diazepino[1,7-a]indole 7-(2,4-dimethylphenyl)-2,3,4,5,11,11a-hexahydro-1H-[1,4]diazepino[1,7-a]indole 7-(2-chloro-4-methoxyphenyl)-2,3,4,5,11,11a-hexahydro-1H-[1,4]diazepino[1,7-a]indole 7-(4-isopropylphenyl)-2,3,4,5,11,11a-hexahydro-1H-[1,4]diazepino[1,7-a]indole 7-(4-butylphenyl)-2,3,4,5,11,11a-hexahydro-1H-[1,4]diazepino[1,7-a]indole 7-(5-fluoro-4-methoxy-2-methylphenyl)-2,3,4,5,11,11a-hexahydro-1H-[1,4]diazepino[1,7-a]indole 7-(4-methoxy-2-methylphenyl)-2,3,4,5,11,11a-hexahydro-1H-[1,4]diazepino[1,7-a]indole 7-[2-chloro-4-(trifluoromethoxy)phenyl]-2,3,4,5,11,11a-hexahydro-1H-[1,4]diazepino[1,7-a]indole 7-(2,4,5-trimethylphenyl)-2,3,4,5,11,11a-hexahydro-1H-[1,4]diazepino[1,7-a]indole 7-(3-chlorophenyl)-2,3,4,5,11,11a-hexahydro-1H-[1,4]diazepino[1,7-a]indole 7-(4-methylphenyl)-2,3,4,5,11,11a-hexahydro-1H-[1,4]diazepino[1,7-a]indole 7-(4-chloro-2-methylphenyl)-2,3,4,5,11,11a-hexahydro-1H-[1,4]diazepino[1,7-a]indole 7-(2,5-dichlorophenyl)-2,3,4,5,11,11a-hexahydro-1H-[1,4]diazepino[1,7-a]indole 7-(4-isopropyl-2-methoxyphenyl)-2,3,4,5,11,11a-hexahydro-1H-[1,4]diazepino[1,7-a]indole 7-(2,6-dichlorophenyl)-2,3,4,5,11,11a-hexahydro-1H-[1,4]diazepino[1,7-a]indole 7-(2,6-difluorophenyl)-2,3,4,5,11,11a-hexahydro-1H-[1,4]diazepino[1,7-a]indole 7-[4-methoxy-2-(trifluoromethyl)phenyl]-2,3,4,5,11,11a-hexahydro-1H-[1,4]diazepino[1,7-a]indole 7-[2-(trifluoromethyl)phenyl]-2,3,4,5,11,11a-hexahydro-1H-[1,4]diazepino[1,7-a]indole 7-(4-pyridinyl)-2,3,4,5,11,11a-hexahydro-1H-[1,4]diazepino[1,7-a]indole 7-(2-furyl)-2,3,4,5,11,11a-hexahydro-1H-[1,4]diazepino[1,7-a]indole 2-(2,3,4,5,11,11a-hexahydro-1H-[1,4]diazepino[1,7-a]indol-7-yl)benzenethiol 7-(2,3-dichlorophenyl)-2,3,4,5,11,11a-hexahydro-1H-[1,4]diazepino[1,7-a]indole 7-(4-ethylphenyl)-2,3,4,5,11,11a-hexahydro-1H-[1,4]diazepino[1,7-a]indole 7-(2,4-dimethoxyphenyl)2,3,4,5,11,11a-hexahydro-1H-[1,4]diazepino[1,7-a]indole 7-(3-chloro-2-fluorophenyl)-2,3,4,5,11,11a-hexahydro-1H-[1,4]diazepino[1,7-a]indole 7-(4-methoxyphenyl)-2,3,4,5,11,11a-hexahydro-1H-[1,4]diazepino[1,7-a]indole 7-[4-(methylsulfanyl)phenyl]-2,3,4,5,11,11a-hexahydro-1H-[1,4]diazepino[1,7-a]indole 4-(2,3,4,5,11,11a-hexahydro-1H-[1,4]diazepino[1,7-a]indol-7-yl)benzonitrile 7-[3-(trifluoromethyl)phenyl]-2,3,4,5,11,11a-hexahydro-1H-[1,4]diazepino[1,7-a]indole 7-(2-naphthyl)-2,3,4,5,11,11a-hexahydro-1H-[1,4]diazepino[1,7-a]indole 1-[4-(2,3,4,5,11,11a-hexahydro-1H-[1,4]diazepino[1,7-a]indol-7-yl)phenyl]ethanone N-[3-(2,3,4,5,11,11a-hexahydro-1H-[1,4]diazepino[1,7-a]indol-7-yl)phenyl]acetamide 7-(2,3-dimethylphenyl)-2,3,4,5,11,11a-hexahydro-1H-[1,4]diazepino[1,7-a]indole 7-(5-fluoro-2-methylphenyl)-2,3,4,5,11,11a-hexahydro-1H-[1,4]diazepino[1,7-a]indole 7-(2-fluoro-5-methylphenyl)-2,3,4,5,11,11a-hexahydro-1H-[1,4]diazepino[1,7-a]indole 7-(5-fluoro-2-methoxyphenyl)-2,3,4,5,11,11a-hexahydro-1H-[1,4]diazepino[1,7-a]indole 7-(3-chloro-2-methylphenyl)-2,3,4,5,11,11a-hexahydro-1H-[1,4]diazepino[1,7-a]indole 7-(3-nitrophenyl)-2,3,4,5,11,11a-hexahydro-1H-[1,4]diazepino[1,7-a]indole 7-(2-nitrophenyl)-2,3,4,5,11,11a-hexahydro-1H-[1,4]diazepino[1,7-a]indole 7-(2-chloro-3-methylphenyl)-2,3,4,5,11,11a-hexahydro-1H-[1,4]diazepino[1,7-a]indole 7-(2-methoxylphenyl)-2,3,4,5,11,11a-hexahydro-1H-[1,4]diazepino[1,7-a]indole 7-(4-ethoxy-2-methylphenyl)-2,3,4,5,11,11a-hexahydro-1H-[1,4]diazepino[1,7-a]indole 7-(4-fluoro-2-methylphenyl)-2,3,4,5,11,11a-hexahydro-1H-[1,4]diazepino[1,7-a]indole 7-(2-chloro-6-fluorophenyl)-2,3,4,5,11,11a-hexahydro-1H-[1,4]diazepino[1,7-a]indole 7-[2-chloro-4-(difluoromethoxy)phenyl]-2,3,4,5,11,11a-hexahydro-1H-[1,4]diazepino[1,7-a]indole 7-[4-(trifluoromethyl)phenyl]-2,3,4,5,11,11a-hexahydro-1H-[1,4]diazepino[1,7-a]indole 7-[4-(trifluoromethoxy)phenyl]-2,3,4,5,11,11a-hexahydro-1H-[1,4]diazepino[1,7-a]indole 7-(6-fluoro-2,4-dimethoxylphenyl)-2,3,4,5,11,11a-hexahydro-1H-[1,4]diazepino[1,7-a]indole 7-(2-methylphenyl)-2,3,4,5,11,11a-hexahydro-1H-[1,4]diazepino[1,7-a]indole 7-[6-fluoro-2-(trifluoromethyl)phenyl]-2,3,4,5,11,11a-hexahydro-1H-[1,4]diazepino[1,7-a]indole 7-[2-(methylsulfanyl)phenyl]-2,3,4,5,11,11a-hexahydro-1H-[1,4]diazepino[1,7-a]indole 7-(2,4,6-trifluorophenyl)-2,3,4,5,11,11a-hexahydro-1H-[1,4]diazepino[1,7-a]indole 7-(2,4,6-trichlorophenyl)-2,3,4,5,11,11a-hexahydro-1H-[1,4]diazepino[1,7-a]indole 7-(2,6-dichloro-4-methoxyphenyl)-2,3,4,5,11,11a-hexahydro-1H-[1,4]diazepino[1,7-a]indole 7-(2,3,4-trifluorophenyl)-2,3,4,5,11,11a-hexahydro-1H-[1,4]diazepino[1,7-a]indole 7-(4-chloro-2,6-difluorophenyl)-2,3,4,5,11,11a-hexahydro-1H-[1,4]diazepino[1,7-a]indole 7-(2,3,4,6-tetrafluorophenyl)-2,3,4,5,11,11a-hexahydro-1H-[1,4]diazepino[1,7-a]indole 7-(2,3,4,5,6-pentafluorophenyl)-2,3,4,5,11,11a-hexahydro-1H-[1,4]diazepino[1,7-a]indole 7-[2,6-di(trifluoromethyl)phenyl]-2,3,4,5,11,11a-hexahydro-1H-[1,4]diazepino[1,7-a]indole 7-[2-(trifluoromethoxy)phenyl]-2,3,4,5,11,11a-hexahydro-1H-[1,4]diazepino[1,7-a]indole 7-[4-ethoxy-2-(trifluoromethoxy)phenyl]-2,3,4,5,11,11a-hexahydro-1H-[1,4]diazepino[1,7-a]indole 7-[4-isopropoxy-2-(trifluoromethyl)phenyl]-2,3,4,5,11,11a-hexahydro-1H-[1,4]diazepino[1,7-a]indole 7-[4-chloro-2-(trifluoromethyl)phenyl]-2,3,4,5,11,11a-hexahydro-1H-[1,4]diazepino[1,7-a]indole 7-[4-fluoro-2-(trifluoromethyl)phenyl]-2,3,4,5,11,11a-hexahydro-1H-[1,4]diazepino[1,7-a]indole 7-[2-chloro-4-ethoxyphenyl]-2,3,4,5,11,11a-hexahydro-1H-[1,4]diazepino[1,7-a]indole 7-[2-chloro-4-isopropoxyphenyl]-2,3,4,5,11,11a-hexahydro-1H-[1,4]diazepino[1,7-a]indole 7-(2-ethyl-4-methoxyphenyl)-2,3,4,5,11,11a-hexahydro-1H-[1,4]diazepino[1,7-a]indole 5-methoxy-2-(2,3,4,5,11,11a-hexahydro-1H-[1,4]diazepino[1,7-a]indol-7-yl)benzaldehyde 7-[4-methoxy-2-(1-hydroxyethyl)phenyl]-2,3,4,5,11,11a-hexahydro-1H-[1,4]diazepino[1,7-a]indole 7-[4-methoxy-2-(1-methoxyethyl)phenyl]-2,3,4,5,11,11a-hexahydro-1H-[1,4]diazepino[1,7-a]indole
1-[5-methoxy-2-(2,3,4,5,11,11a-hexahydro-1H-[1,4]diazepino[1,7-a]indol-7-yl)phenyl]ethanone
[5-methoxy-2-(2,3,4,5,11,11a-hexahydro-1H-[1,4]diazepino[1,7-a]indol-7-yl)phenyl]methanol
7-[4-methoxy-2-(methoxymethyl)phenyl]-2,3,4,5,11,11a-hexahydro-1H-[1,4]diazepino[1,7-a]indole
1-[5-methoxy-2-(2,3,4,5,11,11a-hexahydro-1H-[1,4]diazepino[1,7-a]indol-7-yl)phenyl]-1-propanol
1-[5-methoxy-2-(2,3,4,5,11,11a-hexahydro-1H-[1,4]diazepino[1,7-a]indol-7-yl)phenyl]-1-propanone
methyl (2Z)-3-[5-methoxy-2-(2,3,4,5,11,11a-hexahydro-1H-[1,4]diazepino[1,7-a]indol-7-yl)phenyl]-2-propenoate
methyl 3-[5-methoxy-2-(2,3,4,5,11,11a-hexahydro-1H-[1,4]diazepino[1,7-a]indol-7-yl)phenyl]propanoate
(2Z)-3-[5-methoxy-2-(2,3,4,5,11,11a-hexahydro-1H-[1,4]diazepino[1,7-a]indol-7-yl)phenyl]-2-propen-1-ol
methyl (2E)-3-[5-methoxy-2-(2,3,4,5,11,11a-hexahydro-1H-[1,4]diazepino[1,7-a]indol-7-yl)phenyl]-2-propenoate
(2E)-3-[5-methoxy-2-(2,3,4,5,11,11a-hexahydro-1H-[1,4]diazepino[1,7-a]indol-7-yl)phenyl]-2-propen-1-ol
7-[4-methoxy-2-(2-methoxyethyl)phenyl]-2,3,4,5,11,11a-hexahydro-1H-[1,4]diazepino[1,7-a]indole
7-(2-fluoro-4-methoxyphenyl)-2,3,4,5,11,11a-hexahydro-1H-[1,4]diazepino[1,7-a]indole
7-(2-chloro-4-fluorophenyl)-2,3,4,5,11,11a-hexahydro-1H-[1,4]diazepino[1,7-a]indole
7-benzyl-2,3,4,5,11,11a-hexahydro-1H-[1,4]diazepino[1,7-a]indole
7-(2-fluorobenzyl)-2,3,4,5,11,11a-hexahydro-1H-[1,4]diazepino[1,7-a]indole
7-(3-fluorobenzyl)-2,3,4,5,11,11a-hexahydro-1H-[1,4]diazepino[1,7-a]indole
7-(4-fluorobenzyl)-2,3,4,5,11,11a-hexahydro-1H-[1,4]diazepino[1,7-a]indole
7-(3-methoxybenzyl)-2,3,4,5,11,11a-hexahydro-1H-[1,4]diazepino[1,7-a]indole
3-(2,3,4,5,11,11a-hexahydro-1H-[1,4]diazepino[1,7-a]indol-7-ylmethyl)phenol
7-(2-methoxybenzyl)-2,3,4,5,11,11a-hexahydro-1H-[1,4]diazepino[1,7-a]indole
2-(2,3,4,5,11,11a-hexahydro-1H-[1,4]diazepino[1,7-a]indol-7-ylmethyl)phenol
methyl 2-methoxy-6-(2,3,4,5,11,11a-hexahydro-1H-[1,4]diazepino[1,7-a]indol-7-yl)benzoate
3-(2,3,4,5,11,11a-hexahydro-1H-[1,4]diazepino[1,7-a]indol-7-yl)benzonitrile
3-methyl-4-(2,3,4,5,11,11a-hexahydro-1H-[1,4]diazepino[1,7-a]indol-7-yl)benzonitrile
2-methyl-3-(2,3,4,5,11,11a-hexahydro-1H-[1,4]diazepino[1,7-a]indol-7-yl)benzonitrile
2-(2,3,4,5,11,11a-hexahydro-1H-[1,4]diazepino[1,7-a]indol-7-yl)benzonitrile
3-trifluoromethyl-4-(2,3,4,5,11,11a-hexahydro-1H-[1,4]diazepino[1,7-a]indol-7-yl)benzonitrile
3-(2,3,4,5,11,11a-hexahydro-1H-[1,4]diazepino[1,7-a]indol-7-yl)benzaldehyde
[3-(2,3,4,5,11,11a-hexahydro-1H-[1,4]diazepino[1,7-a]indol-7-yl)phenyl]methanol
7-[3-(methoxymethyl)phenyl]-2,3,4,5,11,11a-hexahydro-1H-[1,4]diazepino[1,7-a]indole
N,N-dimethyl[3-(2,3,4,5,11,11a-hexahydro-1H-[1,4]diazepino[1,7-a]indol-7-yl)phenyl]methanamine
2-fluoro-5-(2,3,4,5,11,11a-hexahydro-1H-[1,4]diazepino[1,7-a]indol-7-yl)benzonitrile
2-fluoro-5-(2,3,4,5,11,11a-hexahydro-1H-[1,4]diazepino[1,7-a]indol-7-yl)benzamide
9-phenyl-2,3,4,5,11,11a-hexahydro-1H-[1,4]diazepino[1,7-a]indole
9-(2,4-dichlorophenyl)-2,3,4,5-tetrahydro-1H-[1,4]diazepino[1,7-a]indole
9-(4-fluorophenyl)-2,3,4,5-tetrahydro-1H-[1,4]diazepino[1,7-a]indole
9-(4-chlorophenyl)-2,3,4,5-tetrahydro-1H-[1,4]diazepino[1,7-a]indole
9-(2-chlorophenyl)-2,3,4,5-tetrahydro-1H-[1,4]diazepino[1,7-a]indole
9-(2-methoxyphenyl)-2,3,4,5-tetrahydro-1H-[1,4]diazepino[1,7-a]indole
9-[2-chloro-4-(trifluoromethyl)phenyl]-2,3,4,5-tetrahydro-1H-[1,4]diazepino[1,7-a]indole
9-(2,4-dimethylphenyl)-2,3,4,5-tetrahydro-1H-[1,4]diazepino[1,7-a]indole
9-(2-chloro-4-methoxyphenyl)-2,3,4,5-tetrahydro-1H-[1,4]diazepino[1,7-a]indole
9-(4-isopropylphenyl)-2,3,4,5-tetrahydro-1H-[1,4]diazepino[1,7-a]indole
9-(4-butylphenyl)-2,3,4,5-tetrahydro-1H-[1,4]diazepino[1,7-a]indole
9-(5-fluoro-4-methoxy-2-methylphenyl)-2,3,4,5-tetrahydro-1H-[1,4]diazepino[1,7-a]indole
9-(4-methoxy-2-methylphenyl)-2,3,4,5-tetrahydro-1H-[1,4]diazepino[1,7-a]indole
9-[2-chloro-4-(trifluoromethoxy)phenyl]-2,3,4,5-tetrahydro-1H-[1,4]diazepino[1,7-a]indole
9-(2,4,5-trimethylphenyl)-2,3,4,5-tetrahydro-1H-[1,4]diazepino[1,7-a]indole
9-(3-chlorophenyl)-2,3,4,5-tetrahydro-1H-[1,4]diazepino[1,7-a]indole
9-(4-methylphenyl)-2,3,4,5-tetrahydro-1H-[1,4]diazepino[1,7-a]indole
9-(4-chloro-2-methylphenyl)-2,3,4,5-tetrahydro-1H-[1,4]diazepino[1,7-a]indole
9-(2,5-dichlorophenyl)-2,3,4,5-tetrahydro-1H-[1,4]diazepino[1,7-a]indole
9-(4-isopropyl-2-methoxyphenyl)-2,3,4,5-tetrahydro-1H-[1,4]diazepino[1,7-a]indole
9-(2,6-dichlorophenyl)-2,3,4,5-tetrahydro-1H-[1,4]diazepino[1,7-a]indole
9-(2,6-difluorophenyl)-2,3,4,5-tetrahydro-1H-[1,4]diazepino[1,7-a]indole
9-[4-methoxy-2-(trifluoromethyl)phenyl]-2,3,4,5-tetrahydro-1H-[1,4]diazepino[1,7-a]indole
9-[2-(trifluoromethyl)phenyl]-2,3,4,5-tetrahydro-1H-[1,4]diazepino[1,7-a]indole
9-(4-pyridinyl)-2,3,4,5-tetrahydro-1H-[1,4]diazepino[1,7-a]indole
9-(2-furyl)-2,3,4,5-tetrahydro-1H-[1,4]diazepino[1,7-a]indole
2-(2,3,4,5-tetrahydro-1H-[1,4]diazepino[1,7-a]indol-9-yl)benzenethiol
9-(2,3-dichlorophenyl)-2,3,4,5-tetrahydro-1H-[1,4]diazepino[1,7-a]indole
9-(4-ethylphenyl)-2,3,4,5-tetrahydro-1H-[1,4]diazepino[1,7-a]indole
9-(2,4-dimethoxyphenyl)-2,3,4,5-tetrahydro-1H-[1,4]diazepino[1,7-a]indole
9-(3-chloro-2-fluorophenyl)-2,3,4,5-tetrahydro-1H-[1,4]diazepino[1,7-a]indole
9-(4-methoxyphenyl)-2,3,4,5-tetrahydro-1H-[1,4]diazepino[1,7-a]indole
9-[4-(methylsulfanyl)phenyl]-2,3,4,5-tetrahydro-1H-[1,4]diazepino[1,7-a]indole 4-(2,3,4,5-tetrahydro-1H-[1,4]diazepino[1,7-a]indol-9-yl)benzonitrile
9-[3-(trifluoromethyl)phenyl]-2,3,4,5-tetrahydro-1H-[1,4]diazepino[1,7-a]indole
9-(2-naphthyl)-2,3,4,5-tetrahydro-1H-[1,4]diazepino[1,7-a]indole
1-[4-(2,3,4,5-tetrahydro-1H-[1,4]diazepino[1,7-a]indol-9-yl)phenyl]ethanone
N-[3-(2,3,4,5-tetrahydro-1H-[1,4]diazepino[1,7-a]indol-9-yl)phenyl]acetamide
9-(2,3-dimethylphenyl)-2,3,4,5-tetrahydro-1H-[1,4]diazepino[1,7-a]indole
9-(5-fluoro-2-methylphenyl)-2,3,4,5-tetrahydro-1H-[1,4]diazepino[1,7-a]indole
9-(2-fluoro-5-methylphenyl)-2,3,4,5-tetrahydro-1H-[1,4]diazepino[1,7-a]indole
9-(5-fluoro-2-methoxylphenyl)-2,3,4,5-tetrahydro-1H-[1,4]diazepino[1,7-a]indole
9-(3-chloro-2-methylphenyl)-2,3,4,5-tetrahydro-1H-[1,4]diazepino[1,7-a]indole
9-(3-nitrophenyl)-2,3,4,5-tetrahydro-1H-[1,4]diazepino[1,7-a]indole
9-(2-nitrophenyl)-2,3,4,5-tetrahydro-1H-[1,4]diazepino[1,7-a]indole
9-(2-chloro-3-methylphenyl)-2,3,4,5-tetrahydro-1H-[1,4]diazepino[1,7-a]indole
9-(2-methoxylphenyl)-2,3,4,5-tetrahydro-1H-[1,4]diazepino[1,7-a]indole
9-(4-ethoxy-2-methylphenyl)-2,3,4,5-tetrahydro-1H-[1,4]diazepino[1,7-a]indole
9-(4-fluoro-2-methylphenyl)-2,3,4,5-tetrahydro-1H-[1,4]diazepino[1,7-a]indole
9-(2-chloro-6-fluorophenyl)-2,3,4,5-tetrahydro-1H-[1,4]diazepino[1,7-a]indole
9-[2-chloro-4-(difluoromethoxy)phenyl]-2,3,4,5-tetrahydro-1H-[1,4]diazepino[1,7-a]indole
9-[4-(trifluoromethyl)phenyl]-2,3,4,5-tetrahydro-1H-[1,4]diazepino[1,7-a]indole
9-[4-(trifluoromethoxy)phenyl]-2,3,4,5-tetrahydro-1H-[1,4]diazepino[1,7-a]indole
9-(6-fluoro-2,4-dimethoxyphenyl)-2,3,4,5-tetrahydro-1H-[1,4]diazepino[1,7-a]indole
9-(2-methylphenyl)-2,3,4,5-tetrahydro-1H-[1,4]diazepino[1,7-a]indole
9-[6-fluoro-2-(trifluoromethyl)phenyl]-2,3,4,5-tetrahydro-1H-[1,4]diazepino[1,7-a]indole
9-[2-(methylsulfanyl)phenyl]-2,3,4,5-tetrahydro-1H-[1,4]diazepino[1,7-a]indole
9-(2,4,6-trifluorophenyl)-2,3,4,5-tetrahydro-1H-[1,4]diazepino[1,7-a]indole
9-(2,4,6-trichlorophenyl)-2,3,4,5-tetrahydro-1H-[1,4]diazepino[1,7-a]indole
9-(2,6-dichloro-4-methoxyphenyl)-2,3,4,5-tetrahydro-1H-[1,4]diazepino[1,7-a]indole
9-(2,3,4-trifluorophenyl)-2,3,4,5-tetrahydro-1H-[1,4]diazepino[1,7-a]indole
9-(4-chloro-2,6-difluorophenyl)-2,3,4,5-tetrahydro-1H-[1,4]diazepino[1,7-a]indole
9-(2,3,4,6-tetrafluorophenyl)-2,3,4,5-tetrahydro-1H-[1,4]diazepino[1,7-a]indole
9-(2,3,4,5,6-pentafluorophenyl)-2,3,4,5-tetrahydro-1H-[1,4]diazepino[1,7-a]indole
9-[2,6-di(trifluoromethyl)phenyl]-2,3,4,5-tetrahydro-1H-[1,4]diazepino[1,7-a]indole
9-[2-(trifluoromethoxy)phenyl]-2,3,4,5-tetrahydro-1H-[1,4]diazepino[1,7-a]indole
9-[4-ethoxy-2-(trifluoromethoxy)phenyl]-2,3,4,5-tetrahydro-1H-[1,4]diazepino[1,7-a]indole
9-[4-isopropoxy-2-(trifluoromethyl)phenyl]-2,3,4,5-tetrahydro-1H-[1,4]diazepino[1,7-a]indole
9-[4-chloro-2-(trifluoromethyl)phenyl]-2,3,4,5-tetrahydro-1H-[1,4]diazepino[1,7-a]indole
9-[4-fluoro-2-(trifluoromethyl)phenyl]-2,3,4,5-tetrahydro-1H-[1,4]diazepino[1,7-a]indole
9-[2-chloro-4-ethoxyphenyl]-2,3,4,5-tetrahydro-1H-[1,4]diazepino[1,7-a]indole
9-[2-chloro-4-isopropoxyphenyl]-2,3,4,5-tetrahydro-1H-[1,4]diazepino[1,7-a]indole
9-(2-ethyl-4-methoxyphenyl)-2,3,4,5-tetrahydro-1H-[14]diazepino[1,7-a]indole
5-methoxy-2-(2,3,4,5-tetrahydro-1H-[1,4]diazepino[1,7-a]indol-9-yl)benzaldehyde
9-[4-methoxy-2-(1-hydroxyethyl)phenyl]-2,3,4,5-tetrahydro-1H-[1,4]diazepino[1,7-a]indole
9-[4-methoxy-2-(1-methoxyethyl)phenyl]-2,3,4,5-tetrahydro-1H-[1,4]diazepino[1,7-a]indole
1-[5-methoxy-2-(2,3,4,5-tetrahydro-1H-[1,4]diazepino[1,7-a]indol-9-yl)phenyl]ethanone
[5-methoxy-2-(2,3,4,5-tetrahydro-1H-[1,4]diazepino[1,7-a]indol-9-yl)phenyl]methanol
9-[4-methoxy-2-(methoxymethyl)phenyl]-2,3,4,5-tetrahydro-1H-[1,4]diazepino[1,7-a]indole
1-[5-methoxy-2-(2,3,4,5-tetrahydro-1H-[1,4]diazepino[1,7-a]indol-9-yl)phenyl]-1-propanol
1-[5-methoxy-2-(2,3,4,5-tetrahydro-1H-[1,4]diazepino[1,7-a]indol-9-yl)phenyl]-1-propanone
methyl (2Z)-3-[5-methoxy-2-(2,3,4,5-tetrahydro-1H-[1,4]diazepino[1,7-a]indol-9-yl)phenyl]-2-propenoate
methyl 3-[5-methoxy-2-(2,3,4,5-tetrahydro-1H-[1,4]diazepino[1,7-a]indol-9-yl)phenyl]propanoate
(2Z)-3-[5-methoxy-2-(2,3,4,5-tetrahydro-1H-[1,4]diazepino[1,7-a]indol-9-yl)phenyl]-2-propen-1-ol
methyl (2E)-3-[5-methoxy-2-(2,3,4,5-tetrahydro-1H-[1,4]diazepino[1,7-a]indol-9-yl)phenyl]-2-propenoate
(2E)-3-[5-methoxy-2-(2,3,4,5-tetrahydro-1H-[1,4]diazepino[1,7-a]indol-9-yl)phenyl]-2-propen-1-ol
9-[4-methoxy-2-(2-methoxyethyl)phenyl]-2,3,4,5-tetrahydro-1H-[1,4]diazepino[1,7-a]indole
9-(2-fluoro-4-methoxyphenyl)-2,3,4,5-tetrahydro-1H-[1,4]diazepino[1,7-a]indole
9-(2-chloro-4-fluorophenyl)-2,3,4,5-tetrahydro-1H-[1,4]diazepino[1,7-a]indole
9-benzyl-2,3,4,5-tetrahydro-1H-[1,4]diazepino[1,7-a]indole
9-(2-fluorobenzyl)-2,3,4,5-tetrahydro-1H-[1,4]diazepino[1,7-a]indole
9-(3-fluorobenzyl)-2,3,4,5-tetrahydro-1H-[1,4]diazepino[1,7-a]indole
9-(4-fluorobenzyl)-2,3,4,5-tetrahydro-1H-[1,4]diazepino[1,7-a]indole
9-(3-methoxybenzyl)-2,3,4,5-tetrahydro-1H-[1,4]diazepino[1,7-a]indole
3-(2,3,4,5-tetrahydro-1H-[1,4]diazepino[1,7-a]indol-9-ylmethyl)phenol
9-(2-methoxybenzyl)-2,3,4,5-tetrahydro-1H-[1,4]diazepino[1,7-a]indole
2-(2,3,4,5-tetrahydro-1H-[1,4]diazepino[1,7-a]indol-9-ylmethyl)phenol
methyl 2-methoxy-6-(2,3,4,5-tetrahydro-1H-[1,4]diazepino[1,7-a]indol-9-yl)benzoate
3-(2,3,4,5-tetrahydro-1H-[1,4]diazepino[1,7-a]indol-9-yl)benzonitrile
3-methyl-4-(2,3,4,5-tetrahydro-1H-[1,4]diazepino[1,7-a]indol-9-yl)benzonitrile
2-methyl-3-(2,3,4,5-tetrahydro-1H-[1,4]diazepino[1,7-a]indol-9-yl)benzonitrile 2-(2,3,4,5-tetrahydro-1H-[1,4]diazepino[1,7-a]indol-9-yl)benzonitrile
3-trifluoromethyl-4-(2,3,4,5-tetrahydro-1H-[1,4]diazepino[1,7-a]indol-9-yl)benzonitrile
3-(2,3,4,5-tetrahydro-1H-[1,4]diazepino[1,7-a]indol-9-yl)benzaldehyde
[3-(2,3,4,5-tetrahydro-1H-[1,4]diazepino[1,7-a]indol-9-yl)phenyl]methanol
9-[3-(methoxymethyl)phenyl]-2,3,4,5-tetrahydro-1H-[1,4]diazepino[1,7-a]indole
N,N-dimethyl[3-(2,3,4,5-tetrahydro-1H-[1,4]diazepino[1,7-a]indol-9-yl)phenyl]methanamine
2-fluoro-5-(2,3,4,5-tetrahydro-1H-[1,4]diazepino[1,7-a]indol-9-yl)benzonitrile
2-fluoro-5-(2,3,4,5-tetrahydro-1H-[1,4]diazepino[1,7-a]indol-9-yl)benzamide
9-phenyl-2,3,4,5,11,11a-hexahydro-1H-[1,4]diazepino[1,7-a]indole
9-(2,4-dichlorophenyl)-2,3,4,5,11,11a-hexahydro-1H-[1,4]diazepino[1,7-a]indole
9-(4-fluorophenyl)-2,3,4,5,11,11a-hexahydro-1H-[1,4]diazepino[1,7-a]indole
9-(4-chlorophenyl)-2,3,4,5,11,11a-hexahydro-1H-[1,4]diazepino[1,7-a]indole
9-(2-chlorophenyl)-2,3,4,5,11,11a-hexahydro-1H-[1,4]diazepino[1,7-a]indole
9-(2-methoxyphenyl)-2,3,4,5,11,11a-hexahydro-1H-[1,4]diazepino[1,7-a]indole
9-[2-chloro-4-(trifluoromethyl)phenyl]-2,3,4,5,11,11a-hexahydro-1H-[1,4]diazepino[1,7-a]indole
9-(2,4-dimethylphenyl)-2,3,4,5,11,11a-hexahydro-1H-[1,4]diazepino[1,7-a]indole
9-(2-chloro-4-methoxyphenyl)-2,3,4,5,11,11a-hexahydro-1H-[1,4]diazepino[1,7-a]indole
9-(4-isopropylphenyl)-2,3,4,5,11,11a-hexahydro-1H-[1,4]diazepino[1,7-a]indole
9-(4-butylphenyl)-2,3,4,5,11,11a-hexahydro-1H-[1,4]diazepino[1,7-a]indole
9-(5-fluoro-4-methoxy-2-methylphenyl)-2,3,4,5,11,11a-hexahydro-1H-[1,4]diazepino[1,7-a]indole
9-(4-methoxy-2-methylphenyl)-2,3,4,5,11,11a-hexahydro-1H-[1,4]diazepino[1,7-a]indole
9-[2-chloro-4-(trifluoromethoxy)phenyl]-2,3,4,5,11,11a-hexahydro-1H-[1,4]diazepino[1,7-a]indole
9-(2,4,5-trimethylphenyl)-2,3,4,5,11,11a-hexahydro-1H-[1,4]diazepino[1,7-a]indole
9-(3-chlorophenyl)-2,3,4,5,11,11a-hexahydro-1H-[1,4]diazepino[1,7-a]indole
9-(4-methylphenyl)-2,3,4,5,11,11a-hexahydro-1H-[1,4]diazepino[1,7-a]indole
9-(4-chloro-2-methylphenyl)-2,3,4,5,11,11a-hexahydro-1H-[1,4]diazepino[1,7-a]indole
9-(2,5-dichlorophenyl)-2,3,4,5,11,11a-hexahydro-1H-[1,4]diazepino[1,7-a]indole
9-(4-isopropyl-2-methoxyphenyl)-2,3,4,5,11,11a-hexahydro-1H-[1,4]diazepino[1,7-a]indole
9-(2,6-dichlorophenyl)-2,3,4,5,11,11a-hexahydro-1H-[1,4]diazepino[1,7-a]indole
9-(2,6-difluorophenyl)-2,3,4,5,11,11a-hexahydro-1H-[1,4]diazepino[1,7-a]indole
9-[4-methoxy-2-(trifluoromethyl)phenyl]-2,3,4,5,11,11a-hexahydro-1H-[1,4]diazepino[1,7-a]indole
9-[2-(trifluoromethyl)phenyl]-2,3,4,5,11,11a-hexahydro-1H-[1,4]diazepino[1,7-a]indole
9-(4-pyridinyl)-2,3,4,5,11,11a-hexahydro-1H-[1,4]diazepino[1,7-a]indole
9-(2-furyl)-2,3,4,5,11,11a-hexahydro-1H-[1,4]diazepino[1,7-a]indole
2-(2,3,4,5,11,11a-hexahydro-1H-[1,4]diazepino[1,7-a]indol-9-yl)benzenethiol
9-(2,3-dichlorophenyl)-2,3,4,5,11,11a-hexahydro-1H-[1,4]diazepino[1,7-a]indole
9-(4-ethylphenyl)-2,3,4,5,11,11a-hexahydro-1H-[1,4]diazepino[1,7-a]indole
9-(2,4-dimethoxyphenyl)-2,3,4,5,11,11a-hexahydro-1H-[1,4]diazepino[1,7-a]indole
9-(3-chloro-2-fluorophenyl)-2,3,4,5,11,11a-hexahydro-1H-[1,4]diazepino[1,7-a]indole
9-(4-methoxyphenyl)-2,3,4,5,11,11a-hexahydro-1H-[1,4]diazepino[1,7-a]indole
9-[4-(methylsulfanyl)phenyl]-2,3,4,5,11,11a-hexahydro-1H-[1,4]diazepino[1,7-a]indole
4-(2,3,4,5,11,11a-hexahydro-1H-[1,4]diazepino[1,7-a]indol-9-yl)benzonitrile
9-[3-(trifluoromethyl)phenyl]-2,3,4,5,11,11a-hexahydro-1H-[1,4]diazepino[1,7-a]indole
9-(2-naphthyl)-2,3,4,5,11,11a-hexahydro-1H-[1,4]diazepino[1,7-a]indole
1-[4-(2,3,4,5,11,11a-hexahydro-1H-[1,4]diazepino[1,7-a]indol-9-yl)phenyl]ethanone
N-[3-(2,3,4,5,11,11a-hexahydro-1H-[1,4]diazepino[1,7-a]indol-9-yl)phenyl]acetamide
9-(2,3-dimethylphenyl)-2,3,4,5,11,11a-hexahydro-1H-[1,4]diazepino[1,7-a]indole
9-(5-fluoro-2-methylphenyl)-2,3,4,5,11,11a-hexahydro-1H-[1,4]diazepino[1,7-a]indole
9-(2-fluoro-5-methylphenyl)-2,3,4,5,11,11a-hexahydro-1H-[1,4]diazepino[1,7-a]indole
9-(5-fluoro-2-methoxylphenyl)-2,3,4,5,11,11a-hexahydro-1H-[1,4]diazepino[1,7-a]indole
9-(3-chloro-2-methylphenyl)-2,3,4,5,11,11a-hexahydro-1H-[1,4]diazepino[1,7-a]indole
9-(3-nitrophenyl)-2,3,4,5,11,11a-hexahydro-1H-[1,4]diazepino[1,7-a]indole
9-(2-nitrophenyl)-2,3,4,5,11,11a-hexahydro-1H-[1,4]diazepino[1,7-a]indole
9-(2-chloro-3-methylphenyl)-2,3,4,5,11,11a-hexahydro-1H-[1,4]diazepino[1,7-a]indole
9-(2-methoxylphenyl)-2,3,4,5,11,11a-hexahydro-1H 1-[1,4]diazepino[1,7-a]indole
9-(4-ethoxy-2-methylphenyl)-2,3,4,5,11,11a-hexahydro-1H-[1,4]diazepino[1,7-a]indole
9-(4-fluoro-2-methylphenyl)-2,3,4,5,11,11a-hexahydro-1H-[1,4]diazepino[1,7-a]indole
9-(2-chloro-6-fluorophenyl)-2,3,4,5,11,11a-hexahydro-1H-[1,4]diazepino[1,7-a]indole
9-[2-chloro-4-(difluoromethoxy)phenyl]-2,3,4,5,11,11a-hexahydro-1H-[1,4]diazepino[1,7-a]indole
9-[4-(trifluoromethyl)phenyl]-2,3,4,5,11,11a-hexahydro-1H-[1,4]diazepino[1,7-a]indole
9-[4-(trifluoromethoxy)phenyl]-2,3,4,5,11,11a-hexahydro-1H-[1,4]diazepino[1,7-a]indole
9-(6-fluoro-2,4-dimethoxylphenyl)-2,3,4,5,11,11a-hexahydro-1H-[1,4]diazepino[1,7-a]indole
9-(2-methylphenyl)-2,3,4,5,11,11a-hexahydro-1H-[1,4]diazepino[1,7-a]indole
9-[6-fluoro-2-(trifluoromethyl)phenyl]-2,3,4,5,11,11a-hexahydro-1H-[1,4]diazepino[1,7-a]indole
9-[2-(methylsulfanyl)phenyl]-2,3,4,5,11,11a-hexahydro-1H-[1,4]diazepino[1,7-a]indole
9-(2,4,6-trifluorophenyl)-2,3,4,5,11,11a-hexahydro-1H-[1,4]diazepino[1,7-a]indole
9-(2,4,6-trichlorophenyl)-2,3,4,5,11,11a-hexahydro-1H-[1,4]diazepino[1,7-a]indole
9-(2,6-dichloro-4-methoxyphenyl)-2,3,4,5,11,11a-hexahydro-1H-[1,4]diazepino[1,7-a]indole 9-(2,3,4-trifluorophenyl)-2,3,4,5,11,11a-hexahydro-1H-[1,4]diazepino[1,7-a]indole
9-(4-chloro-2,6-difluorophenyl)-2,3,4,5,11,11a-hexahydro-1H-[1,4]diazepino[1,7-a]indole
9-(2,3,4,6-tetrafluorophenyl)-2,3,4,5,11,11a-hexahydro-1H-[1,4]diazepino[1,7-a]indole
9-(2,3,4,5,6-pentafluorophenyl)-2,3,4,5,11,11a-hexahydro-1H-[1,4]diazepino[1,7-a]indole
9-[2,6-di(trifluoromethyl)phenyl]-2,3,4,5,11,11a-hexahydro-1H-[1,4]diazepino[1,7-a]indole
9-[2-(trifluoromethoxy)phenyl]-2,3,4,5,11,11a-hexahydro-1H-[1,4]diazepino[1,7-a]indole
9-[4-ethoxy-2-(trifluoromethoxy)phenyl]-2,3,4,5,11,11a-hexahydro-1H-[1,4]diazepino[1,7-a]indole
9-[4-isopropoxy-2-(trifluoromethyl)phenyl]-2,3,4,5,11,11a-hexahydro-1H-[1,4]diazepino[1,7-a]indole
9-[4-chloro-2-(trifluoromethyl)phenyl]-2,3,4,5,11,11a-hexahydro-1H-[1,4]diazepino[1,7-a]indole
9-[4-fluoro-2-(trifluoromethyl)phenyl]-2,3,4,5,11,11a-hexahydro-1H-[1,4]diazepino[1,7-a]indole
9-[2-chloro-4-ethoxyphenyl]-2,3,4,5,11,11a-hexahydro-1H-[1,4]diazepino[1,7-a]indole
9-[2-chloro-4-isopropoxyphenyl]-2,3,4,5,11,11a-hexahydro-1H-[1,4]diazepino[1,7-a]indole
9-(2-ethyl-4-methoxyphenyl)-2,3,4,5,11,11a-hexahydro-1H-[1,4]diazepino[1,7-a]indole
5-methoxy-2-(2,3,4,5,11,11a-hexahydro-1H-[1,4]diazepino[1,7-a]indol-9-yl)benzaldehyde
9-[4-methoxy-2-(1-hydroxyethyl)phenyl]-2,3,4,5,11,11a-hexahydro-1H-[1,4]diazepino[1,7-a]indole
9-[4-methoxy-2-(1-methoxyethyl)phenyl]-2,3,4,5,11,11a-hexahydro-1H-[1,4]diazepino[1,7-a]indole
1-[5-methoxy-2-(2,3,4,5,11,11a-hexahydro-1H-[1,4]diazepino[1,7-a]indol-9-yl)phenyl]ethanone
[5-methoxy-2-(2,3,4,5,11,11a-hexahydro-1H-[1,4]diazepino[1,7-a]indol-9-yl)phenyl]methanol
9-[4-methoxy-2-(methoxymethyl)phenyl]-2,3,4,5,11,11a-hexahydro-1H-[1,4]diazepino[1,7-a]indole
1-[5-methoxy-2-(2,3,4,5,11,11a-hexahydro-1H-[1,4]diazepino[1,7-a]indol-9-yl)phenyl]-1-propanol
1-[5-methoxy-2-(2,3,4,5,11,11a-hexahydro-1H-[1,4]diazepino[1,7-a]indol-9-yl)phenyl]-1-propanone
methyl (2Z)-3-[5-methoxy-2-(2,3,4,5,11,11a-hexahydro-1H-[1,4]diazepino[1,7-a]indol-9-yl)phenyl]-2-propenoate
methyl 3-[5-methoxy-2-(2,3,4,5,11,11a-hexahydro-1H-[1,4]diazepino[1,7-a]indol-9-yl)phenyl]propanoate
(2Z)-3-[5-methoxy-2-(2,3,4,5,11,11a-hexahydro-1H-[1,4]diazepino[1,7-a]indol-9-yl)phenyl]-2-propen-1-ol
methyl (2E)-3-[5-methoxy-2-(2,3,4,5,11,11a-hexahydro-1H-[1,4]diazepino[1,7-a]indol-9-yl)phenyl]-2-propenoate
(2E)-3-[5-methoxy-2-(2,3,4,5,11,11a-hexahydro-1H-[1,4]diazepino[1,7-a]indol-9-yl)phenyl]-2-propen-1-ol
9-[4-methoxy-2-(2-methoxyethyl)phenyl]-2,3,4,5,11,11a-hexahydro-1H-[1,4]diazepino[1,7-a]indole
9-(2-fluoro-4-methoxyphenyl)-2,3,4,5,11,11a-hexahydro-1H-[1,4]diazepino[1,7-a]indole
9-(2-chloro-4-fluorophenyl)-2,3,4,5,11,11a-hexahydro-1H-[1,4]diazepino[1,7-a]indole
9-benzyl-2,3,4,5,11,11a-hexahydro-1H-[1,4]diazepino[1,7-a]indole
9-(2-fluorobenzyl)-2,3,4,5,11,11a-hexahydro-1H-[1,4]diazepino[1,7-a]indole
9-(3-fluorobenzyl)-2,3,4,5,11,11a-hexahydro-1H-[1,4]diazepino[1,7-a]indole
9-(4-fluorobenzyl)-2,3,4,5,11,11a-hexahydro-1H-[1,4]diazepino[1,7-a]indole
9-(3-methoxybenzyl)-2,3,4,5,11,11a-hexahydro-1H-[1,4]diazepino[1,7-a]indole
3-(2,3,4,5,11,11a-hexahydro-1H-[1,4]diazepino[1,7-a]indol-9-ylmethyl)phenol
9-(2-methoxybenzyl)-2,3,4,5,11,11a-hexahydro-1H-[1,4]diazepino[1,7-a]indole
2-(2,3,4,5,11,11a-hexahydro-1H-[1,4]diazepino[1,7-a]indol-9-ylmethyl)phenol
methyl 2-methoxy-6-(2,3,4,5,11,11a-hexahydro-1H-[1,4]diazepino[1,7-a]indol-9-yl)benzoate
3-(2,3,4,5,11,11a-hexahydro-1H-[1,4]diazepino[1,7-a]indol-9-yl)benzonitrile
3-methyl-4-(2,3,4,5,11,11a-hexahydro-1H-[1,4]diazepino[1,7-a]indol-9-yl)benzonitrile
2-methyl-3-(2,3,4,5,11,11a-hexahydro-1H-[1,4]diazepino[1,7-a]indol-9-yl)benzonitrile
2-(2,3,4,5,11,11a-hexahydro-1H-[1,4]diazepino[1,7-a]indol-9-yl)benzonitrile
3-trifluoromethyl-4-(2,3,4,5,11,11a-hexahydro-1H-[1,4]diazepino[1,7-a]indol-9-yl)benzonitrile
3-(2,3,4,5,11,11a-hexahydro-1H-[1,4]diazepino[1,7-a]indol-9-yl)benzaldehyde
[3-(2,3,4,5,11,11a-hexahydro-1H-[1,4]diazepino[1,7-a]indol-9-yl)phenyl]methanol
9-[3-(methoxymethyl)phenyl]-2,3,4,5,11,11a-hexahydro-1H-[1,4]diazepino[1,7-a]indole
N,N-dimethyl[3-(2,3,4,5,11,11a-hexahydro-1H-[1,4]diazepino[1,7-a]indol-9-yl)phenyl]methanamine
2-fluoro-5-(2,3,4,5,11,11a-hexahydro-1H-[1,4]diazepino[1,7-a]indol-9-yl)benzonitrile, and
2-fluoro-5-(2,3,4,5,11,11a-hexahydro-1H-[1,4]diazepino[1,7-a]indol-9-yl)benzamide.

Other compounds which technically are not within the scope of formula I but are considered to be within the scope of the instant invention include:

tert-butyl 1,2,4,5-tertrahydro-3H[1,4]diazepino[1,7-a]-indole-3-carboxylate;
11[(E)-2-nitroethyl]-2,3,4,5-tetrahydro-1H-[1,4]diazepino-[1,7-a]indole;
3-(trifluoroacetyl)-2,3,4,5-tetrahydro-1H-[1,4]diazepino-[1,7-a]indole; and
2-bromo-1-[3-(trifluoroacetyl)-2,3,4,5-tetrahydro-1H-[1,4]diazepino[1–7-a]indole-11-yl]ethanone.

The following describe the preparation of compounds of the present invention. All of the starting materials are prepared by procedures described herein or by procedures that would be well known to one of ordinary skill in organic chemistry.

Compounds of Formula I where R1a, R1b, R2a, R2b, R4, and R3=H can be prepared by reactions outlined in Chart A1. Step 1 involves the reaction of a 2-nitrophenylacetic acid derivative with carbonyl diimidazole followed by the addition of a magnesium salt of ethylhydrogen malonate to provide compound 1. In Step 2, treatment of the β-ketoester with $TiCl_3$ in the presence of water and acetone reduces the nitro group followed by spontaneous dehydrative cyclization with the ketone moiety to provide 3-indoleacetic acid derivatives 2. This dehydrative cyclization is also accomplished under heterogeneous palladium catalyzed hydrogenylitic conditions. In Step 3, reduction of the indole to the corresponding indoline 3 is achieved by the action of $NaCNBH_3$ in the presence of an acid such as acetic acid or trifluoroacetic acid. In Step 4, the aniline moiety is alkylated with 1,2-dibromoethane in the presence of base and a suitable solvent such as CH₃CN or N-methylpyrrolidinone to afford trisubstituted amine derivatives 4. In Step 5, a second annulation occurs by the reaction of 4 with a primary amine of formula R4NH2, where R4 is as defined above, to provide azepinones 5. In Step 6, the carbonyl group of compound 5 is reduced by reaction with a reducing agent such as diisobutylaluminum hydride in a suitable solvent such as tetrahydrofuran or toluene to yield azepines 6. Finally, oxidation of indolines 6 to the corresponding indoles 7 is achieved by the action of an oxidant such as 2,3-dichloro-5,6-dicyano-1,4-benzoquinone (DDQ) in the presence of a suitable solvent such as dixoane (Examples 1–3).

Additionally, compounds of Formula I where R1a, R1b, R2a, R2b, R3 and R4 are as defined above and bond a is a single or double bond can be prepared by reactions outlined in Chart G. Step 1 involves the reaction of 20 (where X can be but is not limited to I, Br, Cl, triflate, organotin, and organoboron) under various catalytic transition metal coupling procedures. These procedures can be performed by one skilled in the art of organic chemistry and include, but are not limited to, the Suzuki coupling (for a review see Snieckus, V.; *Chem. Rev.*; 90; 897; 1990), the Stille coupling (for a review see Beletzkaya, I. P.; *J. Organomet. Chem.*; 250; 551; 1983), the Heck coupling (for a review see de Meijere, A. and Meyer, F. E.; *Angew. Chem. Int. Ed. Engl.*; 33; 2379; 1994), heteroatom carbon coupling reactions (for a review see Buchwald, S. L. and Yang, B. H.; *J. Organomet. Chem.*; 576; 125; 1999), and carbonylation reactions (for an example see Heck, R. F.; Schoenberg, A.; Bartoletti, I.; *J. Org. Chem.*; 39; 3318; 1974).

The present invention also resides in the production of compounds wherein R3 of Formula I is as defined above except for hydrogen. To obtain compounds having specific R3 groups other than hydrogen, 2,3,4,5-tetrahydro-1H-[1,4] diazepino[1,7-a]indole is reacted with appropriate reactants using standard organic chemical synthesis procedures as would be well understood in the art. Examples of such standard procedures are shown in Charts B–E.

For example, Chart B illustrates the preparation of compounds where R1a, R1b, R2a, R2b and R4 are H and R3 is —C(O)C(O)XR5, where X and R5 are as defined above.

In step 1, a N-protected derivative 8 is reacted with oxalyl chloride in dichloromethane at reduced temperatures to produce the corresponding α-keto acid chloride. This uncharacterized intermediate is reacted with various XR5 in the presence of a tertiary amine base such as triethyl amine or diisopropylethyl amine and an appropriate solvent such as dichloromethane or toluene. Upon consumption of the α-keto acid chloride, the protecting group is cleaved under standard deprotection conditions such as trifluoroacetic acid for the tert-butyl carbamate group or alkaline alcoholic conditions for the trifluoro acetamide group to afford α-ketoamide products 9. This sequence can be carried out with non-critical variations utilizing parallel synthetic techniques and employing polymer supported reagents as reactants, scavengers, and capture-release reagents to produce libraries of final products.

Chart C illustrates the preparation of compounds where R1a, R1b, R2a, R2b and R4 are H and R3 is —CH₂C(O) XR5, where X and R5 are as defined above. In step 1, products 9 (Chart B, step 1) are reacted in an appropriate solvent such as 1,2-dichloroethane with a reducing agent such as triethyl silane under acidic conditions and elevated temperatures to afford the selectively reduced products 10.

The production of compounds where R1a, R1b, R2a, R2b and R4 are H and R3 is —CH₂CH₂XR5, where X and R5 are as defined above is depicted in Chart D. In step 1, 3-benzyl-2,3,4,5-tetrahydro-1H-[1,4]diazepino[1,7-a]indole is reacted with oxalyl chloride in an appropriate solvent such as diethyl ether or dichloromethane at reduced temperatures to give an intermediate α-keto acid chloride that is reacted with ethanol to afford compound 12. Reduction of the dicarbonyl moiety is achieved in a two-step procedure involving initial reduction with lithium aluminum hydride in an appropriate solvent such as tetrahydrofuran to the corresponding diol followed by reduction of the secondary alcohol by the action of triethyl silane under acidic conditions in an appropriate solvent such as dichloromethane to afford 13. In step 3, substitution with XR5 as defined above is accomplished under Mitsunobu reaction conditions or by functionalization of the terminal alcohol moiety of 13 to a suitable leaving group such as mesylate followed by nucleophilic displacement to give compounds 14. Finally, debenzylation of the azepino nitrogen is accomplished by palladium catalyzed hydrogenolysis in the presence of a hydrogen source such as ammonium formate to afford compounds 15. Alternatively, conversion of 14 to the corresponding trichloroethyl carbamate derivative followed by cleavage of the newly installed protecting group by the action of zinc in acetic acid affords compounds 15. This sequence can be carried out with non-critical variations utilizing parallel synthetic techniques and employing polymer supported reagents as reactants, scavengers, and capture-release reagents to produce libraries of final products.

Chart E illustrates the preparation of compounds where R1a, R1b, R2a, R2b and R4 are H and R3 is —C(O) CH₂XR5, where X and R5 are as defined above. In step 1, protected intermediate 8 is reacted with bromoacetyl bromide in the presence of a Lewis acid such as aluminum trichloride and an appropriate solvent such as dichloromethane to give 16. This α-bromo ketone is substituted with XR5 as defined above by alkylation in the presence of a suitable base such as potassium carbonate and solvent such as acetonitrile. Upon consumption of the α-keto bromide, the protecting group is cleaved under standard deprotection conditions such as trifluoroacetic acid for the tert-buyl carbamate group or alkaline alcoholic conditions for the trifluoro acetamide group to afford products 17. This sequence can be carried out with non-critical variations utilizing parallel synthetic techniques and employing polymer supported reagents as reactants, scavengers, and capture-release reagents to produce libraries of final products.

The present invention also resides in the production of compounds wherein bond a is a single bond of Formula I and where R1a, R1b, R2a, R2b, R3, and R4 are as defined above. To obtain compounds having bond a as a single bond, derivatives of 2,3,4,5-tetrahydro-1H-[1,4]diazepino[1,7-a] are reacted with appropriate reactants using standard organic chemical synthesis procedures as would be well understood in the art.

Chart F illustrates the preparation of compounds I where bond a is a single bond and R1, R2, R3, and R4 are as defined above. In step 1, the indole products 18 are reduced by the action of a reducing reagent such as sodium cyanoborohydride or triethylsilane in acidic conditions to afford the corresponding indolines 19. Alternatively, reduction can be achieved by catalytic hydrogenation under elevated pressures of hydrogen in the presence of a metal catalyst such as palladium, platinum, rhodium, or nickel, (for an overview of indole reductions to indolines see Sundberg, R. J.; *Indoles*; Academic Press, 145; 1996).

The above compounds are useful in treating diseases or disorders of the central nervous system occurring in animals, preferably mammals. Typically, the mammal is a human being, but the inventive compounds can be used to treat other animals such as food animals (e.g., cows, pigs, sheep, goats, deer, poultry, etc.), companion animals (e.g., dogs, cats, horses, birds and fish), or other animals. The compounds may be administered in their native form, or, more typically, with a pharmaceutically acceptable excipient. The compounds may also be administered in acid or basic salt forms.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, maleate, fumarate, benzenesulfonate and α-glycerophosphate. Suitable inorganic salts may also be formed, including hydrobromide, hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15th Ed., 1975). To the extent necessary for completion, this reference is hereby incorporated by reference. The compounds and compositions of the present invention can be administered parenterally (for example, by intravenous, intraperitoneal or intramuscular injection), topically, nasally, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. The above listing is merely representative and one skilled in the art could envision other binders, excipients, sweetening agents and the like. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices including, but not limited to, those relying on osmotic pressures to obtain a desired release profile (e.g., the OROS drug delivery devices as designed and developed by Alza Corporation).

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions. Sterilization of the powders may also be accomplished through irradiation and aseptic crystallization methods. The sterilization method selected is the choice of the skilled artisan.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. To this extent, the present invention further contemplates the use of the pharmaceutically active materials in personal care compositions such as lotions, cleansers, powders, cosmetics and the like.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can conveniently be administered orally, sublingually, transdermally, or parenterally at dose levels of about 0.01 to about 150 mg/kg, preferably about 0.1 to about 50 mg/kg, and more preferably about 0.1 to about 10 mg/kg of mammal body weight.

For parenteral administration the compounds are presented in aqueous solution in a concentration of from about 0.1 to about 10%, more preferably about 0.1 to about 7%. The solution may contain other ingredients, such as emulsifiers, antioxidants or buffers.

The exact regimen for administration of the compounds and compositions disclosed herein will necessarily be dependent upon the needs of the individual subject being treated, the patient type (i.e., human or animal), the type of treatment and, of course, the judgment of the attending practitioner.

Generally, compounds of the invention are 5-HT ligands. The ability of a compound of the invention to act as a 5-HT receptor agonist, partial agonist or antagonist can also be determined using in vitro and in vivo assays that are known in the art. The invention provides compounds of formula I that act as either agonists, partial agonists or as antagonists of one or more 5-HT receptor subtypes.

The inventive compounds of the present invention may be useful as modulators of 5-HT receptor function. Thus, the compounds are useful for treating diseases or disorders where modulation of 5-HT receptor function is desired. This inventive composition is used to treat any of the diseases or disorders of the central nervous system. Such diseases and disorders are defined in The Diagnostic and Statistical Manual of Mental Disorders-IV (DSM-IV) (American Psychiatric Association (1995)). To the extent necessary for completion, the contents of this reference and all of the defined diseases or disorders are expressly incorporated by reference. Representative diseases or disorders include, but are not limited to the following: obesity, depression, schizophrenia, a stress related disease (e.g. general anxiety disorder), panic disorder, a phobia, obsessive compulsive disorder, post-traumatic-stress syndrome, immune system depression, incontinence, a stress induced problem with the urinary, gastrointestinal or cardiovascular system (e.g., stress incontinence), neurodegenerative disorders, autism, chemotherapy-induced vomiting, hypertension, migraine headaches, cluster headaches, sexual dysfunction in a mammal (e.g. a human), addictive disorder and withdrawal syndrome, an adjustment disorder, an age-associated learning and mental disorder, anorexia nervosa, apathy, an attention-deficit disorder due to general medical conditions, attention-deficit hyperactivity disorder, bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, a movement disorder (e.g., Tourette's syndrome), oppositional defiant disorder, a pain disorder, peripheral neuropathy, post-traumatic stress disorder, premenstrual dysphoric disorder, a psychotic disorder, seasonal affective disorder, a sleep disorder, a specific developmental disorder, and selective serotonin reuptake inhibition (SSRI) "poop out" syndrome. Treatment of the above diseases or disorders is accomplished by delivering a therapeutically effective amount of the inventive composition to a mammal. In most cases this will be a human being, but treatment of food animals (e.g., livestock such as cows, pigs, deer, sheep, goats and the like, and poultry) and companion animals (e.g., dogs, cats, birds, fish and horses) is expressly covered herein.

The invention is described in greater detail by the following non-limiting examples.

EXAMPLE 1

2,3,4,5-Tetrahydro-1H-[1,4]diazepino[1,7-a]indole hydrochloride

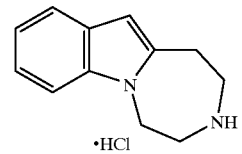

Method 1

(Chart A, Step 1): A solution of ethylhydrogen malonate (19.82 g, 150 mmol) in 375 mL THF is treated with a single portion of magnesium ethoxide (8.58 g, 75 mmol). The resulting light yellow suspension is stirred for 1 hour at RT then concentrated under reduced pressure to give a light golden foam. In a separate vessel, a solution of 2-nitrophenylacetic acid in 750 mL of THF is treated with 1,1-carbonyldiimidazole (26.75 g, 165 mmol). The resulting clear light yellow solution is stirred until TLC indicates no remaining starting acid (4 hours). At this time, the solution of acylimidazole is transferred to the flask containing the crude magnesium salt and is stirred at RT for 18 hours. At this time, the volatiles are removed under reduced pressure with the resulting residue diluted with 60 mL 0.5M hydrochloric acid and extracted twice (600 mL) with dichloromethane. The combined organics are washed once with brine (500 mL), dried over MgSO$_4$, filtered, and concentrated to give 35.44 g of a golden oil. This material is purified by Prep 500 HPLC (250 g silica gel cartridge) eluting with 35% ethyl acetate/heptane to afford 29.48 g (78%) of ethyl 3-(2-nitrophenyl)-3-oxopropanoate as a ligh yellow oil. $^1$H NMR (300 MHz, CDCl$_3$) δ8.14 (dd, J=1, 9

Hz, 1H), 7.62 (dt, J=1, 7 Hz, 1H), 7.49 (dt, J=1, 8 Hz, 1H), 7.32 (dd, J=1, 8 Hz, 1H), 4.27 (s, 2H), 4.22 (qt, J=7 Hz, 2H), 3.64 (s, 2H), 1.31 (t, J=7 Hz, 3H).

(Chart A, Step 2): A solution of ethyl 3-(2-nitrophenyl)-3-oxopropanoate (29.45 g, 117 mmol) in 390 mL acetone is diluted with 2.9 L of a 4 M solution of ammonium acetate resulting in the dissolution of a small amount of the starting β-ketoester. This pale yellow solution is treated with 900 mL of a 15% aqueous solution of titanium trichloride immediately turning an emerald green color. Two additional portions of titanium trichloride (670 mL & 100 mL) are required to completely consume the starting β-ketoester. Within 15 minutes of the final treatment with titanium trichloride, the reaction mixture is washed four times with water (700 mL), once with brine (700 mL), dried over $MgSO_4$, filtered, and concentrated to give a golden oil. This material is purified by Prep 500 HPLC (250 g silica gel cartridge) eluting with 20% ethyl acetate/heptane to afford 21.95 g (92%) of ethyl 2-(1H-indol-2-yl)acetate as a golden oil. $^1$H NMR (300 MHz, $CDCl_3$) δ8.70 (bs, 1H), 7.57 (d, J=8 Hz, 1H), 7.35 (d, J=7 Hz, 1H), 7.13 (m, 2H), 6.37 (d, J=1 Hz, 1H), 4.23 (qrt, J=7 Hz, 2H), 3.83 (s, 2H), 1.31 (t, J=7 Hz, 3H); $^{13}$C NMR (75 MHz, $CDCl_3$) δ170.7, 136.8, 130.6, 128.3, 121.7, 120.2, 119.8, 110.9, 101.8, 61.4, 34.0, 14.2.

(Chart A, Step 3): A solution of ethyl 2-(1H-indol-2-yl)acetate (21.93 g, 108 mmol) in 490 mL acetic acid is treated via solid addition funnel with sodium cyanoborohydride (20.34 g, 324 mmol) with some foaming and a slight exotherm being observed. The resulting clear light yellow solution is stirred 2 hours, quenched with 30 mL water, stirred an additional 30 minutes, basified with saturated $NaHCO_3$, and extracted three times with ethyl acetate (600 mL). The combined organics are dried over $Na_2SO_4$, filtered, and concentrated to give 27.03 g of a yellow oil. This material is purified by Prep 500 HPLC (250 g silica gel cartridge) eluting with 7% ethyl acetate/heptane to afford 17.79 g (80%) of ethyl 2-(2,3-dihydro-1H-indol-2-yl)acetate as a light yellow oil. $^1$H NMR (300 MHz, $CDCl_3$) δ7.09 (d, J=7 Hz, 1H), 7.04 (t, J=8 Hz, 1H), 6.72 (t, J=7 Hz, 1H), 6.63 (d, J=8 Hz, 1H), 4.44 (bs, 1H), 4.23 (m, 3H), 3.21 (dd, J=9, 15 Hz, 1H), 2.71 (dd, J=8, 16 Hz, 1H), 2.64 (d, J=7 Hz, 2H), 1.30 (t, J=7 Hz, 3H); $^{13}$C NMR (75 MHz, $CDCl_3$) δ172.4, 150.6, 127.9, 127.5, 124.7, 118.7, 109.3, 60.6, 55.8, 40, 9, 35.8, 14.3.

(Chart A, Step 4): A solution of ethyl 2-(2,3-dihydro-1H-indol-2-yl)acetate (11.00 g, 53.6 mmol) in 500 mL acetonitrile is charged with powdered potassium carbonate (22.2 g, 161 mmol). The resulting light yellow suspension is treated with dibromoethane (92 mL, 1.07 mol, filtered through basic alumina) followed by heating to reflux for 60 hours. The volatiles are removed under reduced pressure, diluted with water (450 mL), and extracted twice with dichloromethane (300 mL). The combined organics are washed once with brine (300 mL), dried over $MgSO_4$, filtered, and concentrated to give 27.10 g of a golden oil. This material is purified by Prep 500 HPLC (250 g silica gel cartridge) eluting with 7% ethyl acetate/heptane to afford 13.20 g (79%) of ethyl 2-[1-(2-bromoethyl)-2,3-dihydro-1H-indol-2-yl]acetate as a very light lavender oil. $^1$H NMR (300 MHz, $CDCl_3$) δ7.10 (m, 2H), 6.70 (t, J=7 Hz, 1H), 6.45 (d, J=8 Hz, 1H), 4.19 (dqr, J=7, 1 Hz, 2H), 4.13 (m, 1H), 3.53 (m, 4H), 3.32 (dd, J=9, 16 Hz, 1H), 2.80 (m, 2H), 2.57 (dd, J=8, 15 Hz, 1H), 1.30 (t, J=7 Hz, 3H); $^{13}$C NMR (75 MHz, $CDCl_3$) δ171.4, 150.6, 128.0, 127.7, 124.6, 118.3, 106.3, 60.9, 60.8, 49.2, 39.7, 35.5, 28.9, 14.2.

(Chart A, Step 5): A solution of ethyl 2-[1-(2-bromoethyl)-2,3-dihydro-1H-indol-2-yl]acetate (13.18 g, 42.2 mmol) in ammonia saturated methanol (800 mL) is heated to 50° C. in a thick walled sealed tube for 18 hours. The volatiles are removed under reduced pressure, diluted with dichloromethane (400 mL) and washed once with 1N sodium hydroxide (200 mL), once with brine (200 mL), dried over $MgSO_4$, filtered, and concentrated to give 8.30 g of a white solid. This material is purified by LC (230–400 silica gel) eluting with 5% methanol/dichloromethane to afford 7.23 g (85%) of 4,5,11,11a-tetrahydro-1H-[1,4]diazepino[1,7-a]indol-2(3H)-one as a white solid, mp 186–188° C. IR (drift) 3210, 3082, 3047, 2950, 1668, 1606, 1485, 1458, 1383, 1352, 1308, 1280, 1246, 881, 748 $cm^{-1}$. $^1$H NMR (300 MHz, $CDCl_3$) δ7.11 (m, 2H), 7.03 (bs, 1H), 6.74 (t, J=7 Hz, 1H), 6.49 (d, J=8 Hz, 1H), 3.60 (m, 3H), 3.35 (m, 1H), 3.07 (m, 2H), 2.87 (m, 1H), 2.71 (m, 2H); $^{13}$C NMR (75 MHz, $CDCl_3$) δ176.6, 151.7, 128.3, 127.6, 124.5, 118.9, 106.7, 62.1, 48.6, 43.0, 42.6, 36.

(Chart A, Step 6): A solution of 4,5,11,11a-tetrahydro-1H-[1,4]diazepino[1,7-a]indol-2(3H)-one (12.70 g, 63 mmol) in THF (630 mL) is drop-wise treated with borane dimethylsulfide complex (126 mL, 2M THF) with effervescence. The reaction is heated to reflux for 18 hours. At this time, the reaction is quenched by the careful addition of approximately 450 mL ethanol and upon completion of hydrogen evolution the volatiles are removed under reduced pressure. The resulting residue is re-diluted with 650 mL ethanol and 400 mL 1M hydrochloric acid and heated to reflux for 1 hour. The reaction is cooled, concentrated, basified to pH 13, and extracted three times with dichloromethane (500 mL). The combined organics are washed once with brine (200 mL), dried over $MgSO_4$, filtered, and concentrated to give 12.74 g of a pale yellow oil. This material is purified by LC (230–400 silica gel) eluting with 1:15:84 $NH_4OH$/methanol/dichloromethane to afford 11.53 g (97%) of 2,3,4,5,11,11a-hexahydro-1H-[1,4]diazepino[1,7-a]indole as a pale yellow oil. IR (liq.) 2930, 2838, 1608, 1489, 1460, 1383, 1306, 1272, 1236, 1226, 1157, 1022, 745, 723, 708 $cm^{-1}$; MS (FAB) m/z 189 ($MH^+$).

(Chart A, Step 7): A solution of 2,3,4,5,11,11a-hexahydro-1H-[1,4]diazepino[1,7-a]indole (221 mg, 1.2 mmol) in 1,4 dioxane (6 mL) is treated with a single portion of DDQ (266 mg, 1.2 mmol) instantly turning black. HPLC analysis after 15 min indicates 15% remaining indoline and the reaction mixture is treated with additional DDQ (66 mg, 0.3 mmol). After an additional 15 min, the reaction mixture is poured into 2N sodium hydroxide (35 mL) and extracted three times with dichloromethane (30 mL). The combined organics are washed once with brine (30 mL), dried over $MgSO_4$, filtered, and concentrated to give 185 mg of a golden syrup. This material is purified by LC (230–400 silica gel) eluting with 0.5:5:94.5 $NH_4OH$/methanol/dichloromethane to afford 114 mg (52%) of a light golden solid. This material is dissolved in a mixture of dichloromethane/diethyl ether and treated with a solution of hydrochloric acid in methanol. The resulting salt is recrystallized from methanol and ethyl acetate to afford 90 mg of 2,3,4,5-Tetrahydro-1H-[1,4]diazepino[1,7-a]indole hydrochloride as a tan solid, mp 280–283° C. IR (drift) 2962, 2940, 2819, 2736, 2701, 2670, 2653, 2558, 2450, 1458, 1373, 1335, 795, 750, 740 $cm^{-1}$.

Method 2

A solution of 4,5,11,11a-tetrahydro-1H-[1,4]diazepino[1,7-a]indol-2(3H)-one (25.93 g, 128 mmol) in 1,4 dioxane (1.3 L) is heated to 60° C. and treated with a single portion of DDQ (32.02 g, 141 mmol) instantly turning brown with the formation of a percipitate. After 45 min, the reaction mixture is cooled to RT (cooling bath), diluted with ethyl acetate (1 L), and washed once with 5N sodium hydroxide (1.5 L). The alkaline layer is extracted three time with 1:1 ethyl acetate/THF (900 mL) with the combined organics being washed once with water (1 L), once with brine (1 L), dried over MgSO$_4$, filtered, and concentrated to give 24.4 g of an orange solid. This material is purified by LC (biotage 90 g columns) eluting with 3% methanol/dichloromethane to afford 21.27 g (83%) of 4,5-dihydro-1H-[1,4]diazepino [1,7-a]indol-2(3H)-one as an orange solid. IR (drift) 3207, 3097, 1678, 1469, 1453, 1417, 1370, 1356, 1317, 1226, 1147, 796, 771, 757, 749 cm$^{-1}$; MS (EI) m/z 200 (M$^+$).

A solution of 4,5-dihydro-1H-[1,4]diazepino[1,7-a]indol-2(3H)-one (10.50 g, 52.4 mmol) in THF (520 mL) is cooled to −78° C. and treated with a 1M solution of diisobutylaluminum hydride (630 mL, 630 mmol). The cooling bath is removed and the reaction is stirred at rt overnight. After 18 hours, the reaction is cooled to 0° C. and quenched by the addition of methanol (104 mL). Upon completion of gas evolution, the mixture is diluted with dichloromethane (1.2 mL) and saturated Na/K tartrate (1.2 L), and rapidly stirred for 30 min. The solution phases are separated and the aqueous phase is extracted twice with dichloromethane (1 L). The combined organics are washed once with brine (1.2 L), dried over MgSO$_4$, filtered, and concentrated to give 10.24 g of a golden oil. This material is purified by LC (230–400 silica gel) eluting with 0.5:3.5:96 NH$_4$OH/methanol/dichloromethane to afford 7.11 g (73%) of 2,3,4,5-Tetrahydro-1H-[1,4]diazepino[1,7-a]indole as a golden solid. This material is disolved in methanol and treated with a solution of hydrochloric acid in methanol to produce a white solid. This salt is recrystallized from methanol/ethyl acetate to afford a light tan solid, mp 280–283° C. IR (mull) 2817, 2793, 2750, 2735, 2669, 2656, 2559, 2530, 2451, 1445, 1421, 1336, 797, 751, 742 cm$^{-1}$; UV $\lambda_{max}$ 270 (7910, 95% ethanol).

EXAMPLE 2
8-bromo-2,3,4,5-tetrahydro-1H-[1,4]diazepino[1,7-a]indole hydrochloride

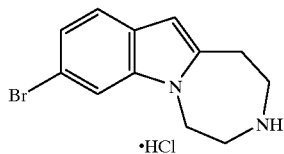

A 60% oil dispersion of sodium hydride (7.83 g, 196 mmol) is washed three times with pentane, suspended in dimethylsulfoxide (200 mL), and treated with neat dimethylmalonate (22.4 mL, 196 mmol) with gas evolution. The grey suspension is heated to 100° C. for 30 min, cooled to rt, and treated with 2,5-dibromonitrobenzene (25.0 g, 89 mmol). The resulting red solution is heated to 100° C. for 1 hour followed by cooling to rt. After 16 hr, the reaction is quenched with 700 mL saturated NH$_4$Cl and extracted once with 1:1 hexane/ethyl acetate. The combined organics are washed once with saturated NH$_4$Cl (300 mL), three times with water (300 mL), once with brine (300 mL), dried over MgSO$_4$, filtered, and concentrated to give 33.94 g of a golden oil. This material crystallizes from ethyl acetate/heptane to afford 23.02 g of dimethyl 2-(4-bromo-2-nitrophenyl)malonate as an off-white solid, mp 86–88° C.

A solution of dimethyl 2-(4-bromo-2-nitrophenyl) malonate (17.98 g, 54 mmol), lithium chloride (4.59 g, 108 mmol), and water (0.97 mL, 54 mmol) in dimethylsulfoxide (360 mL) is heated to 90° C. After 20 hrs, the reaction is cooled to rt, diluted with ethyl acetate (700 mL), washed twice with brine (700 mL), dried over MgSO$_4$, filtered, and concentrated to give 15.21 g of a golden syrup. This material is purified by Prep 500 HPLC (250 g silica gel cartridge) eluting with 7% ethyl acetate/heptane to afford 10.07 g of methyl 2-(4-bromo-2-nitrophenyl)acetate as a light yellow solid.

A solution of methyl 2-(4-bromo-2-nitrophenyl)acetate (11.40 g, 41.6 mmol) in methanol (42 mL) and THF (42 mL) is treated with 5M sodium hydroxide (42 mL, 208 mmol). After 20 hrs, the reaction mixture is acidified with 1 M hydrochloric acid (300 mL) and extracted twice with ethyl acetate (250 mL). The combined organics are washed once with brine (200 mL), dried over MgSO$_4$, filtered, and concentrated to give 10.52 g of an orange solid. This material is recrystallized from ethyl acetate/heptane to afford 9.21 g (85%) of 2-(4-bromo-2-nitrophenyl)acetic acid as a light yellow solid, mp 166–168° C. IR (drift) 3101, 3082, 3029, 2966, 2942, 2866, 1696, 1524, 1431, 1412, 1351, 1335, 1276, 1238, 885 cm$^{-1}$.

(Chart A, Step 1): Following the general procedure of Step 1 of Example 1, and making non-critical variations but substituting 2-(4-bromo-2-nitrophenyl)acetic acid for 2-nitrophenylacetic acid, gives 10.01 of a crude product. This material is purified by LC (230–400 silica gel) eluting with 22% acetone/heptane to afford 9.16 g of ethyl 4-(4-bromo-2-nitrophenyl)-3-oxobutanoate as a white solid, mp 78–80° C. IR (drift) 1743, 1712, 1521, 1419, 1405, 1367, 1348, 1314, 1278, 1262, 1207, 1194, 1073, 1027, 882 cm$^{-1}$.

(Chart A, Step 2): Following the general procedure of Step 2 of Example 1, and making non-critical variations but substituting ethyl 4-(4-bromo-2-nitrophenyl)-3-oxobutanoate for ethyl 3-(2-nitrophenyl)-3-oxopropanoate, gives 8.39 g of a crude product. This material is purified by LC (biotage 90 g column) eluting with 8% acetone/heptane to afford 6.88 g (97%) of ethyl 2-(6-bromo-1H-indol-2-yl)acetate as a white solid, mp 67–69° C. IR (drift) 3378, 2978, 1717, 1456, 1398, 1387, 1374, 1336, 1270, 1221, 1178, 1053, 910, 811, 650 cm$^{-1}$.

(Chart A, Step 3): Following the general procedure of Step 3 of Example 1, and making non-critical variations but substituting ethyl 2-(6-bromo-1H-indol-2-yl)acetate for ethyl 2-(1H-indol-2-yl)acetate and trifluoroacetic acid for acetic acid, gives 6.86 g of a crude product. This material is purified by LC (biotage 90 g column) eluting with 10% ethyl acetate/heptane to afford 5.59 g of ethyl 2-(6-bromo-2,3-dihydro-1H-indol-2-yl)acetate as a pale yellow mobile oil. IR (liq.) 1726, 1606, 1483, 1443, 1398, 1386, 1372, 1318, 1299, 1259, 1232, 1188, 1054, 1027, 898 cm$^{-1}$.

(Chart A, Step 4): Following the general procedure of Step 4 of Example 1, and making non-critical variations but substituting ethyl 2-(6-bromo-2,3-dihydro-1H-indol-2-yl)acetate for ethyl 2-(2,3-dihydro-1H-indol-2-yl)acetate and 1-methyl-2-pyrrolidinone for acetonitrile, gives 8.19 g of a crude product. This material is purified by LC (230–400 silica gel) eluting 10% ethyl acetate/heptane to afford 3.18 g (50%) of ethyl 2-[6-bromo-1-(2-bromoethyl)-2,3-dihydro-1H-indol-2-yl]acetate as a light yellow oil. IR (liq.) 1731, 1604, 1581, 1485, 1455, 1438, 1425, 1375, 1359, 1306, 1266, 1183, 1150, 1135, 1036 cm$^{-1}$.

(Chart A, Step 5): Following the general procedure of Step 5 of Example 1, and making non-critical variations but substituting ethyl 2-[6-bromo-1-(2-bromoethyl)-2,3-dihydro-1H-indol-2-yl]acetate for ethyl 2-[1-(2-bromoethyl)-2,3-dihydro-1H-indol-2-yl]acetate, gives 2.35 g of a crude product. This material is purified by LC (biotage 90 g column) eluting with 45% ethyl acetate/ dichloromethane to afford 1.25 g (56%) of 8-bromo-4,5,11,11a-tetrahydro-1H-[1,4]diazepino[1,7-a]indol-2(3H)-one as a white solid. IR (drift) 3077, 2966, 1662, 1604, 1575, 1490, 1431, 1353, 1322, 1300, 1233, 905, 884, 814, 789 cm$^{-1}$.

(Chart A, Step 6): Following the general procedure of Step 6 of Example 1, and making non-critical variations but substituting 8-bromo-4,5,11,11a-tetrahydro-1H-[1,4] diazepino[1,7-a]indol-2(3H)-one for 4,5,11,11a-tetrahydro-1H-[1,4]diazepino[1,7-a]indol-2(3H)-one, gives 1.10 g of a crude product. This material is purified by LC (230–400 silica gel) eluting with 15% methanol/dichloromethane to afford 989 mg of 8-bromo-2,3,4,5,11,11a-hexahydro-1H-[1,4]diazepino[1,7-a]indole as a white solid. IR (drift) 2940, 2919, 2893, 2867, 2850, 2823, 1602, 1573, 1492, 1452, 1378, 1274, 1216, 787, 732 cm$^{-1}$.

(Chart A, Step 7): Following the general procedure of Step 7 of Example 1, and making non-critical variations but substituting 8-bromo-2,3,4,5,11,11a-hexahydro-1H-[1,4] diazepino[1,7-a]indole for 2,3,4,5,11,11a-hexahydro-1H-[1,4]diazepino[1,7-a]indole, gives 491 mg of a crude product. This material is purified by LC (230–400 silica gel) eluting with 10% methanol/dichloromethane to give a yellow oil. This material is dissolved in a mixture of methanol/ethyl acetate and treated with a solution of hydrochloric acid in methanol. The resulting salt is recrystallized from methanol/ethyl acetate to afford 8-bromo-2,3,4,5-tetrahydro-1H-[1,4]diazepino[1,7-a]indole hydrochloride as a tan solid, mp 292–295° C. IR (drift) 2959, 2850, 2818, 2806, 2773, 2742, 2708, 2670, 2655, 2628, 2564, 2446, 1456, 1371, 817 cm$^{-1}$.

EXAMPLE 3

10-methoxy-2,3,4,5-tetrahydro-1H-[1,4]diazepino[1,7-a]indole hydrochloride

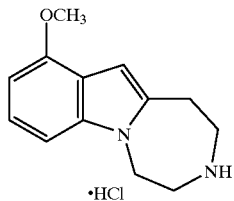

In a dry 25 mL flask 0.17 mg (1.0 mmol) of 2-methyl-3-nitroanisole is combined with 30 mg (0.97 mmol) paraformaldehyde in 7 mL of dimethylsulfoxide (sure-seal). This solution is treated with 1M Potassium t-butoxide/THF (0.20 mL) with the reaction mixture becoming bright red in color. After 2 hours the reaction mixture is diluted with water and ethyl acetate is added. The layers are separated followed by two ethyl acetate extractions. The organics are combined, washed with brine, dried over MgSO$_4$, filtered, and concentrated to give a crude yellow oil that solidifies overnight. This material is purified by LC (45% ethyl acetate/heptane) to yield 140 mg (71%) of 2-(2-methoxy-6-nitrophenyl)-1-ethanol as a pale yellow solid. $^1$H NMR (300 MHz, DMSO-d$_6$) δ2.90 (t, J=7 Hz, 2H), 3.50 (q, J=7 Hz, 2H), 3.88 (s, 3H), 4.74 (t, J=5 Hz, 1H), 7.32 (dd, J=2, 8 Hz, 1H), 7.46–7.36 (m, 2H); $^{13}$C NMR (75 MHz, CDCl$_3$) δ158.5, 127.8, 116.2, 114.2, 62.0, 56.3, 29.2; IR (drift) 1536, 1469, 1458, 1352, 1279, 1266, 1217, 1065, 1040, 1031, 1014, 895, 806, 796, 740 cm$^{-1}$.

A solution of 4.3 g of 2-(2-methoxy-6-nitrophenyl)-1-ethanol acetone (117 mL) is slowly treated with a solution of Jones Reagent (31 mL). The volatiles are removed under reduced pressure, diluted with 5M sodium hydroxide, cooled to 0° C., and treated slowly with concentrated H$_2$SO$_4$. This solution is extracted four times with ethyl acetate with the combine organics washed with brine, dried over NaSO$_4$, filtered, and concentrated. The crude material is purified by LC (10% MeOH/CH$_2$Cl$_2$) to give 3.5 g of 2-(2-methoxy-6-nitrophenyl)acetic acid as a yellow/gold solid. $^1$H NMR (300 MHz, DMSO-d$_6$) δ3.84 (s, 3H), 3.87 (s, 2H), 7.42 (d, J=7 Hz, 1H), 7.52 (t, J=8 Hz, 1H), 7.59 (dd, J=1, 8 Hz, 1H); $^{13}$C NMR (75 MHz, CDCl$_3$) δ157.9, 150.7, 127.5, 120.1, 115.3, 114.8, 56.4, 11.1; IR (drift) 3020, 2983, 2945, 2888, 2840, 1710, 1531, 1471, 1434, 1353, 1274, 1256, 1229, 1058, 799 cm$^{-1}$. HRMS (FAB) calculated for C$_9$H$_9$NO$_5$+H1 212.0559, found 212.0555.

(Chart A, Step 1): Following the general procedure of Step 1 of Example 1, and making non-critical variations but substituting 2-(2-methoxy-6-nitrophenyl)acetic acid for 2-nitrophenylacetic acid gives a crude yellow oil. This material is purified by LC (230–400 silica gel) eluting with 35% ethyl acetate/heptane to afford 1.04 g (74%) of ethyl 4-(2-methoxy-6-nitrophenyl)-3-oxobutanoate as yellow solid. IR (drift) 1746, 1714, 1523, 1466, 1366, 1352, 1317, 1306, 1268, 1229, 1196, 1069, 1053, 1033, 736 cm$^{-1}$; $^1$H NMR (300 MHz, CDCl$_3$) δ1.32 (t, J=7 Hz, 3H), 3.62 (s, 2H), 3.89 (s, 3H), 4.25 (m, 4H), 7.17 (d, J=8 Hz, 1H), 7.42 (t, J=8 Hz, 1H), 7.64 (d, J=8 Hz, 1H); $^{13}$C NMR (75 MHz, CDCl$_3$) δ198.2, 167.0, 158.4, 150.0, 128.7, 118.9, 116.8, 115.2, 61.5, 56.6, 49.3, 39.7, 14.

(Chart A, Step 2): A solution of ethyl 4-(2-methoxy-6-nitrophenyl)-3-oxobutanoate (10.6 g, 37.5 mmol) in MeOH (350 mL) is purged with N$_2$, and treated with 10% Pd/C (1.10 g) turning the yellow solution black. The suspension is treated with ammonium formate (27.4 g, 43.5 mmol) with a slight exotherm and evolution of H$_2$. After 15 minutes, the reaction mixture is filtered through a pad of celite, and concentrated. The residue is diluted with water and extracted 3 times with ethyl acetate. The combined organics are washed with brine, dried over NaSO$_4$, filtered, and concentrated to give 9.4 g of crude material which is combined with the crude material from a previous 1.5 mmol reaction. The crude material is purified by LC (25% ethyl acetate/heptane) to give 8.08 g of substituting ethyl 2-(4-methoxy-1H-indol-2-yl)acetate as an oil that solidifies overnight. IR (liq.) 3389, 1730, 1617, 1594, 1510, 1438, 1367, 1287, 1250, 1217, 1167, 1151, 1097, 1030, 767 cm$^{-1}$.

(Chart A, Step 3): Following the general procedure of Step 3 of Example 1, and making non-critical variations but substituting ethyl 2-(4-methoxy-1H-indol-2-yl)acetate for ethyl 2-(1H-indol-2-yl)acetate, gives 6.83 g of a crude product. This material is purified by LC eluting with 10% ethyl acetate/heptane to afford 4.82 g of ethyl 2-(4-methoxy-2,3-dihydro-1H-indol-2-yl)acetate as a yellow solid. IR (drift) 1727, 1614, 1602, 1493, 1469, 1323, 1296, 1276, 1259, 1235, 1192, 1168, 1148, 1095, 1027 cm$^{-1}$.

(Chart A, Step 4): Following the general procedure of Step 4 of Example 1, and making non-critical variations but substituting ethyl 2-(4-methoxy-2,3-dihydro-1H-indol-2-yl)acetate for ethyl 2-(2,3-dihydro-1H-indol-2-yl)acetate, gives 8.68 g of a crude product. This material is purified by LC to afford 6.95 g of ethyl 2-[1-(2-bromoethyl)-4-methoxy-2,3-dihydro-1H-indol-2-yl]acetate as a light yellow solid. $^{13}$C NMR (75 MHz, DMSO-d$_6$) δ171.0, 155.6, 152.1, 128.9, 113.1, 101.4, 100.3, 65.0, 60.0, 60.0, 54.9, 48.1, 32.0, 30.6, 14.0; IR (drift) 1726, 1712, 1617, 1596, 1477, 1357, 1269, 1255, 1214, 1157, 1080, 1071, 1027, 757, 704 cm$^{-1}$.

(Chart A, Step 5): Following the general procedure of Step 5 of Example 1, and making non-critical variations but substituting ethyl 2-[1-(2-bromoethyl)-4-methoxy-2,3-dihydro-1H-indol-2-yl]acetate for ethyl 2-[1-(2- bromoethyl)-2,3-dihydro-1H-indol-2-yl]acetate and isopropyl alcohol for methanol with a catalytic amount of sodium iodide, gives 3.86 g of a crude product. This material is purified by LC (biotage 90 g column) eluting with dichloromethane to 5% methanol/dichloromethane to afford 3.6 g (82%) of 10-methoxy-4,5,11,11a-tetrahydro-1H-[1,4]diazepino[1,7-a]indol-2(3H)-one as a white solid. IR (drift) 2953, 1666, 1608, 1487, 1473, 1445, 1353, 1305, 1261, 1237, 1223, 1097, 1076, 760, 709 cm$^{-1}$.

(Chart A, Step 6): Following the general procedure of Step 6 of Example 1, and making non-critical variations but substituting 10-methoxy-4,5,11,11a-tetrahydro-1H-[1,4]diazepino[1,7-a]indol-2(3H)-one for 4,5,11,11a-tetrahydro-1H-[1,4]diazepino[1,7-a]indol-2(3H)-one gives 3.03 g of a crude product. This material is purified by LC eluting with 0.5:9.5:90 NHOH$_4$/methanol/dichloromethane to give 2.46 g of 10-methoxy-2,3,4,5,11,11a-hexahydro-1H-[1,4]diazepino[1,7-a]indole as a white solid. IR (drift) 2920, 2895, 2834, 2803, 1614, 1597, 1474, 1453, 1381, 1254, 1244, 1223, 1085, 762, 758 cm$^{-1}$.

(Chart A, Step 7): Following the general procedure of Step 7 of Example 1, and making non-critical variations but substituting 10-methoxy-2,3,4,5,11,11a-hexahydro-1H-[1,4]diazepino[1,7-a]indole for 2,3,4,5,11,11a-hexahydro-1H-[1,4]diazepino[1,7-a]indole, gives 207 mg of a crude product. This material is purified by LC eluting with 0.5:4.0:95.5 NH$_4$OH/methanol/dichloromethane to afford 157 mg of an orange oil. This material is dissolved in ethyl acetate and treated with a solution of 2M hydrochloric acid in methanol to afford 167 mg of 10-methoxy-2,3,4,5-tetrahydro-1H-[1,4]diazepino[1,7-a]indole hydrochloride as a white solid. $^1$H NMR (DMSO-d$_6$) δ3.27 (s, 6H), 3.85 (s, 3H), 4.55 (m, 2H), 6.34 (s, 1H), 6.52 (dd, 1H), 7.04 (m, 2H), 9.65 (br s, 2H); $^{13}$C NMR (DMSO-d$_6$) δ152.3, 138.0, 137.5, 121.7, 117.3, 102.8, 99.6, 97.6, 55.0, 46.7, 45.5, 40.7, 24.4; IR (drift) 2961, 2944, 2832, 2783, 2747, 2732, 2689, 2660, 1584, 1499, 1467, 1355, 1257, 762, 730 cm$^{-1}$.

EXAMPLE 4
2,3,4,5-tetrahydro-1H-[1,4]diazepino[1,7-a]indole-11-carbaldehyde

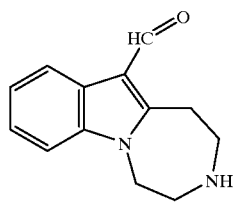

A solution of DMF (10 mL) cooled to 0° C. is treated with phosphorus oxychloride (0.30 mL, 3.3 mmol) and stirred for 10 min. This clear colorless solution of the cloroiminium salt is slowly treated with a solution of tert-butyl 1,2,4,5-tetrahydro-3H-[1,4]diazepino[1,7-a]indole-3-carboxylate in DMF (9 mL) followed by warming to rt. After 18 hr, the reaction is quenched with 5N sodium hydroxide (40 mL), stirred 5 min, and extracted twice with dichloromethane (40 mL). The combined organics are washed twice with water (25 mL), once with brine (25 mL), dried over MgSO$_4$, filtered, and concentrated to give 942 mg of a crude yellow solid. This material is purified by LC (biotage 40 g column) eluting with 35% ethyl acetate/heptane to afford 677 mg of tert-butyl 11-formyl-1,2,4,5-tetrahydro-3H-[1,4]diazepino[1,7-a]indole-3-carboxylate as a pale yellow solid, mp 167–168° C. IR (drift) 1684, 1654, 1469, 1424, 1396, 1370, 1350, 1304, 1248, 1197, 1170, 1121, 762, 757, 752 cm$^{-1}$.

A suspension of tert-butyl 11-formyl-1,2,4,5-tetrahydro-3H-[1,4]diazepino[1,7-a]indole-3-carboxylate (225 mg, 0.72 mmol) in methanol (5 mL) is cooled to 0° C. and treated with a solution of saturated hydrochloric acid in methanol (3 mL). After 15 min, the yellow homogenous solution is treated with an additional portion of the hydrochloric acid solution and warmed to rt. After 1 hr, the reaction is concentrated under reduced pressure, diluted with 2M sodium hydroxide (15 mL), and extracted twice with dichloromethane (20 mL). The combined organics are washed once with brine (20 mL), dried over MgSO$_4$, filtered, and concentrated to give 165 mg of a crude solid. This material is purified by LC (230–400) silica gel eluting with 10% methanol/dichloromethane to afford 118 mg of 2,3,4,5-tetrahydro-1H-[1,4]diazepino[1,7-a]indole-11-carbaldehyde as an off-white solid. This material is recrystallized form ethyl acetate/heptane to give a light yellow solid, mp 167–168° C. IR (drift) 3307, 2941, 1636, 1464, 1429, 1391, 1367, 1350, 1269, 1205, 1124, 1052, 775, 750, 731 cm$^{-1}$.

EXAMPLE 5
2-oxo-2-(2,3,4,5-tetrahydro-1H-[1,4]diazepino[1,7-a]indol-11-yl)acetamide

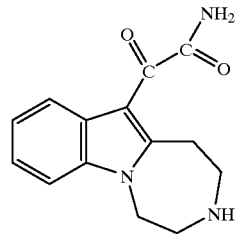

A solution of tert-butyl 1,2,4,5-tetrahydro-3H-[1,4]diazepino[1,7-a]indole-3-carboxylate (286 mg, 1 mmol) in dichloromethane (20 mL) is cooled to 0° C. and treated with oxalyl chloride (0.17 mL, 2.0 mmol) instantly turning a golden color. After 1 hr, the reaction mixture is treated with a 2M solution of ammonia in ethanol (4 mL) with the formation of a white percipitate. After 30 min, the reaction mixture is diluted with dichloromethane (15 mL) and washed once with saturated sodium bicarbonate (25 mL), once with water (20 mL), once with brine (20 mL), dried over MgSO$_4$, filtered, and concentrated to give 389 mg of a yellow solid. This material is purified by LC (230–400) silica gel eluting with 60% ethyl acetate/heptane to afford 294 mg of an off-white solid. This material is dissolved in methanol (5 mL), cooled to 0° C., and treated with a saturated solution of hydrochloric acid in methanol (5 mL). After 3 hrs, the volatiles are removed under reduced pressure, diluted with 5M sodium hydroxide (15 mL), and extracted twice with a 1:1 solution of THF/ethyl acetate (20 mL). The combined organics are dried over MgSO$_4$, filtered, and concentrated to give a yellow solid. This material is recrystallized from methanol/ethyl acetate to afford 100 mg of 2-oxo-2-(2,3,4,5-tetrahydro-1H-[1,4]diazepino[1,7-a]indol-11-yl)acetamide as a white solid, mp 214–215° C. IR (drift) 3363, 1680, 1619, 1588, 1512, 1465, 1407, 1356, 1347, 1335, 1186, 1077, 750, 672, 629 cm$^{-1}$; MS (FAB) m/z 258 (MH$^+$).

EXAMPLE 6

2,2,2-trifluoro-1-(2,3,4,5-tetrahydro-1H-[1,4]diazepino[1,7-a]indol-11-yl)-1-ethanone

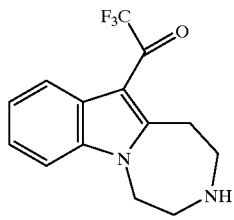

A solution of tert-butyl 11-formyl-1,2,4,5-tetrahydro-3H-[1,4]diazepino[1,7-a]indole-3-carboxylate (286 mg, 1 mmol) in DMF (10 mL) is treated with trifluoroacetic anhydride (0.17 mL, 1.2 mmol). After 24 hrs, a second portion of the anhydride is added with the reaction becoming a darker color. After an additional 18 hrs, the reaction is concentrated under reduced pressure, diluted with water (15 mL), and extracted twice with dichloromethane (15 mL). The combined organics are washed once with saturated sodium bicarbonate (15 mL), once with water (15 mL), once with brine (20 mL), dried over MgSO$_4$, filtered, and concentrated to give 352 mg of a crude solid. This material is purified by LC (230–400) silica gel eluting with 25% ethyl acetate/heptane to afford 315 mg (82%) of a rose colored solid. This material is dissolved in methanol (5 mL), cooled to 0° C., and treated with a saturated solution of hydrochloric acid in methanol (3 mL). After 30 min, the volatiles are removed under reduced pressure, diluted with ethyl acetate (30 mL), washed twice with saturated sodium bicarbonate, dried over MgSO$_4$, filtered, and concentrated to give 232 mg of a crude solid. This material is purified by LC (230–400) silica gel eluting with 10% methanol/dichloromethane to afford 202 mg (87%) of 2,2,2-trifluoro-1-(2,3,4,5-tetrahydro-1H-[1,4]diazepino[1,7-a]indol-11-yl)-1-ethanone as a light yellow solid, mp 131–133° C. IR (drift) 1654, 1504, 1486, 1467, 1428, 1279, 1245, 1212, 1198, 1178, 1134, 1061, 936, 746, 739 cm$^{-1}$.

EXAMPLE 7

11-methyl-2,3,4,5-tetrahydro-1H-[1,4]diazepino[1,7-a]indole hydrochloride

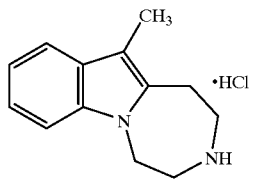

A solution of 2,3,4,5-tetrahydro-1H-[1,4]diazepino[1,7-a]indole-11-carbaldehyde (208 mg, 0.97 mmol) in THF (5 mL) is treated with a 1M solution of lithium aluminum hydride in THF (5 mL, 5 mmol) with instant gas evolution. After 18 hrs at rt, the reaction is heated to reflux for an additional hour, cooled to rt, and quenched by the successive addition of water (0.19 mL), 5M sodium hydroxide (0.17 mL), and water (0.66 mL). The resulting gelatinous solution is diluted with ethyl acetate (25 mL), filtered through a pad of celite, and concentrated to give 185 mg of a yellow oil. This material is purified by LC (230–400) silica gel eluting with 10% methanol/dichloromethane to afford 92 mg of a pink solid. This material is dissolved in a mixture of ethyl acetate/methanol and treated with a solution of hydrochloric acid in methanol to produce a pink solid. The resulting solid is triturated with diethyl ether/ethyl acetate to give 11-methyl-2,3,4,5-tetrahydro-1H-[1,4]diazepino[1,7-a]indole hydrochloride as a light rose solid. IR (drift) 2974, 2954, 2864, 2825, 2749, 2680, 2656, 2444, 1581, 1469, 1425, 1378, 1331, 1186, 738 cm$^{-1}$.

EXAMPLE 8

11-chloro-2,3,4,5-tetrahydro-1H-[1,4]diazepino[1,7-a]indole hydrochloride

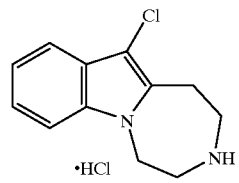

A solution of tert-butyl 11-formyl-1,2,4,5-tetrahydro-3H-[1,4]diazepino[1,7-a]indole-3-carboxylate (286 mg, 1 mmol) in THF (10 mL) is cooled to 0° C. and slowly treated with a solution of N-chlorosuccinimide (134 mg, 1.0 mmol) in THF (10 mL). The resulting florescent yellow solution is warmed to rt. After 18 hrs, the now green reaction mixture is concentrated under reduced pressure, diluted with water (20 mL) and brine (5 mL), and extracted twice with ethyl acetate (20 mL). The combined organics are washed once with brine (20 mL), dried over MgSO$_4$, filtered, and concentrated to give 361 mg of a crude oil. This material is purified by LC (230–400) silica gel eluting with 10% ethyl acetate/heptane to afford 277 mg of a white solid. This material is dissolved in methanol (5 mL), cooled to 0° C., and treated with a saturated solution of hydrochloric acid in methanol (5 mL). After 15 min, the reaction mixture is warmed to rt for an addition 1 hour, followed by removal of the volatiles under reduced pressure to give a white solid. This material is recrystallized from methanol/ethyl acetate to afford 135 mg of 11-chloro-2,3,4,5-tetrahydro-1H-[1,4]diazepino[1,7-a]indole hydrochloride as an off-white solid, mp >250° C. IR (drift) 2982, 2933, 2908, 2888, 2816, 2775, 2719, 2652, 2627, 2564, 2429, 1580, 1462, 1323, 744 cm$^{-1}$.

EXAMPLE 9

2,3,4,5-tetrahydro-1H-[1,4]diazepino[1,7-a]indole-11-carbonitrile

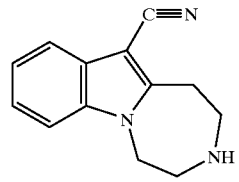

A solution of tert-butyl 11-formyl-1,2,4,5-tetrahydro-3H-[1,4]diazepino[1,7-a]indole-3-carboxylate in formic acid (1 mL) is treated with hydroxylamine hydrochloride (90 mg, 1.3 mmol) and heated to reflux. After 18 hrs, the reaction mixture is cooled to rt, quenched with 1M sodium hydroxide (15 mL), and extracted twice with ethyl acetate (20 mL). The combined organics are washed once with brine (20 mL), dried over MgSO$_4$, filtered, and concentrated to give 224 mg of a crude solid. This material is purified by LC (230–400) silica gel eluting with 5% methanol/dichloromethane to afford 123 mg of 2,3,4,5-tetrahydro-1H-[1,4]diazepino[1,7- a]indole-11-carbonitrile as a red solid, mp 161–164° C. IR (drift) 3313, 2935, 2906, 2203, 1539, 1463, 1421, 1351, 1328, 1272, 1208, 1185, 822, 769, 752 cm$^{-1}$.

EXAMPLE 10

8-bromo-2,3,4,5-tetrahydro-1H-[1,4]diazepino[1,7-a]indole-11-carbaldehyde

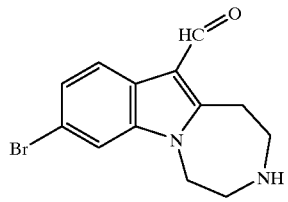

A solution of 8-bromo-2,3,4,5-tetrahydro-1H-[1,4]diazepino[1,7-a]indole in dichloromethane (6 mL) is successively treated with pyridine (0.13 mL, 1.6 mmol) and trifluoroacetic acid anhydride (0.23 mL, 1.6 mmol). After 3 hrs, the resulting black solution is diluted with additional dichloromethane (20 mL) and washed twice with saturated copper sulfate (10 mL), once with water (10 mL), once with brine (10 mL), dried over MgSO$_4$, filtered, and concentrated to give 374 mg of a crude solid. This material is purified by LC (230–400) silica gel eluting with 15% ethyl acetate/heptane to afford 228 mg of 1-(8-bromo-1,2,4,5-tetrahydro-3H-[1,4]diazepino[1,7-a]indol-3-yl)-2,2,2-trifluoro-1-ethanone as a white solid and 109 mg of 1-[8-bromo-11-(2,2,2-trifluoroacetyl)-1,2,4,5-tetrahydro-3H-[1,4]diazepino[1,7-a]indol-3-yl]-2,2,2-trifluoro-1-ethanone as a white solid. Data for 1-(8-bromo-1,2,4,5-tetrahydro-3H-[1,4]diazepino[1,7-a]indol-3-yl)-2,2,2-trifluoro-1-ethanone: $^1$H NMR (300 MHz, CDCl$_3$) δ7.42 (d, J=10 Hz, 2H), 7.22 (dd, J=2, 8 Hz, 1H), 6.34 (d, J=2 Hz, 1H), 4.29 (m, 2H), 3.90 (m, 4H), 3.15 (m, 2H). Data for 1-[8-bromo-11-(2,2,2-trifluoroacetyl)-1,2,4,5-tetrahydro-3H-[1,4]diazepino[1,7-a]indol-3-yl]-2,2,2-trifluoro-1-ethanone: $^1$H NMR (300 MHz, DMSO-d$_6$) δ8.06 (d, J=17 Hz, 1H), 7.79 (d, J=9 Hz, 1H), 7.49 (d, J=9 Hz, 1H), 4.72 (m, 2H), 3.87 (m, 4H), 3.73 (m, 2H).

Following the general procedure of Example 4, and making non-critical variations but substituting 1-(8-bromo-1,2,4,5-tetrahydro-3H-[1,4]diazepino[1,7-a]indol-3-yl)-2,2,2-trifluoro-1-ethanone for tert-butyl 1,2,4,5-tetrahydro-3H-[1,4]diazepino[1,7-a]indole-3-carboxylate, gives 182 mg of a crude solid. This material is purified by LC (230–400 silica gel) eluting with 7% methanol/dichloromethane to afford 130 mg of a tan solid. This solid is recrystallized from methanol/ethyl acetate to give 46 mg of 8-bromo-2,3,4,5-tetrahydro-1H-[1,4]diazepino[1,7-a]indole-11-carbaldehyde as an off-white solid, mp 186–188° C. IR (drift) 1646, 1531, 1468, 1455, 1424, 1391, 1333, 1046, 1037, 954, 862, 837, 820, 753, 738 cm$^{-1}$.

EXAMPLE 11

1-(8-bromo-2,3,4,5-tetrahydro-1H-[1,4]diazepino[1,7-a]indol-11-yl)-2,2,2-trifluoro-1-ethanone

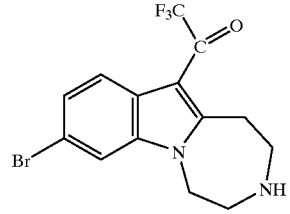

A solution of 1-[8-bromo-11-(2,2,2-trifluoroacetyl)-1,2,4,5-tetrahydro-3H-[1,4]diazepino[1,7-a]indol-3-yl]-2,2,2-trifluoro-1-ethanone (105 mg, 0.23 mmol) in methanol (3 mL) is treated with 1M sodium hydroxide (1 mL, 1 mmol). After 30 min, the reaction is diluted with water (15 mL) and extracted twice with dichloromethane (20 mL). The combined organics are washed with brine (15 mL), dried over MgSO$_4$, filtered, and concentrated to give a crude solid. This material is recrystallized from ethyl acetate/heptane to afford 48 mg of a white solid. IR (drift) 1666, 1508, 1464, 1426, 1282, 1248, 1211, 1201, 1181, 1130, 1060, 1043, 956, 939, 757 cm$^{-1}$.

EXAMPLE 12

2,3,4,5-tetrahydro-1H-[1,4]diazepino[1,7-a]indole-11-carboxamide

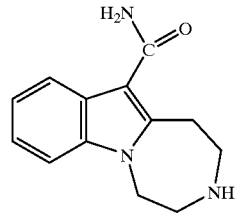

A solution of 2,2,2-trifluoro-1-(1,2,4,5-tetrahydro-3H-[1,4]diazepino[1,7-a]indol-3-yl)-1-ethanone (448 mg, 1.6 mmol) in dichloromethane (20 mL) is treated with chlorosulfonyl isocyanate (0.19 mL, 2.1 mmol). The resulting golden homogenous solution is stirred for 1 hour and treated with methanol (10 mL) and a solution of 25% sodium methoxide in methanol (2 mL, 8.8 mmol). The reaction mixture quickly turns to a white suspension and after 30 min is filtered to give a crude white solid. This material is triturated with hot methanol, filtered through a pad of celite, and concentrated to 184 mg of a white solid that is further purified by LC (230–400 silica gel) eluting with 9:1:89 methanol/NH$_4$OH/dichloromethane to afford 137 mg of 2,3,4,5-tetrahydro-1H-[1,4]diazepino[1,7-a]indole-11-carboxamide as a white solid. IR (drift) 3353, 3341, 3173, 1641, 1602, 1549, 1463, 1432, 1418, 1322, 1314, 778, 740, 729, 654 cm$^{-1}$.

EXAMPLE 13
1-(2,3,4,5-tetrahydro-1H-[1,4]diazepino[1,7-a]indol-11-yl)-1-ethanone hydrochloride

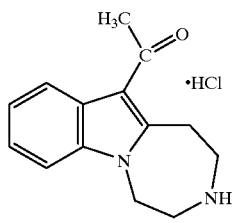

A solution of dimethylacetamide (0.12 mL, 1.3 mmol) in chloroform (2 mL) is cooled to 0° C. and treated with phosphorus oxychloride (0.12 mL, 1.3 mmol) with no observable change. The solution is warmed to rt over 10 min, treated with a solution of 2,2,2-trifluoro-1-(1,2,4,5-tetrahydro-3H-[1,4]diazepino[1,7-a]indol-3-yl)-1-ethanone (120 mg, 0.43 mmol) in chloroform (2 mL), and heated to reflux. After 18 hrs, the reaction mixture is cooled to rt, quenched with 5N sodium hydroxide (20 mL), methanol (10 mL), and reheated to 60° C. for 30 min. At this time, the reaction is cooled to rt, volatiles removed under reduced pressure, and extracted twice with dichloromethane (20 mL). The combined organics are washed with brine (20 mL), dried over MgSO$_4$, filtered, and concentrated to give a crude solid. This material is purified by LC (230–400 silica gel) eluting with 3:0.5:96.5 methanol:NH$_4$OH:dichloromethane to afford 25 mg of an off-white solid. This solid is dissolved in ethyl acetate (10 mL) and treated with 2M hydrochloric acid in methanol (0.2 mL) to afford 1-(2,3,4,5-tetrahydro-1H-[1,4]diazepino[1,7-a]indol-11-yl)-1-ethanone hydrochloride as a light golden solid. IR (drift) 2971, 2805, 2771, 2751, 2729, 2689, 1646, 1521, 1466, 1421, 1352, 1341, 1210, 966, 742 cm$^{-1}$.

EXAMPLE 14
3-methyl-2,3,4,5-tetrahydro-1H-[1,4]diazepino[1,7-a]indole

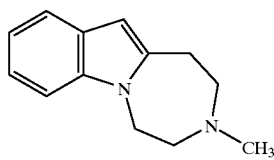

A solution of 2,3,4,5-tetrahydro-1H-[1,4]diazepino[1,7-a]indole (372 mg, 2.0 mmol) in methanol (25 mL) is treated with a solution of 37% aqueous formaldehyde (24 mmol, 2.0 mL). The resulting clear solution is treated with a single portion of sodium cyanoborohydride (251 mg, 4.0 mmol) turning slightly a lighter yellow color. After 40 min, the reaction is quenched with 1M hydrochloric acid (15 mL), stirred over 10 min, basified to pH 13, volatiles removed under reduced pressure, and extracted twice with ethyl acetate (25 mL). The combined organics are washed with brine (20 mL), dried over MgSO$_4$, filtered, and concentrated to give a crude oil. This material is purified by LC (230–400 silica gel) eluting with 70% acetone/heptane to afford 234 mg (58%) of 3-methyl-2,3,4,5-tetrahydro-1H-[1,4]diazepino[1,7-a]indole as a white solid, mp 59–60° C. IR (drift) 2924, 2781, 2758, 2741, 1458, 1413, 1377, 1339, 1326, 1315, 1290, 1133, 1003, 799, 737 cm$^{-1}$. MS (EI) m/z 200 (M$^+$).

EXAMPLE 15
3-ethyl-2,3,4,5-tetrahydro-1H-[1,4]diazepino[1,7-a]indole

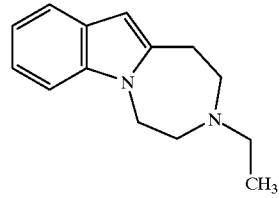

A solution of 2,3,4,5-tetrahydro-1H-[1,4]diazepino[1,7-a]indole (280 mg, 1.5 mmol) in acetonitrile (15 mL) is treated with powdered potassium carbonate (622 mg, 4.5 mmol) and bromoethane (0.12 mL, 1.65 mmol, filtered through a pad of celite). The resulting milky suspenesion is heated to 40° C. After 22 hrs, the volatiles are removed under reduced pressure, diluted with water (20 mL), and extracted twice with ethyl acetate (20 mL). The combined organics are washed with brine (20 mL), dried over MgSO$_4$, filtered, and concentrated to give a crude oil. This material is purified by LC (230–400 silica gel) eluting with 5% methanol/dichloromethane to afford 226 mg of 3-ethyl-2,3,4,5-tetrahydro-1H-[1,4]diazepino[1,7-a]indole as a white solid, mp 44–46° C. IR (drift) 2931, 2808, 1466, 1413, 1373, 1348, 1323, 1315, 1243, 1132, 1104, 776, 749, 732, 688 cm$^{-1}$.

EXAMPLE 16
3-propyl-2,3,4,5-tetrahydro-1H-[1,4]diazepino[1,7-a]indole hydrochloride

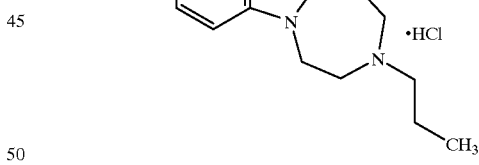

Following the general procedure of Example 15, and making non-critical variations but substituting 1-iodopropane (0.18 mL, 1.8 mmol), gives 421 mg of a crude oil. This material is purified by LC (230–400 silica gel) eluting with 14:1:85 acetone:triethyl amine:heptane to afford 236 mg (69%) of a colorless oil. This material is dissolved in ethyl acetate and treated with 2M hydrochloric acid in methanol (0.75 mL) with immediate formation of a white solid that is collected by filtration and dried to give 3-propyl-2,3,4,5-tetrahydro-1H-[1,4]diazepino[1,7-a]indole hydrochloride as a white solid, mp 257–259° C. IR (drift) 2629, 2603, 2592, 2581, 2535, 2500, 2487, 1463, 1419, 1334, 1318, 920, 785, 749, 736 cm$^{-1}$; MS (EI) m/z 228 (M$^+$).

EXAMPLE 17

3-benzyl-2,3,4,5-tetrahydro-1H-[1,4]diazepino[1,7-a]indole

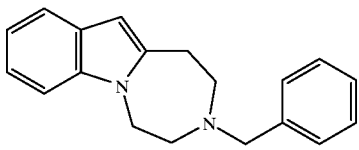

Following the general procedure of Example 15, and making non-critical variations but substituting benzyl chloride (0.38 mL, 3.3 mmol), gives 850 mg of a crude oil. This material is purified by LC (230–400 silica gel) eluting with 15% ethyl acetate/heptane to afford 724 mg of 3-benzyl-2,3,4,5-tetrahydro-1H-[1,4]diazepino[1,7-a]indole as an ivory solid. IR (drift) 2932, 2807, 1460, 1451, 1408, 1365, 1349, 1325, 1317, 1197, 1138, 1027, 789, 736, 699 cm$^{-1}$.

EXAMPLE 18

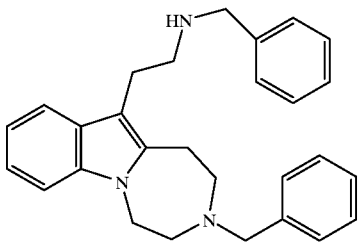

A solution of 2-(3-benzyl-2,3,4,5-tetrahydro-1H-[1,4]diazepino[1,7-a]indol-11-yl)-1-ethanol (320 mg, 1.0 mmol) in dichloromethane (10 mL) is cooled to 0° C., treated with methanesulfonyl chloride (93 µL, 1.2 mmol), and triethylamine (0.21 mL, 1.5 mmol). After 30 min, the yellow solution is diluted with additional dichloromethane (15 mL) and washed once with water (15 mL), once with brine (15 mL), dried over MgSO$_4$, filtered, and concentrated to give a yellow oil. This crude material is diluted with acetonitrile (10 mL) and treated with benzylamine (0.33 mL, 3.0 mmol), and powdered potassium carbonate (415 mg, 3.0 mmol) followed by heating to reflux. After 18 hrs, the yellow suspension is cooled to rt, concentrated, diluted with water (15 mL), and extracted twice with dichloromethane (20 mL). The combined organics are washed with brine (20 mL), dried over MgSO$_4$, filtered, and concentrated to give a crude oil. This material is purified by LC (230–400 silica gel) eluting with 4:0.5:95.5 methanol/NH$_4$OH/dichloromethane to afford 220 mg of N-benzyl-2-(3-benzyl-2,3,4,5-tetrahydro-1H-[1,4]diazepino[1,7-a]indol-11-yl)-1-ethanamine as a yellow oil. IR (liq.) 3025, 2913, 2811, 1494, 1478, 1469, 1453, 1427, 1372, 1363, 1347, 1324, 1120, 733, 698 cm$^{-1}$; MS (EI) m/z 409 (M$^+$).

EXAMPLE 19

2-(2,3,4,5-tetrahydro-1H-[1,4]diazepino[1,7-a]indol-11-yl)-1-ethanamine

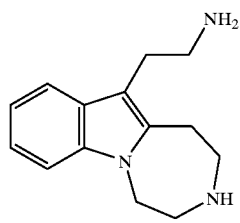

Method 1

A solution of N-benzyl-2-(3-benzyl-2,3,4,5-tetrahydro-1H-[1,4]diazepino[1,7-a]indol-11-yl)-1-ethanamine (195 mg, 0.48 mmol) in methanol (10 mL) is treated with 10% palladium on carbon (40 mg) and ammonium formate (210 mg, 3.3 mmol) followed by heating to reflux. After 18 hrs, the reaction is cooled to rt, filtered through celite, and concentrated to give a crude yellow oil. This material is purified by LC (230–400 silica gel) eluting with 20:2.5:77.5 methanol/ammonuim hydroxide/dichloromethane to afford 51 mg (47%) of 2-(2,3,4,5-tetrahydro-1H-[1,4]diazepino[1,7-a]indol-11-yl)-1-ethanamine as a colorless oil that solidified, mp 77–80° C. MS (EI) m/z 229 (M$^+$); % Water (KF): 0.94; Anal. Calculated for C$_{14}$H$_{19}$N$_3$.0.94 H$_2$O: C, 72.64; H, 8.38; N, 18.15. Found: C, 72.66; H, 8.32; N, 18.03.

Method 2

A solution of 11-[(E)-2-nitroethenyl]-2,3,4,5-tetrahydro-1H-[1,4]diazepino[1,7-a]indole (236 mg, 0.92 mmol) in THF (9 mL) is cooled to 0° C. and treated with lithium aluminum hydride (1M THF, 2.8 mL, 2.8 mmol) with gas evolution. The reaction is heated to reflux for 4 hrs followed by cooling to rt for 16 hrs. At this time, the reaction mixture is quenched by the successive addition of 0.11 mL water, 0.10 mL 5N NaOH, and 0.37 mL water. The resulting thick gelatinous suspension is diluted with dichloromethane (30 mL), filtered through celite, and concentrated to give a crude oil. This material is purified by LC (230–400 silica gel) eluting with 20:2.5:77.5 methanol/ammonuim hydroxide/dichloromethane to afford 92 mg of 2-(2,3,4,5-tetrahydro-1H-[1,4]diazepino[1,7-a]indol-11-yl)-1-ethanamine as a yellow syrup. IR (liq.) 3353, 3307, 3087, 3048, 3025, 2935, 2844, 1469, 1426, 1373, 1340, 1324, 1181, 1015, 742 cm$^{-1}$; MS (FAB) m/z 230 (MH$^+$).

EXAMPLE 20

N-(4-methoxyphenyl)-2-oxo-2-(2,3,4,5-tetrahydro-1H-[1,4]diazepino[1,7-a]indol-11-yl)acetamide

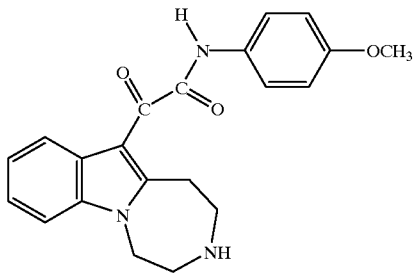

(Chart B, Step 1): A solution 3-(trifluoroacetyl)-2,3,4,5-tetrahydro-1H-[1,4]diazepino[1,7-a]indole in dichloromethane (20 mL) is cooled to 0° C. and treated with oxalylchloride (0.17 mL, 2.0 mmol) instantly becoming a yellow color. After 40 min, the reaction mixture is warmed to rt and volatiles are removed under reduced pressure. The resulting solid is diluted with toluene (20 mL) and dichloromethane (5 mL) and treated with the 4-methoxy aniline (160 mg, 1.3 mmol) and triethylamine (0.42 mL, 3.0 mmol) with immediate smoke/haze forming. After 18 hrs, the reaction mixture is concentrated, diluted with methanol (10 mL) and THF (10 mL) and treated with 1N sodium hydroxide (10 mL). After 15 min, reaction mixture is concentrated, diluted with 1N sodium hydroxide (20 mL), and extracted twice with dichloromethane (25 mL). The combined organics are washed with brine (25 mL), dried over MgSO$_4$, filtered, and concentrated to give a crude solid. This material is purified by LC (230–400 silica gel) eluting with 10% methanol/dichloromethane to afford 359 mg of N-(4-methoxyphenyl)-2-oxo-2-(2,3,4,5-tetrahydro-1H-[1,4]diazepino[1,7-a]indol-11-yl)acetamide as a light yellow solid, mp 177–180° C. IR (drift) 1670, 1621, 1559, 1507, 1465, 1416, 1333, 1264, 1242, 1221, 1211, 1073, 838, 789, 762 cm$^{-1}$; OAMS supporting ions at: ESI+364.1.

EXAMPLE 21
N-(2,4-difluorophenyl)-2-oxo-2-(2,3,4,5-tetrahydro-1H-[1,4]diazepino[1,7-a]indol-11yl)acetamide

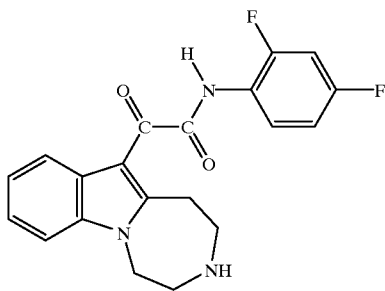

Following the general procedure of Example 20 (Chart B, Step 1), and making non-critical variations but substituting 2,4-difluoroaniline (327 mg, 2.5 mmol), gives 684 mg of a crude solid. This material is recrystallized from methanol/ethyl acetate to afford 597 mg of N-(2,4-difluorophenyl)-2-oxo-2-(2,3,4,5-tetrahydro-1H-[1,4]diazepino[1,7-a]indol-11-yl)acetamide as a white solid, mp 184.5–185.5° C. IR (drift) 1674, 1618, 1566, 1507, 1459, 1423, 1331, 1205, 1099, 1065, 962, 849, 822, 762, 747 cm$^{-1}$.

EXAMPLE 22
N-(3-chloro-4-methoxyphenyl)-2-oxo-2-(2,3,4,5-tetrahydro-1H-[1,4]diazepino[1,7-a]indol-11-yl)acetamide

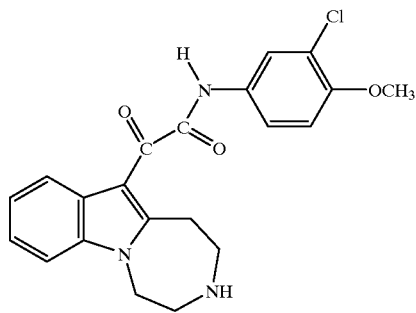

Following the general procedure of Example 20 (Chart B, Step 1), and making non-critical variations but substituting 3-chloro-p-anisidine (399 mg, 2.5 mmol), gives 846 mg of a crude solid. This material is triturated with hot methanol/ethyl acetate to afford 634 mg of N-(3-chloro-4-methoxyphenyl)-2-oxo-2-(2,3,4,5-tetrahydro-1H-[1,4]diazepino[1,7-a]indol-11-yl)acetamide as a tan powder, mp 221–223° C. IR (drift) 1666, 1605, 1499, 1462, 1423, 1309, 1284, 1276, 1249, 1213, 1073, 1058, 837, 802, 753 cm$^{-1}$.

EXAMPLE 23

2-oxo-N-phenyl-2-(2,3,4,5-tetrahydro-1H-[1,4]diazepino[1,7-a]indol-11-yl)acetamide

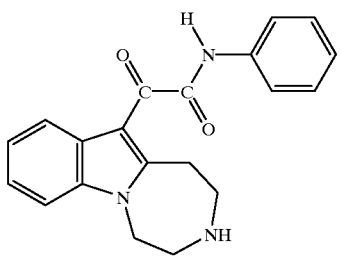

Following the general procedure of Example 20 (Chart B, Step 1), and making non-critical variations but substituting aniline (0.23 mL, 2.5 mmol), gives 684 mg of a crude solid. This material is purified by LC (biotage 400 g column) eluting with 8% methanol/dichloromethane to afford 603 mg of a yellow foam that is recrystallized from ethyl acetate/heptane to afford 2-oxo-N-phenyl-2-(2,3,4,5-tetrahydro-1H-[1,4]diazepino[1,7-a]indol-11-yl)acetamide as a light yellow solid, mp 157–160° C. IR (drift) 1675, 1620, 1611, 1600, 1559, 1509, 1463, 1444, 1420, 1325, 824, 770, 755, 743, 691 cm$^{-1}$.

EXAMPLE 24

N-(2-naphthyl)-2-oxo-2-(2,3,4,5-tetrahydro-1H-[1,4]diazepino[1,7-a]indol-11-yl)acetamide

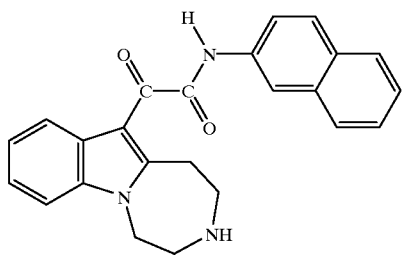

Following the general procedure of Example 20 (Chart B, Step 1), and making non-critical variations but substituting 2-aminonaphthalene (341 mg, 2.4 mmol), gives 940 mg of a crude solid. This material is recrystallized from ethyl acetate/heptane to afford 647 mg of as an off-white powder. IR (drift) 1667, 1620, 1591, 1570, 1521, 1463, 1421, 1356, 1348, 1266, 1075, 856, 804, 758, 743 cm$^{-1}$; OAMS supporting ions at: ESI+384.0.

EXAMPLE 25

N-(4-methoxyphenyl)-2-(2,3,4,5-tetrahydro-1H-[1,4]diazepino[1,7-a]indol-11-yl)acetamide

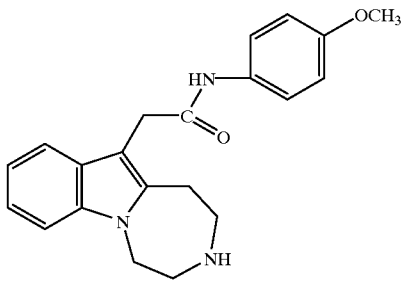

(Chart C, Step 1): A solution of N-(4-methoxyphenyl)-2-oxo-2-(2,3,4,5-tetrahydro-1H-[1,4]diazepino[1,7-a]indol-11-yl)acetamide (355 mg, 0.98 mmol) in 1,2-dichloroethane (20 mL) is treated with TFA (2.5 mL) and triethylsilane (2.5 mL). The resulting clear golden solution is heated to reflux. After 18 hrs, the reaction is cooled to rt, washed twice with saturated sodium bicarbonate (50 mL), once with brine (50 mL), dried over MgSO$_4$, filtered, and concentrated to give a golden oil. This material is purified by LC (230–400 silica gel) eluting with 5:0.5:94.5 methanol/NH$_4$OH/dichloromethane to afford 275 mg of N-(4-methoxyphenyl)-2-(2,3,4,5-tetrahydro-1H-[1,4]diazepino[1,7-a]indol-11-yl)acetamide as a white foam. IR (drift) 1662, 1602, 1535, 1512, 1467, 1411, 1372, 1358, 1323, 1297, 1243, 1180, 1032, 830, 740 cm$^{-1}$; OAMS supporting ions at: ESI+350.2.

EXAMPLE 26

N-(2,4-difluorophenyl)-2-(2,3,4,5-tetrahydro-1H-[1,4]diazepino[1,7-a]indol-11-yl)acetamide

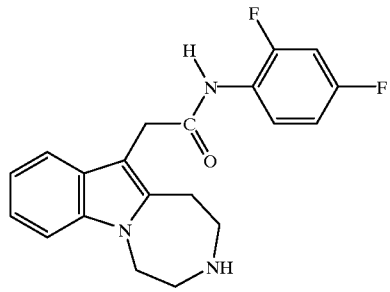

Following the general procedure of Example 25 (Chart C, Step 1), and making non-critical variations but substituting N-(2,4-difluorophenyl)-2-oxo-2-(2,3,4,5-tetrahydro-1H-[1,4]diazepino[1,7-a]indol-11-yl)acetamide (374 mg, 1.0 mmol), gives a crude oil. This material is purified by LC (230–400 silica gel) eluting with 5:0.5:94.5 methanol/NH$_4$OH/dichloromethane to afford 326 mg of N-(2,4-difluorophenyl)-2-(2,3,4,5-tetrahydro-1H-[1,4]diazepino[1,7-a]indol-11-yl)acetamide as a white foam. IR (drift) 1686, 1680, 1610, 1525, 1517, 1467, 1429, 1372, 1360, 1258, 1140, 1096, 969, 848, 741 cm$^{-1}$; OAMS supporting ions at: ESI+ 356.1; MS (FAB) m/z 356 (MH$^+$); HRMS (FAB) calculated for C$_{20}$H$_{19}$F$_2$N$_3$O+H$_1$ 356.1574.

EXAMPLE 27

N-phenyl-2-(2,3,4,5-tetrahydro-1H-[1,4]diazepino[1,7-a]indol-11-yl)acetamide

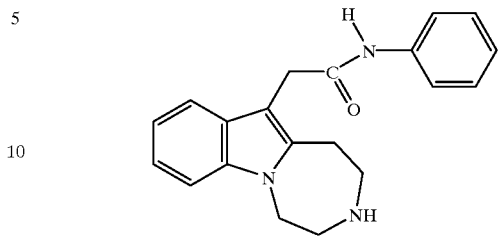

Following the general procedure of Example 25 (Chart C, Step 1), and making non-critical variations but substituting 2-oxo-N-phenyl-2-(2,3,4,5-tetrahydro-1H-[1,4]diazepino[1,7-a]indol-11-yl)acetamide (329 mg, 1.0 mmol), gives a crude oil. This material is purified by LC (230–400 silica gel) eluting with 5:0.5:94.5 methanol/NH$_4$OH/dichloromethane to afford 226 mg of N-phenyl-2-(2,3,4,5-tetrahydro-1H-[1,4]diazepino[1,7-a]indol-11-yl)acetamide as a white foam. IR (drift) 1663, 1598, 1537, 1525, 1498, 1467, 1440, 1372, 1359, 1343, 1323, 1181, 754, 740, 694 cm$^{-1}$; OAMS supporting ions at: ESI+ 320.2.

EXAMPLE 28

4-methoxy-N-[2-(2,3,4,5-tetrahydro-1H-[1,4]diazepino[1,7-a]indol-11-yl)ethyl]aniline dihydrochloride

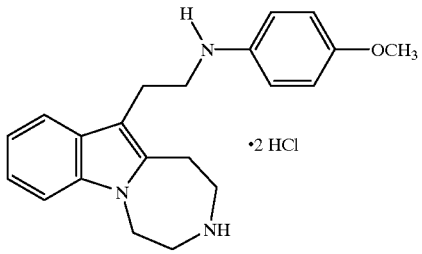

A solution of 1M lithium aluminum hydride (7 mL, 7 mmol) and THF (14 mL) is cooled to 0° C. and portion-wise treated with aluminum trichloride (317 mg, 2.4 mmol) with gas evolution. The resulting colorless solution with a small amount of precipitate is drop-wise treated with a solution of N-(4-methoxyphenyl)-2-oxo-2-(2,3,4,5-tetrahydro-1H-[1,4]diazepino[1,7-a]indol-11-yl)acetamide (433 mg, 1.19 mmol) in THF (10 mL) with additional gas evolution. The resulting yellow suspension is warmed to rt for 20 hr followed by heating to 50° C. for 8 hours. At this time, the reaction is quenched by the successive addition of water (0.27 mL), 5M sodium hydroxide (0.24 mL), and water (0.93 mL). The resulting gelatinous suspension is diluted with dichloromethane, filtered through a pad of celite, with the organics washed once with 1N sodium hydroxide (35 mL), once with brine (35 mL), dried over MgSO$_4$, filtered, and concentrated to give a tan oil. This material is purified by LC (230–400 silica gel) eluting with 5:0.75:94.25 methanol/NH$_4$OH/dichloromethane to afford 330 mg of 4-methoxy-N-[2-(2,3,4,5-tetrahydro-1H-[1,4]diazepino[1,7-a]indol-11-yl)ethyl]aniline as a light golden oil. This material is dissolved in ethyl acetate and treated with 2M hydrochloric acid in methanol (1.1 mL) with immediate formation of a white solid that is collected by filtration and recrystallized from methanol/ethyl acetate to afford 343 mg of 4-methoxy-N-[2-(2,3,4,5-tetrahydro-1H-[1,4]diazepino[1,7-a]indol-11-yl)ethyl]aniline dihydrochloride as a white solid. IR (drift) 2818, 2803, 2746, 2726, 2694, 2669, 2642, 2585, 2552, 2449, 1514, 1471, 1255, 1244, 757 cm$^{-1}$; OAMS supporting ions at: ESI+ 336.2.

EXAMPLE 29
Ethyl-2-(3-benzyl-2,3,4,5-tetrahydro-1H-[1,4]diazepino[1,7-a]indol-11-yl)-2-oxoacetate

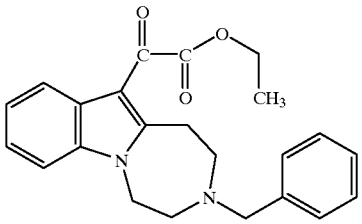

(Chart D, Step 1): A round bottom flask is charged with 3-benzyl-2,3,4,5-tetrahydro-1H-[1,4]diazepino[1,7-a]indole (1.17 g, 4.23 mmol) and ethyl ether (21 mL). The yellow homogeneous solution is cooled with an ice bath for 10 minutes. Oxalyl chloride (0.37 mL, 4.23 mmol) is added drop-wise. A yellow precipitate is observed, turning into a gel. After 10 minutes of stirring the ether is removed under reduced pressure. Ethanol (21 mL) is quickly added to the yellow residue and a nitrogen stream is established on the surface of the reaction to remove excess HCl. Using a syringe, triethylamine (1.30 mL, 9.31 mmol) is added drop-wise forming HCl gas which is carried away by the nitrogen stream. After the triethylamine addition is complete, the flask is adapted with a reflux condenser, and the reaction is heated to reflux for two hours. The reaction is then cooled and concentrated to 2.79 g of a yellow solid. The crude solid is purified on silica gel using a gradient from 25% to 50% ethyl acetate/heptane as the eluent to give 1.293 grams of ethyl 2-(3-benzyl-2,3,4,5-tetrahydro-1H-[1,4]diazepino[1,7-a]indol-11-yl)-2-oxoacetate as a yellow solid. Anal. Calculated for $C_{23}H_{24}N_2O_3$: C, 73.38; H, 6.43; N, 7.44. Found; C, 73.02; H, 6.55; N, 7.38.

EXAMPLE 30
2-(3-benzyl-2,3,4,5-tetrahydro-1H-[1,4]diazepino[1,7-a]indol-11-yl)-1-ethanol

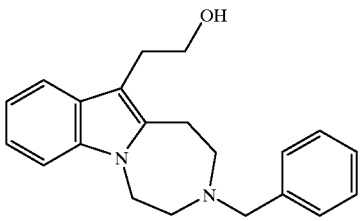

(Chart D, Step 2): A dry round bottom flask is charged with THF (100 mL) and 1M LAH in THF (65.13 mL, 65.13 mmol). A solution of ethyl 2-(3-benzyl-2,3,4,5-tetrahydro-1H-[1,4]diazepino[1,7-a]indol-11-yl)-2-oxoacetate (6.13 g, 16.28 mmol) in THF (75 mL) is slowly added to the reaction via syringe. The addition is exothermic. The reaction mixture is heated to reflux for 5 hours then reaction is quenched with a very slow and sequential addition of a) 2.47 mL $H_2O$, b) 2.22 mL of 5N aq. NaOH, and c) 8.64 mL $H_2O$. The resulting heterogeneous solution is stirred vigorously with excess ethyl acetate for one hour and filtered through a pad of celite. The filtrate is concentrated to give 9.23 g of 1-(3-benzyl-2,3,4,5-tetrahydro-1H-[1,4]diazepino[1,7-a]indol-11-yl)-1,2-ethanediol as a crude yellow solid. A 2 L round bottom is charged with a solution of the crude diol in dichloromethane (541 mL). A semi-dropwise addition of TFA (14.46 mL, 188 mmol) is followed by the slow addition of triethylsilane (9.1 mL, 57 mmol) and the mixture is first refluxed for two hours, then stirred at ambient temperature for 18 hours. The resulting brown solution is concentrated in vacuo, diluted with dichloromethane, basified with sat. aq. $Na_2CO_3$ and vigorously stirred while cooling to 10° C. The mixture is transferred to a round bottom, volatiles are removed in vacuo at 50° C. The residue is partitioned between water and dichloromethane. The organics are combined, dried with $Na_2SO_4$, filtered and concentrated to give 5.57 g of an orange oil. Purification of the crude on silica gel using a gradient of 35%–50% ethyl acetate/heptane as the eluent gives 3.52 g of 2-(3-benzyl-2,3,4,5-tetrahydro-1H-[1,4]diazepino[1,7-a]indol-11-yl)-1-ethanol as a tan oil. IR (liq.) 2933, 2873, 2816, 1469, 1453, 1427, 1376, 1364, 1347, 1325, 1185, 1046, 1015, 733, 699 $cm^{-1}$.

EXAMPLE 31
3-benzyl-11-(2-phenoxyethyl)-2,3,4,5-tetrahydro-1H-[1,4]diazepino[1,7-a]indole

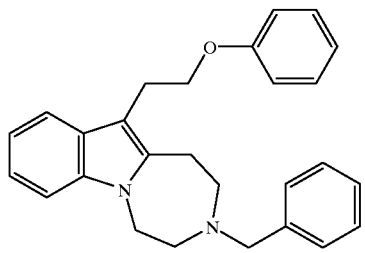

(Chart D, Step 3): A dry round bottom flask is charged with 2-(3-benzyl-2,3,4,5-tetrahydro-1H-[1,4]diazepino[1,7-a]indol-11-yl)-1-ethanol (420 mg, 1.31 mmol), phenol (185.2 mg, 1.97 mmol), triphenylphosphine (413 mg, 1.57 mmol), and THF (12 mL, freshly distilled). After cooling the reaction to 0° C., diethylazodicarboxylate (DEAD) (0.248 mL, 1.57 mmol) is added dropwise via syringe. The ice bath is allowed to expire, and the reaction is stirred at ambient temperature for 18 hours. The reaction is quenched with 30% $H_2O_2$ (0.20 mL), diluted with ethyl ether and washed twice with 10% aq. $NaHSO_3$. The organics are washed twice with aq. 1N NaOH, once with brine, dried with $Na_2SO_4$, filtered and concentrated to 1.08 g of a crude yellow solid. Purification of the crude using silica gel and 10% ethyl acetate in heptane as the eluent gives 392 mg (76%) of 3-benzyl-11-(2-phenoxyethyl)-2,3,4,5-tetrahydro-1H-[1,4]diazepino[1,7-a]indole as a pale yellow oil. HRMS (FAB) calculated for $C_{27}H_{28}N_2O+H_1$ 397.2280, found 397.2271.

EXAMPLE 32
11-(2-phenoxyethyl)-2,3,4,5-tetrahydro-1H-[1,4]diazepino[1,7-a]indole

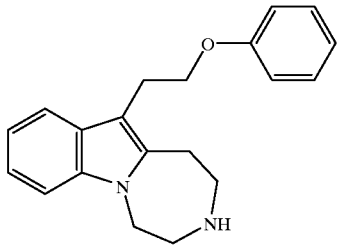

(Chart D, Step 4): A dry round bottom flask is charged with 3-benzyl-11-(2-phenoxyethyl)-2,3,4,5-tetrahydro-1H-

[1,4]diazepino[1,7-a]indole (317 mg, 0.80 mmol), ammonium formate (254 mg, 4.0 mmol), methanol (18 mL) and dichloromethane (3.2 mL). After the addition of 10% Pd/C (64 mg) the reaction is stirred at ambient temperature for two days. The reaction mixture is filtered through a pad of celite, and the catalyst is rinsed with methanol. The filtrates are combined and concentrated to 380 mg of a crude solid. This material is recrystallized from ethyl acetate/methanol/ethyl ether to afford 239 mg of 11-(2-phenoxyethyl)-2,3,4,5-tetrahydro-1H-[1,4]diazepino[1,7-a]indole as a white solid. IR (drift) 3026, 3015, 2998, 2983, 2948, 2910, 2869, 2806, 2781, 2752, 1468, 1451, 1245, 755, 746 cm$^{-1}$.

EXAMPLE 33
3-benzyl-11-[2-(2-methoxyphenoxy)ethyl]-2,3,4,5-tetrahydro-1H-[1,4]diazepino[1,7-a]indole

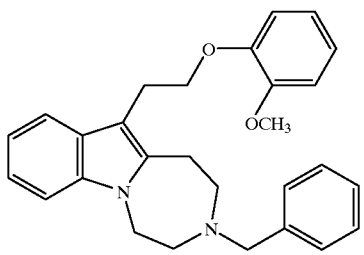

Following the general procedure of Example 31 (Chart D, Step 3), and making non-critical variations but substituting phenol with 2-methoxyphenol, gives 360 mg of a crude oil. This material is purified by LC (230–400 silica gel) eluting with 10% ethyl acetate in heptane to afford 149 mg of 3-benzyl-11-[2-(2-methoxyphenoxy)ethyl]-2,3,4,5-tetrahydro-1H-[1,4]diazepino[1,7-a]indole as a pale yellow oil. HRMS (FAB) calculated for $C_{28}H_{30}N_2O_2+H_1$ 427.2385, found 427.2389.

EXAMPLE 34
3-benzyl-11-[2-(2-fluorophenoxy)ethyl]-2,3,4,5-tetrahydro-1H-[1,4]diazepino[1,7-a]indole

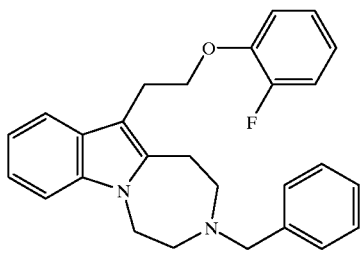

Following the general procedure of Example 31 (Chart D, Step 3) and making non-critical variations but substituting phenol with 2-fluorophenol, gives 326 mg of a yellow solid. This material is purified by LC (230–400 silica gel) eluting with 10% ethyl acetate in heptane to afford 176 mg of 3-benzyl-11-[2-(2-fluorophenoxy)ethyl]-2,3,4,5-tetrahydro-1H-[1,4]diazepino[1,7-a]indole as an ivory solid. HRMS (FAB) calculated for $C_{27}H_{27}FN_2O+H_1$ 415.2185, found 415.2180.

EXAMPLE 35
3-benzyl-11-[2-(8-quinolinyloxy)ethyl]-2,3,4,5-tetrahydro-1H-[1,4]diazepino[1,7-a]indole

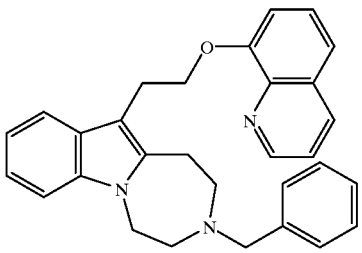

Following the general procedure of Example 31 (Chart D, Step 3) and making non-critical variations but substituting phenol with 8-hydroxyquinoline, gives 312 mg of a crude yellow solid. This material is purified by LC (230–400 silica gel) eluting with 25% acetone in heptane to afford 69 mg 3-benzyl-11-[2-(8-quinolinyloxy)ethyl]-2,3,4,5-tetrahydro-1H-[1,4]diazepino[1,7-a]indole as an oil. HRMS (FAB) calculated for $C_{30}H_{29}N_3O+H_1$ 448.2389, found 448.2383.

EXAMPLE 36
2-(2,3,4,5-tetrahydro-1H-[1,4]diazepino[1,7-a]indol-11-yl)-1-ethanol

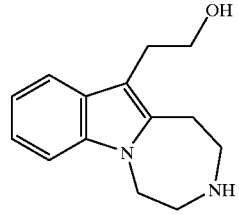

Following the general procedure of Example 32 (Chart D, Step 4) and making non-critical variations but substituting with 2-(3-benzyl-2,3,4,5-tetrahydro-1H-[1,4]diazepino[1,7-a]indol-11-yl)-1-ethanol gives 128 mg of a crude oil. This material is purified by LC (230–400 silica gel) eluting with 0.5% NH$_2$OH and 10% methanol in dichloromethane to afford 119 mg of 2-(2,3,4,5-tetrahydro-1H-[1,4]diazepino[1,7-a]indol-11-yl)-1-ethanol as a tan paste. HRMS (FAB) calculated for $C_{14}H_{18}N_2O+H_1$ 231.1497, found 231.1503.

EXAMPLE 37
3-benzyl-11-[2-(2-methoxy-4-methylphenoxy)ethyl]-2,3,4,5-tetrahydro-1H-[1,4]diazepino[1,7-a]indole

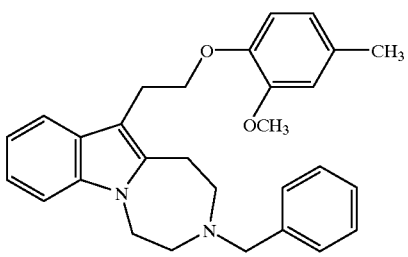

Following the general procedure of Example 31 (Chart D, Step 3) and making non-critical variations but substituting phenol with 2-methoxy-4-methylphenol, gives 460 mg of a crude oil. This material is purified by LC (230–400 silica gel) eluting with 10% ethyl acetate in heptane to afford 158 mg of 3-benzyl-11-[2-(2-methoxy-4-methylphenoxy)ethyl]-2,3,4,5-tetrahydro-1H-[1,4]diazepino[1,7-a]indole as a pale

EXAMPLE 38

3-benzyl-11-[2-(2-fluoro-6-methoxyphenoxy)ethyl]-2,3,4,5-tetrahydro-1H-[1,4]diazepino[1,7-a]indole

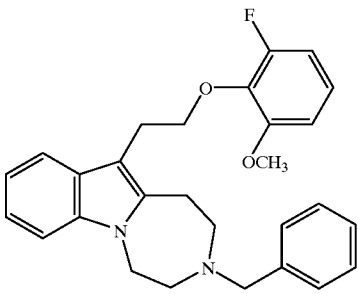

Following the general procedure of Example 31 (Chart D, Step 3) and making non-critical variations but substituting phenol with 2-fluoro-6-methoxyphenol, gives 430 mg of a crude oil. This material is purified by LC (230–400 silica gel) eluting with 10% ethyl acetate in heptane to afford 189 mg of 3-benzyl-11-[2-(2-fluoro-6-methoxyphenoxy)ethyl]-2,3,4,5-tetrahydro-1H-[1,4]diazepino[1,7-a]indole as a pale yellow oil. HRMS (FAB) calculated for $C_{29}H_{32}N_2O_2+H_1$ 441.2542, found 441.2547.

EXAMPLE 39

11-[2-(2-methoxyphenoxy)ethyl]-2,3,4,5-tetrahydro-1H-[1,4]diazepino[1,7-a]indole

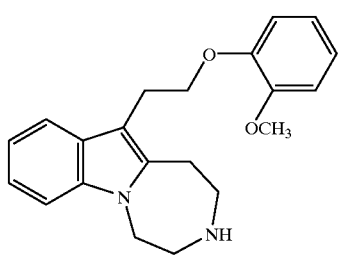

Following the general procedure of Example 32 (Chart D, Step 4) and making non-critical variations but substituting 3-benzyl-11-[2-(2-methoxyphenoxy)ethyl]-2,3,4,5-tetrahydro-1H-[1,4]diazepino[1,7-a]indole with 3-benzyl-11-(2-phenoxyethyl)-2,3,4,5-tetrahydro-1H-[1,4]diazepino[1,7-a]indole gives 146 mg of a crude white solid. This material is purified by LC (230–400 silica gel) eluting with 0.25% NH$_4$OH and 2.5% methanol in dichloromethane to afford 137 mg of 11-[2-(2-methoxyphenoxy)ethyl]-2,3,4,5-tetrahydro-1H-[1,4]diazepino[1,7-a]indole as a tan solid. IR (liq.) 2936, 1591, 1505, 1469, 1455, 1373, 1340, 1326, 1252, 1227, 1179, 1124, 1027, 1015, 740 cm$^{-1}$.

EXAMPLE 40

11-[2-(2-fluorophenoxy)ethyl]-2,3,4,5-tetrahydro-1H-[1,4]diazepino[1,7-a]indole

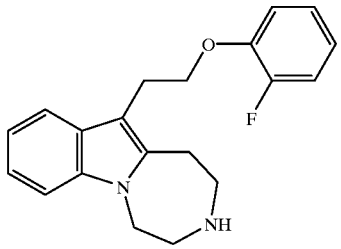

Following the general procedure of Example 32 (Chart D, Step 4) and making non-critical variations but substituting 3-benzyl-11-[2-(2-methoxyphenoxy)ethyl]-2,3,4,5-tetrahydro-1H-[1,4]diazepino[1,7-a]indole with 3-benzyl-11-[2-(2-fluorophenoxy)ethyl]-2,3,4,5-tetrahydro-1H-[1,4]diazepino[1,7-a]indole gives 179 mg of a crude yellow paste. This material is purified by LC (230–400 silica gel) eluting with 0.25 % NH$_4$OH and 2.5 % methanol in dichloromethane to afford 141 mg of 11-[2-(2-fluorophenoxy)ethyl]-2,3,4,5-tetrahydro-1H-[1,4]diazepino[1,7-a]indole as a white solid. IR (drift) 1502, 1466, 1342, 1319, 1307, 1283, 1264, 1255, 1203, 1181, 1106, 804, 772, 751, 742 cm$^{-1}$.

EXAMPLE 41

11-[2-(2-methoxy-4-methylphenoxy)ethyl]-2,3,4,5-tetrahydro-1H-[1,4]diazepino[1,7-a]indole

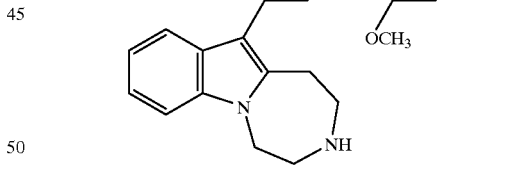

Following the general procedure of Example 32 (Chart D, Step 4) and making non-critical variations but substituting 3-benzyl-11-[2-(2-methoxyphenoxy)ethyl]-2,3,4,5-tetrahydro-1H-[1,4]diazepino[1,7-a]indole with 3-benzyl-11-[2-(2-methoxy-4-methylphenoxy)ethyl]-2,3,4,5-tetrahydro-1H-[1,4]diazepino[1,7-a]indole gives 170 mg of a crude oil. This material is purified by LC (230–400 silica gel) eluting with 0.25% NH$_4$OH and 2.5% methanol in dichloromethane to afford 107 mg of 11-[2-(2-methoxy-4-methylphenoxy)ethyl]-2,3,4,5-tetrahydro-1H-[1,4]diazepino[1,7-a]indole as a pale yellow oil. IR (liq.) 2937, 2918, 1514, 1469, 1374, 1364, 1340, 1325, 1264, 1233, 1159, 1139, 1035, 1015, 741 cm$^{-1}$.

EXAMPLE 42

11-[2-(2-fluoro-6-methoxyphenoxy)ethyl]-2,3,4,5-tetrahydro-1H-[1,4]diazepino[1,7-a]indole

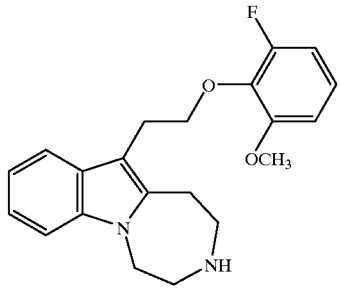

Following the general procedure of Example 32 (Chart D, Step 4) and making non-critical variations but substituting 3-benzyl-11-[2-(2-methoxyphenoxy)ethyl]-2,3,4,5-tetrahydro-1H-[1,4]diazepino[1,7-a]indole with 3-benzyl-11-[2-(2-fluoro-6-methoxyphenoxy)ethyl]-2,3,4,5-tetrahydro-1H-[1,4]diazepino[1,7-a]indole gives 279 mg of a crude solid. This material is purified by LC (230–400 silica gel) eluting with 0.25% $NH_4OH$ and 2.5% methanol in dichloromethane to afford 159 mg of 11-[2-(2-fluoro-6-methoxyphenoxy)ethyl]-2,3,4,5-tetrahydro-1H-[1,4]diazepino[1,7-a]indole as a pale yellow oil. IR (liq.) 2940, 1608, 1497, 1476, 1470, 1440, 1374, 1304, 1283, 1247, 1230, 1086, 992, 775, 740 $cm^{-1}$.

EXAMPLE 43

3-benzyl-11-[2-(2-chlorophenoxy)ethyl]-2,3,4,5-tetrahydro-1H-[1,4]diazepino[1,7-a]indole

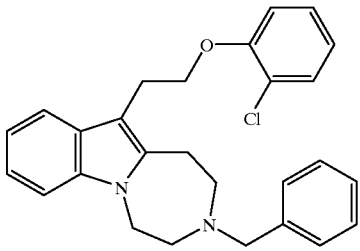

Following the general procedure of Example 31 (Chart D, Step 3) and making non-critical variations but substituting phenol with 2-chlorophenol, gives 445 mg of a crude oil. This material is purified by LC (230–400 silica gel) eluting with 10% ethyl acetate in heptane to afford 192 mg of 3-benzyl-11-[2-(2-chlorophenoxy)ethyl]-2,3,4,5-tetrahydro-1H-[1,4]diazepino[1,7-a]indole as a pale yellow oil. HRMS (FAB) calculated for $C_{27}H_{27}ClN_2O+H_1$ 431.1890, found 431.1888.

EXAMPLE 44

3-benzyl-11-[2-(4-bromo-2-methoxyphenoxy)ethyl]-2,3,4,5-tetrahydro-1H-[1,4]diazepino[1,7-a]indole

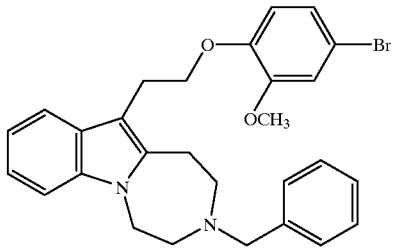

Following the general procedure of Example 31 (Chart D, Step 3) and making non-critical variations but substituting phenol with 4-bromoguaiacol, gives 485 mg of a crude oil. This material is purified by LC (230–400 silica gel) eluting with 10% ethyl acetate in heptane to afford 224 mg of 3-benzyl-11-[2-(4-bromo-2-methoxyphenoxy)ethyl]-2,3,4,5-tetrahydro-1H-[1,4]diazepino[1,7-a]indole as a clear oil. HRMS (FAB) calculated for $C_{28}H_{29}BrN_2O_2+H_1$ 505.1491, found 505.1486.

EXAMPLE 45

11-[2-(2-chlorophenoxy)ethyl]-2,3,4,5-tetrahydro-1H-[1,4]diazepino[1,7-a]indole

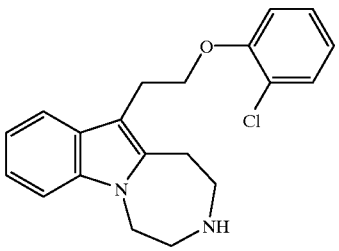

(Chart D, Step 4): A dry round bottom flask is charged with a solution of 3-benzyl-11-[2-(2-chlorophenoxy)ethyl]-2,3,4,5-tetrahydro-1H-[1,4]diazepino[1,7-a]indole (176 mg, 0.41 mmol) in methylene chloride (2 mL) and acetonitrile (5 mL). The addition of 2,2,2-trichloroformate (0.062 mL, 0.45 mmol) immediately turned the solution to a fluorescent green color, which changes to purple within 45 minutes. The reaction is concentrated in vacuo to give 247 mg of a crude purple oil. This material is purified by LC (230–400 silica gel) eluting with 20% ethyl acetate in heptane to afford 203 mg of 2,2,2-trichloroethyl 11-[2-(2-chlorophenoxy)ethyl]-1,2,4,5-tetrahydro-3H-[1,4]diazepino[1,7-a]indole-3-carboxylate as a clear oil. The carboxylate is dissolved in glacial acetic acid (3 mL). Zinc powder (300 mg) is added to the acidic solution, changing the color from light to bright pink. After three hours of stirring at ambient temperature, the reaction is filtered through celite, and the zinc is thoroughly rinsed with water, dichloromethane, 1N aq. NaOH, water and dichloromethane sequentially. The filtrates are combined and neutralized with aq. 5N NaOH to pH 7 then diluted with aq. $NaHCO_3$ and extracted four times with dichloromethane. The extracts are combined, dried over $Na_2SO_4$, filtered and concentrated to 151 mg of a crude opaque oil. The crude is purified by LC (230–400 silica gel) eluting with 1% $NH_4OH$ and 7% methanol in dichloromethane to afford 92 mg (70%) of 11-[2-(2-chlorophenoxy)ethyl]-2,3,4,5-tetrahydro-1H-[1,4]diazepino[1,7-a]indole as a an ivory solid. IR (drift) 1483, 1465, 1340, 1317, 1281, 1261, 1256, 1245, 1059, 1040, 913, 753, 749, 738, 688 $cm^{-1}$.

EXAMPLE 46
11-[2-(4-bromo-2-methoxyphenoxy)ethyl]-2,3,4,5-tetrahydro-1H-[1,4]diazepino[1,7-a]indole

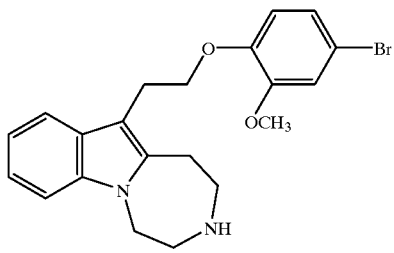

Following the general procedure of Example 45 (Chart D, Step 4) and making non-critical variations but substituting with 3-benzyl-11-[2-(4-bromo-2-methoxyphenoxy)ethyl]-2,3,4,5-tetrahydro-1H-[1,4]diazepino[1,7-a]indole gives 153 mg of a crude opaque oil. This material is purified by LC (230–400 silica gel) eluting with 5% methanol in dichloromethane to afford 98 mg of 11-[2-(4-bromo-2-methoxyphenoxy)ethyl]-2,3,4,5-tetrahydro-1H-[1,4]diazepino[1,7-a]indole as an ivory foam. IR (drift) 2926, 1585, 1500, 1467, 1372, 1323, 1249, 1224, 1179, 1134, 1024, 1014, 838, 799, 739 cm$^{-1}$.

EXAMPLE 47
2-phenoxy-1-(2,3,4,5-tetrahydro-1H-[1,4]diazepino[1,7-a]indol-11-yl)-1-ethanone

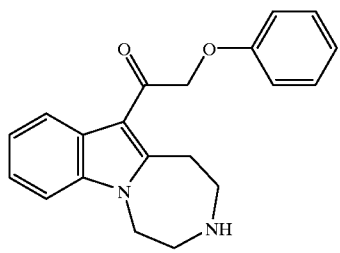

(Chart E, Step 1): A dry round bottom flask is charged with AlCl$_3$ (66.7 mg, 0.5 mmol) and dichloromethane (4 mL) to make a heterogeneous solution. Dropwise addition of bromo-acetylbromide (0.044 mL, 0.5 mmol) turns the reaction into a homogeneous orange solution. After 30 minutes of stirring at ambient temperature, a solution of 2,2,2-trifluoro-1-(1,2,4,5-tetrahydro-3H-[1,4]diazepino[1,7-a]indol-3-yl)-1-ethanone (141.1 mg, 0.5 mmol) in dichloromethane (2 mL) is added dropwise and stirred for three days. The reaction turns dark purple within the first 4 hours of stirring. The reaction is poured in a sat. aq. NaHCO$_3$ solution and extracted three times with dichloromethane. The combined organics are combined, dried with MgSO$_4$, filtered and concentrated to 192 mg of a purple foam. The crude is purified by LC (230–400 silica gel) eluting with 10% ethyl acetate and 20% dichloromethane in heptane to afford 120 mg of 1-[11-(2-bromoacetyl)-1,2,4,5-tetrahydro-3H-[1,4]diazepino[1,7-a]indol-3-yl]-2,2,2-trifluoro-1-ethanone as a white foam.

(Chart E, Step 2): To a dry round bottom charged with a heterogeneous mixture of K$_2$CO$_3$ (40.77 mg, 0.30 mmol) and phenol (27.8 mg, 0.30 mmol) in DMF (1.5 mL) is added a solution of 1-[11-(2-bromoacetyl)-1,2,4,5-tetrahydro-3H-[1,4]diazepino[1,7-a]indol-3-yl]-2,2,2-trifluoro-1-ethanone in DMF (1.5 mL). After stirring at ambient temperature for 18 hours, aq. 1N NaOH (1 mL) is added at once to deprotect the indole in situ. The mixture is stirred for an hour then partitioned between water and ethyl acetate, the aqueous layer is extracted two more times with ethyl acetate. The organics are combined, dried with MgSO$_4$, filtered and concentrated to 95 mg of a crude oil. The crude is purified by LC (230–400 silica gel) eluting with 0.5% NH$_4$OH and 3.5% methanol in dichloromethane to afford 69 mg of 2-phenoxy-1-(2,3,4,5-tetrahydro-1H-[1,4]diazepino[1,7-a]indol-11-yl)-1-ethanone as a white solid. IR (drift) 1662, 1598, 1516, 1495, 1458, 1443, 1420, 1345, 1244, 1198, 1191, 1052, 975, 746, 688 cm$^{-1}$.

EXAMPLE 48
2-(2-methoxyphenoxy)-1-(2,3,4,5-tetrahydro-1H-[1,4]diazepino[1,7-a]indol-11-yl)-1-ethanone

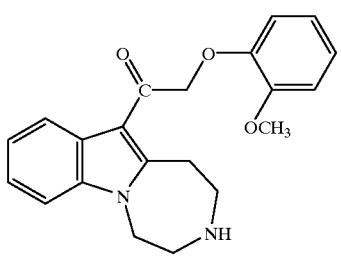

Following the general procedure of Example 47 (Chart E, Step 2) and making non-critical variations but substituting phenol with 2-methoxyphenol, gives 250 mg of a crude oil. This material is purified by LC (230–400 silica gel) eluting with 0.5% NH$_4$OH and 3.5% methanol in dichloromethane to afford 172 mg of 2-(2-methoxyphenoxy)-1-(2,3,4,5-tetrahydro-1H-[1,4]diazepino[1,7-a]indol-11-yl)-1-ethanone as an ivory solid. IR (drift) 1662, 1515, 1505, 1456, 1442, 1422, 1345, 1253, 1225, 1190, 1130, 1032, 975, 758, 737 cm$^{-1}$.

EXAMPLE 49
2-(4-bromo-2-methoxyphenoxy)-1-(2,3,4,5-tetrahydro-1H-[1,4]diazepino[1,7-a]indol-11-yl-1-ethanone

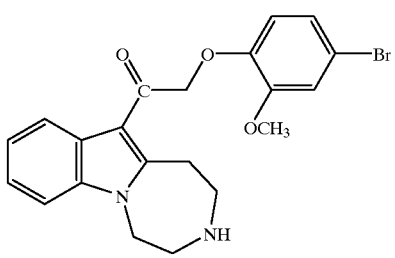

Following the general procedure of Example 47 (Chart E, Step 2) and making non-critical variations but substituting phenol with 4-bromoguaicol, gives 300 mg of a crude oil. This material is purified by LC (230–400 silica gel) eluting with 0.5% NH$_4$OH and 3.5% methanol in dichloromethane to afford 243 mg of 2-(4-bromo-2-methoxyphenoxy)-1-(2,3,4,5-tetrahydro-1H-[1,4]diazepino[1,7-a]indol-11-yl)-1-ethanone as an ivory solid. IR (drift) 1659, 1514, 1501, 1465, 1422, 1343, 1250, 1222, 1189, 1137, 1031, 975, 836, 794, 736 cm$^{-1}$.

EXAMPLE 50

2-(4-methoxyanilino)-1-(2,3,4,5-tetrahydro-1H-[1,4]diazepino[1,7-a]indol-11-yl)-1-ethanone dihydrochloride

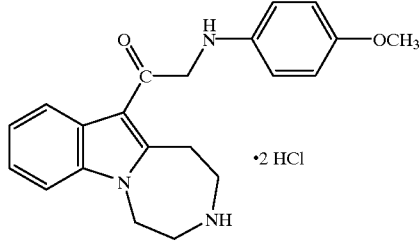

Following the general procedure of Example 47 (Chart E, Step 2) and making non-critical variations but substituting phenol with p-methoxyaniline, gives 350 mg of a crude oil. This material is purified by LC (230–400 silica gel) eluting with 0.5% NH$_4$OH and 3.5% methanol in dichloromethane to afford 169 mg of 2-(4-methoxyanilino)-1-(2,3,4,5-tetrahydro-1H-[1,4]diazepino[1,7-a]indol-11-yl)-1-ethanone as a yellow oil. This material is dissolved in ethyl acetate (15 mL) and treated with a 0.61 M hydrochloric acid solution in methanol (1 mL) to afford 116 mg of 2-(4-methoxyanilino)-1-(2,3,4,5-tetrahydro-1H-[1,4]diazepino[1,7-a]indol-11-yl)-1-ethanone dihydrochloride as a white solid. IR (drift) 2936, 2792, 2767, 2747, 2713, 2684, 2653, 2640, 2595, 2581, 1641, 1512, 1463, 1419, 1257 cm$^{-1}$.

EXAMPLE 51 tert-butyl 1,2,4,5-tetrahydro-3H-[1,4]diazepino[1,7-a]indole-3-carboxylate

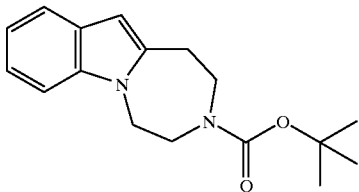

A solution of 2,3,4,5-Tetrahydro-1H-[1,4]diazepino[1,7-a]indole (2.40 g, 12.9 mmol) in dichloromethane (64 mL) is treated with di-tertbutyl dicarbonate (3.37 g, 15.5 mmol) quickly evolving carbon dioxide. After 18 hrs, the reaction mixture is concentrated under reduced pressure to give 4.54 g of a crude solid. This material is purified by LC (biotage 90 g column) eluting with 10:10:80 dichloromethane/ethyl acetate/heptane to afford 3.79 g of tert-butyl 1,2,4,5-tetrahydro-3H-[1,4]diazepino[1,7-a]indole-3-carboxylate as a white solid, mp 129–132° C. IR (drift) 2971, 2934, 1686, 1458, 1406, 1366, 1333, 1255, 1242, 1221, 1195, 1179, 949, 798, 734 cm$^{-1}$.

EXAMPLE 52

11-[(E)-2-nitroethenyl]-2,3,4,5-tetrahydro-1H-[1,4]diazepino[1,7-a]indole

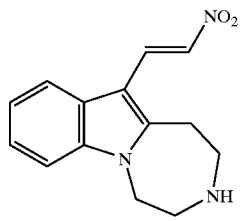

A solution of tert-butyl 11-formyl-1,2,4,5-tetrahydro-3H-[1,4]diazepino[1,7-a]indole-3-carboxylate (314 gm, 1.0 mmol) in nitromethane (1 mL) is treated with ammonium acetate (23 mg, 0.3 mmol) and heated to reflux. After 18 hrs, the resulting dark brown solution is cooled to rt, diluted with water (15 mL), and extracted twice with dichloromethane (20 mL). The combined organics are washed with brine (15 mL), dried over MgSO$_4$, filtered, and concentrated to give a crude solid. This material is purified by LC (230–400 silica gel) eluting with 10:40:50 ethyl acetate/dichloromethane/heptane to afford 240 mg of tert-butyl 11-[(E)-2-nitroethenyl]-1,2,4,5-tetrahydro-3H-[1,4]diazepino[1,7-a]indole-3-carboxylate as a bright yellow solid, mp 227–230° C. IR (drift) 1692, 1621, 1493, 1472, 1419, 1323, 1310, 1302, 1291, 1277, 1259, 1248, 1198, 1164, 751 cm$^{-1}$; MS (EI) m/z 357 (M$^+$).

A solution of tert-butyl 11-[(E)-2-nitroethenyl]-1,2,4,5-tetrahydro-3H-[1,4]diazepino[1,7-a]indole-3-carboxylate (396 mg, 1.1 mmol) in methanol (10 mL) is cooled to 0° C. and treated with a saturated solution of hydrochloric acid in methanol (5 mL). After 3 hrs, the volatiles are removed under reduced pressure, diluted with 5M sodium hydroxide (15 mL), and extracted twice with dichloromethane (20 mL). The combined organics are washed once with brine (15 mL), dried over MgSO$_4$, filtered, and concentrated to give a yellow solid. This material is recrystallized from dichloromethane/ethyl acetate to afford 209 mg of 11-[(E)-2-nitroethenyl]-2,3,4,5-tetrahydro-1H-[1,4]diazepino[1,7-a]indole as a light yellow solid, mp 225–226° C. IR (drift) 1603, 1488, 1469, 1318, 1301, 1281, 1257, 1251, 1206, 1187, 1062, 976, 946, 763, 745 cm$^{-1}$; OAMS supporting ions at: ESI+ 258.1.

EXAMPLE 53

3-(trifluoroacetyl)-2,3,4,5-tetrahydro-1H-[1,4]diazepino[1,7-a]indole

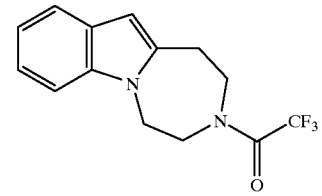

A solution of 2,3,4,5-tetrahydro-1H-[1,4]diazepino[1,7-a]indole hydrochloride (557 mg, 2.5 mmol) in dichloromethane (25 mL) is treated with triethylamine (0.77 mL, 5.5 mmol) followed by cooling to 0° C. The clear golden solution is treated with the trifluoroacetic acid anhydride (0.39 mL, 2.8 mmol) with a smoke/haze forming. After 15 min, the reaction mixture is diluted with additional dichloromethane (25 mL), washed once with water (25 mL), once with brine (25 mL), dried over MgSO$_4$, filtered, and concentrated to give a crude solid. This material is purified by LC (230–400 silica gel) eluting with 25:5:70 dichloromethane/ethyl acetate/heptane to afford 607 mg of 2,2,2-trifluoro-1-(1,2,4,5-tetrahydro-3H-[1,4]diazepino[1,7-a]indol-3-yl)-1-ethanone as a white solid. IR (drift) 1691, 1464, 1449, 1368, 1292, 1203, 1196, 1171, 1161, 1139, 970, 782, 749, 743, 651 cm$^{-1}$; MS (EI) m/z 282 (M$^+$).

EXAMPLE 54

2-bromo-1-[3-(trifluoroacetyl)-2,3,4,5-tetrahydro-1H-[1,4]diazepino[1,7-a]indol-11-yl]ethanone

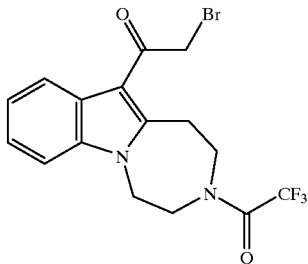

(Chart E, Step 1): A dry round bottom flask is charged with AlCl$_3$ (66.7 mg, 0.5 mmol) and dichloromethane (4 mL) to make a heterogeneous solution. Dropwise addition of bromo-acetylbromide (0.044 mL, 0.5 mmol) turns the reaction into a homogeneous orange solution. After 30 minutes of stirring at ambient temperature, a solution of 2,2,2-trifluoro-1-(1,2,4,5-tetrahydro-3H-[1,4]diazepino[1,7-a]indol-3-yl)-1-ethanone (141.1 mg, 0.5 mmol) in dichloromethane (2 mL) is added dropwise and stirred for three days. The reaction turns dark purple within the first 4 hours of stirring. The reaction is poured in a sat. aq. NaHCO$_3$ solution and extracted three times with dichloromethane. The combined organics are combined, dried with MgSO$_4$, filtered and concentrated to 192 mg of a purple foam. The crude is purified by LC (230–400 silica gel) eluting with 10% ethyl acetate and 20% dichloromethane in heptane to afford 120 mg of 1-[11-(2-bromoacetyl)-1,2,4,5-tetrahydro-3H-[1,4]diazepino[1,7-a]indol-3-yl]-2,2,2-trifluoro-1-ethanone as a white foam.

EXAMPLE 55

N-(1H-benzimidazol-2-yl)-2-oxo-2-(2,3,4,5-tetrahydro-1H-[1,4]diazepino[1,7-a]indol-11-yl)acetamide

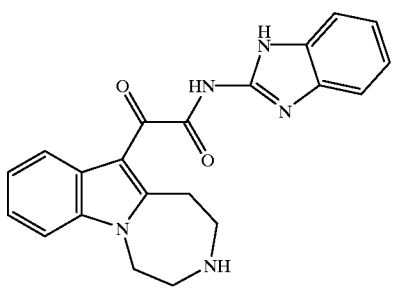

Following the general procedure of Example 20 (Chart B) and making non-critical variations but substituting 4-methoxyaniline with 1H-benzimidazol-2-ylamine gives N-(1H-benzimidazol-2-yl)-2-oxo-2-(2,3,4,5-tetrahydro-1H-[1,4]diazepino[1,7-a]indol-11-yl)acetamide; MS (ESI+) for C$_{21}$H$_{19}$N$_5$O$_2$ m/z 373.9 (M+H)$^+$.

EXAMPLE 56

N-(4-methyl-1,3-thiazol-2-yl)-2-oxo-2-(2,3,4,5-tetrahydro-1H-[1,4]diazepino[1,7-a]indol-11-yl)acetamide

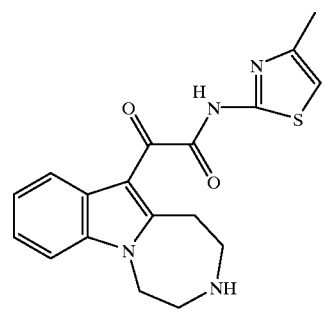

Following the general procedure of Example 20 (Chart B) and making non-critical variations but substituting 4-methoxyaniline with 4-methyl-1,3-thiazol-2-amine gives N-(4-methyl-1,3-thiazol-2-yl)-2-oxo-2-(2,3,4,5-tetrahydro-1H-[1,4]diazepino[1,7-a]indol-11-yl)acetamide; MS (ESI+) for C$_{18}$H$_{18}$N$_4$O$_2$S m/z 355.2 (M+H)$^+$.

EXAMPLE 57

N-[4-(4-morpholinyl)phenyl]-2-oxo-2-(2,3,4,5-tetrahydro-1H-[1,4]diazepino[1,7-a]indol-11-yl)acetamide

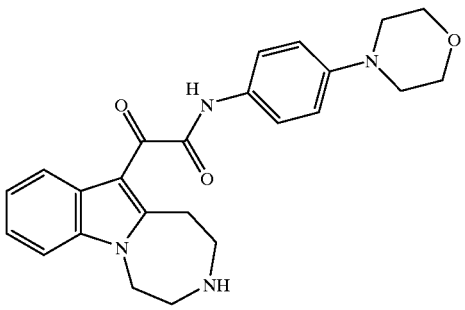

Following the general procedure of Example 20 (Chart B) and making non-critical variations but substituting 4-methoxyaniline with 4-(4-morpholinyl)phenylamine gives N-[4-(4-morpholinyl)phenyl]-2-oxo-2-(2,3,4,5-tetrahydro-1H-[1,4]diazepino[1,7-a]indol-11-yl)acetamide; MS (ESI+) for C$_{24}$H$_{26}$N$_4$O$_3$ m/z 419.1 (M+H)$^+$.

EXAMPLE 58

2-oxo-N-phenyl-2-(2,3,4,5-tetrahydro-1H-[1,4]diazepino[1,7-a]indol-11-yl)acetamide

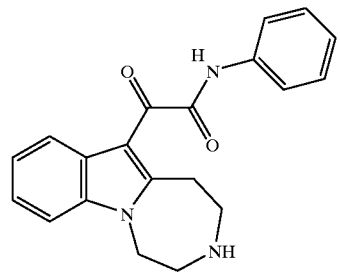

Following the general procedure of Example 20 (Chart B) and making non-critical variations but substituting 4-methoxyaniline with aniline gives 2-oxo-N-phenyl-2-(2, 3,4,5-tetrahydro-1H-[1,4]diazepino[1,7-a]indol-11-yl)acetamide; MS (ESI+) for $C_{20}H_{19}N_3O_2$ m/z 334.2 (M+H)+.

EXAMPLE 59

N-(2-methoxyphenyl)-2-oxo-2-(2,3,4,5-tetrahydro-1H-[1,4]diazepino[1,7-a]indol-11-yl)acetamide

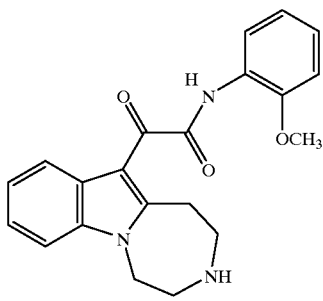

Following the general procedure of Example 20 (Chart B) and making non-critical variations but substituting 4-methoxyaniline with 2-methoxyaniline gives N-(2-methoxyphenyl)-2-oxo-2-(2,3,4,5-tetrahydro-1H-[1,4]diazepino[1,7-a]indol-11-yl)acetamide; MS (ESI+) for $C_{21}H_{21}N_3O_3$ m/z 364.1 (M+H)+.

EXAMPLE 60

N-(4-methoxy-2-methylphenyl)-2-oxo-2-(2,3,4,5-tetrahydro-1H-[1,4]diazepino[1,7-a]indol-11-yl)acetamide

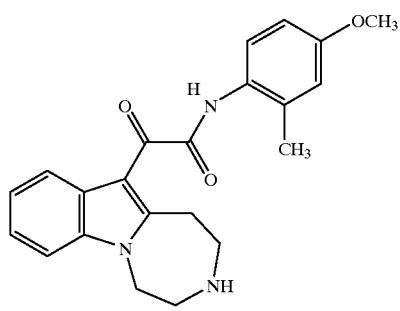

Following the general procedure of Example 20 (Chart B) and making non-critical variations but substituting 4-methoxyaniline with 4-methoxy-2-methylaniline gives N-(4-methoxy-2-methylphenyl)-2-oxo-2-(2,3,4,5-tetrahydro-1H-[1,4]diazepino[1,7-a]indol-11-yl)acetamide; MS (ESI+) for $C_{22}H_{23}N_3O_3$ m/z 378.2 (M+H)+.

EXAMPLE 61

N-(3-cyanophenyl)-2-oxo-2-(2,3,4,5-tetrahydro-1H-[1,4]diazepino[1,7-a]indol-11-yl)acetamide

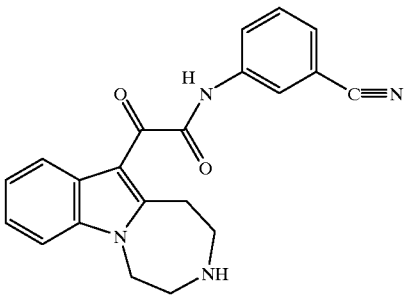

Following the general procedure of Example 20 (Chart B) and making non-critical variations but substituting 4-methoxyaniline with 3-cyanophenylamine gives N-(3-cyanophenyl)-2-oxo-2-(2,3,4,5-tetrahydro-1H-[1,4]diazepino[1,7-a]indol-11-yl)acetamide; MS (ESI+) for $C_{21}H_{18}N_4O_2$ m/z 359.1 (M+H)+.

EXAMPLE 62

N-(3,5-dimethylphenyl)-2-oxo-2-(2,3,4,5-tetrahydro-1H-[1,4]diazepino[1,7-a]indol-11-yl)acetamide

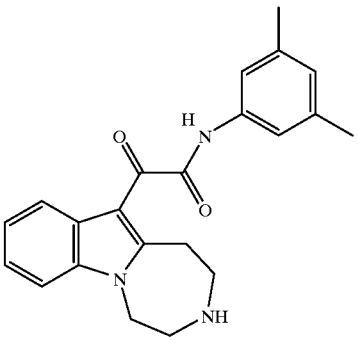

Following the general procedure of Example 20 (Chart B) and making non-critical variations but substituting 4-methoxyaniline with 3,5-dimethylphenylamine gives N-(3,5-dimethylphenyl)-2-oxo-2-(2,3,4,5-tetrahydro-1H-[1,4]diazepino[1,7-a]indol-11-yl)acetamide; MS (ESI+) for $C_{22}H_{23}N_3O_2$ m/z 362.2 (M+H)+.

EXAMPLE 63

N-(4-chlorophenyl)-2-oxo-2-(2,3,4,5-tetrahydro-1H-[1,4]diazepino[1,7-a]indol-11-yl)acetamide

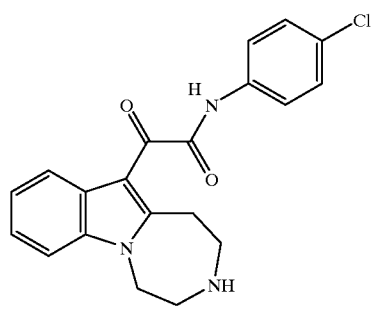

Following the general procedure of Example 20 (Chart B) and making non-critical variations but substituting 4-methoxyaniline with 4-chlorophenylamine gives N-(4-chlorophenyl)-2-oxo-2-(2,3,4,5-tetrahydro-1H-[1,4]diazepino[1,7-a]indol-11-yl)acetamide; MS (ESI+) for $C_{20}H_{18}ClN_3O_2$ m/z 368.1 (M+H)+.

EXAMPLE 64

N-(3-chlorophenyl)-N-methyl-2-oxo-2-(2,3,4,5-tetrahydro-1H-[1,4]diazepino[1,7-a]indol-11-yl)acetamide

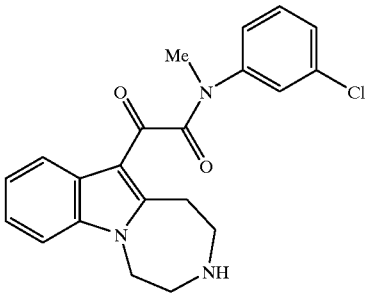

Following the general procedure of Example 20 (Chart B) and making non-critical variations but substituting 4-methoxyaniline with 3-chlorophenylamine gives N-(3-chlorophenyl)-N-methyl-2-oxo-2-(2,3,4,5-tetrahydro-1H-[1,4]diazepino[1,7-a]indol-11-yl)acetamide; MS (ESI+) for $C_{21}H_{20}ClN_3O_2$ m/z 382.1 (M+H)+.

EXAMPLE 65

N-(6-chloro-2-pyrazinyl)-2-oxo-2-(2,3,4,5-tetrahydro-1H-[1,4]diazepino[1,7-a]indol-11-yl)acetamide

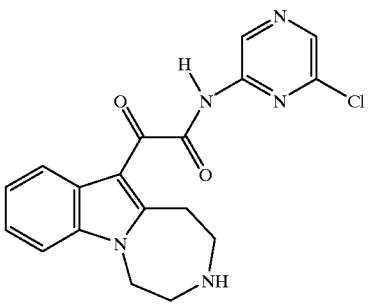

Following the general procedure of Example 20 (Chart B) and making non-critical variations but substituting 4-methoxyaniline with 6-chloro-2-pyrazinylamine gives N-(6-chloro-2-pyrazinyl)-2-oxo-2-(2,3,4,5-tetrahydro-1H-[1,4]diazepino[1,7-a]indol-11-yl)acetamide; MS (ESI+) for $C_{18}H_{16}ClN_5O_2$ m/z 369.9 (M+H)+.

EXAMPLE 66

N-mesityl-2-oxo-2-(2,3,4,5-tetrahydro-1H-[1,4]diazepino[1,7-a]indol-11-yl)acetamide

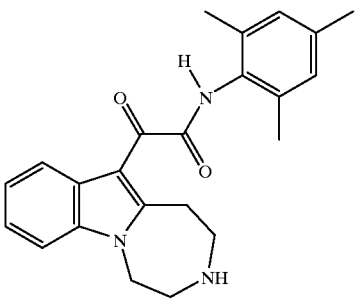

Following the general procedure of Example 20 (Chart B) and making non-critical variations but substituting 4-methoxyaniline with mesitylamine gives N-mesityl-2-oxo-2-(2,3,4,5-tetrahydro-1H-[1,4]diazepino[1,7-a]indol-11-yl)acetamide; MS (ESI+) for $C_{23}H_{25}N_3O_2$ m/z 376.2 (M+H)+.

EXAMPLE 67

N-(2,4-difluorophenyl)-2-oxo-2-(2,3,4,5-tetrahydro-1H-[1,4]diazepino[1,7-a]indol-11-yl)acetamide

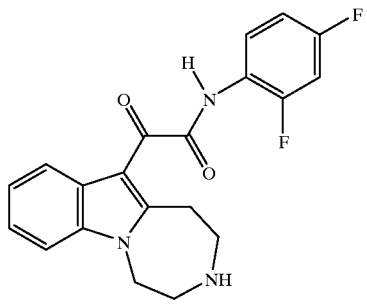

Following the general procedure of Example 20 (Chart B) and making non-critical variations but substituting 4-methoxyaniline with 2,4-difluorophenylamine gives N-(2,4-difluorophenyl)-2-oxo-2-(2,3,4,5-tetrahydro-1H-[1,4]diazepino[1,7-a]indol-11-yl)acetamide; MS (ESI+) for $C_{20}H_{17}F_2N_3O_2$ m/z 370.1 (M+H)+.

EXAMPLE 68

N-methyl-2-oxo-N-phenyl-2-(2,3,4,5-tetrahydro-1H-[1,4]diazepino[1,7-a]indol-11-yl)acetamide

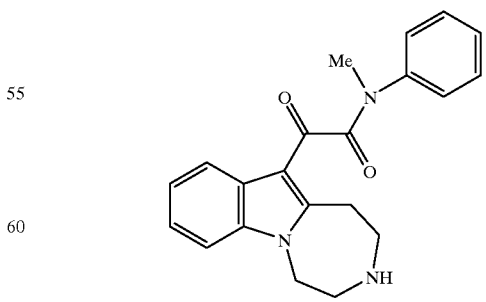

Following the general procedure of Example 20 (Chart B) and making non-critical variations but substituting 4-methoxyaniline with N-methylaniline gives N-methyl-2- oxo-N-phenyl-2-(2,3,4,5-tetrahydro-1H-[1,4]diazepino[1,7-a]indol-11-yl)acetamide; MS (ESI+) for $C_{21}H_{21}N_3O_2$ m/z 348.2 $(M+H)^+$.

EXAMPLE 69
N-(2-ethylphenyl)-2-oxo-2-(2,3,4,5-tetrahydro-1H-[1,4]diazepino[1,7-a]indol-11-yl)acetamide

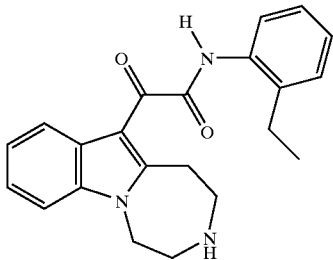

Following the general procedure of Example 20 (Chart B) and making non-critical variations but substituting 4-methoxyaniline with 2-ethylphenylamine gives N-(2-ethylphenyl)-2-oxo-2-(2,3,4,5-tetrahydro-1H-[1,4]diazepino[1,7-a]indol-11-yl)acetamide; MS (ESI+) for $C_{22}H_{23}N_3O_2$ m/z 362.1 $(M+H)^+$.

EXAMPLE 70
N-(4-chlorophenyl)-N-methyl-2-oxo-2-(2,3,4,5-tetrahydro-1H-[1,4]diazepino[1,7-a]indol-11-yl)acetamide

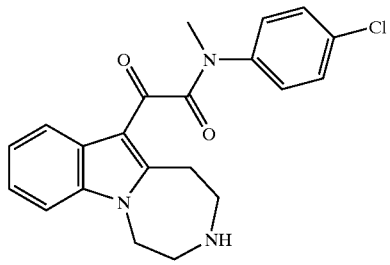

Following the general procedure of Example 20 (Chart B) and making non-critical variations but substituting 4-methoxyaniline with 4-chlorophenylamine gives N-(4-chlorophenyl)-N-methyl-2-oxo-2-(2,3,4,5-tetrahydro-1H-[1,4]diazepino[1,7-a]indol-11-yl)acetamide; MS (ESI+) for $C_{21}H_{20}ClN_3O_2$ m/z 382.0 $(M+H)^+$.

EXAMPLE 71
2-oxo-2-(2,3,4,5-tetrahydro-1H-[1,4]diazepino[1,7-a]indol-11-yl)-N-(5,6,7,8-tetrahydro-1-naphthalenyl)acetamide

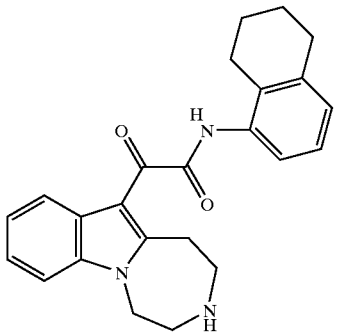

Following the general procedure of Example 20 (Chart B) and making non-critical variations but substituting 4-methoxyaniline with 5,6,7,8-tetrahydro-1-naphthalenylamine gives 2-oxo-2-(2,3,4,5-tetrahydro-1H-[1,4]diazepino[1,7-a]indol-11-yl)-N-(5,6,7,8-tetrahydro-1-naphthalenyl)acetamide; MS (ESI+) for $C_{24}H_{25}N_3O_2$ m/z 388.0 $(M+H)^+$.

EXAMPLE 72
2-oxo-2-(2,3,4,5-tetrahydro-1H-[1,4]diazepino[1,7-a]indol-11-yl)-N-(1,3,4-thiadiazol-2-yl)acetamide

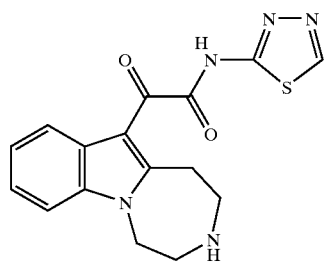

Following the general procedure of Example 20 (Chart B) and making non-critical variations but substituting 4-methoxyaniline with 1,3,4-thiadiazol-2-ylamine gives 2-oxo-2-(2,3,4,5-tetrahydro-1H-[1,4]diazepino[1,7-a]indol-11-yl)-N-(1,3,4-thiadiazol-2-yl)acetamide; MS (ESI+) for $C_{16}H_{15}N_5O_2S$ m/z 349.1 $(M+H)^+$.

EXAMPLE 73
2-oxo-N-(2-pyrazinyl)-2-(2,3,4,5-tetrahydro-1H-[1,4]diazepino[1,7-a]indol-11-yl)acetamide

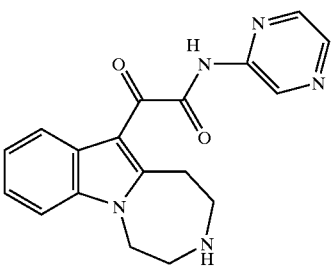

Following the general procedure of Example 20 (Chart B) and making non-critical variations but substituting 4-methoxyaniline with 2-pyrazinylamine gives 2-oxo-N-(2-pyrazinyl)-2-(2,3,4,5-tetrahydro-1H-[1,4]diazepino[1,7-a]indol-11-yl)acetamide; MS (ESI+) for $C_{18}H_{17}N_5O_2$ m/z 336.0 $(M+H)^+$.

EXAMPLE 74
2-oxo-N-(2-pyridinyl)-2-(2,3,4,5-tetrahydro-1H-[1,4]diazepino[1,7-a]indol-11-yl)acetamide

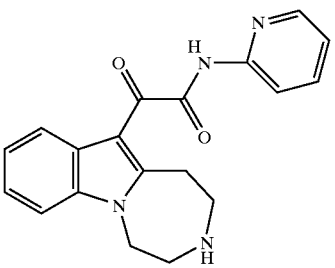

Following the general procedure of Example 20 (Chart B) and making non-critical variations but substituting 4-methoxyaniline with 2-pyridinylamine gives 2-oxo-N-(2-pyridinyl)-2-(2,3,4,5-tetrahydro-1H-[1,4]diazepino[1,7-a]indol-11-yl)acetamide; MS (ESI+) for $C_{19}H_{18}N_4O_2$ m/z 335.0 (M+H)⁺.

EXAMPLE 75
2-oxo-N-(3-pyridinyl)-2-(2,3,4,5-tetrahydro-1H-[1,4]diazepino[1,7-a]indol-11-yl)acetamide

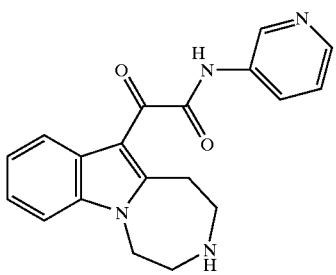

Following the general procedure of Example 20 (Chart B) and making non-critical variations but substituting 4-methoxyaniline with 3-pyridinylamine gives 2-oxo-N-(3-pyridinyl)-2-(2,3,4,5-tetrahydro-1H-[1,4]diazepino[1,7-a]indol-11-yl)acetamide; MS (ESI+) for $C_{19}H_{18}N_4O_2$ m/z 335.0 (M+H)⁺.

EXAMPLE 76
2-oxo-N-(4-pyridinyl)-2-(2,3,4,5-tetrahydro-1H-[1,4]diazepino[1,7-a]indol-11-yl)acetamide

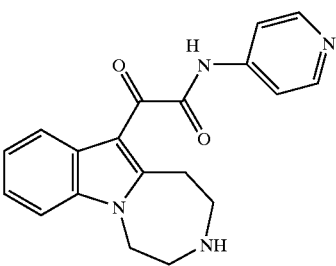

Following the general procedure of Example 20 (Chart B) and making non-critical variations but substituting 4-methoxyaniline with 4-pyridinylamine gives 2-oxo-N-(4-pyridinyl)-2-(2,3,4,5-tetrahydro-1H-[1,4]diazepino[1,7-a]indol-11-yl)acetamide; MS (ESI+) for $C_{19}H_{18}N_4O_2$ m/z 335.0 (M+H)⁺.

EXAMPLE 77
N-(2-cyanophenyl)-2-oxo-2-(2,3,4,5-tetrahydro-1H-[1,4]diazepino[1,7-a]indol-11-yl)acetamide

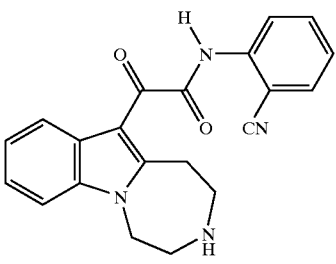

Following the general procedure of Example 20 (Chart B) and making non-critical variations but substituting 4-methoxyaniline with 2-cyanophenylamine gives N-(2-cyanophenyl)-2-oxo-2-(2,3,4,5-tetrahydro-1H-[1,4]diazepino[1,7-a]indol-11-yl)acetamide; MS (ESI+) for $C_{21}H_{18}N_4O_2$ m/z 358.9 (M+H)⁺.

EXAMPLE 78
N-(2-fluoro-5-methylphenyl)-2-oxo-2-(2,3,4,5-tetrahydro-1H-[1,4]diazepino[1,7-a]indol-11-yl)acetamide

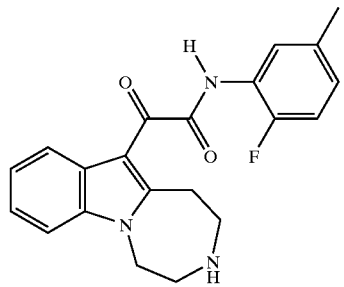

Following the general procedure of Example 20 (Chart B) and making non-critical variations but substituting 4-methoxyaniline with 2-fluoro-5-methylphenylamine gives N-(2-fluoro-5-methylphenyl)-2-oxo-2-(2,3,4,5-tetrahydro-1H-[1,4]diazepino[1,7-a]indol-11-yl)acetamide; MS (ESI+) for $C_{21}H_{20}FN_3O_2$ m/z 366.0 (M+H)⁺.

EXAMPLE 79
N-(2,3-dichlorophenyl)-2-oxo-2-(2,3,4,5-tetrahydro-1H-[1,4]diazepino[1,7-a]indol-11-yl)acetamide

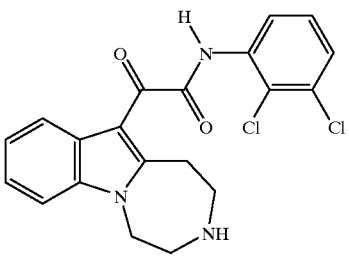

Following the general procedure of Example 20 (Chart B) and making non-critical variations but substituting 4-methoxyaniline with 2,3-dichlorophenylamine gives N-(2,3-dichlorophenyl)-2-oxo-2-(2,3,4,5-tetrahydro-1H-[1,4]diazepino[1,7-a]indol-11-yl)acetamide; MS (ESI+) for $C_{20}H_{17}Cl_2N_3O_2$ m/z 401.8 (M+H)⁺.

EXAMPLE 80
N-(2,6-dichlorophenyl)-2-oxo-2-(2,3,4,5-tetrahydro-1H-[1,4]diazepino[1,7-a]indol-11-yl)acetamide

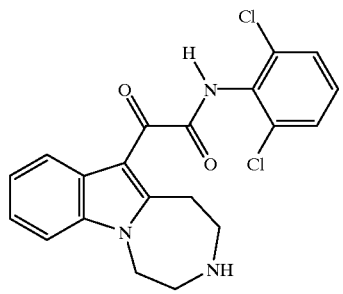

Following the general procedure of Example 20 (Chart B) and making non-critical variations but substituting 4-methoxyaniline with 2,6-dichlorophenylamine gives N-(2,6-dichlorophenyl)-2-oxo-2-(2,3,4,5-tetrahydro-1H-[1,4]diazepino[1,7-a]indol-11-yl)acetamide; MS (ESI+) for $C_{20}H_{17}Cl_2N_3O_2$ m/z 401.8 (M+H)+.

EXAMPLE 81

N-(2,3-dimethylphenyl)-2-oxo-2-(2,3,4,5-tetrahydro-1H-[1,4]diazepino[1,7-a]indol-11-yl)acetamide

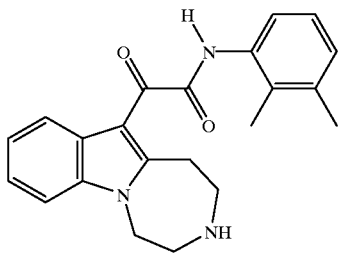

Following the general procedure of Example 20 (Chart B) and making non-critical variations but substituting 4-methoxyaniline with 2,3-dimethylphenylamine gives N-(2,3-dimethylphenyl)-2-oxo-2-(2,3,4,5-tetrahydro-1H-[1,4]diazepino[1,7-a]indol-11-yl)acetamide; MS (ESI+) for $C_{22}H_{23}N_3O_2$ m/z 362.0 (M+H)+.

EXAMPLE 82

N-(2,6-dimethylphenyl)-2-oxo-2-(2,3,4,5-tetrahydro-1H-[1,4]diazepino[1,7-a]indol-11-yl)acetamide

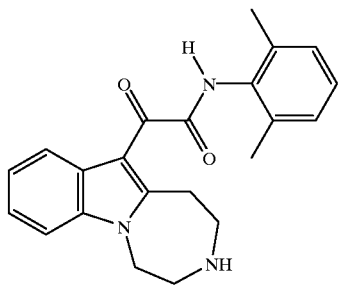

Following the general procedure of Example 20 (Chart B) and making non-critical variations but substituting 4-methoxyaniline with 2,6-dimethylphenylamine gives N-(2,6-dimethylphenyl)-2-oxo-2-(2,3,4,5-tetrahydro-1H-[1,4]diazepino[1,7-a]indol-11-yl)acetamide; MS (ESI+) for $C_{22}H_{23}N_3O_2$ m/z 362.0 (M+H)+.

EXAMPLE 83

N-(3,5-difluorophenyl)-2-oxo-2-(2,3,4,5-tetrahydro-1H-[1,4]diazepino[1,7-a]indol-11-yl)acetamide

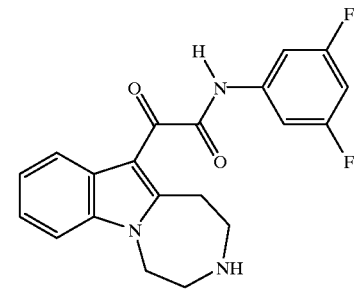

Following the general procedure of Example 20 (Chart B) and making non-critical variations but substituting 4-methoxyaniline with 3,5-difluorophenylamine gives N-(3,5-difluorophenyl)-2-oxo-2-(2,3,4,5-tetrahydro-1H-[1,4]diazepino[1,7-a]indol-11-yl)acetamide; MS (ESI+) for $C_{20}H_{17}F_2N_3O_2$ m/z 370.0 (M+H)+.

EXAMPLE 84

N-(3-chlorophenyl)-2-oxo-2-(2,3,4,5-tetrahydro-1H-[1,4]diazepino[1,7-a]indol-11-yl)acetamide

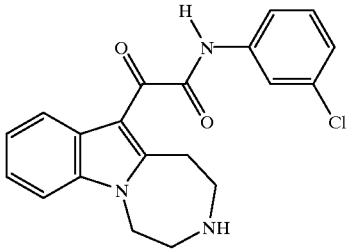

Following the general procedure of Example 20 (Chart B) and making non-critical variations but substituting 4-methoxyaniline with 3-chlorophenylamine gives N-(3-chlorophenyl)-2-oxo-2-(2,3,4,5-tetrahydro-1H-[1,4]diazepino[1,7-a]indol-11-yl)acetamide; MS (ESI+) for $C_{20}H_{18}ClN_3O_2$ m/z 367.9 (M+H)+.

EXAMPLE 85

N-(3-chloro-4-methylphenyl)-2-oxo-2-(2,3,4,5-tetrahydro-1H-[1,4]diazepino[1,7-a]indol-11-yl)acetamide

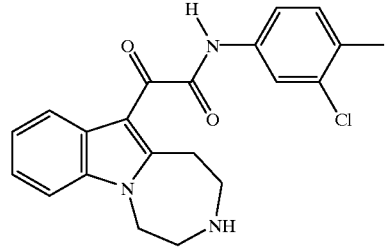

Following the general procedure of Example 20 (Chart B) and making non-critical variations but substituting 4-methoxyaniline with 3-chloro-4-methylphenylamine gives N-(3-chloro-4-methylphenyl)-2-oxo-2-(2,3,4,5-tetrahydro-1H-[1,4]diazepino[1,7-a]indol-11-yl)acetamide; MS (ESI+) for $C_{21}H_{20}ClN_3O_2$ m/z 381.9 (M+H)+.

EXAMPLE 86
N-(3-nitrophenyl)-2-oxo-2-(2,3,4,5-tetrahydro-1H-[1,4]diazepino[1,7-a]indol-11-yl)acetamide

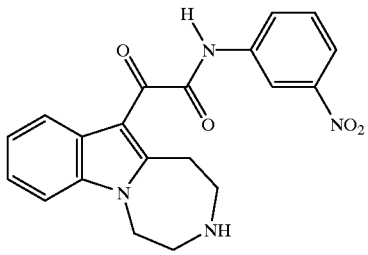

Following the general procedure of Example 20 (Chart B) and making non-critical variations but substituting 4-methoxyaniline with 3-nitrophenylamine gives N-(3-nitrophenyl)-2-oxo-2-(2,3,4,5-tetrahydro-1H-[1,4]diazepino[1,7-a]indol-11-yl)acetamide; MS (ESI+) for $C_{20}H_{18}N_4O_4$ m/z 378.9 (M+H)+.

EXAMPLE 87
N-(3-methoxyphenyl)-2-oxo-2-(2,3,4,5-tetrahydro-1H-[1,4]diazepino[1,7-a]indol-11-yl)acetamide

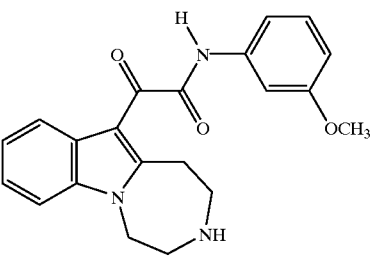

Following the general procedure of Example 20 (Chart B) and making non-critical variations but substituting 4-methoxyaniline with 3-methoxyphenylamine gives N-(3-methoxyphenyl)-2-oxo-2-(2,3,4,5-tetrahydro-1H-[1,4]diazepino[1,7-a]indol-11-yl)acetamide; MS (ESI+) for $C_{21}H_{21}N_3O_3$ m/z 363.9 (M+H)+.

EXAMPLE 88
2-oxo-2-(2,3,4,5-tetrahydro-1H-[1,4]diazepino[1,7-a]indol-11-yl)-N-[3-(trifluoromethyl)phenyl]acetamide

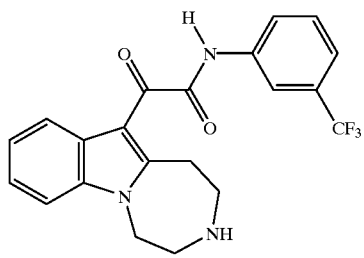

Following the general procedure of Example 20 (Chart B) and making non-critical variations but substituting 4-methoxyaniline with 3-(trifluoromethyl)phenylamine gives 2-oxo-2-(2,3,4,5-tetrahydro-1H-[1,4]diazepino[1,7-a]indol-11-yl)-N-[3-(trifluoromethyl)phenyl]acetamide; MS (ESI+) for $C_{21}H_{18}F_3N_3O_2$ m/z 401.9 (M+H)+.

EXAMPLE 89
N-(3-methylphenyl)-2-oxo-2-(2,3,4,5-tetrahydro-1H-[1,4]diazepino[1,7-a]indol-11-yl)acetamide

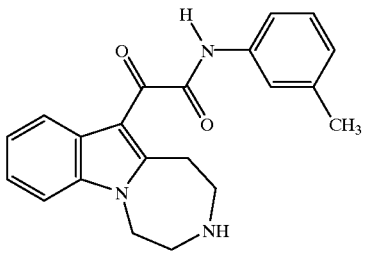

Following the general procedure of Example 20 (Chart B) and making non-critical variations but substituting 4-methoxyaniline with 3-methylphenylamine gives N-(3-methylphenyl)-2-oxo-2-(2,3,4,5-tetrahydro-1H-[1,4]diazepino[1,7-a]indol-11-yl)acetamide; MS (ESI+) for $C_{21}H_{21}N_3O_2$ m/z 348.0 (M+H)+.

EXAMPLE 90
N-(4-cyanophenyl)-2-oxo-2-(2,3,4,5-tetrahydro-1H-[1,4]diazepino[1,7-a]indol-11-yl)acetamide

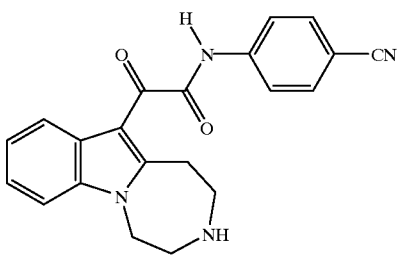

Following the general procedure of Example 20 (Chart B) and making non-critical variations but substituting 4-methoxyaniline with 4-cyanophenylamine gives N-(4-cyanophenyl)-2-oxo-2-(2,3,4,5-tetrahydro-1H-[1,4]diazepino[1,7-a]indol-11-yl)acetamide; MS (ESI+) for $C_{21}H_{18}N_4O_2$ m/z 358.9 (M+H)+.

EXAMPLE 91
N-(2-bromo-4-methylphenyl)-2-oxo-2-(2,3,4,5-tetrahydro-1H-[1,4]diazepino[1,7-a]indol-11-yl)acetamide

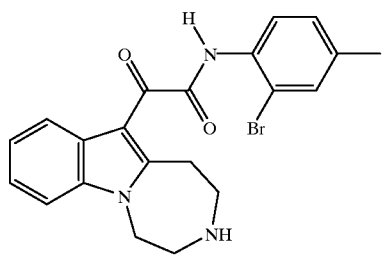

Following the general procedure of Example 20 (Chart B) and making non-critical variations but substituting 4-methoxyaniline with 2-bromo-4-methylphenylamine gives N-(2-bromo-4-methylphenyl)-2-oxo-2-(2,3,4,5-tetrahydro-1H-[1,4]diazepino[1,7-a]indol-11-yl)acetamide; MS (ESI+) for $C_{21}H_{20}BrN_3O_2$ m/z 427.7 (M+H)+.

EXAMPLE 92
N-(4-nitrophenyl)-2-oxo-2-(2,3,4,5-tetrahydro-1H-[1,4]diazepino[1,7-a]indol-11-yl)acetamide

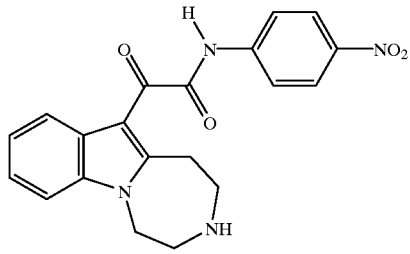

Following the general procedure of Example 20 (Chart B) and making non-critical variations but substituting 4-methoxyaniline with 4-nitrophenylamine gives N-(4-nitrophenyl)-2-oxo-2-(2,3,4,5-tetrahydro-1H-[1,4]diazepino[1,7-a]indol-11-yl)acetamide; MS (ESI+) for $C_{20}H_{18}N_4O_4$ m/z 379.0 (M+H)$^+$.

EXAMPLE 93
2-oxo-N-(4-phenoxyphenyl)-2-(2,3,4,5-tetrahydro-1H-[1,4]diazepino[1,7-a]indol-11-yl)acetamide

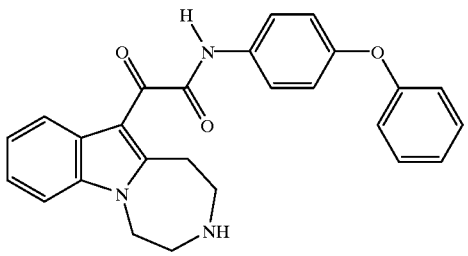

Following the general procedure of Example 20 (Chart B) and making non-critical variations but substituting 4-methoxyaniline with 4-phenoxyphenylamine gives 2-oxo-N-(4-phenoxyphenyl)-2-(2,3,4,5-tetrahydro-1H-[1,4]diazepino[1,7-a]indol-11-yl)acetamide; MS (ESI+) for $C_{26}H_{23}N_3O_3$ m/z 425.9 (M+H)$^+$.

EXAMPLE 94
N-[1,1'-biphenyl]-4-yl-2-oxo-2-(2,3,4,5-tetrahydro-1H-[1,4]diazepino[1,7-a]indol-11-yl)acetamide

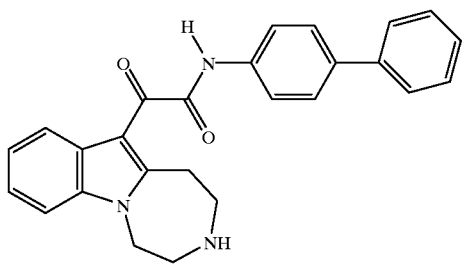

Following the general procedure of Example 20 (Chart B) and making non-critical variations but substituting 4-methoxyaniline with [1,1'-biphenyl]-4-ylamine gives N-[1,1'-biphenyl]-4-yl-2-oxo-2-(2,3,4,5-tetrahydro-1H-[1,4]diazepino[1,7-a]indol-11-yl)acetamide; MS (ESI+) for $C_{26}H_{23}N_3O_2$ m/z 409.9 (M+H)$^+$.

EXAMPLE 95
N-(4-isopropylphenyl)-2-oxo-2-(2,3,4,5-tetrahydro-1H-[1,4]diazepino[1,7-a]indol-11-yl)acetamide

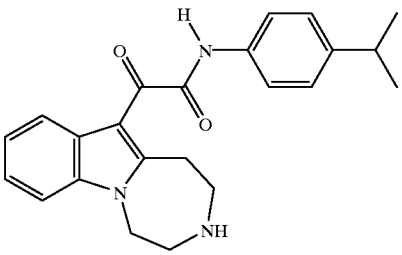

Following the general procedure of Example 20 (Chart B) and making non-critical variations but substituting 4-methoxyaniline with 4-isopropylphenylamine gives N-(4-isopropylphenyl)-2-oxo-2-(2,3,4,5-tetrahydro-1H-[1,4]diazepino[1,7-a]indol-11-yl)acetamide; MS (ESI+) for $C_{23}H_{25}N_3O_2$ m/z 376.0 (M+H)$^+$.

EXAMPLE 96
N-(4-chloro-2-fluorophenyl)-2-oxo-2-(2,3,4,5-tetrahydro-1H-[1,4]diazepino[1,7-a]indol-11-yl)acetamide

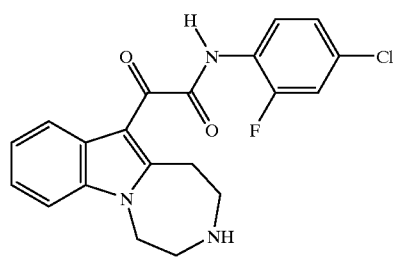

Following the general procedure of Example 20 (Chart B) and making non-critical variations but substituting 4-methoxyaniline with 4-chloro-2-fluorophenylamine gives N-(4-chloro-2-fluorophenyl)-2-oxo-2-(2,3,4,5-tetrahydro-1H-[1,4]diazepino[1,7-a]indol-11-yl)acetamide; MS (ESI+) for $C_{20}H_{17}ClFN_3O_2$ m/z 385.9 (M+H)$^+$.

EXAMPLE 97
N-(2-cyano-3-fluorophenyl)-2-oxo-2-(2,3,4,5-tetrahydro-1H-[1,4]diazepino[1,7-a]indol-11-yl)acetamide

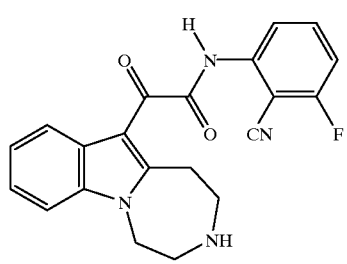

Following the general procedure of Example 20 (Chart B) and making non-critical variations but substituting 4-methoxyaniline with 2-cyano-3-fluorophenylamine gives N-(2-cyano-3-fluorophenyl)-2-oxo-2-(2,3,4,5-tetrahydro-1H-[1,4]diazepino[1,7-a]indol-11-yl)acetamide; MS (ESI+) for $C_{21}H_{17}FN_4O_2$ m/z 376.9 (M+H)$^+$.

EXAMPLE 98
N-(4-chlorophenyl)-N-ethyl-2-oxo-2-(2,3,4,5-tetrahydro-1H-[1,4]diazepino[1,7-a]indol-11-yl)acetamide

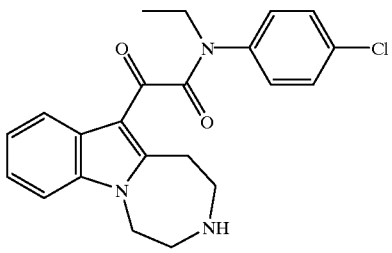

Following the general procedure of Example 20 (Chart B) and making non-critical variations but substituting 4-methoxyaniline with N-(4-chlorophenyl)-N-ethylamine gives N-(4-chlorophenyl)-N-ethyl-2-oxo-2-(2,3,4,5-tetrahydro-1H-[1,4]diazepino[1,7-a]indol-11-yl)acetamide; MS (ESI+) for $C_{22}H_{22}ClN_3O_2$ m/z 395.9 (M+H)$^+$.

EXAMPLE 99
N-(4-bromo-2-chloro-6-methylphenyl)-2-oxo-2-(2,3,4,5-tetrahydro-1H-[1,4]diazepino[1,7-a]indol-11-yl)acetamide

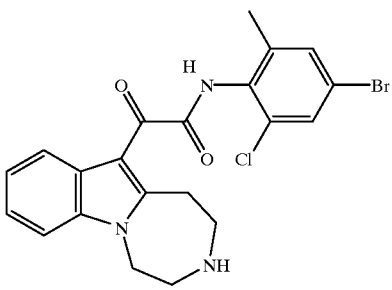

Following the general procedure of Example 20 (Chart B) and making non-critical variations but substituting 4-methoxyaniline with 4-bromo-2-chloro-6-methylphenylamine gives N-(4-bromo-2-chloro-6-methylphenyl)-2-oxo-2-(2,3,4,5-tetrahydro-1H-[1,4]diazepino[1,7-a]indol-11-yl)acetamide; MS (ESI+) for $C_{21}H_{19}BrClN_3O_2$ m/z 461.7 (M+H)$^+$.

EXAMPLE 100
N-(3-chloro-4-iodophenyl)-2-oxo-2-(2,3,4,5-tetrahydro-1H-[1,4]diazepino[1,7-a]indol-11-yl)acetamide

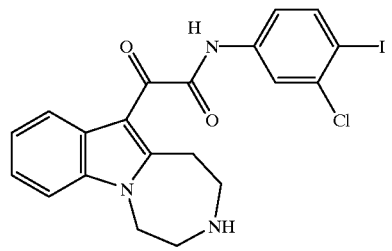

Following the general procedure of Example 20 (Chart B) and making non-critical variations but substituting 4-methoxyaniline with 3-chloro-4-iodophenylamine gives N-(3-chloro-4-iodophenyl)-2-oxo-2-(2,3,4,5-tetrahydro-1H-[1,4]diazepino[1,7-a]indol-11-yl)acetamide; MS (ESI+) for $C_{20}H_{17}ClIN_3O_2$ m/z 493.8 (M+H)$^+$.

EXAMPLE 101
N-ethyl-N-(2-fluorophenyl)-2-oxo-2-(2,3,4,5-tetrahydro-1H-[1,4]diazepino[1,7-a]indol-11-yl)acetamide

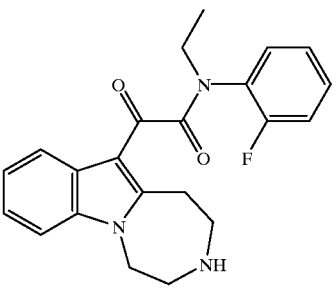

Following the general procedure of Example 20 (Chart B) and making non-critical variations but substituting 4-methoxyaniline with N-ethyl-N-(2-fluorophenyl)amine gives N-ethyl-N-(2-fluorophenyl)-2-oxo-2-(2,3,4,5-tetrahydro-1H-[1,4]diazepino[1,7-a]indol-11-yl)acetamide; MS (ESI+) for $C_{22}H_{22}FN_3O_2$ m/z 380.0 (M+H)$^+$.

EXAMPLE 102
N-(3-benzylphenyl)-2-oxo-2-(2,3,4,5-tetrahydro-1H-[1,4]diazepino[1,7-a]indol-11-yl)acetamide

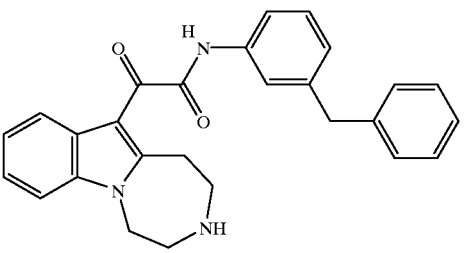

Following the general procedure of Example 20 (Chart B) and making non-critical variations but substituting 4-methoxyaniline with 3-benzylphenylamine gives N-(3-benzylphenyl)-2-oxo-2-(2,3,4,5-tetrahydro-1H-[1,4]diazepino[1,7-a]indol-11-yl)acetamide; MS (ESI+) for $C_{27}H_{25}N_3O_2$ m/z 424.0 (M+H)$^+$.

EXAMPLE 103
N-(4-methylphenyl)-2-oxo-2-(2,3,4,5-tetrahydro-1H-[1,4]diazepino[1,7-a]indol-11-yl)acetamide

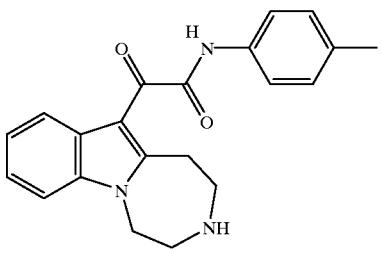

Following the general procedure of Example 20 (Chart B) and making non-critical variations but substituting 4-methoxyaniline with 4-methylphenylamine gives N-(4-methylphenyl)-2-oxo-2-(2,3,4,5-tetrahydro-1H-[1,4]diazepino[1,7-a]indol-11-yl)acetamide; MS (ESI+) for $C_{21}H_{21}N_3O_2$ m/z 348.0 (M+H)$^+$.

EXAMPLE 104
N-(3-ethylphenyl)-2-oxo-2-(2,3,4,5-tetrahydro-1H-[1,4]diazepino[1,7-a]indol-11-yl)acetamide

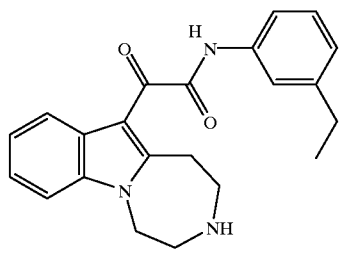

Following the general procedure of Example 20 (Chart B) and making non-critical variations but substituting 4-methoxyaniline with 3-ethylphenylamine gives N-(3-ethylphenyl)-2-oxo-2-(2,3,4,5-tetrahydro-1H-[1,4]diazepino[1,7-a]indol-11-yl)acetamide; MS (ESI+) for $C_{22}H_{23}N_3O_2$ m/z 362.0 (M+H)+.

EXAMPLE 105
N-(1-naphthyl)-2-oxo-2-(2,3,4,5-tetrahydro-1H-[1,4]diazepino[1,7-a]indol-11-yl)acetamide

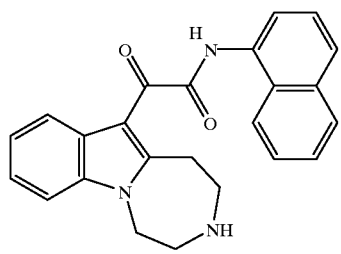

Following the general procedure of Example 20 (Chart B) and making non-critical variations but substituting 4-methoxyaniline with 1-naphthylamine gives N-(1-naphthyl)-2-oxo-2-(2,3,4,5-tetrahydro-1H-[1,4]diazepino[1,7-a]indol-11-yl)acetamide; MS (ESI+) for $C_{24}H_{21}N_3O_2$ m/z 384.0 (M+H)+.

EXAMPLE 106
2-oxo-N-(8-quinolinyl)-2-(2,3,4,5-tetrahydro-1H-[1,4]diazepino[1,7-a]indol-11-yl)acetamide trifluoroacetate

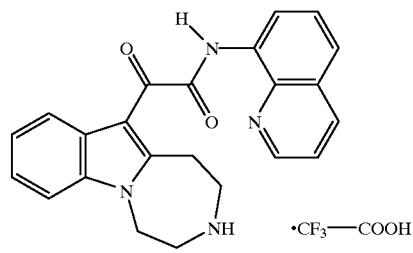

Following the general procedure of Example 20 (Chart B) and making non-critical variations but substituting 4-methoxyaniline with 8-quinolinylamine gives 2-oxo-N-(8-quinolinyl)-2-(2,3,4,5-tetrahydro-1H-[1,4]diazepino[1,7-a]indol-11-yl)acetamide trifluoroacetate; MS (ESI+) for $C_{23}H_{20}N_4O_2$ m/z 385.2 (M+H)+.

EXAMPLE 107
N-(5-methyl-1,3-thiazol-2-yl)-2-oxo-2-(2,3,4,5-tetrahydro-1H-[1,4]diazepino[1,7-a]indol-11-yl)acetamide

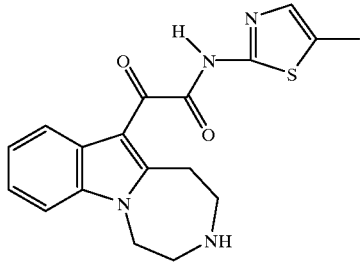

Following the general procedure of Example 20 (Chart B) and making non-critical variations but substituting 4-methoxyaniline with 5-methyl-1,3-thiazol-2-ylamine gives N-(5-methyl-1,3-thiazol-2-yl)-2-oxo-2-(2,3,4,5-tetrahydro-1H-[1,4]diazepino[1,7-a]indol-11-yl)acetamide; MS (ESI+) for $C_{18}H_{18}N_4O_2S$ m/z 355.1 (M+H)+.

EXAMPLE 108
N-(3-methyl-5-isothiazolyl)-2-oxo-2-(2,3,4,5-tetrahydro-1H-[1,4]diazepino[1,7-a]indol-11-yl)acetamide trifluoroacetate

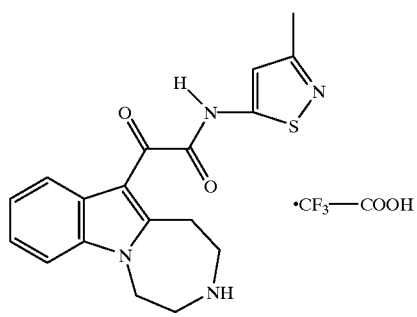

Following the general procedure of Example 20 (Chart B) and making non-critical variations but substituting 4-methoxyaniline with 3-methyl-5-isothiazolylamine gives N-(3-methyl-5-isothiazolyl)-2-oxo-2-(2,3,4,5-tetrahydro-1H-[1,4]diazepino[1,7-a]indol-11-yl)acetamide trifluoroacetate; MS (ESI+) for $C_{18}H_{18}N_4O_2S$ m/z 355.1 (M+H)+.

EXAMPLE 109
N-(3-methyl-5-isoxazolyl)-2-oxo-2-(2,3,4,5-tetrahydro-1H-[1,4]diazepino[1,7-a]indol-11-yl)acetamide

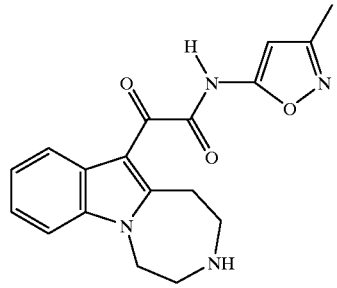

Following the general procedure of Example 20 (Chart B) and making non-critical variations but substituting 4-methoxyaniline with 3-methyl-5-isoxazolylamine gives N-(3-methyl-5-isoxazolyl)-2-oxo-2-(2,3,4,5-tetrahydro-1H-[1,4]diazepino[1,7-a]indol-11-yl)acetamide; MS (ESI+) for $C_{18}H_{18}N_4O_3$ m/z 339.1 (M+H)+.

EXAMPLE 110

N-(1,3-benzothiazol-2-yl)-2-oxo-2-(2,3,4,5-tetrahydro-1H-[1,4]diazepino[1,7-a]indol-11-yl)acetamide

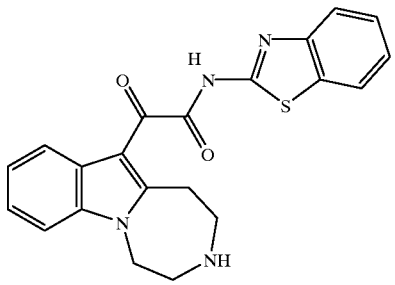

Following the general procedure of Example 20 (Chart B) and making non-critical variations but substituting 4-methoxyaniline with 1,3-benzothiazol-2-ylamine gives N-(1,3-benzothiazol-2-yl)-2-oxo-2-(2,3,4,5-tetrahydro-1H-[1,4]diazepino[1,7-a]indol-11-yl)acetamide; MS (ESI+) for $C_{21}H_{18}N_4O_2S$ m/z 391.1 (M+H)+.

EXAMPLE 111

N-(3-chloro-2-methylphenyl)-2-(2,3,4,5-tetrahydro-1H-[1,4]diazepino[1,7-a]indol-11-yl)acetamide

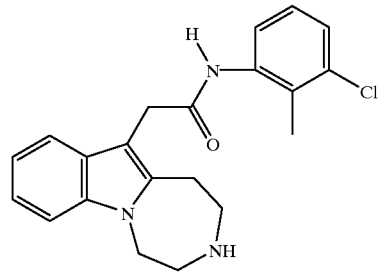

Following the general procedure of Example 20 (Chart B) and making non-critical variations but substituting 4-methoxyaniline with 3-chloro-2-methylphenylamine gives N-(3-chloro-2-methylphenyl)-2-(2,3,4,5-tetrahydro-1H-[1,4]diazepino[1,7-a]indol-11-yl)acetamide; MS (ESI+) for $C_{21}H_{22}ClN_3O$ m/z 368.2 (M+H)+.

EXAMPLE 112

N-(3-chloro-2-methylphenyl)-2-oxo-2-(2,3,4,5-tetrahydro-1H-[1,4]diazepino[1,7-a]indol-11-yl)acetamide

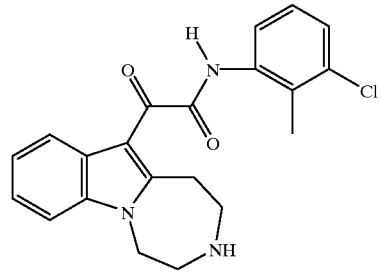

Following the general procedure of Example 20 (Chart B) and making non-critical variations but substituting 4-methoxyaniline with 3-chloro-2-methylphenylamine gives N-(3-chloro-2-methylphenyl)-2-oxo-2-(2,3,4,5-tetrahydro-1H-[1,4]diazepino[1,7-a]indol-11-yl)acetamide; MS (ESI+) for C21 H20 Cl N3 $O_2$ m/z 382.1 (M+H)+.

EXAMPLE 113

N-[2-methyl-3-(trifluoromethyl)phenyl]-2-oxo-2-(2,3,4,5-tetrahydro-1H-[1,4]diazepino[1,7-a]indol-11-yl)acetamide

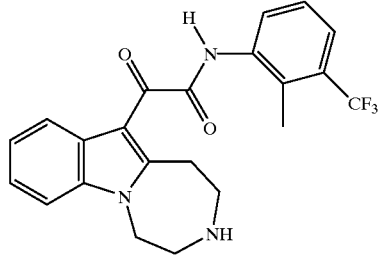

Following the general procedure of Example 20 (Chart B) and making non-critical variations but substituting 4-methoxyaniline with 2-methyl-3-(trifluoromethyl)phenylamine gives N-[2-methyl-3-(trifluoromethyl)phenyl]-2-oxo-2-(2,3,4,5-tetrahydro-1H-[1,4]diazepino[1,7-a]indol-11-yl)acetamide; MS (ESI+) for $C_{22}H_{20}F_3N_3O_2$ m/z 416.0 (M+H)+.

EXAMPLE 114

N-(4-bromo-2-chloro-6-methylphenyl)-2-(2,3,4,5-tetrahydro-1H-[1,4]diazepino[1,7-a]indol-11-yl)acetamide

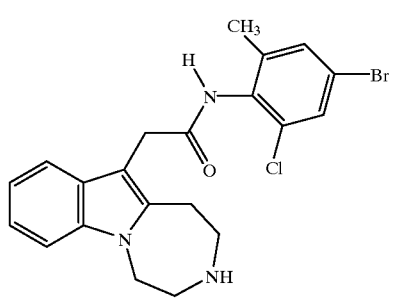

Following the general procedure of Example 20 (Chart B) and making non-critical variations but substituting 4-methoxyaniline with 4-bromo-2-chloro-6-methylphenylamine gives N-(4-bromo-2-chloro-6-methylphenyl)-2-(2,3,4,5-tetrahydro-1H-[1,4]diazepino[1,7-a]indol-11-yl)acetamide; MS (ESI+) for $C_{21}H_{21}BrClN_3O$ m/z 447.8 (M+H)+.

EXAMPLE 115
N-(1-ethyl-1H-pyrazol-5-yl)-2-oxo-2-(2,3,4,5-tetrahydro-1H-[1,4]diazepino[1,7-a]indol-11-yl)acetamide

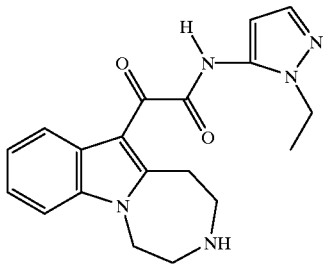

Following the general procedure of Example 20 (Chart B) and making non-critical variations but substituting 4-methoxyaniline with 1-ethyl-1H-pyrazol-5-ylamine gives N-(1-ethyl-1H-pyrazol-5-yl)-2-oxo-2-(2,3,4,5-tetrahydro-1H-[1,4]diazepino[1,7-a]indol-11-yl)acetamide; MS (ESI+) for $C_{19}H_{21}N_5O_2$ m/z 352.2 (M+H)$^+$.

EXAMPLE 116
2-oxo-N-(4-phenyl-1,3-thiazol-2-yl)-2-(2,3,4,5-tetrahydro-1H-[1,4]diazepino[1,7-a]indol-11-yl)acetamide

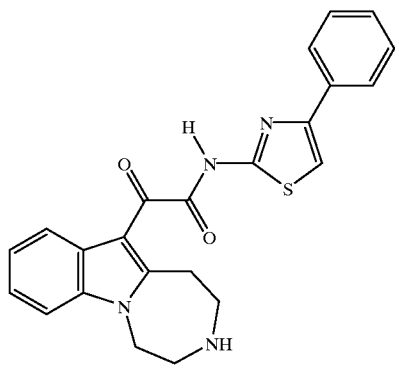

Following the general procedure of Example 20 (Chart B) and making non-critical variations but substituting 4-methoxyaniline with 4-phenyl-1,3-thiazol-2-ylamine gives 2-oxo-N-(4-phenyl-1,3-thiazol-2-yl)-2-(2,3,4,5-tetrahydro-1H-[1,4]diazepino[1,7-a]indol-11-yl)acetamide; MS (ESI+) for $C_{23}H_{20}N_4O_2S$ m/z 417.0 (M+H)$^+$.

EXAMPLE 117
N-(5-methyl-3-isoxazolyl)-2-oxo-2-(2,3,4,5-tetrahydro-1H-[1,4]diazepino[1,7-a]indol-11-yl)acetamide

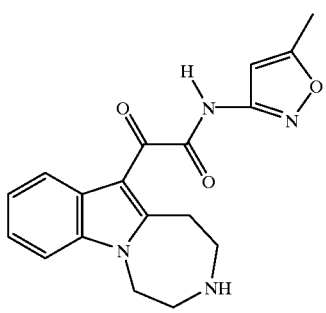

Following the general procedure of Example 20 (Chart B) and making non-critical variations but substituting 4-methoxyaniline with 5-methyl-3-isoxazolylamine gives N-(5-methyl-3-isoxazolyl)-2-oxo-2-(2,3,4,5-tetrahydro-1H-[1,4]diazepino[1,7-a]indol-11-yl)acetamide; MS (ESI+) for $C_{18}H_{18}N_4O_3$ m/z 339.1 (M+H)$^+$.

EXAMPLE 118
1-(2,3,4,5-tetrahydro-1H-[1,4]diazepino[1,7-a]indol-11-yl)-2-(5,6,7,8-tetrahydro-1-naphthalenyloxy)ethanone

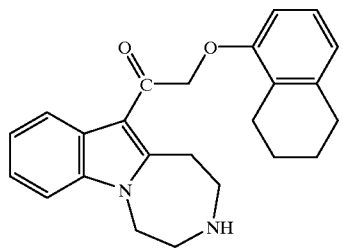

Following the general procedure of Example 47 (Chart E, Step 2) and making non-critical variations but substituting phenol with 5,6,7,8-tetrahydro-1-naphthalenol gives 1-(2,3,4,5-tetrahydro-1H-[1,4]diazepino[1,7-a]indol-11-yl)-2-(5,6,7,8-tetrahydro-1-naphthalenyloxy)ethanone; MS (ESI+) for $C_{24}H_{26}N_2O_2$ m/z 375.1 (M+H)$^+$.

EXAMPLE 119
2-(2-bromophenoxy)-1-(2,3,4,5-tetrahydro-1H-[1,4]diazepino[1,7-a]indol-11-yl)ethanone

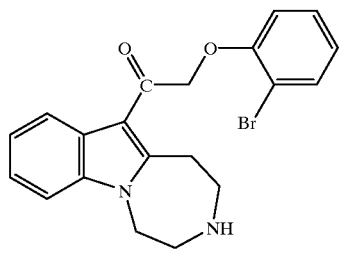

Following the general procedure of Example 47 (Chart E, Step 2) and making non-critical variations but substituting phenol with 2-bromophenol gives 2-(2-bromophenoxy)-1-(2,3,4,5-tetrahydro-1H-[1,4]diazepino[1,7-a]indol-11-yl)ethanone; MS (ESI+) for $C_{20}H_{19}BrN_2O_2$ m/z 400.9 (M+H)$^+$.

EXAMPLE 120
2-(2-isopropylphenoxy)-1-(2,3,4,5-tetrahydro-1H-[1,4]diazepino[1,7-a]indol-11-yl)ethanone

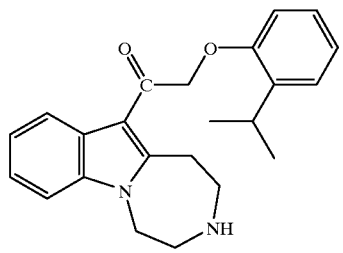

Following the general procedure of Example 47 (Chart E, Step 2) and making non-critical variations but substituting phenol with 2-isopropylphenol gives 2-(2- isopropylphenoxy)-1-(2,3,4,5-tetrahydro-1H-[1,4]diazepino[1,7-a]indol-11-yl)ethanone; MS (ESI+) for $C_{23}H_{26}N_2O_2$ m/z 363.1 (M+H)$^+$.

EXAMPLE 121
2-(2-ethylphenoxy)-1-(2,3,4,5-tetrahydro-1H-[1,4]diazepino[1,7-a]indol-11-yl)ethanone

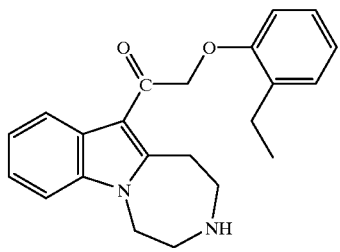

Following the general procedure of Example 47 (Chart E, Step 2) and making non-critical variations but substituting phenol with 2-ethylphenol gives 2-(2-ethylphenoxy)-1-(2,3,4,5-tetrahydro-1H-[1,4]diazepino[1,7-a]indol-11-yl)ethanone; MS (ESI+) for $C_{22}H_{24}N_2O_2$ m/z 349.1 (M+H)$^+$.

EXAMPLE 122
2-(3-bromophenoxy)-1-(2,3,4,5-tetrahydro-1H-[1,4]diazepino[1,7-a]indol-11-yl)ethanone

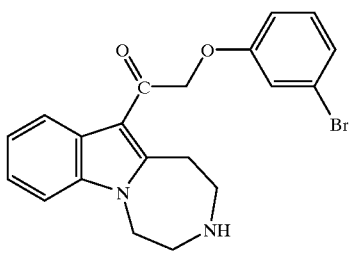

Following the general procedure of Example 47 (Chart E, Step 2) and making non-critical variations but substituting phenol with 3-bromophenol gives 2-(3-bromophenoxy)-1-(2,3,4,5-tetrahydro-1H-[1,4]diazepino[1,7-a]indol-11-yl)ethanone; MS (ESI+) for $C_{20}H_{19}BrN_2O_2$ m/z 400.9 (M+H)$^+$.

EXAMPLE 123
2-(3-fluorophenoxy)-1-(2,3,4,5-tetrahydro-1H-[1,4]diazepino[1,7-a]indol-11-yl)ethanone

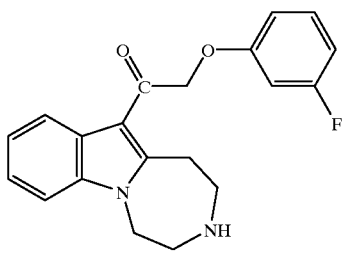

Following the general procedure of Example 47 (Chart E, Step 2) and making non-critical variations but substituting phenol with 3-fluorophenol gives 2-(3-fluorophenoxy)-1-(2,3,4,5-tetrahydro-1H-[1,4]diazepino[1,7-a]indol-11-yl)ethanone; MS (ESI+) for $C_{20}H_{19}FN_2O_2$ m/z 339.1 (M+H)$^+$.

EXAMPLE 124
2-(3-methoxyphenoxy)-1-(2,3,4,5-tetrahydro-1H-[1,4]diazepino[1,7-a]indol-11-yl)ethanone

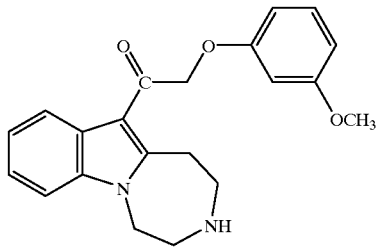

Following the general procedure of Example 47 (Chart E, Step 2) and making non-critical variations but substituting phenol with 3-methoxyphenol gives 2-(3-methoxyphenoxy)-1-(2,3,4,5-tetrahydro-1H-[1,4]diazepino[1,7-a]indol-11-yl)ethanone; MS (ESI+) for $C_{21}H_{22}N_2O_3$ m/z 351.1 (M+H)$^+$.

EXAMPLE 125
1-(2,3,4,5-tetrahydro-1H-[1,4]diazepino[1,7-a]indol-11-yl)-2-[3-(trifluoromethyl)phenoxy]ethanone

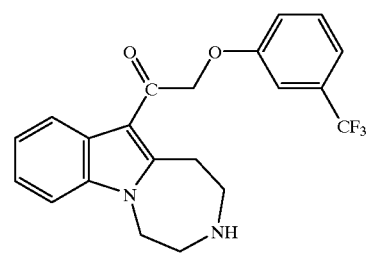

Following the general procedure of Example 47 (Chart E, Step 2) and making non-critical variations but substituting phenol with 3-(trifluoromethyl)phenol gives 1-(2,3,4,5-tetrahydro-1H-[1,4]diazepino[1,7-a]indol-11-yl)-2-[3-(trifluoromethyl)phenoxy]ethanone; MS (ESI+) for $C_{21}H_{19}F_3N_2O_2$ m/z 389.0 (M+H)$^+$.

EXAMPLE 126
2-(3-isopropylphenoxy)-1-(2,3,4,5-tetrahydro-1H-[1,4]diazepino[1,7-a]indol-11-yl)ethanone

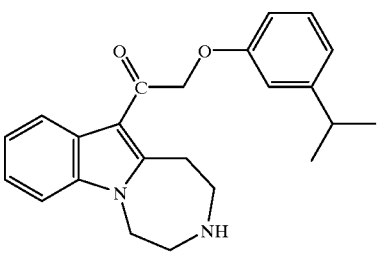

Following the general procedure of Example 47 (Chart E, Step 2) and making non-critical variations but substituting phenol with 3-isopropylphenol gives 2-(3-isopropylphenoxy)-1-(2,3,4,5-tetrahydro-1H-[1,4]diazepino[1,7-a]indol-11-yl)ethanone; MS (ESI+) for $C_{23}H_{26}N_2O_2$ m/z 363.1 (M+H)$^+$.

EXAMPLE 127

2-(3-ethylphenoxy)-1-(2,3,4,5-tetrahydro-1H-[1,4]diazepino[1,7-a]indol-11-yl)ethanone

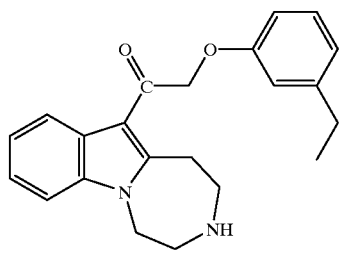

Following the general procedure of Example 47 (Chart E, Step 2) and making non-critical variations but substituting phenol with 3-ethylphenol gives 2-(3-ethylphenoxy)-1-(2,3,4,5-tetrahydro-1H-[1,4]diazepino[1,7-a]indol-11-yl)ethanone; MS (ESI+) for $C_{22}H_{24}N_2O_2$ m/z 349.2 (M+H)$^+$.

EXAMPLE 128

2-(4-fluorophenoxy)-1-(2,3,4,5-tetrahydro-1H-[1,4]diazepino[1,7-a]indol-11-yl)ethanone

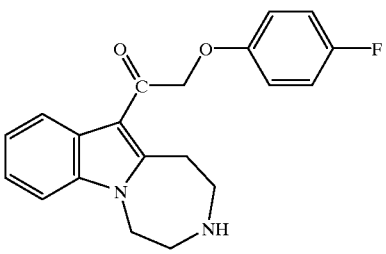

Following the general procedure of Example 47 (Chart E, Step 2) and making non-critical variations but substituting phenol with 4-fluorophenol gives 2-(4-fluorophenoxy)-1-(2,3,4,5-tetrahydro-1H-[1,4]diazepino[1,7-a]indol-11-yl)ethanone; MS (ESI+) for $C_{20}H_{19}FN_2O_2$ m/z 339.1 (M+H)$^+$.

EXAMPLE 129

2-(4-iodophenoxy)-1-(2,3,4,5-tetrahydro-1H-[1,4]diazepino[1,7-a]indol-11-yl)ethanone

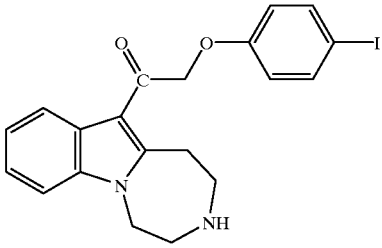

Following the general procedure of Example 47 (Chart E, Step 2) and making non-critical variations but substituting phenol with 4-iodophenol gives 2-(4-iodophenoxy)-1-(2,3,4,5-tetrahydro-1H-[1,4]diazepino[1,7-a]indol-11-yl)ethanone; MS (ESI+) for $C_{20}H_{19}IN_2O_2$ m/z 446.8 (M+H)$^+$.

EXAMPLE 130

2-[4-(benzyloxy)phenoxy]-1-(2,3,4,5-tetrahydro-1H-[1,4]diazepino[1,7-a]indol-11-yl)ethanone

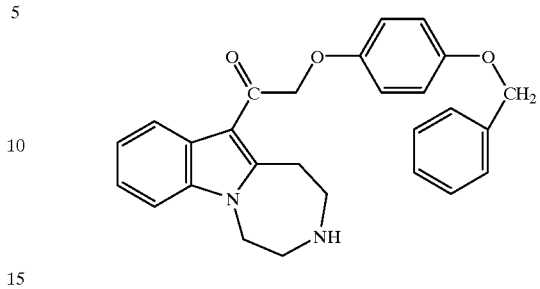

Following the general procedure of Example 47 (Chart E, Step 2) and making non-critical variations but substituting phenol with 4-(benzyloxy)phenol gives 2-[4-(benzyloxy)phenoxy]-1-(2,3,4,5-tetrahydro-1H-[1,4]diazepino[1,7-a]indol-11-yl)ethanone; MS (ESI+) for $C_{27}H_{26}N_2O_3$ m/z 427.0 (M+H)$^+$.

EXAMPLE 131

2-(4-butoxyphenoxy)-1-(2,3,4,5-tetrahydro-1H-[1,4]diazepino[1,7-a]indol-11-yl)ethanone

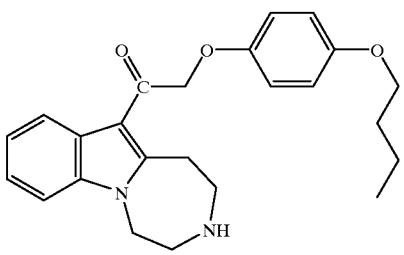

Following the general procedure of Example 47 (Chart E, Step 2) and making non-critical variations but substituting phenol with 4-butoxyphenol gives 2-(4-butoxyphenoxy)-1-(2,3,4,5-tetrahydro-1H-[1,4]diazepino[1,7-a]indol-11-yl)ethanone; MS (ESI+) for $C_{24}H_{28}N_2O_3$ m/z 393.0 (M+H)$^+$.

EXAMPLE 132

2-(3-tert-butylphenoxy)-1-(2,3,4,5-tetrahydro-1H-[1,4]diazepino[1,7-a]indol-11-yl)ethanone

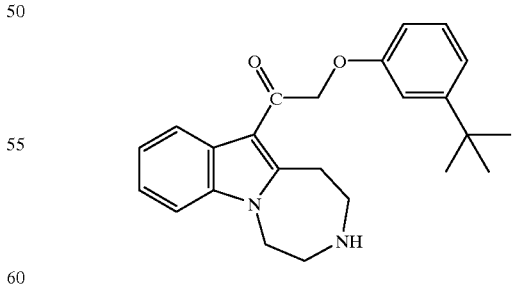

Following the general procedure of Example 47 (Chart E, Step 2) and making non-critical variations but substituting phenol with 3-tert-butylphenol gives 2-(3-tert-butylphenoxy)-1-(2,3,4,5-tetrahydro-1H-[1,4]diazepino[1,7-a]indol-11-yl)ethanone; MS (ESI+) for $C_{24}H_{28}N_2O_2$ m/z 377.0 (M+H)$^+$.

EXAMPLE 133

2-(4-ethylphenoxy)-1-(2,3,4,5-tetrahydro-1H-[1,4]diazepino[1,7-a]indol-11-yl)ethanone

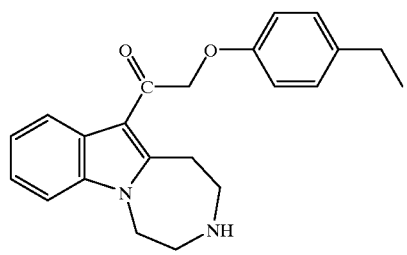

Following the general procedure of Example 47 (Chart E, Step 2) and making non-critical variations but substituting phenol with 4-ethylphenol gives 2-(4-ethylphenoxy)-1-(2,3,4,5-tetrahydro-1H-[1,4]diazepino[1,7-a]indol-11-yl)ethanone; MS (ESI+) for $C_{22}H_{24}N_2O_2$ m/z 349.1 $(M+H)^+$.

EXAMPLE 134

2-(1-naphthyloxy)-1-(2,3,4,5-tetrahydro-1H-[1,4]diazepino[1,7-a]indol-11-yl)ethanone

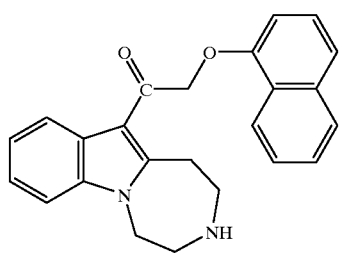

Following the general procedure of Example 47 (Chart E, Step 2) and making non-critical variations but substituting phenol with 1-naphthol gives 2-(1-naphthyloxy)-1-(2,3,4,5-tetrahydro-1H-[1,4]diazepino[1,7-a]indol-11-yl)ethanone; MS (ESI+) for $C_{24}H_{22}N_2O_2$ m/z 371.0 $(M+H)^+$.

EXAMPLE 135

2-[(4-chloro-1-naphthyl)oxy]-1-(2,3,4,5-tetrahydro-1H-[1,4]diazepino[1,7-a]indol-11-yl)ethanone

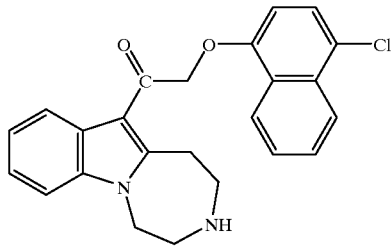

Following the general procedure of Example 47 (Chart E, Step 2) and making non-critical variations but substituting phenol with 4-chloro-1-naphthol gives 2-[(4-chloro-1-naphthyl)oxy]-1-(2,3,4,5-tetrahydro-1H-[1,4]diazepino[1,7-a]indol-11-yl)ethanone; MS (ESI+) for $C_{24}H_{21}ClN_2O_2$ m/z 405.0 $(M+H)^+$.

EXAMPLE 136

2-(2-naphthyloxy)-1-(2,3,4,5-tetrahydro-1H-[1,4]diazepino[1,7-a]indol-11-yl)ethanone

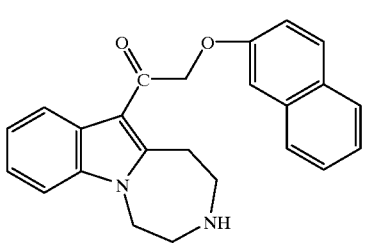

Following the general procedure of Example 47 (Chart E, Step 2) and making non-critical variations but substituting phenol with 2-naphthol gives 2-(2-naphthyloxy)-1-(2,3,4,5-tetrahydro-1H-[1,4]diazepino[1,7-a]indol-11-yl)ethanone; MS (ESI+) for $C_{24}H_{22}N_2O_2$ m/z 371.1 $(M+H)^+$.

EXAMPLE 137

2-(1,3-benzodioxol-5-yloxy)-1-(2,3,4,5-tetrahydro-1H-[1,4]diazepino[1,7-a]indol-11-yl)ethanone

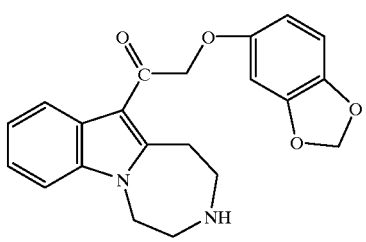

Following the general procedure of Example 47 (Chart E, Step 2) and making non-critical variations but substituting phenol with 1,3-benzodioxol-5-ol gives 2-(1,3-benzodioxol-5-yloxy)-1-(2,3,4,5-tetrahydro-1H-[1,4]diazepino[1,7-a]indol-11-yl)ethanone; MS (ESI+) for $C_{21}H_{20}N_2O_4$ m/z 365.1 $(M+H)^+$.

EXAMPLE 138

2-(4-quinolinyloxy)-1-(2,3,4,5-tetrahydro-1H-[1,4]diazepino[1,7-a]indol-11-yl)ethanone

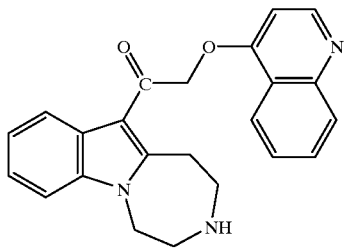

Following the general procedure of Example 47 (Chart E, Step 2) and making non-critical variations but substituting phenol with 4-quinolinol gives 2-(4-quinolinyloxy)-1-(2,3,4,5-tetrahydro-1H-[1,4]diazepino[1,7-a]indol-11-yl)ethanone; MS (ESI+) for $C_{23}H_{21}N_3O_2$ m/z 372.2 $(M+H)^+$.

EXAMPLE 139

2-(8-quinolinyloxy)-1-(2,3,4,5-tetrahydro-1H-[1,4]diazepino[1,7-a]indol-11-yl)ethanone

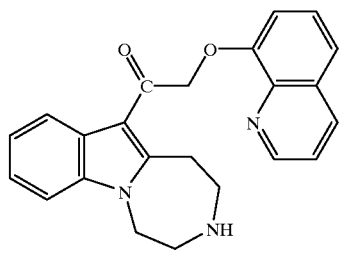

Following the general procedure of Example 47 (Chart E, Step 2) and making non-critical variations but substituting phenol with 8-quinolinol gives 2-(8-quinolinyloxy)-1-(2,3,4,5-tetrahydro-1H-[1,4]diazepino[1,7-a]indol-11-yl)ethanone; MS (ESI+) for $C_{23}H_{21}N_3O_2$ m/z 372.2 $(M+H)^+$.

EXAMPLE 140

2-(5-isoquinolinyloxy)-1-(2,3,4,5-tetrahydro-1H-[1,4]diazepino[1,7-a]indol-11-yl)ethanone

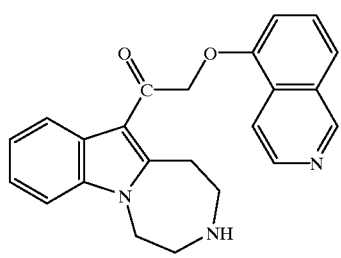

Following the general procedure of Example 47 (Chart E, Step 2) and making non-critical variations but substituting phenol with 5-isoquinolinol gives 2-(5-isoquinolinyloxy)-1-(2,3,4,5-tetrahydro-1H-[1,4]diazepino[1,7-a]indol-11-yl)ethanone; MS (ESI+) for $C_{23}H_{21}N_3O_2$ m/z 372.3 $(M+H)^+$.

EXAMPLE 141

1-(2,3,4,5-tetrahydro-1H-[1,4]diazepino[1,7-a]indol-11-yl)-2-(2,3,6,7-tetrahydro-1H,5H-pyrido[3,2,1-ij]quinolin-8-yloxy)ethanone

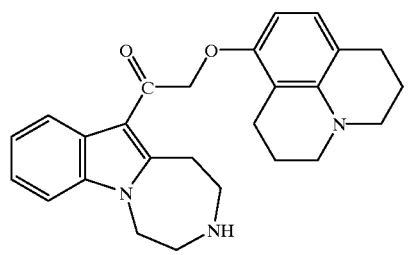

Following the general procedure of Example 47 (Chart E, Step 2) and making non-critical variations but substituting phenol with 2,3,6,7-tetrahydro-1H,5H-pyrido[3,2,1-ij]quinolin-8-ol gives 1-(2,3,4,5-tetrahydro-1H-[1,4]diazepino[1,7-a]indol-11-yl)-2-(2,3,6,7-tetrahydro-1H,5H-pyrido[3,2,1-ij]quinolin-8-yloxy)ethanone; MS (ESI+) for $C_{26}H_{29}N_3O_2$ m/z 416.4 $(M+H)^+$.

EXAMPLE 142

2-(4-nitrophenoxy)-1-(2,3,4,5-tetrahydro-1H-[1,4]diazepino[1,7-a]indol-11-yl)ethanone

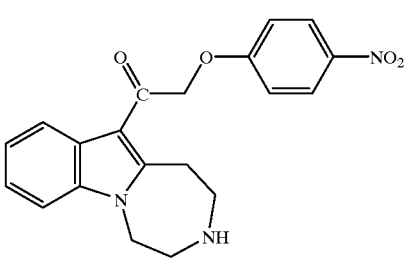

Following the general procedure of Example 47 (Chart E, Step 2) and making non-critical variations but substituting phenol with 4-nitrophenol gives 2-(4-nitrophenoxy)-1-(2,3,4,5-tetrahydro-1H-[1,4]diazepino[1,7-a]indol-11-yl)ethanone; MS (ESI+) for $C_{20}H_{19}N_3O_4$ m/z 366.0 $(M+H)^+$.

EXAMPLE 143

2-(2-iodophenoxy)-1-(2,3,4,5-tetrahydro-1H-[1,4]diazepino[1,7-a]indol-11-yl)ethanone

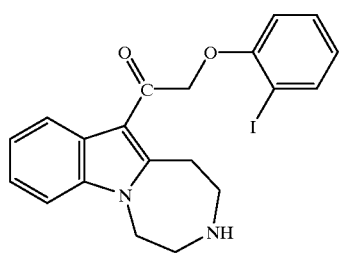

Following the general procedure of Example 47 (Chart E, Step 2) and making non-critical variations but substituting phenol with 2-iodophenol gives 2-(2-iodophenoxy)-1-(2,3,4,5-tetrahydro-1H-[1,4]diazepino[1,7-a]indol-11-yl)ethanone; MS (ESI+) for $C_{20}H_{19}IN_2O_2$ m/z 446.9 $(M+H)^+$.

EXAMPLE 144

2-[(4'-bromo[1,1'-biphenyl]-4-yl)oxy]-1-(2,3,4,5-tetrahydro-1H-[1,4]diazepino[1,7-a]indol-11-yl)ethanone

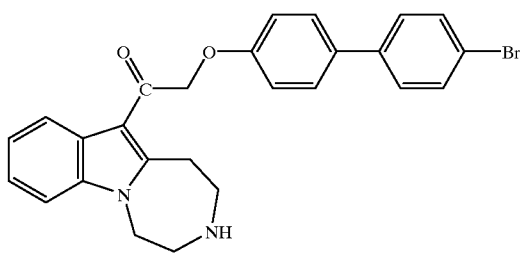

Following the general procedure of Example 47 (Chart E, Step 2) and making non-critical variations but substituting phenol with 4'-bromo[1,1'-biphenyl]-4-ol gives 2-[(4'-bromo[1,1'-biphenyl]-4-yl)oxy]-1-(2,3,4,5-tetrahydro-1H-[1,4]diazepino[1,7-a]indol-11-yl)ethanone; MS (ESI+) for $C_{26}H_{23}BrN_2O_2$ m/z 476.8 $(M+H)^+$.

EXAMPLE 145

5-methoxy-6-[2-oxo-2-(2,3,4,5-tetrahydro-1H-[1,4]diazepino[1,7-a]indol-11-yl)ethoxy]-1-indanone

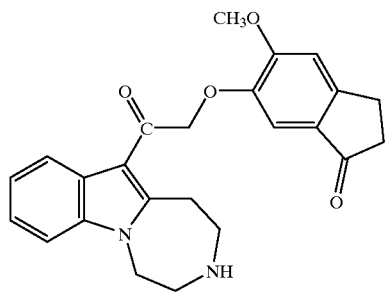

Following the general procedure of Example 47 (Chart E, Step 2) and making non-critical variations but substituting phenol with 6-hydroxy-5-methoxy-1-indanone gives 5-methoxy-6-[2-oxo-2-(2,3,4,5-tetrahydro-1H-[1,4]diazepino[1,7-a]indol-11-yl)ethoxy]-1-indanone; MS (ESI+) for $C_{24}H_{24}N_2O_4$ m/z 405.0 (M+H)$^+$.

EXAMPLE 146

7-[2-oxo-2-(2,3,4,5-tetrahydro-1H-[1,4]diazepino[1,7-a]indol-11-yl)ethoxy]-1-indanone

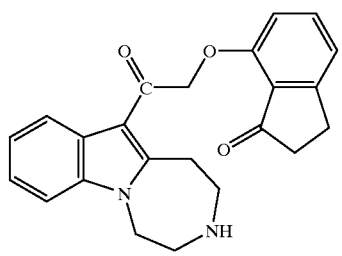

Following the general procedure of Example 47 (Chart E, Step 2) and making non-critical variations but substituting phenol with 7-hydroxy-1-indanone gives 7-[2-oxo-2-(2,3,4,5-tetrahydro-1H-[1,4]diazepino[1,7-a]indol-11-yl)ethoxy]-1-indanone; MS (ESI+) for $C_{23}H_{22}N_2O_3$ m/z 375.1 (M+H)$^+$.

EXAMPLE 147

5-[2-oxo-2-(2,3,4,5-tetrahydro-1H-[1,4]diazepino[1,7-a]indol-11-yl)ethoxy]-1-indanone

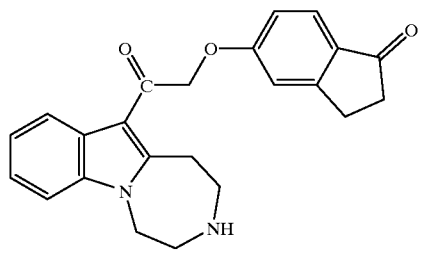

Following the general procedure of Example 47 (Chart E, Step 2) and making non-critical variations but substituting phenol with 5-hydroxy-1-indanone gives 5-[2-oxo-2-(2,3,4,5-tetrahydro-1H-[1,4]diazepino[1,7-a]indol-11-yl)ethoxy]-1-indanone; MS (ESI+) for $C_{23}H_{22}N_2O_3$ m/z 375.0 (M+H)$^+$.

EXAMPLE 148

2-[(2-acetyl-1,2,3,4-tetrahydro-5-isoquinolinyl)oxy]-1-(2,3,4,5-tetrahydro-1H-[1,4]diazepino[1,7-a]indol-11-yl)ethanone

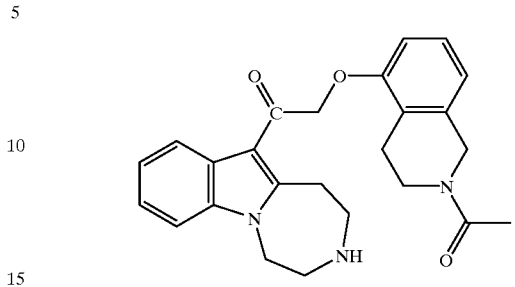

Following the general procedure of Example 47 (Chart E, Step 2) and making non-critical variations but substituting phenol with 2-acetyl-1,2,3,4-tetrahydro-5-isoquinolinol gives 2-[(2-acetyl-1,2,3,4-tetrahydro-5-isoquinolinyl)oxy]-1-(2,3,4,5-tetrahydro-1H-[1,4]diazepino[1,7-a]indol-11-yl)ethanone; MS (ESI+) for $C_{25}H_{27}N_3O_3$ m/z 418.1 (M+H)$^+$.

EXAMPLE 149

2-([1,1'-biphenyl]-2-yloxy)-1-(2,3,4,5-tetrahydro-1H-[1,4]diazepino[1,7-a]indol-11-yl)ethanone

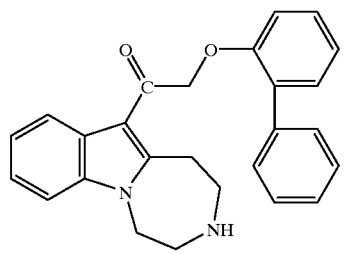

Following the general procedure of Example 47 (Chart E, Step 2) and making non-critical variations but substituting phenol with [1,1'-biphenyl]-2-ol gives 2-([1,1'-biphenyl]-2-yloxy)-1-(2,3,4,5-tetrahydro-1H-[1,4]diazepino[1,7-a]indol-11-yl)ethanone; MS (ESI+) for $C_{26}H_{24}N_2O_2$ m/z 397.1 (M+H)$^+$.

EXAMPLE 150

2-[2-oxo-2-(2,3,4,5-tetrahydro-1H-[1,4]diazepino[1,7-a]indol-11-yl)ethoxy]-N-phenylbenzamide

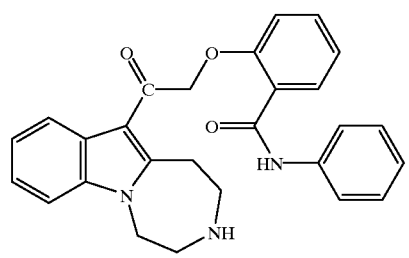

Following the general procedure of Example 47 (Chart E, Step 2) and making non-critical variations but substituting phenol with 2-hydroxy-N-phenylbenzamide gives 2-[2-oxo-2-(2,3,4,5-tetrahydro-1H-[1,4]diazepino[1,7-a]indol-11-yl)ethoxy]-N-phenylbenzamide; MS (ESI+) for $C_{27}H_{25}N_3O_3$ m/z 440.0 (M+H)$^+$.

EXAMPLE 151
2-[2-(4-morpholinylcarbonyl)phenoxy]-1-(2,3,4,5-tetrahydro-1H-[1,4]diazepino[1,7-a]indol-11-yl)ethanone

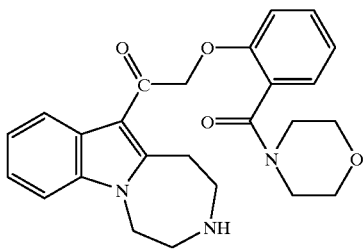

Following the general procedure of Example 47 (Chart E, Step 2) and making non-critical variations but substituting phenol with 2-(4-morpholinylcarbonyl)phenol gives 2-[2-(4-morpholinylcarbonyl)phenoxy]-1-(2,3,4,5-tetrahydro-1H-[1,4]diazepino[1,7-a]indol-11-yl)ethanone; MS (ESI+) for $C_{25}H_{27}N_3O_4$ m/z 434.0 $(M+H)^+$.

EXAMPLE 152
2-[2-methoxy-5-(1-pyrrolidinylmethyl)phenoxy]-1-(2,3,4,5-tetrahydro-1H-[1,4]diazepino[1,7-a]indol-11-yl)ethanone

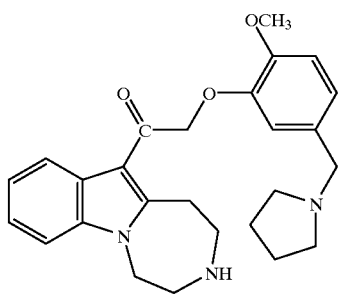

Following the general procedure of Example 47 (Chart E, Step 2) and making non-critical variations but substituting phenol with 2-methoxy-5-(1-pyrrolidinylmethyl)phenol gives 2-[2-methoxy-5-(1-pyrrolidinylmethyl)phenoxy]-1-(2,3,4,5-tetrahydro-1H-[1,4]diazepino[1,7-a]indol-11-yl)ethanone; MS (ESI+) for $C_{26}H_{31}N_3O_3$ m/z 434.0 $(M+H)^+$.

EXAMPLE 153
2-[(5-chloro-8-quinolinyl)oxy]-1-(2,3,4,5-tetrahydro-1H-[1,4]diazepino[1,7-a]indol-11-yl)ethanone

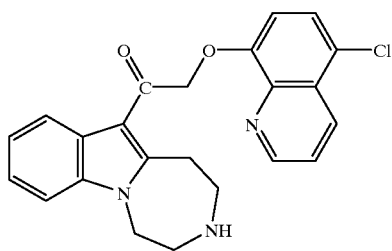

Following the general procedure of Example 47 (Chart E, Step 2) and making non-critical variations but substituting phenol with 5-chloro-8-quinolinol gives 2-[(5-chloro-8-quinolinyl)oxy]-1-(2,3,4,5-tetrahydro-1H-[1,4]diazepino[1,7-a]indol-11-yl)ethanone; MS (ESI+) for $C_{23}H_{20}ClN_3O_2$ m/z 406.0 $(M+H)^+$.

EXAMPLE 154
N-{4-[2-oxo-2-(2,3,4,5-tetrahydro-1H-[1,4]diazepino[1,7-a]indol-11-yl)ethoxy]phenyl}urea

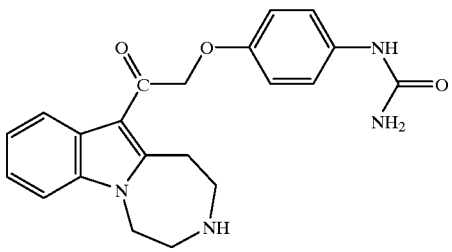

Following the general procedure of Example 47 (Chart E, Step 2) and making non-critical variations but substituting phenol with N-(4-hydroxyphenyl)urea gives N-{4-[2-oxo-2-(2,3,4,5-tetrahydro-1H-[1,4]diazepino[1,7-a]indol-11-yl)ethoxy]phenyl}urea; MS (ESI+) for $C_{21}H_{22}N_4O_3$ m/z 379.1 $(M+H)^+$.

EXAMPLE 155
N-{2-methyl-3-[2-oxo-2-(2,3,4,5-tetrahydro-1H-[1,4]diazepino[1,7-a]indol-11 -yl)ethoxy]phenyl}acetamide

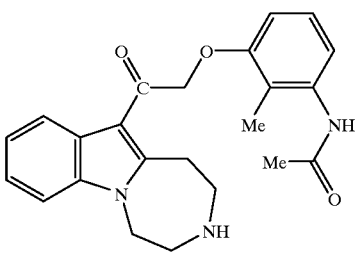

Following the general procedure of Example 47 (Chart E, Step 2) and making non-critical variations but substituting phenol with N-(3-hydroxy-2-methylphenyl)acetamide gives N-{2-methyl-3-[2-oxo-2-(2,3,4,5-tetrahydro-1H-[1,4]diazepino[1,7-a]indol-11-yl)ethoxy]phenyl}acetamide; MS (ESI+) for $C_{23}H_{25}N_3O_3$ m/z 392.1 $(M+H)^+$.

EXAMPLE 156
2-phenoxy-1-(2,3,4,5-tetrahydro-1H-[1,4]diazepino[1,7-a]indol-11-yl)ethanone

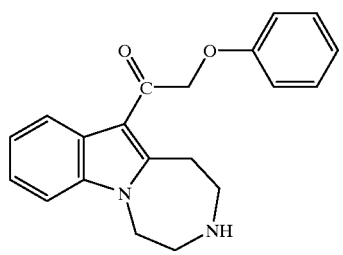

Following the general procedure of Example 47 (Chart E, Step 2) and making non-critical variations and without substituting for phenol gives 2-phenoxy-1-(2,3,4,5-tetrahydro-1H-[1,4]diazepino[1,7-a]indol-11-yl)ethanone; MS (ESI+) for $C_{20}H_{20}N_2O_2$ m/z 321.2 $(M+H)^+$.

EXAMPLE 157
2-(2,6-dimethylphenoxy)-1-(2,3,4,5-tetrahydro-1H-[1,4]diazepino[1,7-a]indol-11-yl)ethanone

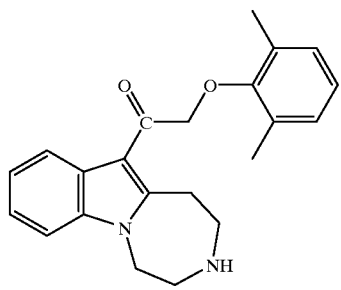

Following the general procedure of Example 47 (Chart E, Step 2) and making non-critical variations but substituting phenol with 2,6-dimethylphenol gives 2-(2,6-dimethylphenoxy)-1-(2,3,4,5-tetrahydro-1H-[1,4]diazepino[1,7-a]indol-11-yl)ethanone; MS (ESI+) for $C_{22}H_{24}N_2O_2$ m/z 349.3 (M+H)$^+$.

EXAMPLE 158
2-(4-methoxyphenoxy)-1-(2,3,4,5-tetrahydro-1H-[1,4]diazepino[1,7-a]indol-11-yl)ethanone

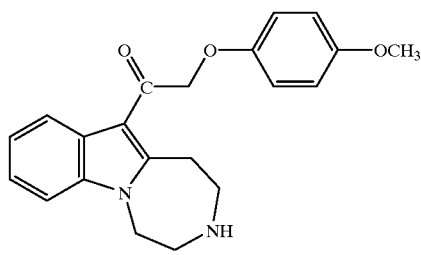

Following the general procedure of Example 47 (Chart E, Step 2) and making non-critical variations but substituting phenol with 4-methoxyphenol gives 2-(4-methoxyphenoxy)-1-(2,3,4,5-tetrahydro-1H-[1,4]diazepino[1,7-a]indol-11-yl)ethanone; MS (ESI+) for $C_{21}H_{22}N_2O_3$ m/z 351.2 (M+H)$^+$.

EXAMPLE 159
2-(2,4-difluorophenoxy)-1-(2,3,4,5-tetrahydro-1H-[1,4]diazepino[1,7-a]indol-11-yl)ethanone

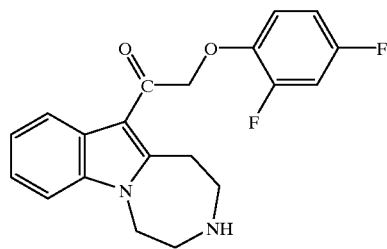

Following the general procedure of Example 47 (Chart E, Step 2) and making non-critical variations but substituting phenol with 2,4-difluorophenol gives 2-(2,4-difluorophenoxy)-1-(2,3,4,5-tetrahydro-1H-[1,4]diazepino[1,7-a]indol-11-yl)ethanone; MS (ESI+) for $C_{20}H_{18}F_2N_2O_2$ m/z 357.2 (M+H)$^+$.

EXAMPLE 160
2-(2,4-dibromophenoxy)-1-(2,3,4,5-tetrahydro-1H-[1,4]diazepino[1,7-a]indol-11-yl)ethanone

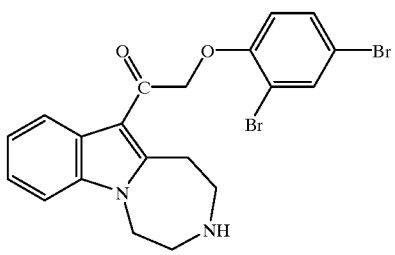

Following the general procedure of Example 47 (Chart E, Step 2) and making non-critical variations but substituting phenol with 2,4-dibromophenol gives 2-(2,4-dibromophenoxy)-1-(2,3,4,5-tetrahydro-1H-[1,4]diazepino[1,7-a]indol-11-yl)ethanone; MS (ESI+) for $C_{20}H_{18}Br_2N_2O_2$ m/z 478.9 (M+H)$^+$.

EXAMPLE 161
2-(4-methylphenoxy)-1-(2,3,4,5-tetrahydro-1H-[1,4]diazepino[1,7-a]indol-11-yl)ethanone

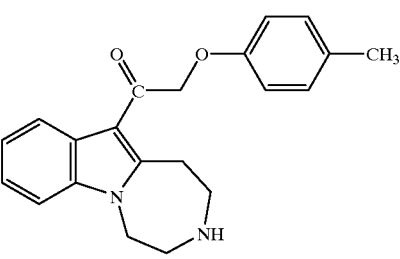

Following the general procedure of Example 47 (Chart E, Step 2) and making non-critical variations but substituting phenol with 4-methylphenol gives 2-(4-methylphenoxy)-1-(2,3,4,5-tetrahydro-1H-[1,4]diazepino[1,7-a]indol-11-yl)ethanone; MS (ESI+) for $C_{21}H_{22}N_2O_2$ m/z 335.3 (M+H)$^+$.

EXAMPLE 162
2-(2-chlorophenoxy)-1-(2,3,4,5-tetrahydro-1H-[1,4]diazepino[1,7-a]indol-11-yl)ethanone

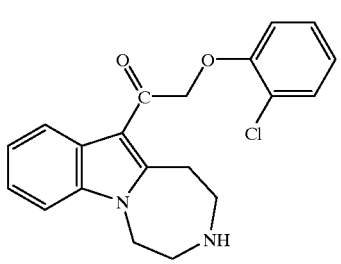

Following the general procedure of Example 47 (Chart E, Step 2) and making non-critical variations but substituting phenol with 2-chlorophenol gives 2-(2-chlorophenoxy)-1-(2,3,4,5-tetrahydro-1H-[1,4]diazepino[1,7-a]indol-11-yl)ethanone; MS (ESI+) for $C_{20}H_{19}ClN_2O_2$ m/z 355.1 (M+H)$^+$.

EXAMPLE 163

2-(2,4-dichlorophenoxy)-1-(2,3,4,5-tetrahydro-1H-[1,4]diazepino[1,7-a]indol-11-yl)ethanone

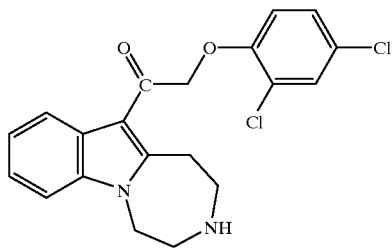

Following the general procedure of Example 47 (Chart E, Step 2) and making non-critical variations but substituting phenol with 2,4-dichlorophenol gives 2-(2,4-dichlorophenoxy)-1-(2,3,4,5-tetrahydro-1H-[1,4]diazepino[1,7-a]indol-11-yl)ethanone; MS (ESI+) for $C_{20}H_{18}Cl_2N_2O_2$ m/z 389.0 (M+H)$^+$.

EXAMPLE 164

2-(mesityloxy)-1-(2,3,4,5-tetrahydro-1H-[1,4]diazepino[1,7-a]indol-11-yl)ethanone

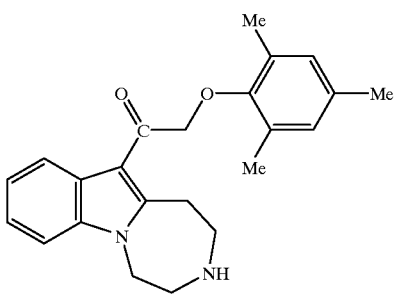

Following the general procedure of Example 47 (Chart E, Step 2) and making non-critical variations but substituting phenol with 2,4,6-trimethylphenol gives 2-(mesityloxy)-1-(2,3,4,5-tetrahydro-1H-[1,4]diazepino[1,7-a]indol-11-yl)ethanone; MS (ESI+) for $C_{23}H_{26}N_2O_2$ m/z 363.1 (M+H)$^+$.

EXAMPLE 165

2-(3-nitrophenoxy)-1-(2,3,4,5-tetrahydro-1H-[1,4]diazepino[1,7-a]indol-11-yl)ethanone

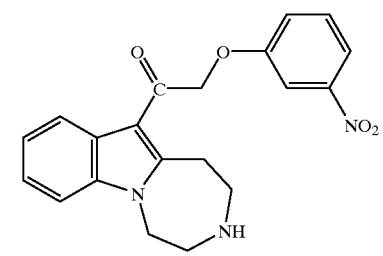

Following the general procedure of Example 47 (Chart E, Step 2) and making non-critical variations but substituting phenol with 3-nitrophenol gives 2-(3-nitrophenoxy)-1-(2,3,4,5-tetrahydro-1H-[1,4]diazepino[1,7-a]indol-11-yl)ethanone; MS (ESI+) for $C_{20}H_{19}N_3O_4$ m/z 366.1 (M+H)$^+$.

EXAMPLE 166

5-[2-oxo-2-(2,3,4,5-tetrahydro-1H-[1,4]diazepino[1,7-a]indol-11-yl)ethoxy]-3,4-dihydro-1(2H)-naphthalenone

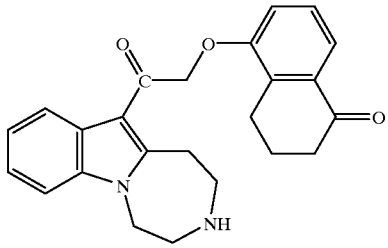

Following the general procedure of Example 47 (Chart E, Step 2) and making non-critical variations but substituting phenol with 5-hydroxy-3,4-dihydro-1(2H)-naphthalenone gives 5-[2-oxo-2-(2,3,4,5-tetrahydro-1H-[1,4]diazepino[1,7-a]indol-11-yl)ethoxy]-3,4-dihydro-1(2H)-naphthalenone; MS (ESI+) for $C_{24}H_{24}N_2O_3$ m/z 389.0 (M+H)$^+$.

EXAMPLE 167

2-(2,3-dimethylphenoxy)-1-(2,3,4,5-tetrahydro-1H-[1,4]diazepino[1,7-a]indol-11-yl)ethanone

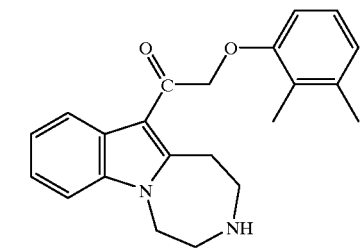

Following the general procedure of Example 47 (Chart E, Step 2) and making non-critical variations but substituting phenol with 2,3-dimethylphenol gives 2-(2,3-dimethylphenoxy)-1-(2,3,4,5-tetrahydro-1H-[1,4]diazepino[1,7-a]indol-11-yl)ethanone; MS (ESI+) for $C_{22}H_{24}N_2O_2$ m/z 349.1 (M+H)$^+$.

EXAMPLE 168

2-[(2-methyl-8-quinolinyl)oxy]-1-(2,3,4,5-tetrahydro-1H-[1,4]diazepino[1,7-a]indole-11-yl)ethanone

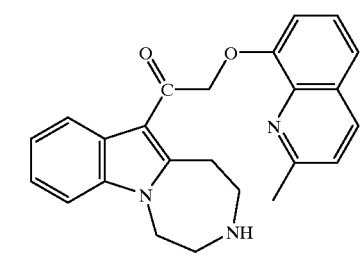

Following the general procedure of Example 47 (Chart E, Step 2) and making non-critical variations but substituting phenol with 2-methyl-8-quinolinol gives 2-[(2-methyl-8-quinolinyl)oxy]-1-(2,3,4,5-tetrahydro-1H-[1,4]diazepino[1,7-a]indol-11-yl)ethanone; MS (ESI+) for $C_{24}H_{23}N_3O_2$ m/z 386.0 (M+H)$^+$.

EXAMPLE 169
2-[(5,7-dibromo-8-quinolinyl)oxy]-1-(2,3,4,5-tetrahydro-1H-[1,4]diazepino[1,7-a]indol-11-yl)ethanone

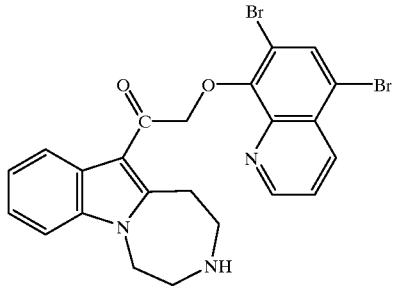

Following the general procedure of Example 47 (Chart E, Step 2) and making non-critical variations but substituting phenol with 5,7-dibromo-8-quinolinol gives 2-[(5,7-dibromo-8-quinolinyl)oxy]-1-(2,3,4,5-tetrahydro-1H-[1,4]diazepino[1,7-a]indol-11-yl)ethanone; MS (ESI+) for $C_{23}H_{19}Br_2N_3O_2$ m/z 529.7 (M+H)$^+$.

EXAMPLE 170
2-[(5,7-dichloro-8-quinolinyl)oxy]-1-(2,3,4,5-tetrahydro-1H-[1,4]diazepino[1,7-a]indol-11-yl)ethanone

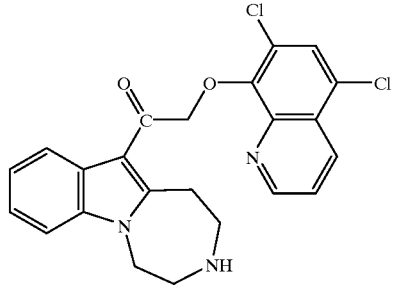

Following the general procedure of Example 47 (Chart E, Step 2) and making non-critical variations but substituting phenol with 5,7-dichloro-8-quinolinol gives 2-[(5,7-dichloro-8-quinolinyl)oxy]-1-(2,3,4,5-tetrahydro-1H-[1,4]diazepino[1,7-a]indol-11-yl)ethanone; MS (ESI+) for $C_{23}H_{19}Cl_2N_3O_2$ m/z 439.8 (M+H)$^+$.

EXAMPLE 171
2-(2,3-dimethoxyphenoxy)-1-(2,3,4,5-tetrahydro-1H-[1,4]diazepino[1,7-a]indol-11-yl)ethanone

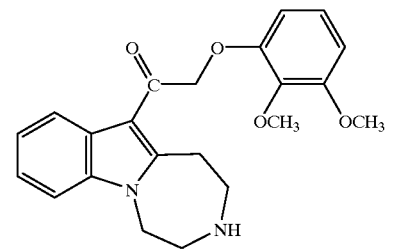

Following the general procedure of Example 47 (Chart E, Step 2) and making non-critical variations but substituting phenol with 2,3-dimethoxyphenol gives 2-(2,3-dimethoxyphenoxy)-1-(2,3,4,5-tetrahydro-1H-[1,4]diazepino[1,7-a]indol-11-yl)ethanone, MS (ESI+) for $C_{22}H_{24}N_2O_4$ m/z 381.0 (M+H)$^+$.

EXAMPLE 172
2-[(5,7-dibromo-2-methyl-8-quinolinyl)oxy]-1-(2,3,4,5-tetrahydro-1H-[1,4]diazepino[1,7-a]indol-11-yl)ethanone

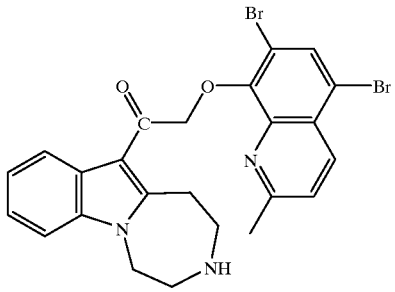

Following the general procedure of Example 47 (Chart E, Step 2) and making non-critical variations but substituting phenol with 5,7-dibromo-2-methyl-8-quinolinol gives 2-[(5,7-dibromo-2-methyl-8-quinolinyl)oxy]-1-(2,3,4,5-tetrahydro-1H-[1,4]diazepino[1,7-a]indol-11-yl)ethanone; MS (ESI+) for $C_{24}H_{21}Br_2N_3O_2$ m/z 543.6 (M+H)$^+$.

EXAMPLE 173
2-[(5,7-dichloro-2-methyl-8-quinolinyl)oxy]-1-(2,3,4,5-tetrahydro-1H-[1,4]diazepino[1,7-a]indol-11-yl)ethanone

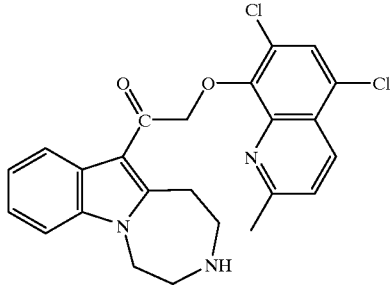

Following the general procedure of Example 47 (Chart E, Step 2) and making non-critical variations but substituting phenol with 5,7-dichloro-2-methyl-8-quinolinol gives 2-[(5,7-dichloro-2-methyl-8-quinolinyl)oxy]-1-(2,3,4,5-tetrahydro-1H-[1,4]diazepino[1,7-a]indol-11-yl)ethanone; MS (ESI+) for $C_{24}H_{21}Cl_2N_3O_2$ m/z 453.8 (M+H)$^+$.

EXAMPLE 174
2-[(5-fluoro-8-quinolinyl)oxy]-1-(2,3,4,5-tetrahydro-1H-[1,4]diazepino[1,7-a]indol-11-yl)ethanone

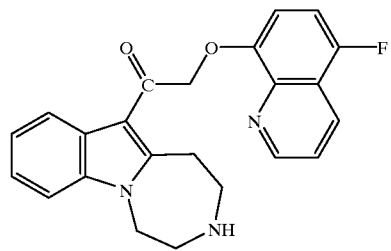

Following the general procedure of Example 47 (Chart E, Step 2) and making non-critical variations but substituting phenol with 5-fluoro-8-quinolinol gives 2-[(5-fluoro-8-quinolinyl)oxy]-1-(2,3,4,5-tetrahydro-1H-[1,4]diazepino[1,7-a]indol-11-yl)ethanone; MS (ESI+) for $C_{23}H_{20}FN_3O_2$ m/z 389.9 (M+H)$^+$.

EXAMPLE 175
2-[(7-propyl-8-quinolinyl)oxy]-1-(2,3,4,5-tetrahydro-1H-[1,4]diazepino[1,7-a]indol-11-yl)ethanone

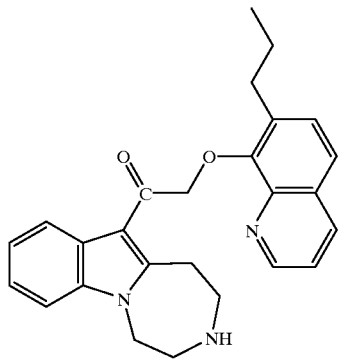

Following the general procedure of Example 47 (Chart E, Step 2) and making non-critical variations but substituting phenol with 7-propyl-8-quinolinol gives 2-[(7-propyl-8-quinolinyl)oxy]-1-(2,3,4,5-tetrahydro-1H-[1,4]diazepino[1,7-a]indol-11-yl)ethanone; MS (ESI+) for $C_{26}H_{27}N_3O_2$ m/z 414.0 (M+H)$^+$.

EXAMPLE 176
2-[(2,2-dimethyl-2,3-dihydro-1-benzofuran-7-yl)oxy]-1-(2,3,4,5-tetrahydro-1H-[1,4]diazepino[1,7-a]indol-11-yl)ethanone

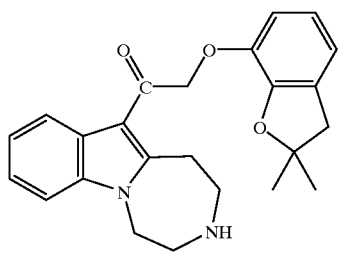

Following the general procedure of Example 47 (Chart E, Step 2) and making non-critical variations but substituting phenol with 2,2-dimethyl-2,3-dihydro-1-benzofuran-7-ol gives 2-[(2,2-dimethyl-2,3-dihydro-1-benzofuran-7-yl)oxy]-1-(2,3,4,5-tetrahydro-1H-[1,4]diazepino[1,7-a]indol-11-yl)ethanone; MS (ESI+) for $C_{24}H_{26}N_2O_3$ m/z 391.0 (M+H)$^+$.

EXAMPLE 177
2-[2-fluoro-3-(trifluoromethyl)phenoxy]-1-(2,3,4,5-tetrahydro-1H-[1,4]diazepino[1,7-a]indol-11-yl)ethanone

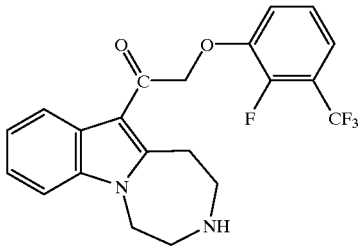

Following the general procedure of Example 47 (Chart E, Step 2) and making non-critical variations but substituting phenol with 2-fluoro-3-(trifluoromethyl)phenol gives 2-[2-fluoro-3-(trifluoromethyl)phenoxy]-1-(2,3,4,5-tetrahydro-1H-[1,4]diazepino[1,7-a]indol-11-yl)ethanone; MS (ESI+) for $C_{21}H_{18}F_4N_2O_2$ m/z 406.9 (M+H)$^+$.

EXAMPLE 178
4-[2-oxo-2-(2,3,4,5-tetrahydro-1H-[1,4]diazepino[1,7-a]indol-11-yl)ethoxy]-1-indanone

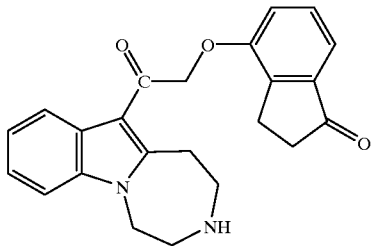

Following the general procedure of Example 47 (Chart E, Step 2) and making non-critical variations but substituting phenol with 4-hydroxy-1-indanone gives 4-[2-oxo-2-(2,3,4,5-tetrahydro-1H-[1,4]diazepino[1,7-a]indol-11-yl)ethoxy]-1-indanone; MS (ESI+) for $C_{23}H_{22}N_2O_3$ m/z 375.0 (M+H)$^+$.

EXAMPLE 179
3-methyl-7-[2-oxo-2-(2,3,4,5-tetrahydro-1H-[1,4]diazepino[1,7-a]indol-11-yl)ethoxy]-2-benzofuran-1 (3H)-one

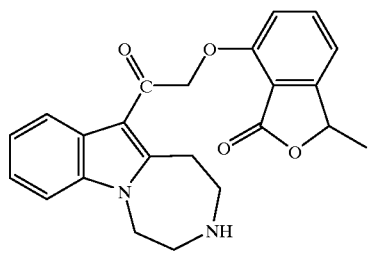

Following the general procedure of Example 47 (Chart E, Step 2) and making non-critical variations but substituting phenol with 7-hydroxy-3-methyl-2-benzofuran-1(3H)-one gives 3-methyl-7-[2-oxo-2-(2,3,4,5-tetrahydro-1H-[1,4]diazepino[1,7-a]indol-11-yl)ethoxy]-2-benzofuran-1(3H)-one; MS (ESI+) for $C_{23}H_{22}N_2O_4$ m/z 390.9 (M+H)$^+$.

EXAMPLE 180
2-[(5,7-dimethyl-8-quinolinyl)oxy]-1-(2,3,4,5-tetrahydro-1H-[1,4]diazepino[1,7-a]indol-11-yl)ethanone

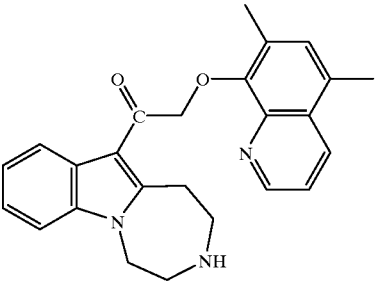

Following the general procedure of Example 47 (Chart E, Step 2) and making non-critical variations but substituting phenol with 5,7-dimethyl-8-quinolinol gives 2-[(5,7- dimethyl-8-quinolinyl)oxy]-1-(2,3,4,5-tetrahydro-1H-[1,4]diazepino[1,7-a]indol-11-yl)ethanone; MS (ESI+) for C$_{25}$H$_{25}$N$_3$O$_2$ m/z 400.0 (M+H)$^+$.

EXAMPLE 181
2-[(5,5-dimethyl-5,6,7,8-tetrahydro-1-naphthalenyl)oxy]-1-(2,3,4,5-tetrahydro-1H-[1,4]diazepino[1,7-a]indol-11-yl)ethanone

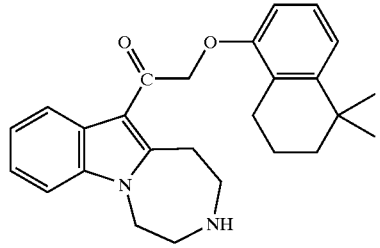

Following the general procedure of Example 47 (Chart E, Step 2) and making non-critical variations but substituting phenol with 5,5-dimethyl-5,6,7,8-tetrahydro-1-naphthalenol gives 2-[(5,5-dimethyl-5,6,7,8-tetrahydro-1-naphthalenyl)oxy]-1-(2,3,4,5-tetrahydro-1H-[1,4]diazepino[1,7-a]indol-11-yl)ethanone; MS (ESI+) for C$_{26}$H$_{30}$N$_2$O$_2$ m/z 403.0 (M+H)$^+$.

EXAMPLE 182
2-[(2-chloro-3-pyridinyl)oxy]-1-(2,3,4,5-tetrahydro-1H-[1,4]diazepino[1,7-a]indol-11-yl)ethanone

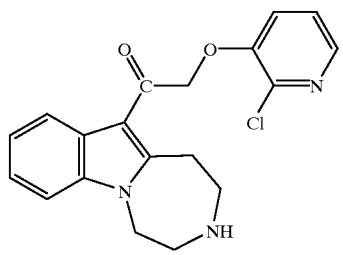

Following the general procedure of Example 47 (Chart E, Step 2) and making non-critical variations but substituting phenol with 2-chloro-3-pyridinol gives 2-[(2-chloro-3-pyridinyl)oxy]-1-(2,3,4,5-tetrahydro-1H-[1,4]diazepino[1,7-a]indol-11-yl)ethanone; MS (ESI+) for C$_{19}$H$_{18}$ClN$_3$O$_2$ m/z 356.0 (M+H)$^+$.

EXAMPLE 183
3-[2-oxo-2-(2,3,4,5-tetrahydro-1H-[1,4]diazepino[1,7-a]indol-11-yl)ethoxy]benzonitrile

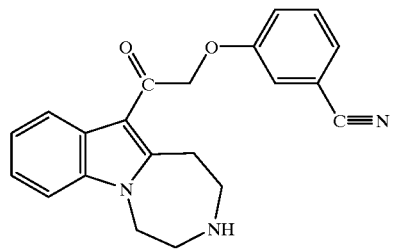

Following the general procedure of Example 47 (Chart E, Step 2) and making non-critical variations but substituting phenol with 3-hydroxybenzonitrile gives 3-[2-oxo-2-(2,3,4,5-tetrahydro-1H-[1,4]diazepino[1,7-a]indol-11-yl)ethoxy]benzonitrile; MS (ESI+) for C$_{21}$H$_{19}$N$_3$O$_2$ m/z 346.1 (M+H)$^+$.

EXAMPLE 184
7-[2-oxo-2-(2,3,4,5-tetrahydro-1H-[1,4]diazepino[1,7-a]indol-11-yl)ethoxy]-2H-chromen-2-one

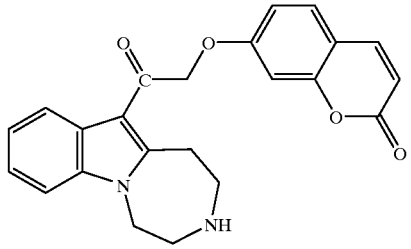

Following the general procedure of Example 47 (Chart E, Step 2) and making non-critical variations but substituting phenol with 7-hydroxy-2H-chromen-2-one gives 7-[2-oxo-2-(2,3,4,5-tetrahydro-1H-[1,4]diazepino[1,7-a]indol-11-yl)ethoxy]-2H-chromen-2-one; MS (ESI+) for C$_{23}$H$_{20}$N$_2$O$_4$ m/z 389.0 (M+H)$^+$.

EXAMPLE 185
2-(phenylsulfanyl)-1-(2,3,4,5-tetrahydro-1H-[1,4]diazepino[1,7-a]indol-11-yl)ethanone

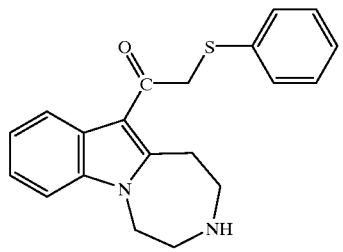

Following the general procedure of Example 47 (Chart E, Step 2) and making non-critical variations but substituting phenol with benzenethiol gives 2-(phenylsulfanyl)-1-(2,3,4,5-tetrahydro-1H-[1,4]diazepino[1,7-a]indol-11-yl)ethanone; MS (ESI+) for C$_{20}$H$_{20}$N$_2$OS m/z 337.2 (M+H)$^+$.

EXAMPLE 186
2-(2,3-dihydro-1,4-benzodioxin-5-yloxy)-1-(2,3,4,5-tetrahydro-1H-[1,4]diazepino[1,7-a]indol-11-yl)ethanone

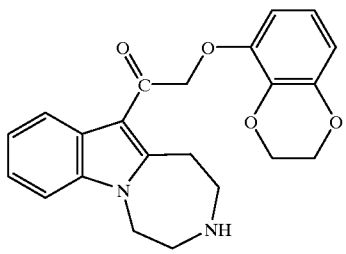

Following the general procedure of Example 47 (Chart E, Step 2) and making non-critical variations but substituting phenol with 2,3-dihydro-1,4-benzodioxin-5-ol gives 2-(2,3-dihydro-1,4-benzodioxin-5-yloxy)-1-(2,3,4,5-tetrahydro-1H-[1,4]diazepino[1,7-a]indol-11-yl)ethanone; MS (ESI+) for C$_{22}$H$_{22}$N$_2$O$_4$ m/z 379.1 (M+H)$^+$.

EXAMPLE 187

2-[(8,8-dimethyl-5,6,7,8-tetrahydro-2-naphthalenyl)oxy]-1-(2,3,4,5-tetrahydro-1H-[1,4]diazepino[1,7-a]indol-11-yl)ethanone

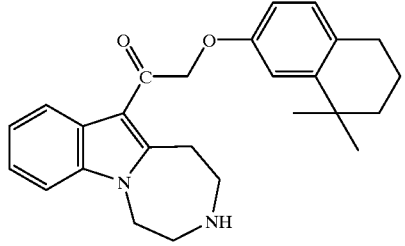

Following the general procedure of Example 47 (Chart E, Step 2) and making non-critical variations but substituting phenol with 8,8-dimethyl-5,6,7,8-tetrahydro-2-naphthalenol gives 2-[(8,8-dimethyl-5,6,7,8-tetrahydro-2-naphthalenyl)oxy]-1-(2,3,4,5-tetrahydro-1H-[1,4]diazepino[1,7-a]indol-11-yl)ethanone; MS (ESI+) for $C_{26}H_{30}N_2O_2$ m/z 403.2 (M+H)+.

EXAMPLE 188

2-(4-pyridinyloxy)-1-(2,3,4,5-tetrahydro-1H-[1,4]diazepino[1,7-a]indol-11-yl)ethanone

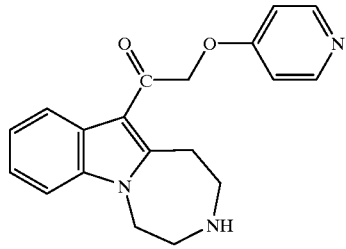

Following the general procedure of Example 47 (Chart E, Step 2) and making non-critical variations but substituting phenol with 4-pyridinol gives 2-(4-pyridinyloxy)-1-(2,3,4,5-tetrahydro-1H-[1,4]diazepino[1,7-a]indol-11-yl)ethanone; MS (ESI+) for $C_{19}H_{19}N_3O_2$ m/z 322.1 (M+H)+.

EXAMPLE 189

2-(2-pyrimidinyloxy)-1-(2,3,4,5-tetrahydro-1H-[1,4]diazepino[1,7-a]indol-11-yl)ethanone

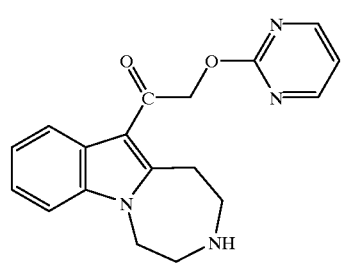

Following the general procedure of Example 47 (Chart E, Step 2) and making non-critical variations but substituting phenol with 2-pyrimidinol gives 2-(2-pyrimidinyloxy)-1-(2,3,4,5-tetrahydro-1H-[1,4]diazepino[1,7-a]indol-11-yl)ethanone; MS (ESI+) for $C_{18}H_{18}N_4O_2$ m/z 323.2 (M+H)+.

EXAMPLE 190

2-(8-quinolinylsulfanyl)-1-(2,3,4,5-tetrahydro-1H-[1,4]diazepino[1,7-a]indol-11-yl)ethanone

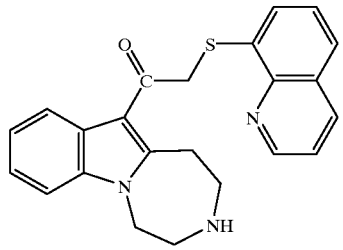

Following the general procedure of Example 47 (Chart E, Step 2) and making non-critical variations but substituting phenol with 8-quinolinethiol gives 2-(8-quinolinylsulfanyl)-1-(2,3,4,5-tetrahydro-1H-[1,4]diazepino[1,7-a]indol-11-yl)ethanone; MS (ESI+) for $C_{23}H_{21}N_3OS$ m/z 388.2 (M+H)+.

EXAMPLE 191

N-(6-methoxy-1,3-benzothiazol-2-yl)-2-oxo-2-(2,3,4,5-tetrahydro-1H-[1,4]diazepino[1,7-a]indol-11-yl)acetamide

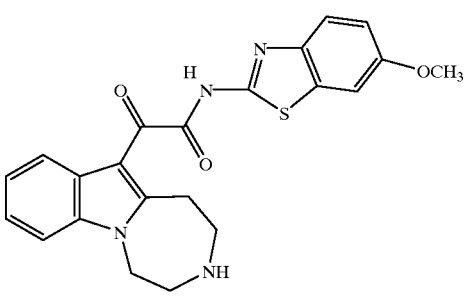

Following the general procedure of Example 20 (Chart B) and making non-critical variations but substituting 4-methoxyaniline with 6-methoxy-1,3-benzothiazol-2-ylamine gives N-(6-methoxy-1,3-benzothiazol-2-yl)-2-oxo-2-(2,3,4,5-tetrahydro-1H-[1,4]diazepino[1,7-a]indol-11-yl)acetamide, MS (ESI+) for $C_{22}H_{20}N_4O_3S$ m/z 421.2 (M+H)+.

EXAMPLE 192

2-oxo-2-(2,3,4,5-tetrahydro-1H-[1,4]diazepino[1,7-a]indol-11-yl)-N-[6-(trifluoromethoxy)-1,3-benzothiazol-2-yl]acetamide

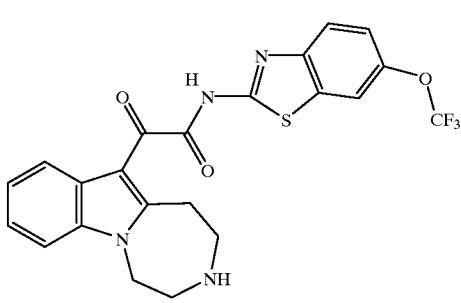

Following the general procedure of Example 20 (Chart B) and making non-critical variations but substituting 4-methoxyaniline with 6-(trifluoromethoxy)-1,3-benzothiazol-2-ylamine gives 2-oxo-2-(2,3,4,5-tetrahydro-1H-[1,4]diazepino[1,7-a]indol-11-yl)-N-[6-

(trifluoromethoxy)-1,3-benzothiazol-2-yl]acetamide, MS (ESI+) for $C_{22}H_{17}F_3N_4O_3S$ m/z 475.0 (M+H)+.

EXAMPLE 193

2-oxo-2-(2,3,4,5-tetrahydro-1H-[1,4]diazepino[1,7-a]indol-11-yl)-N-[6-(trifluoromethyl)-1,3-benzothiazol-2-yl]acetamide

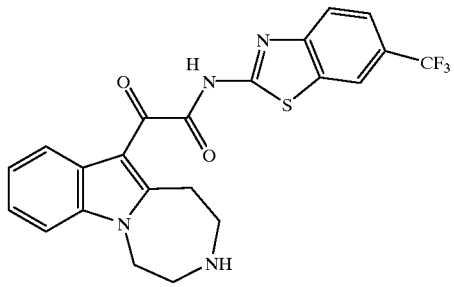

Following the general procedure of Example 20 (Chart B) and making non-critical variations but substituting 4-methoxyaniline with 6-(trifluoromethyl)-1,3-benzothiazol-2-ylamine gives 2-oxo-2-(2,3,4,5-tetrahydro-1H-[1,4]diazepino[1,7-a]indol-11-yl)-N-[6-(trifluoromethyl)-1,3-benzothiazol-2-yl]acetamide, MS (ESI+) for $C_{22}H_{17}F_3N_4O_2S$ m/z 459.1 (M+H)+.

EXAMPLE 194

2-oxo-2-(2,3,4,5-tetrahydro-1H-[1,4]diazepino[1,7-a]indol-11-yl)-N-{6-[(trifluoromethyl)sulfanyl]-1,3-benzothiazol-2-yl}acetamide

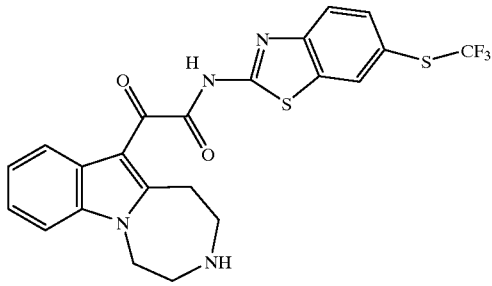

Following the general procedure of Example 20 (Chart B) and making non-critical variations but substituting 4-methoxyaniline with 6-[(trifluoromethyl)sulfanyl]-1,3-benzothiazol-2-ylamine gives 2-oxo-2-(2,3,4,5-tetrahydro-1H-[1,4]diazepino[1,7-a]indol-11-yl)-N-{6-[(trifluoromethyl)sulfanyl]-1,3-benzothiazol-2-yl}acetamide, MS (ESI+) for $C_{22}H_{17}F_3N_4O_2S_2$ m/z 491.1 (M+H)+.

EXAMPLE 195

N-(6-ethoxy-1,3-benzothiazol-2-yl)-2-oxo-2-(2,3,4,5-tetrahydro-1H-[1,4]diazepino[1,7-a]indol-11-yl)acetamide

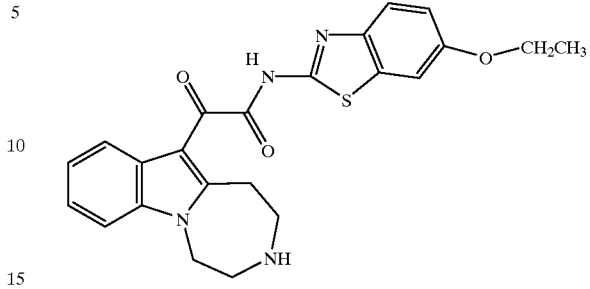

Following the general procedure of Example 20 (Chart B) and making non-critical variations but substituting 4-methoxyaniline with 6-ethoxy-1,3-benzothiazol-2-ylamine gives N-(6-ethoxy-1,3-benzothiazol-2-yl)-2-oxo-2-(2,3,4,5-tetrahydro-1H-[1,4]diazepino[1,7-a]indol-11-yl)acetamide, MS (ESI+) for $C_{23}H_{22}N_4O_3S$ m/z 435.2 (M+H)+.

EXAMPLE 196

N-(6-fluoro-1,3-benzothiazol-2-yl)-2-oxo-2-(2,3,4,5-tetrahydro-1H-[1,4]diazepino[1,7-a]indol-11-yl)acetamide

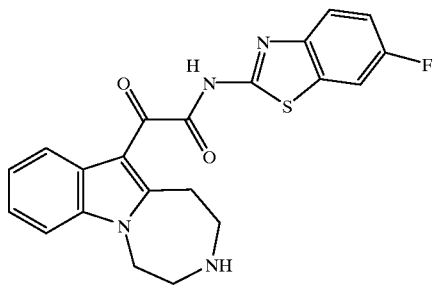

Following the general procedure of Example 20 (Chart B) and making non-critical variations but substituting 4-methoxyaniline with 6-fluoro-1,3-benzothiazol-2-ylamine gives N-(6-fluoro-1,3-benzothiazol-2-yl)-2-oxo-2-(2,3,4,5-tetrahydro-1H-[1,4]diazepino[1,7-a]indol-11-yl)acetamide, MS (ESI+) for $C_{21}H_{17}FN_4O_2S$ m/z 409.1 (M+H)+.

EXAMPLE 197

N-(6-chloro-1,3-benzothiazol-2-yl)-2-oxo-2-(2,3,4,5-tetrahydro-1H-[1,4]diazepino[1,7-a]indol-11-yl)acetamide

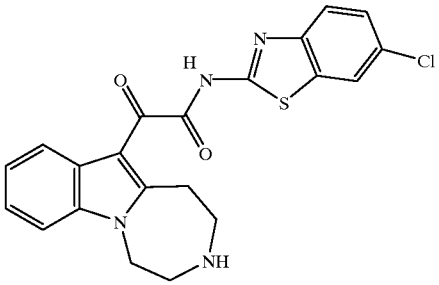

Following the general procedure of Example 20 (Chart 13) and making non-critical variations but substituting 4-methoxyaniline with 6-chloro-1,3-benzothiazol-2-ylamine gives N-(6-chloro-1,3-benzothiazol-2-yl)-2-oxo-2-(2,3,4,5-tetrahydro-1H-[1,4]diazepino[1,7-a]indol-11-yl)acetamide, MS (ESI+) for $C_{21}H_{17}ClN_4O_2S$ m/z 425.1 (M+H)+.

EXAMPLE 198

N-(6-methyl-1,3-benzothiazol-2-yl)-2-oxo-2-(2,3,4,5-tetrahydro-1H-[1,4]diazepino[1,7-a]indol-11-yl)acetamide

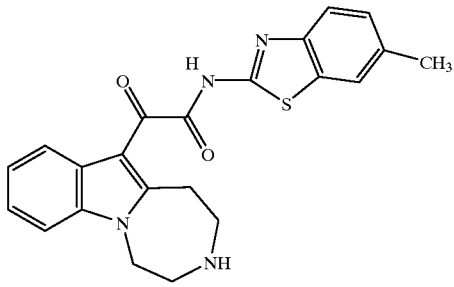

Following the general procedure of Example 20 (Chart B) and making non-critical variations but substituting 4-methoxyaniline with 6-methyl-1,3-benzothiazol-2-ylamine gives N-(6-methyl-1,3-benzothiazol-2-yl)-2-oxo-2-(2,3,4,5-tetrahydro-1H-[1,4]diazepino[1,7-a]indol-11-yl)acetamide, MS (ESI+) for $C_{22}H_{20}N_4O_2S$ m/z 405.2 (M+H)$^+$.

EXAMPLE 199

N-(4-chloro-1,3-benzothiazol-2-yl)-2-oxo-2-(2,3,4,5-tetrahydro-1H-[1,4]diazepino[1,7-a]indol-11-yl)acetamide

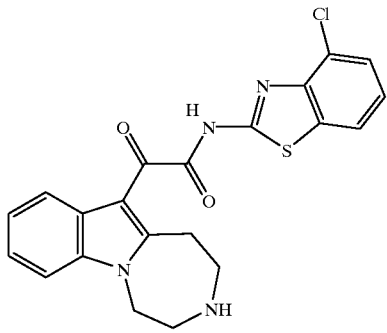

Following the general procedure of Example 20 (Chart B) and making non-critical variations but substituting 4-methoxyaniline with 4-chloro-1,3-benzothiazol-2-ylamine gives N-(4-chloro-1,3-benzothiazol-2-yl)-2-oxo-2-(2,3,4,5-tetrahydro-1H-[1,4]diazepino[1,7-a]indol-11-yl)acetamide, MS (ESI+) for $C_{21}H_{17}ClN_4O_2S$ m/z 425.2 (M+H)$^+$.

EXAMPLE 200

N-(4-methoxy-1,3-benzothiazol-2-yl)-2-oxo-2-(2,3,4,5-tetrahydro-1H-[1,4]diazepino[1,7-a]indol-11-yl)acetamide

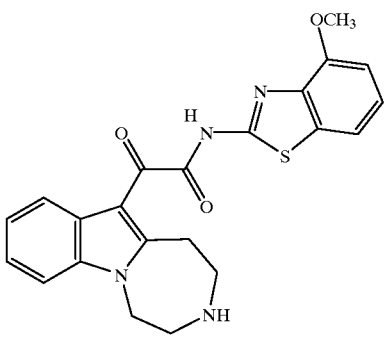

Following the general procedure of Example 20 (Chart B) and making non-critical variations but substituting 4-methoxyaniline with 4-methoxy-1,3-benzothiazol-2-ylamine gives N-(4-methoxy-1,3-benzothiazol-2-yl)-2-oxo-2-(2,3,4,5-tetrahydro-1H-[1,4]diazepino[1,7-a]indol-11-yl)acetamide, MS (ESI+) for $C_{22}H_{20}N_4O_3S$ m/z 421.2 (M+H)$^+$.

EXAMPLE 201

N-(4-methyl-1,3-benzothiazol-2-yl)-2-oxo-2-(2,3,4,5-tetrahydro-1H-[1,4]diazepino[1,7-a]indol-11-yl)acetamide

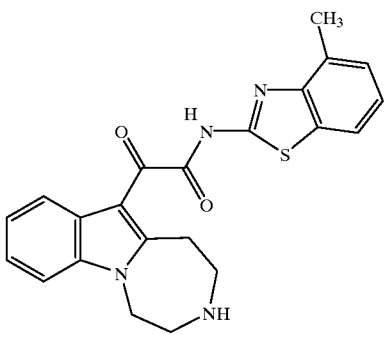

Following the general procedure of Example 20 (Chart B) and making non-critical variations but substituting 4-methoxyaniline with 4-methyl-1,3-benzothiazol-2-ylamine gives N-(4-methyl-1,3-benzothiazol-2-yl)-2-oxo-2-(2,3,4,5-tetrahydro-1H-[1,4]diazepino[1,7-a]indol-11-yl)acetamide, MS (ESI+) for $C_{22}H_{20}N_4O_2S$ m/z 405.2 (M+H)$^+$.

EXAMPLE 202

N-(5,6-dichloro-1,3-benzothiazol-2-yl)-2-oxo-2-(2,3,4,5-tetrahydro-1H-[1,4]diazepino[1,7-a]indol-11-yl)acetamide

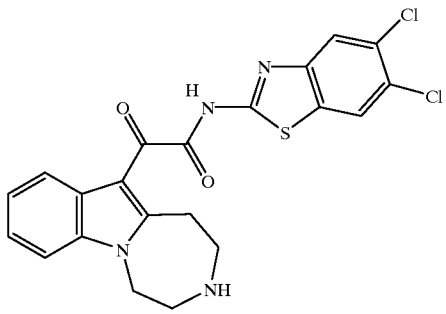

Following the general procedure of Example 20 (Chart B) and making non-critical variations but substituting 4-methoxyaniline with 5,6-dichloro-1,3-benzothiazol-2-ylamine gives N-(5,6-dichloro-1,3-benzothiazol-2-yl)-2-oxo-2-(2,3,4,5-tetrahydro-1H-[1,4]diazepino[1,7-a]indol-11-yl)acetamide, MS (ESI+) for $C_{21}H_{16}Cl_2N_4O_2S$ m/z 459.1 (M+H)$^+$.

EXAMPLE 203
N-(5,6-dimethyl-1,3-benzothiazol-2-yl)-2-oxo-2-(2,3,4,5-tetrahydro-1H-[1,4]diazepino[1,7-a]indol-11-yl)acetamide

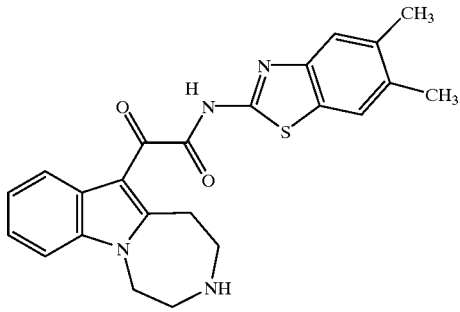

Following the general procedure of Example 20 (Chart B) and making non-critical variations but substituting 4-methoxyaniline with 5,6-dimethyl-1,3-benzothiazol-2-ylamine gives N-(5,6-dimethyl-1,3-benzothiazol-2-yl)-2-oxo-2-(2,3,4,5-tetrahydro-1H-[1,4]diazepino[1,7-a]indol-11-yl)acetamide, MS (ESI+) for $C_{23}H_{22}N_4O_2S$ m/z 419.2 (M+H)+.

EXAMPLE 204
N-(7-bromo-6-fluoro-1,3-benzothiazol-2-yl)-2-oxo-2-(2,3,4,5-tetrahydro-1H-[1,4]diazepino[1,7-a]indol-11-yl)acetamide

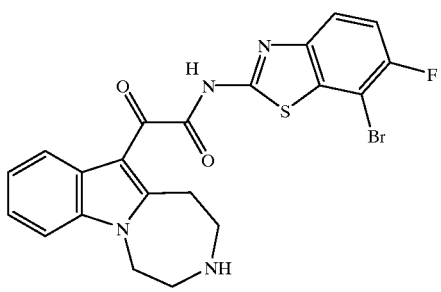

Following the general procedure of Example 20 (Chart B) and making non-critical variations but substituting 4-methoxyaniline with 7-bromo-6-fluoro-1,3-benzothiazol-2-ylamine gives N-(7-bromo-6-fluoro-1,3-benzothiazol-2-yl)-2-oxo-2-(2,3,4,5-tetrahydro-1H-[1,4]diazepino[1,7-a]indol-11-yl)acetamide, MS (ESI+) for $C_{21}H_{16}BrFN_4O_2S$ m/z 489.1 (M+H)+.

EXAMPLE 205
N-(4,6-dichloro-1,3-benzothiazol-2-yl)-2-oxo-2-(2,3,4,5-tetrahydro-1H-[1,4]diazepino[1,7-a]indol-11-yl)acetamide

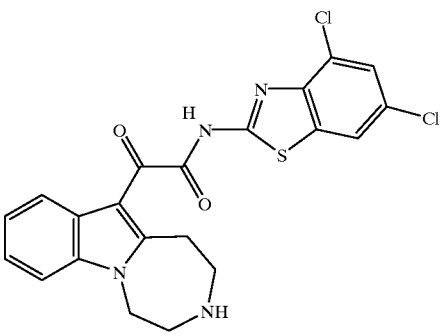

Following the general procedure of Example 20 (Chart B) and making non-critical variations but substituting 4-methoxyaniline with 4,6-dichloro-1,3-benzothiazol-2-ylamine gives N-(4,6-dichloro-1,3-benzothiazol-2-yl)-2-oxo-2-(2,3,4,5-tetrahydro-1H-[1,4]diazepino[1,7-a]indol-11-yl)acetamide, MS (ESI+) for $C_{21}H_{16}Cl_2N_4O_2S$ m/z 459.1 (M+H)+.

EXAMPLE 206
N-(4,6-dimethyl-1,3-benzothiazol-2-yl)-2-oxo-2-(2,3,4,5-tetrahydro-1H-[1,4]diazepino[1,7-a]indol-11-yl)acetamide

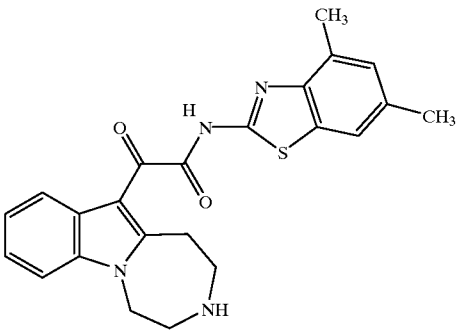

Following the general procedure of Example 20 (Chart B) and making non-critical variations but substituting 4-methoxyaniline with 4,6-dimethyl-1,3-benzothiazol-2-ylamine gives N-(4,6-dimethyl-1,3-benzothiazol-2-yl)-2-oxo-2-(2,3,4,5-tetrahydro-1H-[1,4]diazepino[1,7-a]indol-11-yl)acetamide, MS (ESI+) for $C_{23}H_{22}N_4O_2S$ m/z 419.2 (M+H)+.

EXAMPLE 208
N-(4,6-difluoro-1,3-benzothiazol-2-yl)-2-oxo-2-(2,3,4,5-tetrahydro-1H-[1,4]diazepino[1,7-a]indol-11-yl)acetamide

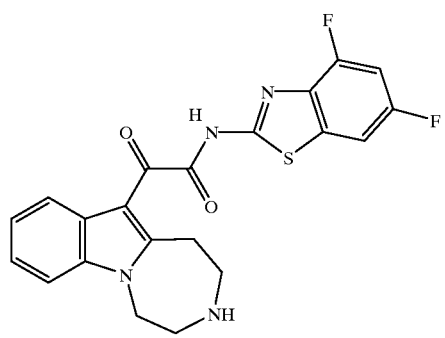

Following the general procedure of Example 20 (Chart B) and making non-critical variations but substituting 4-methoxyaniline with 4,6-difluoro-1,3-benzothiazol-2-ylamine gives N-(4,6-difluoro-1,3-benzothiazol-2-yl)-2-oxo-2-(2,3,4,5-tetrahydro-1H-[1,4]diazepino[1,7-a]indol-11-yl)acetamide, MS (ESI+) for $C_{21}H_{16}F_2N_4O_2S$ m/z 427.1 (M+H)+.

EXAMPLE 209
N-(6-nitro-1,3-benzothiazol-2-yl)-2-oxo-2-(2,3,4,5-tetrahydro-1H-[1,4]diazepino[1,7-a]indol-11-yl)acetamide

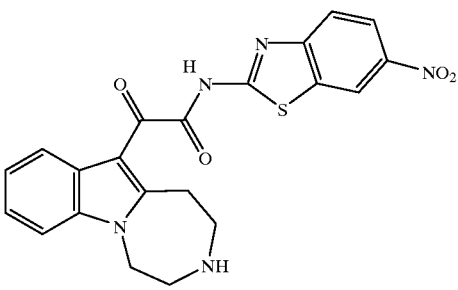

Following the general procedure of Example 20 (Chart B) and making non-critical variations but substituting 4-methoxyaniline with 6-nitro-1,3-benzothiazol-2-ylamine gives N-(6-nitro-1,3-benzothiazol-2-yl)-2-oxo-2-(2,3,4,5-tetrahydro-1H-[1,4]diazepino[1,7-a]indol-11-yl)acetamide, MS (ESI+) for $C_{21}H_{17}N_5O_4S$ m/z 436.2 (M+H)$^+$.

EFFICACY DATA

All of the Example compounds provided above are believed to be 5-HT ligands, with the ability to displace >50% of a radiolabeled test ligand from one or more 5-HT receptor subtypes at a concentration of 1 μM. The procedures used for testing such displacement are well known and would be readily available to one skilled in the art.

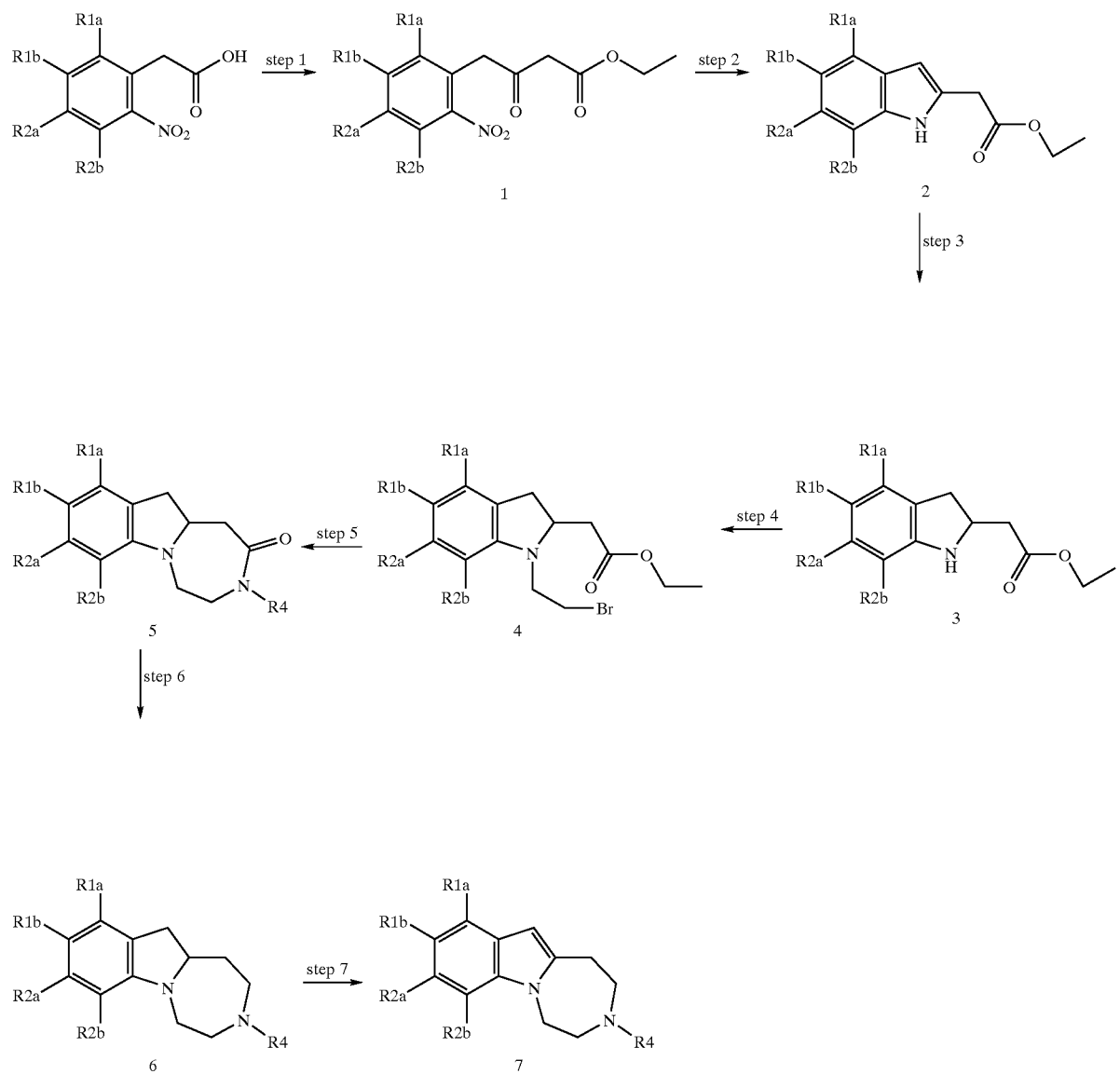

Chart A

Chart B
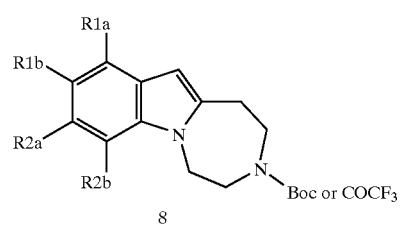
8
↓ step 1
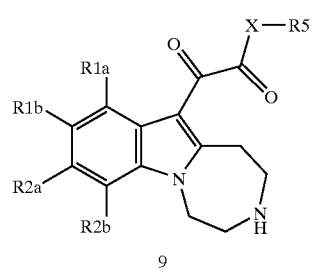
9
Chart C
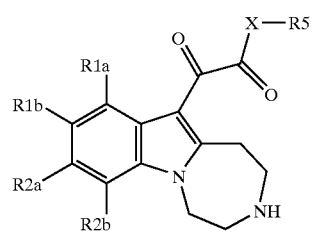
9
↓ step 1
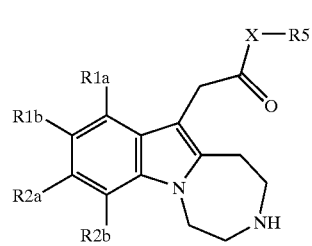
10
Chart D
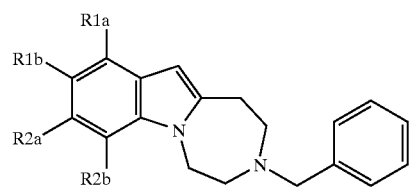
11
↓ step 1
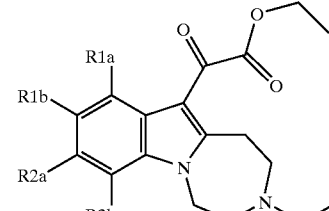
12
↓ step 2
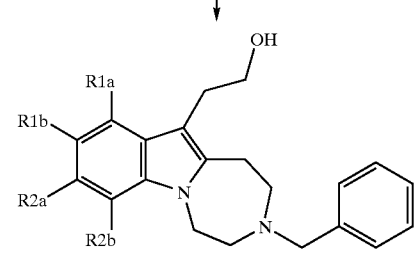
13
↓ step 3
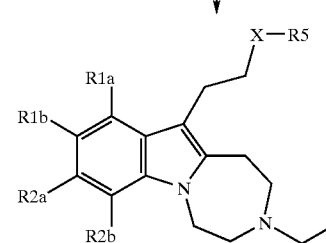
14
↓ step 4
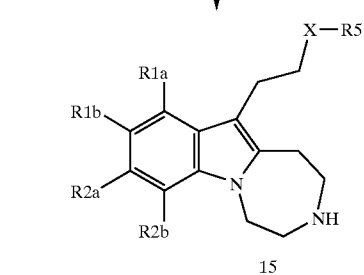
15

Chart E

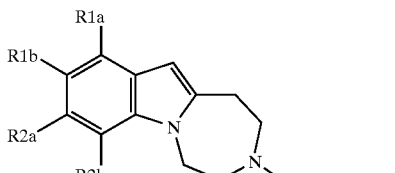
8

↓ step 1

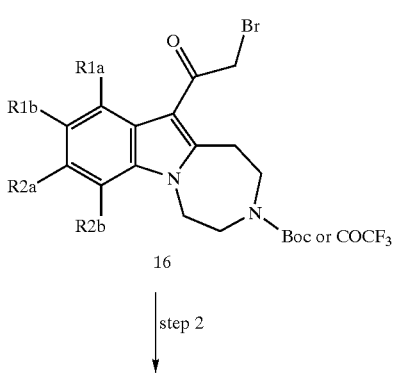
16

↓ step 2

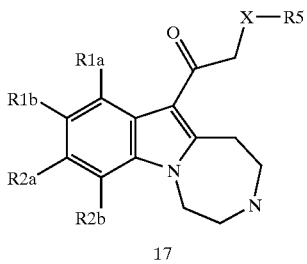
17

Chart F

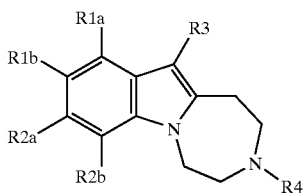
18

↓ step 1

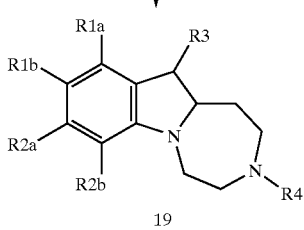
19

Chart G

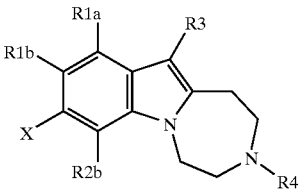
20

↓ step 1

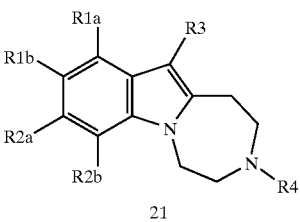
21

Having described the invention in detail and by reference to the preferred embodiments thereof, it will be apparent that modifications and variations are possible without departing from the scope of the appended claims.

What is claimed is:

1. A compound of formula I:

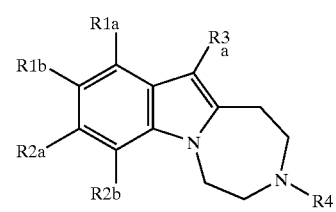

I where a is a single bond or double bond, and where R1a, R1b, R2a and R2b are each independently (a) H, Cl, Br, I, F, CN, $CF_3$, $OCF_3$, OR5, CONR5R6, COR5, $CO_2$R5, $Y(CH_2)_m$XR5 or $YC(O)(CH_2)_m$XR5, where m=0–3, Y=$CH_2$, S, O, or NR6, X=$CH_2$, S, O, NR6;

(b) $(CH_2)_p$Ar where p =0–3 and Ar is aryl or heteroaryl optionally substituted with one or more of the following: H, halogen, CN, $NO_2$, OR7, $CF_3$, $OCF_3$, SR7, $SO_2$R7, $SO_2$NR7R8, NR7R8, CONR7R8, NR7COR8, NR7CONR8R9, $CO_2$R7, COR7, or R7; or (c) linear or branched $C_1$–$C_8$ alkyl, linear or branched $C_2$–$C_8$ alkenyl, linear or branched $C_2$–$C_8$ alkynyl, $C_3$–$C_8$ cycloalkyl, $C_3$–$C_8$ cycloalkenyl, or $C_3$–$C_8$ cycloalkynyl; wherein any of these groups may be optionally substituted with one or more of the following: halogen, CN, $NO_2$, COR7, OR7, NR7R8, SR7, $CO_2$R7, CONR7R8 or NR7COR8; and where R3 is (a) H, Cl, Br, I, F, CN, $CF_3$, $OCF_3$, alkyl, OR5, SR5, CHO, CONR5R6, COR5, $CO_2$R5, $(Y)_o(CH_2)_n$XR5, C(O)C(O)XR5, $(Y)_o(CH_2)_n$C(O)XR5, $C(O)(CH_2)_n$XR5, $(Y)_o(CH_2)_n$N(R6)C(O)NR5R6 where o=0 or 1, n=0–3, X=$CH_2$, S, O, or NR6 and Y=$CH_2$, S, O or NR6; or (b) linear or branched $C_1$–$C_8$ alkyl, linear or branched $C_2$–$C_8$ alkenyl, linear or branched $C_2$–$C_8$ alkynyl, $C_3$–$C_8$ cycloalkyl, $C_3$–$C_8$ cycloalkenyl, or $C_3$–$C_8$ cycloalkynyl; wherein any of these groups may be optionally substituted with one or more of the following: halogen, CN, $NO_2$, COR10, OR10, NR10R8, SR10, $CO_2$R10, CONR10R8 or NR10COR8; and where R4, R5 and R6 are each independently (a) H, linear or branched $C_1$–$C_8$ alkyl, linear or branched $C_2$–$C_8$ alkenyl, linear or branched $C_2$–$C_8$ alkynyl, $C_3$–$C_8$ cycboalkyl, $C_3$–$C_8$ cycloalkenyl, or $C_3$–$C_8$ cycloalkynyl; wherein any of these groups other than H may be optionally substituted with one or more of the following: halogen, CN, $NO_2$, COR10, OR10, NR10R11, SR10, $CO_2$R10, CONR10R11 or NR10COR11; or where R5 and R6 are linked to form a 3 to 8 member ring; or (b) $(CH_2)_p$Ar where p=0–3 and Ar is aryl or heteroaryl optionally substituted with one or more of the following: H, halogen, CN, $NO_2$, OR7, $CF_3$, $OCF_3$, SR7, $SO_2$R7, $SO_2$NR7R8, NR7R8, CONR7R8, NR7COR8, NR7CONR8R9, $CO_2$R7, COR7, or R7; and where R7, R8, and R9 are each independently (a) H, linear or branched $C_1$–$C_8$ alkyl, linear or branched $C_2$–$C_8$ alkenyl, linear or branched $C_2$–$C_8$ alkynyl, $C_3$–$C_8$ cycloalkyl, $C_3$–$C_8$ cycloalkenyl, or $C_3$–$C_8$ cycloalkynyl groups, wherein any of these groups other than H may be optionally substituted with halogen, CN, $NO_2$, COR10, OR10, NR10R11, SR10, $CO_2$R10, CONR10R11, NR10COR11, NR10CONR11R12, or where R7, R8, or R9 are linked to form a ring; or (b) $(CH_2)_p$Ar where p=0–3 and Ar is aryl or heteroaryl optionally substituted with one or more of the following: H, halogen, CN, $NO_2$, OR10, $CF_3$, $OCF_3$, SR10, $SO_2$R10, $SO_2$NR10R11, NR10R11, CONR10R11, NR10COR11, NR10CONR11R12, $CO_2$R10, COR10, or R10; and where R10, R11 and R12 are each independently H, linear or branched $C_1$–$C_8$ alkyl, linear or branched $C_2$–$C_8$ alkenyl, linear or branched $C_2$–$C_8$ alkynyl, $C_3$–$C_8$ cycloalkyl, $C_3$–$C_8$ cycloalkenyl, or $C_3$–$C_8$ cycloalkynyl;

or a stereoisomer or pharmaceutically acceptable salt thereof.

2. The compound of claim 1 wherein R1a, R1b, R2a, R2b and R4 are H and R3 is selected from either H, —C(O)C(O)XAr, —CH$_2$C(O)XAr or —C(O)CH$_2$XAr.

3. The compound of claim 1 which is selected from the group consisting of:

2,3,4,5-tetrahydro-1H-[1,4]diazepino[1,7-a]indole hydrochloride 8-bromo-2,3,4,5-tetrahydro-1H-[1,4]diazepino[1,7-a]indole hydrochloride 2,3,4,5-tetrahydro-1H-[1,4]diazepino[1,7-a]indole-11-carbaldehyde 2-oxo-2-(2,3,4,5-tetrahydro-1H-[1,4]diazepino[1,7-a]indol-11-yl)acetamide 2,2,2-trifluoro-1-(2,3,4,5-tetrahydro-1H-[1,4]diazepino[1,7-a]indol-11-yl)-1-ethanone 11-methyl-2,3,4,5-tetrahydro-1H-[1,4]diazepino[1,7-a]indole hydrochloride 11-chloro-2,3,4,5-tetrahydro-1H-[1,4]diazepino[1,7-a]indole 2,3,4,5-tetrahydro-1H-[1,4]diazepino[1,7-a]indole-11-carbonitrile 8-bromo-2,3,4,5-tetrahydro-1H-[1,4]diazepino[1,7-a]indole-11-carbaldehyde 1-(8-bromo-2,3,4,5-tetrahydro-1H-[1,4]diazepino[1,7-a]indol-11-yl)-2,2,2-trifluoro-1-ethanone 2,3,4,5-tetrahydro-1H-[1,4]diazepino[1,7-a]indole-11-carboxamide 1-(2,3,4,5-tetrahydro-1H-[1,4]diazepino[1,7-a]indol-11-yl)-1-ethanone hydrochloride 3-methyl-2,3,4,5-tetrahydro-1H-[1,4]diazepino[1,7-a]indole 3-ethyl-2,3,4,5-tetrahydro-1H-[1,4]diazepino[1,7-a]indole 3-benzyl-2,3,4,5-tetrahydro-1H-[1,4]diazepino[1,7-a]indole 10-methoxy-2,3,4,5-tetrahydro-1H-[1,4]diazepino[1,7-a]indole hydrochloride ethyl 2-(3-benzyl-2,3,4,5-tetrahydro-1H-[1,4]diazepino[1,7-a]indol-11-yl)-2-oxoacetate 3-propyl-2,3,4,5-tetrahydro-1H-[1,4]diazepino[1,7-a]indole hydrochloride 2-(2,3,4,5-tetrahydro-1H-[1,4]diazepino[1,7-a]indol-11-yl)-1-ethanamine 2-(3-benzyl-2,3,4,5-tetrahydro-1H-[1,4]diazepino[1,7-a]indol-11-yl)-1-ethanol 3-benzyl-11-(2-phenoxyethyl)-2,3,4,5-tetrahydro-1H-[1,4]diazepino[1,7-a]indole 11-(2-phenoxyethyl)-2,3,4,5-tetrahydro-1H-[1,4]diazepino[1,7-a]indole 3-benzyl-11-[2-(2-methoxyphenoxy)ethyl]-2,3,4,5-tetrahydro-1H-[1,4]diazepino[1,7-a]indole 3-benzyl-11-[2-(2-fluorophenoxy)ethyl]-2,3,4,5-tetrahydro-1H-[1,4]diazepino[1,7-a]indole 3-benzyl-11-[2-(8-quinolinyloxy)ethyl]-2,3,4,5-tetrahydro-1H-[1,4]diazepino[1,7-a]indole 2-(2,3,4,5-tetrahydro-1H-[1,4]diazepino[1,7-a]indol-11-yl)-1-ethanol 3-benzyl-11-[2-(2-methoxy-4-methylphenoxy)ethyl]-2,3,4,5-tetrahydro-1H-[1,4]diazepino[1,7-a]indole 3-benzyl-11-[2-(2-fluoro-6-methoxyphenoxy)ethyl]-2,3,4,5-tetrahydro-1H-[1,4]diazepino[1,7-a]indole 11-[2-(2-methoxyphenoxy)ethyl]-2,3,4,5-tetrahydro-1H-[1,4]diazepino[1,7-a]indole 11-[2-(2-methoxyphenoxy)ethyl]-2,3,4,5-tetrahydro-1H-[1,4]diazepino[1,7-a]indole hydrochloride 11-[2-(2-fluorophenoxy)ethyl]-2,3,4,5-tetrahydro-1H-[1,4]diazepino[1,7-a]indole 11-[2-(2-methoxy-4-methylphenoxy)ethyl]-2,3,4,5-tetrahydro-1H-[1,4]diazepino[1,7-a]indole 11-[2-(2-fluoro-6-methoxyphenoxy)ethyl]-2,3,4,5-tetrahydro-1H-[1,4]diazepino[1,7-a]indole 3-benzyl-11-[2-(2-chlorophenoxy)ethyl]-2,3,4,5-tetrahydro-1H-[1,4]diazepino[1,7-a]indole 3-benzyl-11-[2-(4-bromo-2-methoxyphenoxy)ethyl]-2,3,4,5-tetrahydro-1H-[1,4]diazepino[1,7-a]indole N-benzyl-2-(3-benzyl-2,3,4,5-tetrahydro-1H-[1,4]diazepino[1,7-a]indol-11-yl)-1-ethanamine 11-[2-(2-chlorophenoxy)ethyl]-2,3,4,5-tetrahydro-1H-[1,4]diazepino[1,7-a]indole 11-[2-(4-bromo-2-methoxyphenoxy)ethyl]-2,3,4,5-tetrahydro-1H-[1,4]diazepino[1,7-a]indole 2-phenoxy-1-(2,3,4,5-tetrahydro-1H-[1,4]diazepino[1,7-a]indol-11-yl)-1-ethanone N-(4-methoxyphenyl)-2-oxo-2-(2,3,4,5-tetrahydro-1H-[1,4]diazepino[1,7-a]indol-11-yl)acetamide 4-methoxy-N-[2-(2,3,4,5-tetrahydro-1H-[1,4]diazepino[1,7-a]indol-11-yl)ethyl]aniline dihydrochloride 2-hydroxy-N-(4-methoxyphenyl)-2-(2,3,4,5-tetrahydro-1H-[1,4]diazepino[1,7-a]indol-11-yl)acetamide 2-(2-methoxyphenoxy)-1-(2,3,4,5-tetrahydro-1H-[1,4]diazepino[1,7-a]indol-11-yl)-1-ethanone 2-(4-bromo-2-methoxyphenoxy)-1-(2,3,4,5-tetrahydro-1H-[1,4]diazepino[1,7-a]indol-11-yl)-1-ethanone N-(4-methoxyphenyl)-2-(2,3,4,5-tetrahydro-1H-[1,4]diazepino[1,7-a]indol-11-yl)acetamide 2-(4-methoxyanilino)-1-(2,3,4,5-tetrahydro-1H-[1,4]diazepino[1,7-a]indol-11-yl)-1-ethanone dihydrochloride N-(2,4-difluorophenyl)-2-oxo-2-(2,3,4,5-tetrahydro-1H-[1,4]diazepino[1,7-a]indol-11-yl)acetamide N-(3-chloro-4-methoxyphenyl)-2-oxo-2-(2,3,4,5-tetrahydro-1H-[1,4]diazepino[1,7-a]indol-11-yl)acetamide 2-oxo-N-phenyl-2-(2,3,4,5-tetrahydro-1H-[1,4]diazepino[1,7-a]indol-11-yl)acetamide N-(2-naphthyl)-2-oxo-2-(2,3,4,5-tetrahydro-1H-[1,4]diazepino[1,7-a]indol-11-yl)acetamide N-(2,4-difluorophenyl)-2-(2,3,4,5-tetrahydro-1H-[1,4]diazepino[1,7-a]indol-11-yl)acetamide 8-phenyl-2,3,4,5-tetrahydro-1H-[1,4]diazepino[1,7-a]indole 8-(2,4-dichlorophenyl)-2,3,4,5-tetrahydro-1H-[1,4]diazepino[1,7-a]indole 8-(4-fluorophenyl)-2,3,4,5-tetrahydro-1H-[1,4]diazepino[1,7-a]indole 8-(4-chlorophenyl)-2,3,4,5-tetrahydro-1H-[1,4]diazepino[1,7-a]indole 8-(2-chlorophenyl)-2,3,4,5-tetrahydro-1H-[1,4]diazepino[1,7-a]indole 8-(2-methoxyphenyl)-2,3,4,5-tetrahydro-1H-[1,4]diazepino[1,7-a]indole 8-[2-chloro-4-(trifluoromethyl)phenyl]-2,3,4,5-tetrahydro-1H-[1,4]diazepino[1,7-a]indole 8-(2,4-dimethylphenyl)-2,3,4,5-tetrahydro-1H-[1,4]diazepino[1,7-a]indole 8-(2-chloro-4-methoxyphenyl)-2,3,4,5-tetrahydro-1H-[1,4]diazepino[1,7-a]indole 8-(4-isopropylphenyl)-2,3,4,5-tetrahydro-1H-[1,4]diazepino[1,7-a]indole 8-(4-butylphenyl)-2,3,4,5-tetrahydro-1H-[1,4]diazepino[1,7-a]indole 8-(5-fluoro-4-methoxy-2-methylphenyl)-2,3,4,5-tetrahydro-1H-[1,4]diazepino[1,7-a]indole 8-(4-methoxy-2-methylphenyl)-2,3,4,5-tetrahydro-1H-[1,4]diazepino[1,7-a]indole 8-[2-chloro-4-(trifluoromethoxy)phenyl]-2,3,4,5-tetrahydro-1H-[1,4]diazepino[1,7-a]indole 8-(2,4,5-trimethylphenyl)-2,3,4,5-tetrahydro-1H-[1,4]diazepino[1,7-a]indole 8-(3-chlorophenyl)-2,3,4,5-tetrahydro-1H-[1,4]diazepino[1,7-a]indole 8-(4-methylphenyl)-2,3,4,5-tetrahydro-1H-[1,4]diazepino[1,7-a]indole 8-(4-chloro-2-methylphenyl)-2,3,4,5-tetrahydro-1H-[1,4]diazepino[1,7-a]indole 8-(2,5-dichlorophenyl)-2,3,4,5-tetrahydro-1H-[1,4]diazepino[1,7-a]indole 8-(4-isopropyl-2-methoxyphenyl)-2,3,4,5-tetrahydro-1H-[1,4]diazepino[1,7-a]indole 8-(2,6-dichlorophenyl)-2,3,4,5-tetrahydro-1H-[1,4]diazepino[1,7-a]indole 8-(2,6-difluorophenyl)-2,3,4,5-tetrahydro-1H-[1,4]diazepino[1,7-a]indole 8-[4-methoxy-2-(trifluoromethyl)phenyl]-2,3,4,5-tetrahydro-1H-[1,4]diazepino[1,7-a]indole 8-[2-(trifluoromethyl)phenyl]-2,3,4,5-tetrahydro-1H-[1,4]diazepino[1,7-a]indole 8-(4-pyridinyl)-2,3,4,5-tetrahydro-1H-[1,4]diazepino[1,7-a]indole 8-(2-furyl)-2,3,4,5-tetrahydro-1H-[1,4]diazepino[1,7-a]indole 2-(2,3,4,5-tetrahydro-1H-[1,4]diazepino[1,7-a]indol-8-yl)benzenethiol 8-(2,3-dichlorophenyl)-2,3,4,5-tetrahydro-1H-[1,4]diazepino[1,7-a]indole 8-(4-ethylphenyl)-2,3,4,5-tetrahydro-1H-[1,4]diazepino[1,7-a]indole 8-(2,4-dimethoxyphenyl)-2,3,4,5-tetrahydro-1H-[1,4]diazepino[1,7-a]indole 8-(3-chloro-2-fluorophenyl)-2,3,4,5-tetrahydro-1H-[1,4]diazepino[1,7-a]indole 8-(4-methoxyphenyl)-2,3,4,5-tetrahydro-1H-[1,4]diazepino[1,7-a]indole 8-[4-(methylsulfanyl)phenyl]-2,3,4,5-tetrahydro-1H-[1,4]diazepino[1,7-a]indole 4-(2,3,4,5-tetrahydro-1H-[1,4]diazepino[1,7-a]indol-8-yl)benzonitrile 8-[3-(trifluoromethyl)phenyl]-2,3,4,5-tetrahydro-1H-[1,4]diazepino[1,7-a]indole 8-(2-naphthyl)-2,3,4,5-tetrahydro-1H-[1,4]diazepino[1,7-a]indole 1-[4-(2,3,4,5-tetrahydro-1H-[1,4]diazepino[1,7-a]indol-8-yl)phenyl]ethanone N-[3-(2,3,4,5-tetrahydro-1H-[1,4]diazepino[1,7-a]indol-8-yl)phenyl]acetamide 8-(2,3-dimethylphenyl)-2,3,4,5-tetrahydro-1H-[1,4]diazepino[1,7-a]indole 8-(5-fluoro-2-methylphenyl)-2,3,4,5-tetrahydro-1H-[1,4]diazepino[1,7-a]indole 8-(2-fluoro-5-methylphenyl)-2,3,4,5-tetrahydro-1H-[1,4]diazepino[1,7-a]indole 8-(5-fluoro-2-methoxyphenyl)-2,3,4,5-tetrahydro-1H-[1,4]diazepino[1,7-a]indole 8-(3-chloro-2-methylphenyl)-2,3,4,5-tetrahydro-1H-[1,4]diazepino[1,7-a]indole 8-(3-nitrophenyl)-2,3,4,5-tetrahydro-1H-[1,4]diazepino[1,7-a]indole 8-(2-nitrophenyl)-2,3,4,5-tetrahydro-1H-[1,4]diazepino[1,7-a]indole 8-(2-chloro-3-methylphenyl)-2,3,4,5-tetrahydro-1H-[1,4]diazepino[1,7-a]indole 8-(2-methoxyphenyl)-2,3,4,5-tetrahydro-1H-[1,4]diazepino[1,7-a]indole 8-(4-ethoxy-2-methylphenyl)-2,3,4,5-tetrahydro-1H-[1,4]diazepino[1,7-a]indole 8-(4-fluoro-2-methylphenyl)-2,3,4,5-tetrahydro-1H-[1,4]diazepino[1,7-a]indole 8-(2-chloro-6-fluorophenyl)-2,3,4,5-tetrahydro-1H-[1,4]diazepino[1,7-a]indole 8-[2-chloro-4-(difluoromethoxy)phenyl]-2,3,4,5-tetrahydro-1H-[1,4]diazepino[1,7-a]indole 8-[4-(trifluoromethyl)phenyl]-2,3,4,5-tetrahydro-1H-[1,4]diazepino[1,7-a]indole 8-[4-(trifluoromethoxy)phenyl]-2,3,4,5-tetrahydro-1H-[1,4]diazepino[1,7-a]indole 8-(6-fluoro-2,4-dimethoxyphenyl)-2,3,4,5-tetrahydro-1H-[1,4]diazepino[1,7-a]indole 8-(2-methylphenyl)-2,3,4,5-tetrahydro-1H-[1,4]diazepino[1,7-a]indole 8-[6-fluoro-2-(trifluoromethyl)phenyl]-2,3,4,5-tetrahydro-1H-[1,4]diazepino[1,7-a]indole 8-[2-(methylsulfanyl)phenyl]-2,3,4,5-tetrahydro-1H-[1,4]diazepino[1,7-a]indole 8-(2,4,6-trifluorophenyl)-2,3,4,5-tetrahydro-1H-[1,4]diazepino[1,7-a]indole 8-(2,4,6-trichlorophenyl)-2,3,4,5-tetrahydro-1H-[1,4]diazepino[1,7-a]indole 8-(2,6-dichloro-4-methoxyphenyl)-2,3,4,5-tetrahydro-1H-[1,4]diazepino[1,7-a]indole 8-(2,3,4-trifluorophenyl)-2,3,4,5-tetrahydro-1H-[1,4]diazepino[1,7-a]indole 8-(4-chloro-2,6-difluorophenyl)-2,3,4,5-tetrahydro-1H-[1,4]diazepino[1,7-a]indole 8-(2,3,4,6-tetrafluorophenyl)-2,3,4,5-tetrahydro-1H-[1,4]diazepino[1,7-a]indole 8-(2,3,4,5,6-pentafluorophenyl)-2,3,4,5-tetrahydro-1H-[1,4]diazepino[1,7-a]indole 8-[2,6-di(trifluoromethyl)phenyl]-2,3,4,5-tetrahydro-1H-[1,4]diazepino[1,7-a]indole 8-[2-(trifluoromethoxy)phenyl]-2,3,4,5-tetrahydro-1H-[1,4]diazepino[1,7-a]indole 8-[4-ethoxy-2-(trifluoromethoxy)phenyl]-2,3,4,5-tetrahydro-1H-[1,4]diazepino[1,7-a]indole 8-[4-isopropoxy-2-(trifluoromethyl)phenyl]-2,3,4,5-tetrahydro-1H-[1,4]diazepino[1,7-a]indole 8-[4-chloro-2-(trifluoromethyl)phenyl]-2,3,4,5-tetrahydro-1H-[1,4]diazepino[1,7-a]indole 8-[4-fluoro-2-(trifluoromethyl)phenyl]-2,3,4,5-tetrahydro-1H-[1,4]diazepino[1,7-a]indole 8-[2-chloro-4-ethoxyphenyl]-2,3,4,5-tetrahydro-1H-[1,4]diazepino[1,7-a]indole 8-[2-chloro-4-isopropoxyphenyl]-2,3,4,5-tetrahydro-1H-[1,4]diazepino[1,7-a]indole 8-(2-ethyl-4-methoxyphenyl)-2,3,4,5-tetrahydro-1H-[1,4]diazepino[1,7-a]indole 5-methoxy-2-(2,3,4,5-tetrahydro-1H-[1,4]diazepino[1,7-a]indol-8-yl)benzaldehyde 8-[4-methoxy-2-(1-hydroxyethyl)phenyl]-2,3,4,5-tetrahydro-1H-[1,4]diazepino[1,7-a]indole 8-[4-methoxy-2-(1-methoxyethyl)phenyl]-2,3,4,5-tetrahydro-1H-[1,4]diazepino[1,7-a]indole 1-[5-methoxy-2-(2,3,4,5-tetrahydro-1H-[1,4]diazepino[1,7-a]indol-8-yl)phenyl]ethanone

[5-methoxy-2-(2,3,4,5-tetrahydro-1H-[1,4]diazepino[1,7-a]indol-8-yl)phenyl]methanol 8-[4-methoxy-2-(methoxymethyl)phenyl]-2,3,4,5-tetrahydro-1H-[1,4]diazepino[1,7-a]indole 1-[5-methoxy-2-(2,3,4,5-tetrahydro-1H-[1,4]diazepino[1,7-a]indol-8-yl)phenyl]-1-propanol 1-[5-methoxy-2-(2,3,4,5-tetrahydro-1H-[1,4]diazepino[1,7-a]indol-8-yl)phenyl]-1-propanone methyl (2Z)-3-[5-methoxy-2-(2,3,4,5-tetrahydro-1H-[1,4]diazepino[1,7-a]indol-8-yl)phenyl]-2-propenoate methyl-3-[5-methoxy-2-(2,3,4,5-tetrahydro-1H-[1,4]diazepino[1,7-a]indol-8-yl)phenyl]propanoate (2Z)-3-[5-methoxy-2-(2,3,4,5-tetrahydro-1H-[1,4]diazepino[1,7-a]indol-8-yl)phenyl]-2-propen-1-ol methyl (2E)-3-[5-methoxy-2-(2,3,4,5-tetrahydro-1H-[1,4]diazepino[1,7-a]indol-8-yl)phenyl]-2-propenoate (2E)-3-[5-methoxy-2-(2,3,4,5-tetrahydro-1H-[1,4]diazepino[1,7-a]indol-8-yl)phenyl]-2-propen-1-ol 8-[4-methoxy-2-(2-methoxyethyl)phenyl]2,3,4,5-tetrahydro-1H-[1,4]diazepino[1,7-a]indole 8-(2-fluoro-4-methoxyphenyl)-2,3,4,5-tetrahydro-1H-[1,4]diazepino[1,7-a]indole 8-(2-chloro-4-fluorophenyl)-2,3,4,5-tetrahydro-1H-[1,4]diazepino[1,7-a]indole 8-benzyl-2,3,4,5-tetrahydro-1H-[1,4]diazepino[1,7-a]indole 8-(2-fluorobenzyl)-2,3,4,5-tetrahydro-1H-[1,4]diazepino[1,7-a]indole 8-(3-fluorobenzyl)-2,3,4,5-tetrahydro-1H-[1,4]diazepino[1,7-a]indole 8-(4-fluorobenzyl)-2,3,4,5-tetrahydro-1H-[1,4]diazepino[1,7-a]indole 8-(3-methoxybenzyl)-2,3,4,5-tetrahydro-1H-[1,4]diazepino[1,7-a]indole 3-(2,3,4,5-tetrahydro-1H-[1,4]diazepino[1,7-a]indol-8-ylmethyl)phenol 8-(2-methoxybenzyl)-2,3,4,5-tetrahydro-1H-[1,4]diazepino[1,7-a]indole 2-(2,3,4,5-tetrahydro-1H-[1,4]diazepino[1,7-a]indol-8-ylmethyl)phenol methyl 2-methoxy-6-(2,3,4,5-tetrahydro-1H-[1,4]diazepino[1,7-a]indol-8-yl)benzoate 3-(2,3,4,5-tetrahydro-1H-[1,4]diazepino[1,7-a]indol-8-yl)benzonitrile 3-methyl-4-(2,3,4,5-tetrahydro-1H-[1,4]diazepino[1,7-a]indol-8-yl)benzonitrile 2-methyl-3-(2,3,4,5-tetrahydro-1H-[1,4]diazepino[1,7-a]indol-8-yl)benzonitrile 2-(2,3,4,5-tetrahydro-1H-[1,4]diazepino[1,7-a]indol-8-yl)benzonitrile 3-trifluoromethyl-4-(2,3,4,5-tetrahydro-1H-[1,4]diazepino[1,7-a]indol-8-yl)benzonitrile 3-(2,3,4,5-tetrahydro-1H-[1,4-]diazepino[1,7-a]indol-8-yl)benzaldehyde

[3-(2,3,4,5-tetrahydro-1H-[1,4]diazepino[1,7-a]indol-8-yl)phenyl]methanol

8-[3-(methoxymethyl)phenyl]-2,3,4,5-tetrahydro-1H-[1,4]diazepino[1,7-a]indole

N,N-dimethyl[3-(2,3,4,5-tetrahydro-1H-[1,4]diazepino[1,7-a]indol-8-yl)phenyl]methanamine 2-fluoro-5-(2,3,4,5-tetrahydro-1H-[1,4]diazepino[1,7-a]indol-8-yl)benzonitrile 2-fluoro-5-(2,3,4,5-tetrahydro-1H-[1,4]diazepino[1,7-a]indol-8-yl)benzamide 8-phenyl-2,3,4,5,11,11a-hexahydro-1H-[1,4]diazepino[1,7-a]indole 8-(2,4-dichlorophenyl)-2,3,4,5,11,11a-hexahydro-1H-[1,4]diazepino[1,7-a]indole 8-(4-fluorophenyl)-2,3,4,5,11,11a-hexahydro-1H-[1,4]diazepino[1,7-a]indole 8-(4-chlorophenyl)-2,3,4,5,11,11a-hexahydro-1H-[1,4]diazepino[1,7-a]indole 8-(2-chlorophenyl)-2,3,4,5,11,11a-hexahydro-1H-[1,4]diazepino[1,7-a]indole 8-(2-methoxyphenyl)-2,3,4,5,11,11a-hexahydro-1H-[1,4]diazepino[1,7-a]indole 8-[2-chloro-4-(trifluoromethyl)phenyl]-2,3,4,5,11,11a-hexahydro-1H-[1,4]diazepino[1,7-a]indole 8-(2,4-dimethylphenyl)-2,3,4,5,11,11a-hexahydro-1H-[1,4]diazepino[1,7-a]indole 8-(2-chloro-4-methoxyphenyl)-2,3,4,5,11,11a-hexahydro-1H-[1,4]diazepino[1,7-a]indole 8-(4-isopropylphenyl)-2,3,4,5,11,11a-hexahydro-1H-[1,4]diazepino[1,7-a]indole 8-(4-butylphenyl)-2,3,4,5,11,11a-hexahydro-1H-[1,4]diazepino[1,7-a]indole 8-(5-fluoro-4-methoxy-2-methylphenyl)-2,3,4,5,11,11a-hexahydro-1H-[1,4]diazepino[1,7-a]indole 8-(4-methoxy-2-methylphenyl)-2,3,4,5,11,11a-hexahydro-1H-[1,4]diazepino[1,7-a]indole 8-[2-chloro-4-(trifluoromethoxy)phenyl]-2,3,4,5,11,11a-hexahydro-1H-[1,4]diazepino[1,7-a]indole 8-(2,4,5-trimethylphenyl)-2,3,4,5,11,11a-hexahydro-1H-[1,4]diazepino[1,7-a]indole 8-(3-chlorophenyl)-2,3,4,5,11,11a-hexahydro-1H-[1,4]diazepino[1,7-a]indole 8-(4-methylphenyl)-2,3,4,5,11,11a-hexahydro-1H-[1,4]diazepino[1,7-a]indole 8-(4-chloro-2-methylphenyl)-2,3,4,5,11,11a-hexahydro-1H-[1,4]diazepino[1,7-a]indole 8-(2,5-dichlorophenyl)-2,3,4,5,11,11a-hexahydro-1H-[1,4]diazepino[1,7-a]indole 8-(4-isopropyl-2-methoxyphenyl)-2,3,4,5,11,11a-hexahydro-1H-[1,4]diazepino[1,7-a]indole 8-(2,6-dichlorophenyl)-2,3,4,5,11,11a-hexahydro-1H-[1,4]diazepino[1,7-a]indole 8-(2,6-difluorophenyl)-2,3,4,5,11,11a-hexahydro-1H-[1,4]diazepino[1,7-a]indole 8-[4-methoxy-2-(trifluoromethyl)phenyl]-2,3,4,5,11,11a-hexahydro-1H-[1,4]diazepino[1,7-a]indole 8-[2-(trifluoromethyl)phenyl]-2,3,4,11,11a-hexahydro-1H-[1,4]diazepino[1,7-a]indole 8-(4-pyridinyl)-2,3,4,5,11,11a-hexahydro-1H-[1,4]diazepino[1,7a]indole 8-(2-furyl)-2,3,4,5,11,11a-hexahydro-1H-[1,4]diazepino[1,7-a]indole 2-(2,3,4,5,11,11a-hexahydro-1H-[1,4]diazepino[1,7-a]indol-8-yl)benzenethiol 8-(2,3-dichlorophenyl)-2,3,4,5,11,11a-hexahydro-1H-[1,4]diazepino[1,7-a]indole 8-(4-ethylphenyl)-2,3,4,5,11,11a-hexahydro-1H-[1,4]diazepino[1,7-a]indole 8-(2,4-dimethoxyphenyl)-2,3,4,5,11,11a-hexahydro-1H-[1,4]diazepino[1,7-a]indole 8-(3-chloro-2-fluorophenyl)-2,3,4,5,11,11a-hexahydro-1H-[1,4]diazepino[1,7-a]indole 8-(4-methoxyphenyl)-2,3,4,5,11,11a-hexahydro-1H-[1,4]diazepino[1,7-a]indole 8-[4-(methylsulfanyl)phenyl]-2,3,4,5,11,11a-hexahydro-1H-[1,4]diazepino[1,7-a]indole 4-(2,3,4,5,11,11a-hexahydro-1H-[1,4]diazepino[1,7-a]indol-8-yl)benzonitrile 8-[3-(trifluoromethyl)phenyl]-2,3,4,5,11,11a-hexahydro-1H-[1,4]diazepino[1,7-a]indole 8-(2-naphthyl)-2,3,4,5,11,11a-hexahydro-1H-[1,4]diazepino[1,7-a]indole 1-[4-(2,3,4,5,11,11a-hexahydro-1H-[1,4]diazepino[1,7-a]indol-8-yl)phenyl]ethanone N-[3-(2,3,4,5,11,11a-hexahydro-1H-[1,4]diazepino[1,7-a]indol-8-yl)phenyl]acetamide 8-(2,3-dimethylphenyl)-2,3,4,5,11,11a-hexahydro-1H-[1,4]diazepino[1,7-a]indole 8-(5-fluoro-2-methylphenyl)-2,3,4,5,11,11a-hexahydro-1H-[1,4]diazepino[1,7-a]indole 8-(2-fluoro-5-methylphenyl)-2,3,4,5,11,11a-hexahydro-1H-[1,4]diazepino[1,7-a]indole 8-(5-fluoro-2-methoxyphenyl)-2,3,4,5,11,11a-hexahydro-1H-[1,4]diazepino[1,7-a]indole 8-(3-chloro-2-methylphenyl)-2,3,4,5,11,11a-hexahydro-1H-[1,4]diazepino[1,7-a]indole 8-(3-nitrophenyl)-2,3,4,5,11,11a-hexahydro-1H-[1,4]diazepino[1,7-a]indole 8-(2-nitrophenyl)-2,3,4,5,11,11a-hexahydro-1H-[1,4]diazepino[1,7-a]indole 8-(2-chloro-3-methylphenyl)-2,3,4,5,11,11a-hexahydro-1H-[1,4]diazepino[1,7-a]indole 8-(2-methoxyphenyl)-2,3,4,5,11,11a-hexahydro-1H-[1,4]diazepino[1,7-a]indole 8-(4-ethoxy-2-methylphenyl)-2,3,4,5,11,11a-hexahydro-1H-[1,4]diazepino[1,7-a]indole 8-(4-fluoro-2-methylphenyl)-2,3,4,5,11,11a-hexahydro-1H-[1,4]diazepino[1,7-a]indole 8-(2-chloro-6-fluorophenyl)-2,3,4,5,11,11a-hexahydro-1H-[1,4]diazepino[1,7-a]indole 8-[2-chloro-4-(difluoromethoxy)phenyl]-2,3,4,5,11,11a-hexahydro-1H-[1,4]diazepino[1,7-a]indole 8-[4-(trifluoromethyl)phenyl]-2,3,4,5,11,11a-hexahydro-1H-[1,4]diazepino[1,7-a]indole 8-[4-(trifluoromethoxy)phenyl]-2,3,4,5,11,11a-hexahydro-1H-[1,4]diazepino[1,7-a]indole 8-(6-fluoro-2,4-dimethoxyphenyl)-2,3,4,5,11,11a-hexahydro-1H-[1,4]diazepino[1,7-a]indole 8-(2-methylphenyl)-2,3,4,5,11,11a-hexahydro-1H-[1,4]diazepino[1,7-a]indole 8-[6-fluoro-2-(trifluoromethyl)phenyl]-2,3,4,5,11,11a-hexahydro-1H-[1,4]diazepino[1,7-a]indole 8-[2-(methylsulfanyl)phenyl]-2,3,4,5,11,11a-hexahydro-1H-[1,4]diazepino[1,7-a]indole 8-(2,4,6-trifluorophenyl)-2,3,4,5,11,11a-hexahydro-1H-[1,4]diazepino[1,7-a]indole 8-(2,4,6-trichlorophenyl)-2,3,4,5,11,11a-hexahydro-1H-[1,4]diazepino[1,7-a]indole 8-(2,6-dichloro-4-methoxyphenyl)-2,3,4,5,11,11a-hexahydro-1H-[1,4]diazepino[1,7-a]indole 8-(2,3,4-trifluorophenyl)-2,3,4,5,11,11a-hexahydro-1H-[1,4]diazepino[1,7-a]indole 8-(4-chloro-2,6-difluorophenyl)-2,3,4,5,11,11a-hexahydro-1H-[1,4]diazepino[1,7-a]indole 8-(2,3,4,6-tetrafluorophenyl)-2,3,4,5,11,11a-hexahydro-1H-[1,4]diazepino[1,7-a]indole 8-(2,3,4,5,6-pentafluorophenyl)-2,3,4,5,11,11a-hexahydro-1H-[1,4]diazepino[1,7-a]indole 8-[2,6-di(trifluoromethyl)phenyl]-2,3,4,5,11,11a-hexahydro-1H-[1,4]diazepino[1,7-a]indole 8-[2-(trifluoromethoxy)phenyl]-2,3,4,5,11,11a-hexahydro-1H-[1,4]diazepino[1,7-a]indole 8-[4-ethoxy-2-(trifluoromethoxy)phenyl]-2,3,4,5,11,11a-hexahydro-1H-[1,4]diazepino[1,7-a]indole 8-[4-isopropoxy-2-(trifluoromethyl)phenyl]-2,3,4,5,11,11a-hexahydro-1H-[1,4]diazepino[1,7-a]indole 8-[4-chloro-2-(trifluoromethyl)phenyl]-2,3,4,5,11,11a-hexahydro-1H-[1,4]diazepino[1,7-a]indole 8-[4-fluoro-2-(trifluoromethyl)phenyl]-2,3,4,5,11,11a-hexahydro-1H-[1,4]diazepino[1,7-a]indole 8-[2-chloro-4-ethoxyphenyl]-2,3,4,5,11,11a-hexahydro-1H-[1,4]diazepino[1,7-a]indole 8-[2-chloro-4-isopropoxyphenyl]-2,3,4,5,11,11a-hexahydro-1H-[1,4]diazepino[1,7-a]indole 8-(2-ethyl-4-methoxyphenyl)-2,3,4,5,11,11a-hexahydro-1H-[1,4]diazepino[1,7-a]indole 5-methoxy-2-(2,3,4,5,11,11a-hexahydro-1H-[1,4]diazepino[1,7-a]indol-8-yl)benzaldehyde 8-[4-methoxy-2-(1-hydroxyethyl)phenyl]-2,3,4,5,11,11a-hexahydro-1H-[1,4]diazepino[1,7-a]indole 8-[4-methoxy-2-(1-methoxyethyl)phenyl]-2,3,4,5,11,11a-hexahydro-1H-[1,4]diazepino[1,7-a]indole 1-[5-methoxy-2-(2,3,4,5,11,11a-hexahydro-1H-[1,4]diazepino[1,7-a]indol-8-yl)phenyl]ethanone

[5-methoxy-2-(2,3,4,5,11,11a-hexahydro-1H-[1,4]diazepino[1,7-a]indol-8-yl)phenyl]methanol 8-[4-methoxy-2-(methoxymethyl)phenyl]-2,13,4,5,11,11a-hexahydro-1H-[1,4]diazepino[1,7-a]indole 1-[5-methoxy-2-(2,3,4,5,11,11a-hexahydro-1H-[1,4]diazepino[1,7-a]indol-8-yl)phenyl]-1-propanol 1-[5-methoxy-2-(2,3,4,5,11,11a-hexahydro-1H-[1,4]diazepino[1,7-a]indol-8-yl)phenyl]-1-propanone methyl (2Z)-3-[5-methoxy-2-(2,3,4,5,11,11a-hexahydro-1H-[1,4]diazepino[1,7-a]indol-8-yl)phenyl]-2-propenoate methyl 3-[5-methoxy-2-(2,3,4,5,11,11a-hexahydro-1H-[1,4]diazepino[1,7a]indol-8-yl)phenyl]propanoate (2Z)-3-[5-methoxy-2-(2,3,4,5,11,11a-hexahydro-1H-[1,4]diazepino[1,7-a]indol-8-yl)phenyl]-2-propen-1-ol methyl (2E)-3-[5-methoxy-2-(2,3,4,5,11,11a-hexahydro-1H-[1,4]diazepino[1,7-a]indol-8-yl)phenyl]-2-propenoate (2E)-3-[5-methoxy-2-(2,3,4,5,11,11a-hexahydro-1H-[1,4]diazepino[1,7-a]indol-8-yl)phenyl]-2-propen-1-ol 8-[4-methoxy-2-(2-methoxyethyl)phenyl]-2,3,4,5,11,11a-hexahydro-1H-[1,4]diazepino[1,7-a]indole 8-(2-fluoro-4-methoxyphenyl)-2,3,4,5,11,11a-hexahydro-1H-[1,4]diazepino[1,7-a]indole 8-(2-chloro-4-fluorophenyl)-2,3,4,5,11,11a-hexahydro-1H-[1,4]diazepino[1,7-a]indole 8-benzyl-2,3,4,5,11,11a-hexahydro-1H-[1,4]diazepino[1,7-a]indole 8-(2-fluorobenzyl)-2,3,4,5,11,11a-hexahydro-1H-[1,4]diazepino[1,7-a]indole 8-(3-fluorobenzyl)-2,3,4,5,11,11a-hexahydro-1H-[1,4]diazepino[1,7-a]indole 8-(4-fluorobenzyl)-2,3,4,5,11,11a-hexahydro-1H-[1,4]diazepino[1,7-a]indole 8-(3-methoxybenzyl)-2,3,4,5,11,11a-hexahydro-1H-[1,4]diazepino[1,7-a]indole 3-(2,3,4,5,11,11a-hexahydro-1H-[1,4]diazepino[1,7-a]indol-8-ylmethyl)phenol 8-(2-methoxybenzyl)-2,3,4,5,11,11a-hexahydro-1H-[1,4]diazepino[1,7-a]indole 2-(2,3,4,5,11,11a-hexahydro-1H-[1,4]diazepino[1,7-a]indol-8-ylmethyl)phenol methyl 2-methoxy-6-(2,3,4,5,11,11a-hexahydro-1H-[1,4]diazepino[1,7-a]indol-8-yl)benzoate 3-(2,3,4,5,11,11a-hexahydro-1H-[1,4]diazepino[1,7-a]indol-8-yl)benzonitrile 3-methyl-4-(2,3,4,5,11,11a-hexahydro-1H-[1,4]diazepino[1,7-a]indol-8-yl)benzonitrile 2-methyl-3-(2,3,4,5,11,11a-hexahydro-1H-[1,4]diazepino[1,7-a]indol-8-yl)benzonitrile 2-(2,3,4,5,11,11a-hexahydro-1H-[1,4]diazepino[1,7-a]indol-8-yl)benzonitrile 3-trifluoromethyl-4-(2,3,4,5,11,11a-hexahydro-1H-[1,4]diazepino[1,7-a]indol-8-yl)benzonitrile 3-(2,3,4,5,11,11a-hexahydro-1H-[1,4]diazepino[1,7-a]indol-8-yl)benzaldehyde

[3-(2,3,4,5,11,11a-hexahydro-1H-[1,4]diazepino[1,7-a]indol-8-yl)phenyl]methanol

8-[3-(methoxymethyl)phenyl]-2,3,4,5,11,11a-hexahydro-1H-[1,4]diazepino[1,7-a]indole N,N-dimethyl[3-(2,3,4,5,11,11a-hexahydro-1H-[1,4]diazepino[1,7-a]indol-8-yl)phenyl]methanamine 2-fluoro-5-(2,3,4,5,11,11a-hexahydro-1H-[1,4]diazepino[1,7-a]indol-8-yl)benzonitrile 2-fluoro-5-(2,3,4,5,11,11a-hexahydro-1H-[1,4]diazepino[1,7-a]indol-8-yl)benzamide 7-phenyl-2,3,4,5-tetrahydro-1H-[1,4]diazepino[1,7-a]indole 7-(2,4-dichlorophenyl)-2,3,4,5-tetrahydro-1H-[1,4]diazepino[1,7-a]indole 7-(4-fluorophenyl)-2,3,4,5-tetrahydro-1H-[1,4]diazepino[1,7-a]indole 7-(4-chlorophenyl)-2,3,4,5-tetrahydro-1H-[1,4]diazepino[1,7-a]indole 7-(2-chlorophenyl)-2,3,4,5-tetrahydro-1H-[1,4]diazepino[1,7-a]indole 7-(2-methoxyphenyl)-2,3,4,5-tetrahydro-1H-[1,4]diazepino[1,7-a]indole 7-[2-chloro-4-(trifluoromethyl)phenyl]-2,3,4,5-tetrahydro-1H-[1,4]diazepino[1,7-a]indole 7-(2,4-dimethylphenyl)-2,3,4,5-tetrahydro-1H-[1,4]diazepino[1,7-a]indole 7-(2-chloro-4-methoxyphenyl)-2,3,4,5-tetrahydro-1H-[1,4]diazepino[1,7-a]indole 7-(4-isopropylphenyl)-2,3,4,5-tetrahydro-1H-[1,4]diazepino[1,7-a]indole 7-(4-butylphenyl)-2,3,4,5-tetrahydro-1H-[1,4]diazepino[1,7-a]indole 7-(5-fluoro-4-methoxy-2-methylphenyl)-2,3,4,5-tetrahydro-1H-[1,4]diazepino[1,7-a]indole 7-(4-methoxy-2-methylphenyl)-2,3,4,5-tetrahydro-1H-[1,4]diazepino[1,7-a]indole 7-[2-chloro-4-(trifluoromethoxy)phenyl]-2,3,4,5-tetrahydro-1H-[1,4]diazepino[1,7-a]indole 7-(2,4,5-trimethylphenyl)-2,3,4,5-tetrahydro-1H-[1,4]diazepino[1,7-a]indole 7-(3-chlorophenyl)-2,3,4,5-tetrahydro-1H-[1,4]diazepino[1,7-a]indole 7-(4-methylphenyl)-2,3,4,5-tetrahydro-1H-[1,4]diazepino[1,7-a]indole 7-(4-chloro-2-methylphenyl)-2,3,4,5-tetrahydro-1H-[1,4]diazepino[1,7-a]indole 7-(2,5-dichlorophenyl)-2,3,4,5-tetrahydro-1H-[1,4]diazepino[1,7-a]indole 7-(4-isopropyl-2-methoxyphenyl)-2,3,4,5-tetrahydro-1H-[1,4]diazepino[1,7-a]indole 7-(2,6-dichlorophenyl)-2,3,4,5-tetrahydro-1H-[1,4]diazepino[1,7-a]indole 7-(2,6-difluorophenyl)-2,3,4,5-tetrahydro-1H-[1,4]diazepino[1,7-a]indole 7-[4-methoxy-2-(trifluoromethyl)phenyl]-2,3,4,5-tetrahydro-1H-[1,4]diazepino[1,7-a]indole 7-[2-(trifluoromethyl)phenyl]-2,3,4,5-tetrahydro-1H-[1,4]diazepino[1,7-a]indole 7-(4-pyridinyl)-2,3,4,5-tetrahydro-1H-[1,4]diazepino[1,7-a]indole 7-(2-furyl)-2,3,4,5-tetrahydro-1H-[1,4]diazepino[1,7-a]indole 2-(2,3,4,5-tetrahydro-1H-[1,4]diazepino[1,7-a]indol-7-yl)benzenethiol 7-(2,3-dichlorophenyl)-2,3,4,5-tetrahydro-1H-[1,4]diazepino[1,7-a]indole 7-(4-ethylphenyl)-2,3,4,5-tetrahydro-1H-[1,4]diazepino[1,7-a]indole 7-(2,4-dimethoxyphenyl)-2,3,4,5-tetrahydro-1H-[1,4]diazepino[1,7-a]indole 7-(3-chloro-2-fluorophenyl)-2,3,4,5-tetrahydro-1H-[1,4]diazepino[1,7-a]indole 7-(4-methoxyphenyl)-2,3,4,5-tetrahydro-1H-[1,4]diazepino[1,7-a]indole 7-[4-(methylsulfanyl)phenyl]-2,3,4,5-tetrahydro-1H-[1,4]diazepino[1,7-a]indole 4-(2,3,4,5-tetrahydro-1H-[1,4]diazepino[1,7-a]indol-7-yl)benzonitrile 7-[3-(trifluoromethyl)phenyl]-2,3,4,5-tetrahydro-1H-[1,4]diazepino[1,7-a]indole 7-(2-naphthyl)-2,3,4,5-tetrahydro-1H-[1,4]diazepino[1,7-a]indole 1-[4-(2,3,4,5-tetrahydro-1H-[1,4]diazepino[1,7-a]indol-7-yl)phenyl]ethanone N-[3-(2,3,4,5-tetrahydro-1H-[1,4]diazepino[1,7-a]indol-7-yl)phenyl]acetamide 7-(2,3-dimethylphenyl)-2,3,4,5-tetrahydro-1H-[1,4]diazepino[1,7-a]indole 7-(5-fluoro-2-methylphenyl)-2,3,4,5-tetrahydro-1H-[1,4]diazepino[1,7-a]indole 7-(2-fluoro-5-methylphenyl)-2,3,4,5-tetrahydro-1H-[1,4]diazepino[1,7-a]indole 7-(5-fluoro-2-methoxyphenyl)-2,3,4,5-tetrahydro-1H-[1,4]diazepino[1,7-a]indole 7-(3-chloro-2-methylphenyl)-2,3,4,5-tetrahydro-1H-[1,4]diazepino[1,7-a]indole 7-(3-nitrophenyl)-2,3,4,5-tetrahydro-1H-[1,4]diazepino[1,7-a]indole 7-(2-nitrophenyl)-2,3,4,5-tetrahydro-1H-[1,4]diazepino[1,7-a]indole 7-(2-chloro-3-methylphenyl)-2,3,4,5-tetrahydro-1H-[1,4]diazepino[1,7-a]indole 7-(2-methoxyphenyl)-2,3,4,5-tetrahydro-1H-[1,4]diazepino[1,7-a]indole 7-(4-ethoxy-2-methylphenyl)-2,3,4,5-tetrahydro-1H-[1,4]diazepino[1,7-a]indole 7-(4-fluoro-2-methylphenyl)-2,3,4,5-tetrahydro-1H-[1,4]diazepino[1,7-a]indole 7-(2-chloro-6-fluorophenyl)-2,3,4,5-tetrahydro-1H-[1,4]diazepino[1,7-a]indole 7-[2-chloro-4-(difluoromethoxy)phenyl[23,4,5-tetrahydro-1H-[1,4]diazepino[1,7-a]indole 7-[4-(trifluoromethyl)phenyl]-2,3,4,5-tetrahydro-1H-[1,4]diazepino[1,7-a]indole 7-[4-(trifluoromethoxy)phenyl]-2,3,4,5-tetrahydro-1H-[1,4]diazepino[1,7-a]indole 7-(6-fluoro-2,4-dimethoxyphenyl)-2,3,4,5-tetrahydro-1H-[1,4]diazepino[1,7-a]indole 7-(2-methylphenyl)-2,3,4,5-tetrahydro-1H-[1,4]diazepino[1,7-a]indole 7-[6-fluoro-2-(trifluoromethyl)phenyl]-2,3,4,5-tetrahydro-1H-[1,4]diazepino[1,7-a]indole 7-[2-(methylsulfanyl)phenyl]-2,3,4,5-tetrahydro-1H-[1,4]diazepino[1,7-a]indole 7-(2,4,6-trifluorophenyl)-2,3,4,5-tetrahydro-1H-[1,4]diazepino[1,7-a]indole 7-(2,4,6-trichlorophenyl)-2,3,4,5-tetrahydro-1H-[1,4]diazepino[1,7-a]indole 7-(2,6-dichloro-4-methoxyphenyl)-2,3,4,5-tetrahydro-1H-[1,4]diazepino[1,7-a]indole 7-(2,3,4-trifluorophenyl)-2,3,4,5-tetrahydro-1H-[1,4]diazepino[1,7-a]indole 7-(4-chloro-2,6-difluorophenyl)-2,3,4,5-tetrahydro 1H-[1,4]diazepino[1,7-a]indole 7-(2,3,4,6-tetrafluorophenyl)-2,3,4,5-tetrahydro-1H-[1,4]diazepino[1,7-a]indole 7-(2,3,4,5,6-pentafluorophenyl)-2,3,4,5-tetrahydro-1H-[1,4]diazepino[1,7-a]indole 7-[2,6-di(trifluoromethyl)phenyl]-2,3,4,5-tetrahydro-1H-[-1,4]diazepino[1,7-a]indole 7-[2-(trifluoromethoxy)phenyl]-2,3,4,5-tetrahydro-1H-[1,4]diazepino[1,7-a]indole 7-[4-ethoxy-2-(trifluoromethoxy)phenyl]-2,3,4,5-tetrahydro-1 n-[1,4]diazepino[1,7-a]indole 7-[4-isopropoxy-2-(trifluoromethyl)phenyl]-2,3,4,5-tetrahydro-1 n-[1,4]diazepino[1,7-a]indole 7-[4-chloro-2-(trifluoromethyl)phenyl]-2,3,4,5-tetrahydro-1H-[1,4]diazepino[1,7-a]indole 7-[4-fluoro-2-(trifluoromethyl)phenyl]-2,3,4,5-tetrahydro-1H-[1,4]diazepino[1,7-a]indole 7-(2-chloro-4-ethoxyphenyl)-2,3,4,5-tetrahydro-1H-[1,4]diazepino[1,7-a]indole 7-(2-chloro-4-isopropoxyphenyl)-2,3,4,5-tetrahydro-1H-[1,4]diazepino[1,7-a]indole 7-(2-ethyl-4-methoxyphenyl)-2,3,4,5-tetrahydro-1H-[1,4]diazepino[1,7-a]indole 5-methoxy-2-(2,3,4,5-tetrahydro-1H-[1,4]diazepino[1,7-a]indol-7-yl)benzaldehyde 7-[4-methoxy-2-(1-hydroxyethyl)phenyl]-2,3,4,5-tetrahydro-1H-[1,4]diazepino[1,7-a]indole 7-[4-methoxy-2-(1-methoxyethyl)phenyl]-2,3,4,5-tetrahydro-1H-[1,4]diazepino[1,7-a]indole 1-[5-methoxy-2-(2,3,4,5-tetrahydro-1H-[1,4]diazepino[1,7-a]indol-7-yl)phenyl]ethanone

[5-methoxy-2-(2,3,4,5-tetrahydro-1H-[1,4]diazepino[1,7-a]indol-7-yl)phenyl]methanol 7-[4-methoxy-2-(methoxymethyl)phenyl]-2,3,4,5-tetrahydro-1H-[1,4]diazepino[1,7-a]indole 1-[5-methoxy-2-(2,3,4,5-tetrahydro-1H-[1,4]diazepino[1,7-a]indol-7-yl)phenyl]-1-propanol 1-[5-methoxy-2-(2,3,4,5-tetrahydro-1H-[1,4]diazepino[1,7-a]indol-7-yl)phenyl]-1-propanone methyl (2Z)-3-[5-methoxy-2-(2,3,4,5-tetrahydro-1H-[1,4]diazepino[1,7-a]indol-7-yl)phenyl]-2-propenoate methyl 3-[5-methoxy-2-(2,3,4,5-tetrahydro-1H-[1,4]diazepino[1,7-a]indol-7-yl)phenyl]propanoate (2Z)-3-[5-methoxy-2-(2,3,4,5-tetrahydro-1H-[1,4]diazepino[1,7-a]indol-7-yl)phenyl]2-propen-1-ol methyl (2E)-3-[5-methoxy-2-(2,3,4,5-tetrahydro-1H-[1,4]diazepino[1,7-a]indol-7-yl)phenyl]-2-propenoate (2E)-3-[5-methoxy-2-(2,3,4,5-tetrahydro-1H-[1,4]diazepino[1,7-a]indol-7-yl)phenyl]-2-propen-1-ol 7-[4-methoxy-2-(2-methoxyethyl)phenyl]-2,3,4,5-tetrahydro-1H-[1,4]diazepino[1,7-a]indole 7-(2-fluoro-4-methoxyphenyl)-2,3,4,5-tetrahydro-1H-[1,4]diazepino[1,7-a]indole 7-(2-chloro-4-fluorophenyl)-2,3,4,5-tetrahydro-1H-[1,4]diazepino[1,7-a]indole 7-benzyl-2,3,4,5-tetrahydro-1H-[1,4]diazepino[1,7-a]indole 7-(2-fluorobenzyl)-2,3,4,5-tetrahydro-1H-[1,4]diazepino[1,7-a]indole 7-(3-fluorobenzyl)-2,3,4,5-tetrahydro-1H-[1,4]diazepino[1,7-a]indole 7-(4-fluorobenzyl)-2,3,4,5-tetrahydro-1H-[1,4]diazepino[1,7-a]indole 7-(3-methoxybenzyl)-2,3,4,5-tetrahydro-1H-[1,4]diazepino[1,7-a]indole 3-(2,3,4,5-tetrahydro-1H-[1,4]diazepino[1,7-a]indol-7-ylmethyl)phenol 7-(2-methoxybenzyl)-2,3,4,5-tetrahydro-1H-[1,4]diazepino[1,7-a]indole 2-(2,3,4,5-tetrahydro-1H-[1,4]diazepino[1,7-a]indol-7-ylmethyl)phenol methyl 2-methoxy-6-(2,3,4,5-tetrahydro-1H-[1,4]diazepino[1,7-a]indol-7-yl)benzoate 3-(2,3,4,5-tetrahydro-1H-[1,4]diazepino[1,7-a]indol-7-yl)benzonitrile 3-methyl-4-(2,3,4,5-tetrahydro-1H-[1,4]diazepino[1,7-a]indol-7-yl)benzonitrile 2-methyl-3-(2,3,4,5-tetrahydro-1H-[1,4]diazepino[1,7-a]indol-7-yl)benzonitrile 2-(2,3,4,5-tetrahydro-1H-[1,4]diazepino[1,7-a]indol-7-yl)benzonitrile 3-trifluoromethyl-4-(2,3,4,5-tetrahydro-1H-[1,4]diazepino[1,7-a]indol-7-yl)benzonitrile 3-(2,3,4,5-tetrahydro-1H-[1,4]diazepino[1,7-a]indol-7-yl)benzaldehyde

[3-(2,3,4,5-tetrahydro-1H-[1,4]diazepino[1,7-a]indol-7-yl)phenyl]methanol

7-[3-(methoxymethyl)phenyl]-2,3,4,5-tetrahydro-1H-[1,4]diazepino[1,7-a]indole

N,N-dimethyl[3-(2,3,4,5-tetrahydro-1H-[1,4]diazepino[1,7-a]indol-7-yl)phenyl]methanamine 2-fluoro-5-(2,3,4,5-tetrahydro-1H-[1,4]diazepino[1,7-a]indol-7-yl)benzonitrile 2-fluoro-5-(2,3,4,5-tetrahydro-1H-[1,4]diazepino[1,7-a]indol-7-yl)benzamide 7-phenyl-2,3,4,5,11,11a-hexahydro-1H-[1,4]diazepino[1,7-a]indole 7-(2,4-dichlorophenyl)-2,3,4,5,11,11a-hexahydro-1H-[1,4]diazepino[1,7-a]indole 7-(4-fluorophenyl)-2,3,4,5,11,11a-hexahydro-1H-[1,4]diazepino[1,7-a]indole 7-(4-chlorophenyl)-2,3,4,5,11,11a-hexahydro-1H-[1,4]diazepino[1,7-a]indole 7-(2-chlorophenyl)-2,3,4,5,11,11a-hexahydro-1H-[1,4]diazepino[1,7-a]indole 7-(2-methoxyphenyl)-2,3,4,5,11,11a-hexahydro-1H-[1,4]diazepino[1,7-a]indole 7-[2-chloro-4-(trifluoromethyl)phenyl]-2,3,4,5,11,11a-hexahydro-1H-[1,4]diazepino[1,7-a]indole 7-(2,4-dimethylphenyl)-2,3,4,5,11,11a-hexahydro-1H-[1,4]diazepino[1,7-a]indole 7-(2-chloro-4-methoxyphenyl)-2,3,4,5,11,11a-hexahydro-1H-[1,4]diazepino[1,7-a]indole 7-(4-isopropylphenyl)-2,3,4,5,11,11a-hexahydro-1H-[1,4]diazepino[1,7-a]indole 7-(4-butylphenyl)-2,3,4,5,11,11a-hexahydro-1H-[1,4]diazepino[1,7-a]indole 7-(5-fluoro-4-methoxy-2-methylphenyl)-2,3,4,5,11,11a-hexahydro-1H-[1,4]diazepino[1,7-a]indole 7-(4-methoxy-2-methylphenyl)-2,3,4,5,11,11a-hexahydro-1H-[1,4]diazepino[1,7-a]indole 7-[2-chloro-4-(trifluoromethoxy)phenyl]-2,3,4,5,11,11a-hexahydro-1H-[1,4]diazepino[1,7-a]indole 7-(2,4,5-trimethylphenyl)-2,3,4,5,11,11a-hexahydro-1H-[1,4]diazepino[1,7-a]indole 7-(3-chlorophenyl)-2,3,4,5,11,11a-hexahydro-1H-[1,4]diazepino[1,7-a]indole 7-(4-methylphenyl)-2,3,4,5,11,11a-hexahydro-1H-[1,4]diazepino[1,7-a]indole 7-(4-chloro-2-methylphenyl)-2,3,4,5,11,11a-hexahydro-1H-[1,4]diazepino[1,7-a]indole 7-(2,5-dichlorophenyl)-2,3,4,5,11,11a-hexahydro-1H-[1,4]diazepino[1,7-a]indole 7-(4-isopropyl-2-methoxyphenyl)-2,3,4,5,11,11a-hexahydro-1H-[1,4]diazepino[1,7-a]indole 7-(2,6-dichlorophenyl)-2,3,4,5,11,11a-hexahydro-1H-[1,4]diazepino[1,7-a]indole 7-(2,6-difluorophenyl)-2,3,4,5,11,11a-hexahydro-1H-[1,4]diazepino[1,7-a]indole 7-[4-methoxy-2-(trifluoromethyl)phenyl]-2,3,4,5,11,11a-hexahydro-1H-[1,4]diazepino[1,7-a]indole 7-[2-(trifluoromethyl)phenyl]-2,3,4,5,11,11a-hexahydro-1H-[1,4]diazepino[1,7-a]indole 7-(4-pyridinyl)-2,3,4,5,11,11a-hexahydro-1H-[1,4]diazepino[1,7-a]indole 7-(2-furyl)-2,3,4,5,11,11a-hexahydro-1H-[1,4]diazepino[1,7-a]indole 2-(2,3,4,5,11,11a-hexahydro-1H-[1,4]diazepino[1,7-a]indol-7-yl)benzenethiol 7-(2,3-dichlorophenyl)-2,3,4,5,11,11a-hexahydro-1H-[1,4]diazepino[1,7-a]indole 7-(4-ethylphenyl)-2,3,4,5,11,11a-hexahydro-1H-[1,4]diazepino[1,7-a]indole 7-(2,4-dimethoxyphenyl)-2,3,4,5,11,11a-hexahydro-1H-[1,4]diazepino[1,7-a]indole 7-(3-chloro-2-fluorophenyl)-2,3,4,5,11,11a-hexahydro-1H-[1,4]diazepino[1,7-a]indole 7-(4-methoxyphenyl)-2,3,4,5,11,11a-hexahydro-1H-[1,4]diazepino[1,7-a]indole 7-[4-(methylsulfanyl)phenyl]-2,3,4,5,11,11a-hexahydro-1H-[1,4]diazepino[1,7-a]indole 4-(2,3,4,5,11,11a-hexahydro-1H-[1,4]diazepino[1,7-a]indol-7-yl)benzonitrile 7-[3-(trifluoromethyl)phenyl]-2,3,4,5,11,11a-hexahydro-1H-[1,4]diazepino[1,7-a]indole 7-(2-naphthyl)-2,3,4,5,11,11a-hexahydro-1H-[1,4]diazepino[1,7-a]indole 1-[4-(2,3,4,5,11,11a-hexahydro-1H-[1,4]diazepino[1,7-a]indol7yl)phenyl]ethanone N-[3-(2,3,4,5,11,11a-hexahydro-1H-[1,4]diazepino[1,7-a]indol-7-yl)phenyl]acetamide 7-(2,3-dimethylphenyl)-2,3,4,5,11,11a-hexahydro-1H-[1,4]diazepino[1,7-a]indole 7-(5-fluoro-2-methylphenyl)-2,3,4,5,11,11a-hexahydro-1H-[1,4]diazepino[1,7-a]indole 7-(2-fluoro-5-methylphenyl)-2,3,4,5,11,11a-hexahydro-1H-[1,4]diazepino[1,7-a]indole 7-(5-fluoro-2-methoxyphenyl)-2,3,4,5,11,11a-hexahydro-1H-[1,4]diazepino[1,7-a]indole 7-(3-chloro-2-methylphenyl)-2,3,4,5,11,11a-hexahydro-1H-[1,4]diazepino[1,7-a]indole 7-(3-nitrophenyl)-2,3,4,5,11,11a-hexahydro-1H-[1,4]diazepino[1,7-a]indole 7-(2-nitrophenyl)-2,3,4,5,11,11a-hexahydro-1H-[1,4]diazepino[1,7-a]indole 7-(2-chloro-3-methylphenyl)-2,3,4,5,11,11a-hexahydro-1H-[1,4]diazepino[1,7-a]indole 7-(2-methoxyphenyl)-2,3,4,5,11,11a-hexahydro-1H-[1,4]diazepino[1,7-a]indole 7-(4-ethoxy-2-methylphenyl)-2,3,4,5,11,11a-hexahydro-1H-[1,4]diazepino[1,7-a]indole 7-(4-fluoro-2-methylphenyl)-2,3,4,5,11,11a-hexahydro-1H-[1,4]diazepino[1,7-a]indole 7-(2-chloro-6-fluorophenyl)-2,3,4,5,11,11a-hexahydro-1H-[1,4]diazepino[1,7-a]indole 7-[2-chloro-4-(difluoromethoxy)phenyl]-2,3,4,5,11,11a-hexahydro-1H-[1,4]diazepino[1,7-a]indole 7-[4-(trifluoromethyl)phenyl]-2,3,4,5,11,11a-hexahydro-1H-[1,4]diazepino[1,7-a]indole 7-[4-(trifluoromethoxy)phenyl]-2,3,4,5,11,11a-hexahydro-1H-[1,4]diazepino[1,7-a]indole 7-(6-fluoro-2,4-dimethoxyphenyl)-2,3,4,5,11,11a-hexahydro-1H-[1,4]diazepino[1,7-a]indole 7-(2-methylphenyl)-2,3,4,5,11,11a-hexahydro-1H-[1,4]diazepino[1,7-a]indole 7-[6-fluoro-2-(trifluoromethyl)phenyl]-2,3,4,5,11,11a-hexahydro-1H-[1,4]diazepino[1,7-a]indole 7-[2-(methylsulfanyl)phenyl]-2,3,4,5,11,11a-hexahydro-1H-[1,4]diazepino[1,7-a]indole 7-(2,4,6-trifluorophenyl)-2,3,4,5,11,11a-hexahydro-1H-[1,4]diazepino[1,7-a]indole 7-(2,4,6-trichlorophenyl)-2,3,4,5,11,11a-hexahydro-1H-[1,4]diazepino[1,7-a]indole 7-(2,6-dichloro-4-methoxyphenyl)-2,3,4,5,11,11a-hexahydro-1H-[1,4]diazepino[1,7-a]indole 7-(2,3,4-trifluorophenyl)-2,3,4,5,11,11a-hexahydro-1H-[1,4]diazepino[1,7-a]indole 7-(4-chloro-2,6-difluorophenyl)-2,3,4,5,11,11a-hexahydro-1H-[1,4]diazepino[1,7-a]indole 7-(2,3,4,6-tetrafluorophenyl)-2,3,4,5,11,11a-hexahydro-1H-[1,4]diazepino[1,7-a]indole 7-(2,3,4,5,6-pentafluorophenyl)-2,3,4,5,11,11a-hexahydro-1H-[1,4]diazepino[1,7-a]indole 7-[2,6-di(trifluoromethyl)phenyl]-2,3,4,5,11,11a-hexahydro-1H-[1,4]diazepino[1,7-a]indole 7-[2-(trifluoromethoxy)phenyl]-2,3,4,5,11,11a-hexahydro-1H-[1,4]diazepino[1,7-a]indole 7-[4-ethoxy-2-(trifluoromethoxy)phenyl]-2,3,4,5,11,11a-hexahydro-1H-[1,4]diazepino[1,7-a]indole 7-[4-isopropoxy-2-(trifluoromethyl)phenyl]-2,3,4,5,11,11a-hexahydro-1H-[1,4]diazepino[1,7-a]indole 7-[4-chloro-2-(trifluoromethyl)phenyl]-2,3,4,5,11,11a-hexahydro-1H-[1,4]diazepino[1,7-a]indole 7-[4-fluoro-2-(trifluoromethyl)phenyl]-2,3,4,5,11,11a-hexahydro-1H-[1,4]diazepino[1,7-a]indole 7-[2-chloro-4-ethoxyphenyl]-2,3,4,5,11,11a-hexahydro-1H-[1,4]diazepino[1,7-a]indole 7-[2-chloro-4-isopropoxyphenyl]-2,3,4,5,11,11a-hexahydro-1H-[1,4]diazepino[1,7-a]indole 7-(2-ethyl-4-methoxyphenyl)-2,3,4,5,11,11a-hexahydro-1H-[1,4]diazepino[1,7-a]indole 5-methoxy-2-(2,3,4,5,11,11a-hexahydro-1H-[1,4]diazepino[1,7-a]indol-7-yl)benzaldehyde 7-[4-methoxy-2-(1-hydroxyethyl)phenyl]-2,3,4,5,11,11a-hexahydro-1H-[1,4]diazepino[1,7-a]indole 7-[4-methoxy-2-(1-methoxyethyl)phenyl]-2,3,4,5,11,11a-hexahydro-1H-[1,4]diazepino[1,7-a]indole 1-[5-methoxy-2-(2,3,4,5,11,11a-hexahydro-1H-[1,4]diazepino[1,7-a]indol-7-yl)phenyl]ethanone

[5-methoxy-2-(2,3,4,5,11,11a-hexahydro-1H-[1,4]diazepino[1,7-a]indol-7-yl)phenyl]methanol 7-[4-methoxy-2-(methoxymethyl)phenyl]-2,3,4,5,11,11a-hexahydro-1H-[1,4]diazepino[1,7-a]indole 1-[5-methoxy-2-(2,3,4,5,11,11a-hexahydro-1H-[1,4]diazepino[1,7-a]indol-7-yl)phenyl]-1-propanol 1-[5-methoxy-2-(2,3,4,5,11,11a-hexahydro-1H-[1,4]diazepino[1,7-a]indol-7-yl)phenyl]-1-propanone methyl (2Z)-3-[5-methoxy-2-(2,3,4,5,11,11a-hexahydro-1H-[1,4]diazepino[1,7-a]indol-7-yl)phenyl]-2-propenoate methyl 3-[5-methoxy-2-(2,3,4,5,11,11a-hexahydro-1H-[1,4]diazepino[1,7-a]indol-7-yl)phenyl]propanoate (2Z)-3-[5-methoxy-2-(2,3,4,5,11,11a-hexahydro-1H-[1,4]diazepino[1,7-a]indole yl)phenyl]-2-propen-1-ol methyl (2E)-3-[5-methoxy-2-(2,3,4,5,11,11a-hexahydro-1H-[1,4]diazepino[1,7-a]indol-7-yl)phenyl]-2-propenoate (2E)-3-[5-methoxy-2-(2,3,4,5,11,11a-hexahydro-1H-[1,4]diazepino[1,7-a]indol-7-yl)phenyl]-2-propen-1-ol 7-[4-methoxy-2-(2-methoxyethyl)phenyl]-2,3,4,5,11,11a-hexahydro-1H-[1,4]diazepino[1,7-a]indole 7-(2-fluoro-4-methoxyphenyl)-2,3,4,5,11,11a-hexahydro-1H-[1,4]diazepino[1,7-a]indole 7-(2-chloro-4-fluorophenyl)-2,3,4,5,11,11a-hexahydro-1H-[1,4]diazepino[1,7-a]indole 7-benzyl-2,3,4,5,11,11a-hexahydro-1H-[1,4]diazepino[1,7-a]indole 7-(2-fluorobenzyl)-2,3,4,5,11,11a-hexahydro-1H-[1,4]diazepino[1,7-a]indole 7-(3-fluorobenzyl)-2,3,4,5,11,11a-hexahydro-1H-[1,4]diazepino[1,7-a]indole
7-(4-fluorobenzyl)-2,3,4,5,11,11a-hexahydro-1H-[1,4]diazepino[1,7-a]indole
7-(3-methoxybenzyl)-2,3,4,5,11,11a-hexahydro-1H-[1,4]diazepino[1,7-a]indole
3-(2,3,4,5,11,11a-hexahydro-1H-[1,4]diazepino[1,7-a]indol-7-ylmethyl)phenol
7-(2-methoxybenzyl)-2,3,4,5,11,11a-hexahydro-1H-[1,4]diazepino[1,7-a]indole
2-(2,3,4,5,11,11a-hexahydro-1H-[1,4]diazepino[1,7-a]indol-7-ylmethyl)phenol
methyl 2-methoxy-6-(2,3,4,5,11,11a-hexahydro-1H-[1,4]diazepino[1,7-a]indol-7-yl)benzoate
3-(2,3,4,5,11,11a-hexahydro-1H-[1,4]diazepino[1,7-a]indol-7-yl)benzonitrile
3-methyl-4-(2,3,4,5,11,11a-hexahydro-1H-[1,4]diazepino[1,7-a]indol-7-yl)benzonitrile
2-methyl-3-(2,3,4,5,11,11a-hexahydro-1H-[1,4]diazepino[1,7-a]indol-7-yl)benzonitrile
2-(2,3,4,5,11,11a-hexahydro-1H-[1,4]diazepino[1,7-a]indol-7-yl)benzonitrile
3-trifluoromethyl-4-(2,3,4,5,11,11a-hexahydro-1H-[1,4]diazepino[1,7-a]indol-7-yl)benzonitrile
3-(2,3,4,5,11,11a-hexahydro-1H-[1,4]diazepino[1,7-a]indol-7-yl)benzaldehyde
[3-(2,3,4,5,11,11a-hexahydro-1H-[1,4]diazepino[1,7-a]indol-7-yl)phenyl]methanol
7-[3-(methoxymethyl)phenyl]-2,3,4,5,11,11a-hexahydro-1H-[1,4]diazepino[1,7-a]indole
N,N-dimethyl[3-(2,3,4,5,11,11a-hexahydro-1H-[1,4]diazepino[1,7-a]indol-7-yl)phenyl]methanamine
2-fluoro-5-(2,3,4,5,11,11a-hexahydro-1H-[1,4]diazepino[1,7-a]indol-7-yl)benzonitrile
2-fluoro-5-(2,3,4,5,11,11a-hexahydro-1H-[1,4]diazepino[1,7-a]indol-7-yl)benzamide
9-(2,4-dichlorophenyl)-2,3,4,5-tetrahydro-1H-[1,4]diazepino[1,7-a]indole
9-(4-fluorophenyl)-2,3,4,5-tetrahydro-1H-[1,4]diazepino[1,7-a]indole
9-(4-chlorophenyl)-2,3,4,5-tetrahydro-1H-[1,4]diazepino[1,7-a]indole
9-(2-chlorophenyl)-2,3,4,5-tetrahydro-1H-[1,4]diazepino[1,7-a]indole
9-(2-methoxyphenyl)-2,3,4,5-tetrahydro-1H-[1,4]diazepino[1,7-a]indole
9-[2-chloro-4-(trifluoromethyl)phenyl]-2,3,4,5-tetrahydro-1H-[1,4]diazepino[1,7-a]indole
9-(2,4-dimethylphenyl)-2,3,4,5-tetrahydro-1H-[1,4]diazepino[1,7-a]indole
9-(2-chloro-4-methoxyphenyl)-2,3,4,5-tetrahydro-1H-[1,4]diazepino[1,7-a]indole
9-(4-isopropylphenyl)-2,3,4,5-tetrahydro-1H-[1,4]diazepino[1,7-a]indole
9-(4-butylphenyl)-2,3,4,5-tetrahydro-1H-[1,4]diazepino[1,7-a]indole
9-(5-fluoro-4-methoxy-2-methylphenyl)-2,3,4,5-tetrahydro-1H-[1,4]diazepino[1,7-a]indole
9-(4-methoxy-2-methylphenyl)-2,3,4,5-tetrahydro-1H-[1,4]diazepino[1,7-a]indole
9-[2-chloro-4-(trifluoromethoxy)phenyl]-2,3,4,5-tetrahydro-1H-[1,4]diazepino[1,7-a]indole
9-(2,4,5-trimethylphenyl)-2,3,4,5-tetrahydro-1H-[1,4]diazepino[1,7-a]indole
9-(3-chlorophenyl)-2,3,4,5-tetrahydro-1H-[1,4]diazepino[1,7-a]indole
9-(4-methylphenyl)-2,3,4,5-tetrahydro-1H-[1,4]diazepino[1,7-a]indole
9-(4-chloro-2-methylphenyl)-2,3,4,5-tetrahydro-1H-[1,4]diazepino[1,7-a]indole
9-(2,5-dichlorophenyl)-2,3,4,5-tetrahydro-1H-[1,4]diazepino[1,7-a]indole
9-(4-isopropyl-2-methoxyphenyl)-2,3,4,5-tetrahydro-1H-[1,4]diazepino[1,7-a]indole
9-(2,6-dichlorophenyl)-2,3,4,5-tetrahydro-1H-[1,4]diazepino[1,7-a]indole
9-(2,6-difluorophenyl)-2,3,4,5-tetrahydro-1H-[1,4]diazepino[1,7-a]indole
9-[4-methoxy-2-(trifluoromethyl)phenyl]-2,3,4,5-tetrahydro-1H-[1,4]diazepino[1,7-a]indole
9-[2-(trifluoromethyl)phenyl]-2,3,4,5-tetrahydro-1H-[1,4]diazepino[1,7-a]indole
9-(4-pyridinyl)-2,3,4,5-tetrahydro-1H-[1,4]diazepino[1,7-a]indole
9-(2-furyl)-2,3,4,5-tetrahydro-1H-[1,4]diazepino[1,7-a]indole
2-(2,3,4,5-tetrahydro-1H-[1,4]diazepino[1,7-a]indol-9-yl)benzenethiol
9-(2,3-dichlorophenyl)-2,3,4,5-tetrahydro-1H-[1,4]diazepino[1,7-a]indole
9-(4-ethylphenyl)-2,3,4,5-tetrahydro-1H-[1,4]diazepino[1,7-a]indole
9-(2,4-dimethoxyphenyl)-2,3,4,5-tetrahydro-1H-[1,4]diazepino[1,7-a]indole
9-(3-chloro-2-fluorophenyl)-2,3,4,5-tetrahydro-1H-[1,4]diazepino[1,7-a]indole
9-(4-methoxyphenyl)-2,3,4,5-tetrahydro-1H-[1,4]diazepino[1,7-a]indole
9-[4-(methylsulfanyl)phenyl]-2,3,4,5-tetrahydro-1H-[1,4]diazepino[1,7-a]indole
4-(2,3,4,5-tetrahydro-1H-[1,4]diazepino[1,7-a]indol-9-yl)benzonitrile
9-[3-(trifluoromethyl)phenyl]-2,3,4,5-tetrahydro-1H-[1,4]diazepino[1,7-a]indole
9-(2-naphthyl)-2,3,4,5-tetrahydro-1H-[1,4]diazepino[1,7-a]indole
1-[4-(2,3,4,5-tetrahydro-1H-[1,4]diazepino[1,7-a]indol-9-yl)phenyl]ethanone
N-[3-(2,3,4,5-tetrahydro-1H-[1,4]diazepino[1,7-a]indol-9-yl)phenyl]acetamide
9-(2,3-dimethylphenyl)-2,3,4,5-tetrahydro-1H-[1,4]diazepino[1,7-a]indole
9-(5-fluoro-2-methylphenyl)-2,3,4,5-tetrahydro-1H-[1,4]diazepino[1,7-a]indole
9-(2-fluoro-5-methylphenyl)-2,3,4,5-tetrahydro-1H-[1,4]diazepino[1,7-a]indole
9-(5-fluoro-2-methoxyphenyl)-2,3,4,5-tetrahydro-1H-[1,4]diazepino[1,7-a]indole
9-(3-chloro-2-methylphenyl)-2,3,4,5-tetrahydro-1H-[1,4]diazepino[1,7-a]indole
9-(3-nitrophenyl)-2,3,4,5-tetrahydro-1H-[1,4]diazepino[1,7-a]indole
9-(2-nitrophenyl)-2,3,4,5-tetrahydro-1H-[1,4]diazepino[1,7-a]indole 9-(2-chloro-3-methylphenyl)-2,3,4,5-tetrahydro-1H-[1,4]diazepino[1,7-a]indole 9-(2-methoxyphenyl)-2,3,4,5-tetrahydro-1H-[1,4]diazepino[1,7-a]indole 9-(4-ethoxy-2-methylphenyl)-2,3,4,5-tetrahydro-1H-[1,4]diazepino[1,7-a]indole 9-(4-fluoro-2-methylphenyl)-2,3,4,5-tetrahydro-1H-[1,4]diazepino[1,7-a]indole 9-(2-chloro-6-fluorophenyl)-2,3,4,5-tetrahydro-1H-[1,4]diazepino[1,7-a]indole 9-[2-chloro-4-(difluoromethoxy)phenyl]-2,3,4,5-tetrahydro-1H-[1,4]diazepino[1,7-a]indole 9-[4-(trifluoromethyl)phenyl]-2,3,4,5-tetrahydro-1H-[1,4]diazepino[1,7-a]indole 9-[4-(trifluoromethoxy)phenyl]-2,3,4,5-tetrahydro-1H-[1,4]diazepino[1,7-a]indole 9-(6-fluoro-2,4-dimethoxyphenyl)-2,3,4,5-tetrahydro-1H-[1,4]diazepino[1,7-a]indole 9-(2-methylphenyl)-2,3,4,5-tetrahydro-1H-[1,4]diazepino[1,7-a]indole 9-[6-fluoro-2-(trifluoromethyl)phenyl]-2,3,4,5-tetrahydro-1H-[1,4]diazepino[1,7-a]indole 9-[2-(methylsulfanyl)phenyl]-2,3,4,5-tetrahydro-1H-[1,4]diazepino[1,7-a]indole 9-(2,4,6-trifluorophenyl)-2,3,4,5-tetrahydro-1H-[1,4]diazepino[1,7-a]indole 9-(2,4,6-trichlorophenyl)-2,3,4,5-tetrahydro-1H-[1,4]diazepino[1,7-a]indole 9-(2,6-dichloro-4-methoxyphenyl)-2,3,4,5-tetrahydro-1H-[1,4]diazepino[1,7-a]indole 9-(2,3,4-trifluorophenyl)-2,3,4,5-tetrahydro-1H-[1,4]diazepino[1,7-a]indole 9-(4-chloro-2,6-difluorophenyl)-2,3,4,5-tetrahydro-1H-[1,4]diazepino[1,7-a]indole 9-(2,3,4,6-tetrafluorophenyl)-2,3,4,5-tetrahydro-1H-[1,4]diazepino[1,7-a]indole 9-(2,3,4,5,6-pentafluorophenyl)-2,3,4,5-tetrahydro-1H-[1,4]diazepino[1,7-a]indole 9-[2,6-di(trifluoromethyl)phenyl]-2,3,4,5-tetrahydro-1H-[1,4]diazepino[1,7-a]indole 9-[2-(trifluoromethoxy)phenyl]-2,3,4,5-tetrahydro-1H-[1,4]diazepino[1,7-a]indole 9-[4-ethoxy-2-(trifluoromethoxy)phenyl]-2,3,4,5-tetrahydro-1H-[1,4]diazepino[1,7-a]indole 9-[4-isopropoxy-2-(trifluoromethyl)phenyl]-2,3,4,5-tetrahydro-1H-[1,4]diazepino[1,7-a]indole 9-[4-chloro-2-(trifluoromethyl)phenyl]-2,3,4,s-tetrahydro-1H-[1,4]diazepino[1,7-a]indole 9-[4-fluoro-2-(trifluoromethyl)phenyl]-2,3,4,5-tetrahydro-1H-[1,4]diazepino[1,7-a]indole 9-[2-chloro-4-ethoxyphenyl]-2,3,4,5-tetrahydro-1H-[1,4]diazepino[1,7-a]indole 9-[2-chloro-4-isopropoxyphenyl]-2,3,4,5-tetrahydro-1H-[1,4]diazepino[1,7-a]indole 9-(2-ethyl-4-methoxyphenyl)-2,3,4,5-tetrahydro-1H-[1,4]diazepino[1,7-a]indole 5-methoxy-2-(2,3,4,5-tetrahydro-1H-[1,4]diazepino[1,7-a]indol-9-yl)benzaldehyde 9-[4-methoxy-2-(1-hydroxyethyl)phenyl]-2,3,4,5-tetrahydro-1H-[1,4]diazepino[1,7-a]indole 9-[4-methoxy-2-(1-methoxyethyl)phenyl]-2,3,4,5-tetrahydro-1H-[1,4]diazepino[1,7-a]indole 1-[5-methoxy-2-(2,3,4,5-tetrahydro-1H-[1,4]diazepino[1,7-a]indol-9-yl)phenyl]ethanone

[5-methoxy-2-(2,3,4,5-tetrahydro-1H-[1,4]diazepino[1,7-a]indol-9-yl)phenyl]methanol 9-[4-methoxy-2-(methoxymethyl)phenyl]-2,3,4,5-tetrahydro-1H-[1,4]diazepino[1,7-a]indole 1-[5-methoxy-2-(2,3,4,5-tetrahydro-1H-[1,4]diazepino[1,7-a]indol-9-yl)phenyl]-1-propanol 1-[5-methoxy-2-(2,3,4,5-tetrahydro-1H-[1,4]diazepino[1,7-a]indol-9-yl)phenyl]-1-propanone methyl (2Z)-3-[5-methoxy-2-(2,3,4,5-tetrahydro-1H-[1,4]diazepino[1,7-a]indol-9-yl)phenyl]-2-propenoate methyl 3-[5-methoxy-2-(2,3,4,5-tetrahydro-1H-[1,4]diazepino[1,7-a]indol-9-yl)phenyl]propanoate (2Z)-3-[5-methoxy-2-(2,3,4,5-tetrahydro-1H-[1,4]diazepino[1,7-a]indol-9-yl)phenyl]-2-propen-1-ol methyl (2E)-3-[5-methoxy-2-(2,3,4,5-tetrahydro-1H-[1,4]diazepino[1,7-a]indol-9-yl)phenyl]-2-propenoate (2E)-3-[5-methoxy-2-(2,3,4,5-tetrahydro-1H-[1,4]diazepino[1,7-a]indol-9-yl)phenyl]-2-propen-1-ol 9-[4-methoxy-2-(2-methoxyethyl)phenyl]-2,3,4,5-tetrahydro-1H-[1,4]diazepino[1,7-a]indole 9-(2-fluoro-4-methoxyphenyl)-2,3,4,5-tetrahydro-1H-[1,4]diazepino[1,7-a]indole 9-(2-chloro-4-fluorophenyl)-2,3,4,5-tetrahydro-1H-[1,4]diazepino[1,7-a]indole 9-benzyl-2,3,4,5-tetrahydro-1H-[1,4]diazepino[1,7-a]indole 9-(2-fluorobenzyl)-2,3,4,5-tetrahydro-1H-[1,4]diazepino[1,7-a]indole 9-(3-fluorobenzyl)-2,3,4,5-tetrahydro-1H-[1,4]diazepino[1,7-a]indole 9-(4-fluorobenzyl)-2,3,4,5-tetrahydro-1H-[1,4]diazepino[1,7-a]indole 9-(3-methoxybenzyl)-2,3,4,5-tetrahydro-1H-[1,4]diazepino[1,7-a]indole 3-(2,3,4,5-tetrahydro-1H-[1,4]diazepino[1,7-a]indol-9-ylmethyl)phenol 9-(2-methoxybenzyl)-2,3,4,5-tetrahydro-1H-[1,4]diazepino[1,7-a]indole 2-(2,3,4,5-tetrahydro-1H-[1,4]diazepino[1,7-a]indol-9-ylmethyl)phenol methyl 2-methoxy-6-(2,3,4,5-tetrahydro-1H-[1,4]diazepino[1,7-a]indol-9-yl)benzoate 3-(2,3,4,5-tetrahydro-1H-[1,4]diazepino[1,7-a]indol-9-yl)benzonitrile 3-methyl-4-(2,3,4,5-tetrahydro-1H-[1,4]diazepino[1,7-a]indol-9-yl)benzonitrile 2-methyl-3-(2,3,4,5-tetrahydro-1H-[1,4]diazepino[1,7-a]indol-9-yl)benzonitrile 2-(2,3,4,5-tetrahydro-1H-[1,4]diazepino[1,7-a]indol-9-yl)benzonitrile 3-trifluoromethyl-4-(2,3,4,5-tetrahydro-1H-[1,4]diazepino[1,7-a]indol-9-yl)benzonitrile 3-(2,3,4,5-tetrahydro-1H-[1,4]diazepino[1,7-a]indol-9-yl)benzaldehyde

[3-(2,3,4,5-tetrahydro-1H-[1,4]diazepino[1,7-a]indol-9-yl)phenyl]methanol

9-[3-(methoxymethyl)phenyl]-2,3,4,5-tetrahydro-1H-[1,4]diazepino[1,7-a]indole

N,N-dimethyl[3-(2,3,4,5-tetrahydro-1H-[1,4]diazepino[1,7-a]indol-9-yl)phenyl]methanamine 2-fluoro-5-(2,3,4,5-tetrahydro-1H-[1,4]diazepino[1,7-a]indol-9-yl)benzonitrile 2-fluoro-5-(2,3,4,5-tetrahydro-1H-[1,4]diazepino[1,7-a]indol-9-yl)benzamide 9-phenyl-2,3,4,5,11,11a-hexahydro-1H-[1,4]diazepino[1,7-a]indole 9-(2,4-dichlorophenyl)-2,3,4,5,11,11a-hexahydro-1H-[1,4]diazepino[1,7-a]indole 9-(4-fluorophenyl)-2,3,4,5,11,11a-hexahydro-1H-[1,4]diazepino[1,7-a]indole 9-(4-chlorophenyl)-2,3,4,5,11,11a-hexahydro-1H-[1,4]diazepino[1,7-a]indole 9-(2-chlorophenyl)-2,3,4,5,11,11a-hexahydro-1H-[1,4]diazepino[1,7-a]indole 9-(2-methoxyphenyl)-2,3,4,5,11,11a-hexahydro-1H-[1,4]diazepino[1,7-a]indole 9-[2-chloro-4-(trifluoromethyl)phenyl]-2,3,4,5,11,11a-hexahydro-1H-[1,4]diazepino[1,7-a]indole 9-(2,4-dimethylphenyl)-2,3,4,5,11,11a-hexahydro-1H-[1,4]diazepino[1,7-a]indole 9-(2-chloro-4-methoxyphenyl)-2,3,4,5,11,11a-hexahydro-1H-[1,4]diazepino[1,7-a]indole 9-(4-isopropylphenyl)-2,3,4,5,11,11a-hexahydro-1H-[1,4]diazepino[1,7-a]indole 9-(4-butylphenyl)-2,3,4,5,11,11a-hexahydro-1H-[1,4]diazepino[1,7-a]indole 9-(5-fluoro-4-methoxy-2-methylphenyl)-2,3,4,5,11,11a-hexahydro-1H-[1,4]diazepino[1,7-a]indole 9-(4-methoxy-2-methylphenyl)-2,3,4,5,11,11a-hexahydro-1H-[1,4]diazepino[1,7-a]indole 9-[2-chloro-4-(trifluoromethoxy)phenyl]-2,3,4,5,11,11a-hexahydro-1H-[1,4]diazepino[1,7-a]indole 9-(2,4,5-trimethylphenyl)-2,3,4,5,11,11a-hexahydro-1H-[1,4]diazepino[1,7-a]indole 9-(3-chlorophenyl)-2,3,4,5,11,11a-hexahydro-1H-[1,4]diazepino[1,7-a]indole 9-(4-methylphenyl)-2,3,4,5,11,11a-hexahydro-1H-[1,4]diazepino[1,7-a]indole 9-(4-chloro-2-methylphenyl)-2,3,4,5,11,11a-hexahydro-1H-[1,4]diazepino[1,7-a]indole 9-(2,5-dichlorophenyl)-2,3,4,5,11,11a-hexahydro-1H-[1,4]diazepino[1,7-a]indole 9-(4-isopropyl-2-methoxyphenyl)-2,3,4,5,11,11a-hexahydro-1H-[1,4]diazepino[1,7-a]indole 9-(2,6-dichlorophenyl)-2,3,4,5,11,11a-hexahydro-1H-[1,4]diazepino[1,7-a]indole 9-(2,6-difluorophenyl)-2,3,4,5,11,11a-hexahydro-1H-[1,4]diazepino[1,7-a]indole 9-[4-methoxy-2-(trifluoromethyl)phenyl]-2,3,4,5,11,11a-hexahydro-1H-[1,4]diazepino[1,7-a]indole 9-[2-(trifluoromethyl)phenyl]-2,3,4,5,11,11a-hexahydro-1H-[1,4]diazepino[1,7-a]indole 9-(4-pyridinyl)-2,3,4,5,11,11a-hexahydro-1H-[1,4]diazepino[1,7-a]indole 9-(2-furyl)-2,3,4,5,11,11a-hexahydro-1H-[1,4]diazepino[1,7-a]indole 2-(2,3,4,5,11,11a-hexahydro-1H-[1,4]diazepino[1,7-a]indol-9-yl)benzenethiol 9-(2,3-dichlorophenyl)-2,3,4,5,11,11a-hexahydro-1H-[1,4]diazepino[1,7-a]indole 9-(4-ethylphenyl)-2,3,4,5,11,11a-hexahydro-1H-[1,4]diazepino[1,7-a]indole 9-(2,4-dimethoxyphenyl)-2,3,4,5,11,11a-hexahydro-1H-[1,4]diazepino[1,7-a]indole 9-(3-chloro-2-fluorophenyl)-2,3,4,5,11,11a-hexahydro-1H-[1,4]diazepino[1,7-a]indole 9-(4-methoxyphenyl)-2,3,4,5,11,11a-hexahydro-1H-[1,4]diazepino[1,7-a]indole 9-[4-(methylsulfanyl)phenyl]-2,3,4,5,11,11a-hexahydro-1H-[1,4]diazepino[1,7-a]indole 4-(2,3,4,5,11,11a-hexahydro-1H-[1,4]diazepino[1,7-a]indol-9-yl)benzonitrile 9-[3-(trifluoromethyl)phenyl]-2,3,4,5,11,11a-hexahydro-1H-[1,4]diazepino[1,7-a]indole 9-(2-naphthyl)-2,3,4,5,11,11a-hexahydro-1H-[1,4]diazepino[1,7-a]indole 1-[4-(2,3,4,5,11,11a-hexahydro-1H-[1,4]diazepino[1,7-a]indol-9-yl)phenyl]ethanone N-[3-(2,3,4,5,11,11a-hexahydro-1H-[1,4]diazepino[1,7-a]indol-9-yl)phenyl]acetamide 9-(2,3-dimethylphenyl)-2,3,4,5,11,11a-hexahydro-1H-[1,4]diazepino[1,7-a]indole 9-(5-fluoro-2-methylphenyl)-2,3,4,5,11,11a-hexahydro-1H-[1,4]diazepino[1,7-a]indole 9-(2-fluoro-5-methylphenyl)-2,3,4,5,11,11a-hexahydro-1H-[1,4]diazepino[1,7-a]indole 9-(5-fluoro-2-methoxyphenyl)-2,3,4,5,11,11a-hexahydro-1H-[1,4]diazepino[1,7-a]indole 9-(3-chloro-2-methylphenyl)-2,3,4,5,11,11a-hexahydro-1H-[1,4]diazepino[1,7-a]indole 9-(3-nitrophenyl)-2,3,4,5,11,11a-hexahydro-1H-[1,4]diazepino[1,7-a]indole 9-(2-nitrophenyl)-2,3,4,5,11,11a-hexahydro-1H-[1,4]diazepino[1,7-a]indole 9-(2-chloro-3-methylphenyl)-2,3,4,5,11,11a-hexahydro-1H-[1,4]diazepino[1,7-a]indole 9-(2-methoxyphenyl)-2,3,4,5,11,11a-hexahydro-1H-[1,4]diazepino[1,7-a]indole 9-(4-ethoxy-2-methylphenyl)-2,3,4,5,11,11a-hexahydro-1H-[1,4]diazepino[1,7-a]indole 9-(4-fluoro-2-methylphenyl)-2,3,4,5,11,11a-hexahydro-1H-[1,4]diazepino[1,7-a]indole 9-(2-chloro-6-fluorophenyl)-2,3,4,5,11,11a-hexahydro-1H-[1,4]diazepino[1,7-a]indole 9-[2-chloro-4-(difluoromethoxy)phenyl]-2,3,4,5,11,11a-hexahydro-1H-[1,4]diazepino[1,7-a]indole 9-[4-(trifluoromethyl)phenyl]-2,3,4,5,11,11a-hexahydro-1H-[1,4]diazepino[1,7-a]indole 9-[4-(trifluoromethoxy)phenyl]-2,3,4,5,11,11a-hexahydro-1H-[1,4]diazepino[1,7-a]indole 9-(6-fluoro-2,4-dimethoxyphenyl)-2,3,4,5,11,11a-hexahydro-1H-[1,4]diazepino[1,7-a]indole 9-(2-methylphenyl)-2,3,4,5,11,11a-hexahydro-1H-[1,4]diazepino[1,7-a]indole 9-[6-fluoro-2-(trifluoromethyl)phenyl]-2,3,4,5,11,11a-hexahydro-1H-[1,4]diazepino[1,7-a]indole 9-[2-(methylsulfanyl)phenyl]-2,3,4,5,11,11a-hexahydro-1H-[1,4]diazepino[1,7-a]indole 9-(2,4,6-trifluorophenyl)-2,3,4,5,11,11a-hexahydro-1H-[1,4]diazepino[1,7-a]indole 9-(2,4,6-trichlorophenyl)-2,3,4,5,11,11a-hexahydro-1H-[1,4]diazepino[1,7-a]indole 9-(2,6-dichloro-4-methoxyphenyl)-2,3,4,5,11,11a-hexahydro-1H-[1,4]diazepino[1,7-a]indole 9-(2,3,4-trifluorophenyl)-2,3,4,5,11,11a-hexahydro-1H-E1,4]diazepino[1,7-a]indole
9-(4-chloro-2,6-difluorophenyl)-2,3,4,5,11,11a-hexahydro-1H-[1,4]diazepino[1,7-a]indole
9-(2,3,4,6-tetrafluorophenyl)-2,3,4,5,11,11a-hexahydro-1H-[1,4]diazepino[1,7-a]indole
9-(2,3,4,5,6-pentafluorophenyl)-2,3,4,5,11,11a-hexahydro-1H-[1,4]diazepino[1,7-a]indole
9-[2,6-di(trifluoromethyl)phenyl]-2,3,4,5,11,11a-hexahydro-1H-[1,4]diazepino[1,7-a]indole
9-[2-(trifluoromethoxy)phenyl]-2,3,4,5,11,11a-hexahydro-1H-[1,4]diazepino[1,7-a]indole
9-[4-ethoxy-2-(trifluoromethoxy)phenyl]-2,3,4,5,11,11a-hexahydro-1H-[1,4]diazepino[1,7-a]indole
9-[4-isopropoxy-2-(trifluoromethyl)phenyl]-2,3,4,5,11,11a-hexahydro-1H-[1,4]diazepino[1,7-a]indole
9-[4-chloro-2-(trifluoromethyl)phenyl]-2,3,4,5,11,11a-hexahydro-1H-[1,4]diazepino[1,7-a]indole
9-[4-fluoro-2-(trifluoromethyl)phenyl]-2,3,4,5,11,11a-hexahydro-1H-[1,4]diazepino[1,7-a]indole
9-[2-chloro-4-ethoxyphenyl]-2,3,4,5,11,11a-hexahydro-1H-[1,4]diazepino[1,7-a]indole
9-[2-chloro-4-isopropoxyphenyl]-2,3,4,5,11,11a-hexahydro-1H-[1,4]diazepino[1,7-a]indole
9-(2-ethyl-4-methoxyphenyl)-2,3,4,5,11,11a-hexahydro-1H-[1,4]diazepino[1,7-a]indole
5-methoxy-2-(2,3,4,5,11,11a-hexahydro-1H-[1,4]diazepino[1,7-a]indol-9-yl)benzaldehyde
9-[4-methoxy-2-(1-hydroxyethyl)phenyl]-2,3,4,5,11,11a-hexahydro-1H-[1,4]diazepino[1,7-a]indole
9-[4-methoxy-2-(1-methoxyethyl)phenyl]-2,3,4,5,11,11a-hexahydro-1H-[1,4]diazepino[1,7-a]indole
1-[5-methoxy-2-(2,3,4,5,11,11a-hexahydro-1H-[1,4]diazepino[1,7-a]indol-9-yl)phenyl]ethanone
[5-methoxy-2-(2,3,4,5,11,11a-hexahydro-1H-[1,4]diazepino[1,7-a]indol-9-yl)phenyl]methanol
9-[4-methoxy-2-(methoxymethyl)phenyl]-2,3,4,5,11,11a-hexahydro-1H-[1,4]diazepino[1,7-a]indole
1-[5-methoxy-2-(2,3,4,5,11,11a-hexahydro-1H-[1,4]diazepino[1,7-a]indol-9-yl)phenyl]-1-propanol
1-[5-methoxy-2-(2,3,4,5,11,11a-hexahydro-1H-[1,4]diazepino[1,7-a]indol-9-yl)phenyl]-1-propanone
methyl (2Z)-3-[5-methoxy-2-(2,3,4,5,11,11a-hexahydro-1H-[1,4]diazepino[1,7-a]indol-9-yl)phenyl]-2-propenoate
methyl 3-[5-methoxy-2-(2,3,4,5,11,11a-hexahydro-1H-[1,4]diazepino[1,7-a]indol-9-yl)phenyl]propanoate
(2Z)-3-[5-methoxy-2-(2,3,4,5,11,11a-hexahydro-1H-[1,4]diazepino[1,7-a]indol-9-yl)phenyl]-2-propen-1-ol
methyl (2E)-3-[5-methoxy-2-(2,3,4,5,11,11a-hexahydro-1H-[1,4]diazepino[1,7-a]indol-9-yl)phenyl]-2-propenoate
(2E)-3-[5-methoxy-2-(2,3,4,5,11,11a-hexahydro-1H-[1,4]diazepino[1,7-a]indol-9-yl)phenyl]-2-propen-1-ol
9-[4-methoxy-2-(2-methoxyethyl)phenyl]-2,3,4,5,11,11a-hexahydro-1H-[1,4]diazepino[1,7-a]indole
9-(2-fluoro-4-methoxyphenyl)-2,3,4,5,11,11a-hexahydro-1H-[1,4]diazepino[1,7-a]indole
9-(2-chloro-4-fluorophenyl)-2,3,4,5,11,11a-hexahydro-1H-[1,4]diazepino[1,7-a]indole
9-benzyl-2,3,4,5,11,11a-hexahydro-1H-[1,4]diazepino[1,7-a]indole
9-(2-fluorobenzyl)-2,3,4,5,11,11a-hexahydro-1H-[1,4]diazepino[1,7-a]indole
9-(3-fluorobenzyl)-2,3,4,5,11,11a-hexahydro-1H-[1,4]diazepino[1,7-a]indole
9-(4-fluorobenzyl)-2,3,4,5,11,11a-hexahydro-1H-[1,4]diazepino[1,7-a]indole
9-(3-methoxybenzyl)-2,3,4,5,11,11a-hexahydro-1H-[1,4]diazepino[1,7-a]indole
3-(2,3,4,5,11,11a-hexahydro-1H-[1,4]diazepino[1,7-a]indol-9-ylmethyl)phenol
9-(2-methoxybenzyl)-2,3,4,5,11,11a-hexahydro-1H-[1,4]diazepino[1,7-a]indole
2-(2,3,4,5,11,11a-hexahydro-1H-[1,4]diazepino[1,7-a]indol-9-ylmethyl)phenol
methyl 2-methoxy-6-(2,3,4,5,11,11a-hexahydro-1H-[1,4]diazepino[1,7-a]indol-9-yl)benzoate
3-(2,3,4,5,11,11a-hexahydro-1H-[1,4]diazepino[1,7-a]indol-9-yl)benzonitrile
3-methyl-4-(2,3,4,5,11,11a-hexahydro-1H-[1,4]diazepino[1,7-a]indol-9-yl)benzonitrile
2-methyl-3-(2,3,4,5,11,11a-hexahydro-1H-[1,4]diazepino[1,7-a]indol-9-yl)benzonitrile
2-(2,3,4,5,11,11a-hexahydro-1H-[1,4]diazepino[1,7-a]indol-9-yl)benzonitrile
3-trifluoromethyl-4-(2,3,4,5,11,11a-hexahydro-1H-[1,4]diazepino[1,7-a]indol-9-yl)benzonitrile
3-(2,3,4,5,11,11a-hexahydro-1H-[1,4]diazepino[1,7-a]indol-9-yl)benzaldehyde
[3-(2,3,4,5,11,11a-hexahydro-1H-[1,4]diazepino[1,7-a]indol-9-yl)phenyl]methanol
9-[3-(methoxymethyl)phenyl]-2,3,4,5,11,11a-hexahydro-1H-[1,4]diazepino[1,7-a]indole
N,N-dimethyl[3-(2,3,4,5,11,11a-hexahydro-1H-[1,4]diazepino[1,7-a]indol-9-yl)phenyl]methanamine
2-fluoro-5-(2,3,4,5,11,11a-hexahydro-1H-[1,4]diazepino[1,7-a]indol-9-yl)benzonitrile
2-fluoro-5-(2,3,4,5,11,11a-hexahydro-1H-[1,4]diazepino[1,7-a]indol-9-yl)benzamide
N-phenyl-2-(2,3,4,5-tetrahydro-1H-[1,4]diazepino[1,7-a]indol-11-yl)acetamide
N-(1H-benzimidazol-2-yl)-2-oxo-2-(2,3,4,5-tetrahydro-1H-[1,4]diazepino[1,7-a]indol-11-yl)acetamide
N-(4-methyl-1,3-thiazol-2-yl)-2-oxo-2-(2,3,4,5-tetrahydro-1H-[1,4]diazepino[1,7-a]indol-11-yl)acetamide
N-[4-(4-morpholinyl)phenyl]-2-oxo-2-(2,3,4,5-tetrahydro-1H-[1,4]diazepino[1,7-a]indol-11-yl)acetamide
N-(2-methoxyphenyl)-2-oxo-2-(2,3,4,5-tetrahydro-1H-[1,4]diazepino[1,7-a]indol-11-yl)acetamide
N-(4-methoxy-2-methylphenyl)-2-oxo-2-(2,3,4,5-tetrahydro-1H-[1,4]diazepino[1,7-a]indol-11-yl)acetamide
N-(3-cyanophenyl)-2-oxo-2-(2,3,4,5-tetrahydro-1H-[1,4]diazepino[1,7-a]indol-11-yl)acetamide
N-(3,5-dimethylphenyl)-2-oxo-2-(2,3,4,5-tetrahydro-1H-[1,4]diazepino[1,7-a]indol-11-yl)acetamide
N-(4-chlorophenyl)-2-oxo-2-(2,3,4,5-tetrahydro-1H-[1,4]diazepino[1,7-a]indol-11-yl)acetamide
N-(3-chlorophenyl)-N-methyl-2-oxo-2-(2,3,4,5-tetrahydro-1H-[1,4]diazepino[1,7-a]indol-11-yl)acetamide N-(6-chloro-2-pyrazinyl)-2-oxo-2-(2,3,4,5-tetrahydro-1H-[1,4]diazepino[1,7-a]indol-11-yl)acetamide N-mesityl-2-oxo-2-(2,3,4,5-tetrahydro-1H-[1,4]diazepino[1,7-a]indol-11-yl)acetamide N-methyl-2-oxo-N-phenyl-2-(2,3,4,5-tetrahydro-1H-[1,4]diazepino[1,7-a]indol-11-yl)acetamide N-(2-ethylphenyl)-2-oxo-2-(2,3,4,5-tetrahydro-1H-[1,4]diazepino[1,7-a]indol-11-yl)acetamide N-(4-chlorophenyl)-N-methyl-2-oxo-2-(2,3,4,5-tetrahydro-1H-[1,4]diazepino[1,7-a]indol-11-yl)acetamide 2-oxo-2-(2,3,4,5-tetrahydro-1H-[1,4]diazepino[1,7-a]indol-11-yl)-N-(5,6,7,8-tetrahydro-1-naphthalenyl)acetamide 2-oxo-2-(2,3,4,5-tetrahydro-1H-[1,4]diazepino[1,7-a]indol-11-yl)-N-(1,3,4-thiadiazol-2-y1)acetamide 2-oxo-N-(2-pyrazinyl)-2-(2,3,4,5-tetrahydro-1H-[1,4]diazepino[1,7-a]indol-11-yl)acetamide 2-oxo-N-(2-pyridinyl)-2-(2,3,4,5-tetrahydro-1H-[1,4]diazepino[1,7-a]indol-11-yl)acetamide 2-oxo-N-(3-pyridinyl)-2-(2,3,4,5-tetrahydro-1H-[1,4]diazepino[1,7-a]indol-11-yl)acetamide 2-oxo-N-(4-pyridinyl)-2-(2,3,4,5-tetrahydro-1H-[1,4]diazepino[1,7-a]indol-11-yl)acetamide N-(2-cyanophenyl)-2-oxo-2-(2,3,4,5-tetrahydro-1H-[1,4]diazepino[1,7-a]indol-11-yl)acetamide N-(2-fluoro-5-methylphenyl)-2-oxo-2-(2,3,4,5-tetrahydro-1H-[1,4]diazepino[1,7-a]indol-11-yl)acetamide N-(2,3-dichlorophenyl)-2-oxo-2-(2,3,4,5-tetrahydro-1H-[1,4]diazepino[1,7-a]indol-11-yl)acetamide N-(2,6-dichlorophenyl)-2-oxo-2-(2,3,4,5-tetrahydro-1H-[1,4]diazepino[1,7-a]indol-11-yl)acetamide N-(2,3-dimethylphenyl)-2-oxo-2-(2,3,4,5-tetrahydro-1H-[1,4]diazepino[1,7-a]indol-11-yl)acetamide N-(2,6-dimethylphenyl)-2-oxo-2-(2,3,4,5-tetrahydro-1H-[1,4]diazepino[1,7-a]indol-11-yl)acetamide N-(3,5-difluorophenyl)-2-oxo-2-(2,3,4,5-tetrahydro-1H-[1,4]diazepino[1,7-a]indol-11-yl)acetamide N-(3-chlorophenyl)-2-oxo-2-(2,3,4,5-tetrahydro-1H-[1,4]diazepino[1,7-a]indol-11-yl)acetamide N-(3-chloro-4-methylphenyl)-2-oxo-2-(2,3,4,5-tetrahydro-1H-[1,4]diazepino[1,7-a]indol-11-yl)acetamide N-(3-nitrophenyl)-2-oxo-2-(2,3,4,5-tetrahydro-1H-[1,4]diazepino[1,7-a]indol-11-yl)acetamide N-(3-methoxyphenyl)-2-oxo-2-(2,3,4,5-tetrahydro-1H-[1,4]diazepino[1,7-a]indol-11-yl)acetamide 2-oxo-2-(2,3,4,5-tetrahydro-1H-[1,4]diazepino[1,7-a]indol-11-yl)-N-[3-(trifluoromethyl)phenyl]acetamide N-(3-methylphenyl)-2-oxo-2-(2,3,4,5-tetrahydro-1H-[1,4]diazepino[1,7-a]indol-11-yl)acetamide N-(4-cyanophenyl)-2-oxo-2-(2,3,4,5-tetrahydro-1H-[1,4]diazepino[1,7-a]indol-11-yl)acetamide N-(2-bromo-4-methylphenyl)-2-oxo-2-(2,3,4,5-tetrahydro-1H-[1,4]diazepino[1,7-a]indol-11-yl)acetamide N-(4-nitrophenyl)-2-oxo-2-(2,3,4,5-tetrahydro-1H-[1,4]diazepino[1,7-a]indol-11-yl)acetamide 2-oxo-N-(4-phenoxyphenyl)-2-(2,3,4,5-tetrahydro-1H-[1,4]diazepino[1,7-a]indol-11-yl)acetamide N-[1,1'-biphenyl]-4-yl-2-oxo-2-(2,3,4,5-tetrahydro-1H-[1,4]diazepino[1,7-a]indol-11-yl)acetamide N-(4-isopropylphenyl)-2-oxo-2-(2,3,4,5-tetrahydro-1H-[1,4]diazepino[1,7-a]indol-11-yl)acetamide N-(4-chloro-2-fluorophenyl)-2-oxo-2-(2,3,4,5-tetrahydro-1H-[1,4]diazepino[1,7-a]indol-11-yl)acetamide N-(2-cyano-3-fluorophenyl)-2-oxo-2-(2,3,4,5-tetrahydro-1H-[1,4]diazepino[1,7-a]indol-11-yl)acetamide N-(4-chlorophenyl)-N-ethyl-2-oxo-2-(2,3,4,5-tetrahydro-1H-[1,4]diazepino[1,7-a]indol-11-yl)acetamide N-(4-bromo-2-chloro-6-methylphenyl)-2-oxo-2-(2,3,4,5-tetrahydro-1H-[1,4]diazepino[1,7-a]indol-11-yl)acetamide N-(3-chloro-4-iodophenyl)-2-oxo-2-(2,3,4,5-tetrahydro-1H-[1,4]diazepino[1,7-a]indol-11-yl)acetamide N-ethyl-N-(2-fluorophenyl)-2-oxo-2-(2,3,4,5-tetrahydro-1H-[1,4]diazepino[1,7-a]indol-11-yl)acetamide N-(3-benzylphenyl)-2-oxo-2-(2,3,4,5-tetrahydro-1H-[1,4]diazepino[1,7-a]indol-11-yl)acetamide N-(4-methylphenyl)-2-oxo-2-(2,3,4,5-tetrahydro-1H-[1,4]diazepino[1,7-a]indol-11-yl)acetamide N-(3-ethylphenyl)-2-oxo-2-(2,3,4,5-tetrahydro-1H-[1,4]diazepino[1,7-a]indol-11-yl)acetamide N-(1-naphthyl)-2-oxo-2-(2,3,4,5-tetrahydro-1H-[1,4]diazepino[1,7-a]indol-11-yl)acetamide 2-oxo-N-(8-quinolinyl)-2-(2,3,4,5-tetrahydro-1H-[1,4]diazepino[1,7-a]indol-11-yl)acetamide: trifluoroacetate N-(5-methyl-1,3-thiazol-2-yl)-2-oxo-2-(2,3,4,5-tetrahydro-1H-[1,4]diazepino[1,7-a]indol-11-yl)acetamide N-(3-methyl-5-isothiazolyl)-2-oxo-2-(2,3,4,5-tetrahydro-1H-[1,4]diazepino[1,7-a]indol-11-yl)acetamide: trifluoroacetate N-(3-methyl-5-isoxazolyl)-2-oxo-2-(2,3,4,5-tetrahydro-1H-[1,4]diazepino[1,7-a]indol-11-yl)acetamide N-(1,3-benzothiazol-2-yl)-2-oxo-2-(2,3,4,5-tetrahydro-1H-[1,4]diazepino[1,7-a]indol-11-yl)acetamide N-(3-chloro-2-methylphenyl)-2-(2,3,4,5-tetrahydro-1H-[1,4]diazepino[1,7-a]indol-11-yl)acetamide N-(3-chloro-2-methylphenyl)-2-oxo-2-(2,3,4,5-tetrahydro-1H-[1,4]diazepino[1,7-a]indol-11-yl)acetamide N-[2-methyl-3-(trifluoromethyl)phenyl]-2-oxo-2-(2,3,4,5-tetrahydro-1H-[1,4]diazepino[1,7-a]indol-11-yl)acetamide N-(4-bromo-2-chloro-6-methylphenyl)2(2,3,4,5-tetrahydro-1H-[1,4]diazepino[1,7-a]indol-11-yl)acetamide N-(1-ethyl-1H-pyrazol-5-yl)-2-oxo-2-(2,3,4,5-tetrahydro-1H-[1,4]diazepino[1,7-a]indol-11-yl)acetamide 2-oxo-N-(4-phenyl-1,3-thiazol-2-yl)-2-(2,3,4,5-tetrahydro-1H-[1,4]diazepino[1,7-a]indol-11-yl)acetamide N-(5-methyl-3-isoxazolyl)-2-oxo-2-(2,3,4,5-tetrahydro-1H-[1,4]diazepino[1,7-a]indol-11-yl)acetamide 1-(2,3,4,5-tetrahydro-1H-[1,4]diazepino[1,7-a]indol-11-yl)-2-(5,6,7,8-tetrahydro-1-naphthalenyloxy)ethanone 2-(2-bromophenoxy)-1-(2,3,4,5-tetrahydro-1H-[1,4]diazepino[1,7-a]indol-11-yl)ethanone 2-(2-isopropylphenoxy)-1-(2,3,4,5-tetrahydro-1H-[1,4]diazepino[1,7-a]indol-11-yl)ethanone 2-(2-ethylphenoxy)-1-(2,3,4,5-tetrahydro-1H-[1,4]diazepino[1,7-a]indol-11-yl)ethanone 2-(3-bromophenoxy)-1-(2,3,4,5-tetrahydro-1H-[1,4]
diazepino[1,7-a]indol-11-yl)ethanone
2-(3-fluorophenoxy)-1-(2,3,4,5-tetrahydro-1H-[1,4]
diazepino[1,7-a]indol-11-yl)ethanone
2-(3-methoxyphenoxy)-1-(2,3,4,5-tetrahydro-1H-[1,4]
diazepino[1,7-a]indol-11-yl)ethanone
1-(2,3,4,5-tetrahydro-1H-[1,4]diazepino[1,7-a]indol-11-
yl)-2-[3-(trifluoromethyl)phenoxy]ethanone
2-(3-isopropylphenoxy)-1-(2,3,4,5-tetrahydro-1H-[1,4]
diazepino[1,7-a]indol-11-yl)ethanone
2-(3-ethylphenoxy)-1-(2,3,4,5-tetrahydro-1H-[1,4]
diazepino[1,7-a]indol-11-yl)ethanone
2-(4-fluorophenoxy)-1-(2,3,4,5-tetrahydro-1H-[1,4]
diazepino[1,7-a]indol-11-yl)ethanone
2-(4-iodophenoxy)-1-(2,3,4,5-tetrahydro-1H-[1,4]
diazepino[1,7-a]indol-11-yl)ethanone
2-[4-(benzyloxy)phenoxy]-1-(2,3,4,5-tetrahydro-1H-[1,
4]diazepino[1,7-a]indol-11-yl)ethanone
2-(4-butoxyphenoxy)-1-(2,3,4,5-tetrahydro-1H-[1,4]
diazepino[1,7-a]indol-11-yl)ethanone
2-(3-tert-butylphenoxy)-1-(2,3,4,5-tetrahydro-1H-[1,4]
diazepino[1,7-a]indol-11-yl)ethanone
2-(4-ethylphenoxy)-1-(2,3,4,5-tetrahydro-1H-[1,4]
diazepino[1,7-a]indol-11-yl)ethanone
2-(1-naphthyloxy)-1-(2,3,4,5-tetrahydro-1H-[1,4]
diazepino[1,7-a]indol-11-yl)ethanone
2-[(4-chloro-1-naphthyl)oxy]-1-(2,3,4,5-tetrahydro-1H-
[1,4]diazepino[1,7-a]indol-11-yl)ethanone
2-(2-naphthyloxy)-1-(2,3,4,5-tetrahydro-1H-[1,4]
diazepino[1,7-a]indol-11-yl)ethanone
2-(1,3-benzodioxol-5-yloxy)-1-(2,3,4,5-tetrahydro-1H-
[1,4]diazepino[1,7-a]indol-11-yl)ethanone
2-(4-quinolinyloxy)-1-(2,3,4,5-tetrahydro-1H-[1,4]
diazepino[1,7-a]indol-11-yl)ethanone
2-(8-quinolinyloxy)-1-(2,3,4,5-tetrahydro-1H-[1,4]
diazepino[1,7-a]indol-11-yl)ethanone
2-(5-isoquinolinyloxy)-1-(2,3,4,5-tetrahydro-1H-[1,4]
diazepino[1,7-a]indol-11-yl)ethanone
2-(4-nitrophenoxy)-1-(2,3,4,5-tetrahydro-1H-[1,4]
diazepino[1,7-a]indol-11-yl)ethanone
2-(2-iodophenoxy)-1-(2,3,4,5-tetrahydro-1H-[1,4]
diazepino[1,7-a]indol-11-yl)ethanone
2-[(4'-bromo[1,1'-biphenyl]-4-yl)oxy]-1-(2,3,4,5-
tetrahydro-1H-[1,4]diazepino[1,7-a]indol-11-yl)
ethanone
5-methoxy-6-[2-oxo-2-(2,3,4,5-tetrahydro-1H-[1,4]
diazepino[1,7-a]indol-11-yl)ethoxy]-1-indanone
7-[2-oxo-2-(2,3,4,5-tetrahydro-1H-[1,4]diazepino[1,7-a]
indol-11-yl)ethoxy]-1-indanone 5-[2-oxo-2-(2,3,4,5-
tetrahydro-1H-[1,4]diazepino[1,7-a]indol-11-yl)
ethoxy]-1-indanone
2-[(2-acetyl-1,2,3,4-tetrahydro-5-isoquinolinyl)oxy]-1-
(2,3,4,5-tetrahydro-1H-[1,4]diazepino[1,7-a]indol-11-
yl)ethanone
2-([1,1'-biphenyl]-2-yloxy)-1-(2,3,4,5-tetrahydro-1H-[1,
4]diazepino[1,7-a]indol-11-yl)ethanone
2-[2-oxo-2-(2,3,4,5-tetrahydro-1H-[1,4]diazepino[1,7-a]
indol-11-yl)ethoxy]-N-phenylbenzamide
2-[2-(4-morpholinylcarbonyl)phenoxy]-1-(2,3,4,5-
tetrahydro-1H-[1,4]diazepino[1,7-a]indol-11-yl)
ethanone
2-[(5-chloro-8-quinolinyl)oxy]-1-(2,3,4,5-tetrahydro-1H-
[1,4]diazepino[1,7-a]indol-11-yl)ethanone
N-{4-[2-oxo-2-(2,3,4,5-tetrahydro-1H-[1,4]diazepino[1,
7-a]indol-11-yl)ethoxy]phenyl}urea
N-{2-methyl-3-[2-oxo-2-(2,3,4,5-tetrahydro-1H-[1,4]
diazepino[1,7-a]indol-11-yl)ethoxy]phenyl}acetamide
2-phenoxy-1-(2,3,4,5-tetrahydro-1H-[1,4]diazepino[1,7-
a]indol-11-yl)ethanone
2-(2,6-dimethylphenoxy)-1-(2,3,4,5-tetrahydro-1H-[1,4]
diazepino[1,7-a]indol-11-yl)ethanone
2-(4-methoxyphenoxy)-1-(2,3,4,5-tetrahydro-1H-[1,4]
diazepino[1,7-a]indol-11-yl)ethanone
2-(2,4-difluorophenoxy)-1-(2,3,4,5-tetrahydro-1H-[1,4]
diazepino[1,7-a]indol-11-yl)ethanone
2-(2,4-dibromophenoxy)-1-(2,3,4,5-tetrahydro-1H-[1,4]
diazepino[1,7-a]indol-11-yl)ethanone
2-(4-methylphenoxy)-1-(2,3,4,5-tetrahydro-1H-[1,4]
diazepino[1,7-a]indol-11-yl)ethanone
2-(2-chlorophenoxy)-1-(2,3,4,5-tetrahydro-1H-[1,4]
diazepino[1,7-a]indol-11-yl)ethanone
2-(2,4-dichlorophenoxy)-1-(2,3,4,5-tetrahydro-1H-[1,4]
diazepino[1,7-a]indol-11-yl)ethanone
2-(mesityloxy)-1-(2,3,4,5-tetrahydro-1H-[1,4]diazepino
[1,7-a]indol-11-yl)ethanone
2-(3-nitrophenoxy)-1-(2,3,4,5-tetrahydro-1H-[1,4]
diazepino[1,7-a]indol-11-yl)ethanone
5-[2-oxo-2-(2,3,4,5-tetrahydro-1H-[1,4]diazepino[1,7-a]
indol-11-yl)ethoxy]-3,4-dihydro-1 (2H)-naphthalenone
2-(2,3-dimethylphenoxy)-1-(2,3,4,5-tetrahydro-1H-[1,4]
diazepino[1,7-a]indol-11-yl)ethanone
2-[(2-methyl-8-quinolinyl)oxy]-1-(2,3,4,5-tetrahydro-
1H-[1,4]diazepino[1,7-a]indol-11-yl)ethanone
2-[(5,7-dibromo-8-quinolinyl)oxy]-1-(2,3,4,5-tetrahydro-
1H-[1,4]diazepino[1,7-a]indol-11-yl)ethanone
2-[(5,7-dichloro-8-quinolinyl)oxy]-1-(2,3,4,5-tetrahydro-
1H-[1,4]diazepino[1,7-a]indol-11-yl)ethanone
2-(2,3-dimethoxyphenoxy)-1-(2,3,4,5-tetrahydro-1H-[1,
4]diazepino[1,7-a]indol-11-yl)ethanone
2-[(5,7-dibromo-2-methyl-8-quinolinyl)oxy]-1-(2,3,4,5-
tetrahydro-1H-[1,4]diazepino[1,7-a]indol-11-yl)
ethanone
2-[(5,7-dichloro-2-methyl-8-quinolinyl)oxy]-1-(2,3,4,5-
tetrahydro-1H-[1,4]diazepino[1,7-a]indol-11-yl)
ethanone
2-[(5-fluoro-8-quinolinyl)oxy]-1-(2,3,4,5-tetrahydro-1H-
[1,4]diazepino[1,7-a]indol-11-yl)ethanone
2-[(7-propyl-8-quinolinyl)oxy]-1-(2,3,4,5-tetrahydro-1H-
[1,4]diazepino[1,7-a]indol-11-yl)ethanone
2-[(2,2-dimethyl-2,3-dihydro-1-benzofuran-7-yl)oxy]-1-
(2,3,4,5-tetrahydro-1H-[1,4]diazepino[1,7-a]indol-11-
yl)ethanone
2-[2-fluoro-3-(trifluoromethyl)phenoxy]-1-(2,3,4,5-
tetrahydro-1H-[1,4]diazepino[1,7-a]indol-11-yl)
ethanone
4-[2-oxo-2-(2,3,4,5-tetrahydro-1H-[1,4]diazepino[1,7-a]
indol-11-yl)ethoxy]-1-indanone
2-[(5,7-dimethyl-8-quinolinyl)oxy]-1-(2,3,4,5-
tetrahydro-1H-[1,4]diazepino[1,7-a]indol-11-yl)
ethanone
2-[(5,5-dimethyl-5,6,7,8-tetrahydro-1-naphthalenyl)oxy]-
1-(2,3,4,5-tetrahydro-1H-[1,4]diazepino[1,7-a]indol-
11-yl)ethanone
2-[(2-chloro-3-pyridinyl)oxy]-1-(2,3,4,5-tetrahydro-1H-
[1,4]diazepino[1,7-a]indol-yl)ethanone 3-[2-oxo-2-(2,3,4,5-tetrahydro-1H-[1,4]diazepino[1,7-a]indol-11-yl)ethoxy]benzonitrile 2-(phenylsulfanyl)-1-(2,3,4,5-tetrahydro-1H-[1,4]diazepino[1,7-a]indol-11-yl)ethanone 2-(2,3-dihydro-1,4-benzodioxin-5-yloxy)-1-(2,3,4,5-tetrahydro-1H-[1,4]diazepino[1,7-a]indol-11-yl)ethanone 2-[(8,8-dimethyl-5,6,7,8-tetrahydro-2-naphthalenyl)oxy]-1-(2,3,4,5-tetrahydro-1H-[1,4]diazepino[1,7-a]indol-11-yl)ethanone 2-(4-pyridinyloxy)-1-(2,3,4,5-tetrahydro-1H-[1,4]diazepino[1,7-a]indol-11-yl)ethanone 2-(2-pyrimidinyloxy)-1-(2,3,4,5-tetrahydro-1H-[1,4]diazepino[1,7-a]indol-11-yl)ethanone 2-(8-quinolinylsulfanyl)-1-(2,3,4,5-tetrahydro-1H-[1,4]diazepino[1,7-a]indol-11-yl)ethanone N-(6-methoxy-1,3-benzothiazol-2-yl)-2-oxo-2-(2,3,4,5-tetrahydro-1H-[1,4]diazepino[1,7-a]indol-11-yl)acetamide 2-oxo-2-(2,3,4,5-tetrahydro-1H-[1,4]diazepino[1,7-a]indol-11-yl)-N-[6-(trifluoromethoxy)-1,3-benzothiazol-2-yl]acetamide 2-oxo-2-(2,3,4,5-tetrahydro-1H-[1,4]diazepino[1,7-a]indol-11-yl)-N-[6-(trifluoromethyl)-1,3-benzothiazol-2-yl]acetamide 2-oxo-2-(2,3,4,5-tetrahydro-1H-[1,4]diazepino[1,7-a]indol-11-yl)-N-{6-[(trifluoromethyl)sulfanyl]-1,3-benzothiazol-2-yl}acetamide N-(6-ethoxy-1,3-benzothiazol-2-y1)-2-oxo-2-(2,3,4,5-tetrahydro-1H-[1,4]diazepino[1,7-a]indol-11-yl)acetamide N-(6-fluoro-1,3-benzothiazol-2-yl)-2-oxo-2-(2,3,4,5-tetrahydro-1H-[1,4]diazepino[1,7-a]indol-11-yl)acetamide N-(6-chloro-1,3-benzothiazol-2-yl)-2-oxo-2-(2,3,4,5-tetrahydro-1H-[1,4]diazepino[1,7-a]indol-11-yl)acetamide N-(6-methyl-1,3-benzothiazol-2-yl)-2-oxo-2-(2,3,4,5-tetrahydro-1H-[1,4]diazepino[1,7-a]indol-11-yl)acetamide N-(4-chloro-1,3-benzothiazol-2-yl)-2-oxo-2-(2,3,4,5-tetrahydro-1H-[1,4]diazepino[1,7-a]indol-11-yl)acetamide N-(4-methoxy-1,3-benzothiazol-2-yl)-2-oxo-2-(2,3,4,5-tetrahydro-1H-[1,4]diazepino[1,7-a]indol-11-yl)acetamide N-(4-methyl-1,3-benzothiazol-2-yl)-2-oxo-2-(2,3,4,5-tetrahydro-1H-[1,4]diazepino[1,7-a]indol-11-yl)acetamide N-(5,6-dichloro-1,3-benzothiazol-2-yl)-2-oxo-2-(2,3,4,5-tetrahydro-1H-[1,4]diazepino[1,7-a]indol-11-yl)acetamide N-(5,6-dimethyl-1,3-benzothiazol-2-yl)-2-oxo-2-(2,3,4,5-tetrahydro-1H-[1,4]diazepino[1,7-a]indol-11-yl)acetamide N-(7-bromo-6-fluoro-1,3-benzothiazol-2-yl)-2-oxo-2-(2,3,4,5-tetrahydro-1H-[1,4]diazepino[1,7-a]indol-11-yl)acetamide N-(4,6-dichloro-1,3-benzothiazol-2-yl)-2-oxo-2-(2,3,4,5-tetrahydro-1H-[1,4]diazepino[1,7-a]indol-11-yl)acetamide N-(4,6-dimethyl-1,3-benzothiazol-2-yl)-2-oxo-2-(2,3,4,5-tetrahydro-1H-[1,4]diazepino[1,7-a]indol-11-yl)acetamide N-(4,6-difluoro-1,3-benzothiazol-2-yl)-2-oxo-2-(2,3,4,5-tetrahydro-1H-[1,4]diazepino[1,7-a]indol-11-yl)acetamide; and N-(6-nitro-1,3-benzothiazol-2-yl)-2-oxo-2-(2,3,4,5-tetrahydro-1H-[1,4]diazepino[1,7-a]indol-11-yl)acetamide.

4. The compound of claim 1 in native form, acid salt form or base salt form.

5. A compound selected from the group consisting of:

tert-butyl 1,2,4,5-tetrahydro-3H-[1,4]diazepino[1,7-a]-indole-3-carboxylate;

11-[(E)-2-nitroethyl]-2,3,4,5-tetrahydro-1H-[1,4]diazepino-[1,7-a]indole;

3-(trifluoroacetyl)-2,3,4,5-tetrahydro-1H-[1,4]diazepino-[1,7a]indole; and 2-bromo-1-[3-trifluoroacetyl)-2,3,4,5-tetrahydro-1H-[1,4]diazepino[1-a]indole-11-yl]ethanone;

or a pharmaceutically effective salt thereof.

6. A compound of the formula

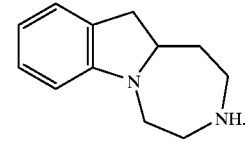

7. A compound of the formula

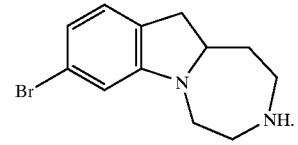

8. A compound of the formula

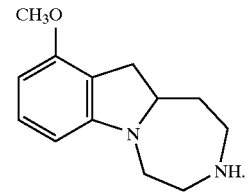

* * * * *